(12) United States Patent
Bitner et al.

(10) Patent No.: US 8,993,632 B2
(45) Date of Patent: *Mar. 31, 2015

(54) INHIBITORS OF THE 11-BETA-HYDROXYSTEROID DEHYDROGENASE TYPE 1 ENZYME

(75) Inventors: R. Scott Bitner, Pleasant Prairie, WI (US); Kaitlin E. Browman, Deerfield, IL (US); Michael E. Brune, Mundelein, IL (US); Steven Fung, Mount Prospect, IL (US); Peer B. Jacobson, Libertyville, IL (US); Lynne E. Rueter, Round Lake Beach, IL (US); Marina I. Strakhova, Vernon Hills, IL (US); Jiahong Wang, Lake Bluff, IL (US); Jeffrey J. Rohde, Evanston, IL (US); Qi Shuai, Dekalb, IL (US); James T. Link, Stanford, CA (US); Jyoti R. Patel, Libertyville, IL (US); Jurgen Dinges, Wadsworth, IL (US); Bryan K. Sorensen, Antioch, IL (US); Hong Yong, Libertyville, IL (US); Vince S. Yeh, San Diego, CA (US); Ravi Kurukulasuriya, East Lyme, CT (US)

(73) Assignee: AbbVie Inc., North Chicago, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/469,021

(22) Filed: May 10, 2012

(65) Prior Publication Data

US 2012/0289512 A1     Nov. 15, 2012

Related U.S. Application Data

(60) Division of application No. 12/390,286, filed on Feb. 20, 2009, now Pat. No. 8,198,331, which is a continuation-in-part of application No. 11/733,636, filed on Apr. 10, 2007, now Pat. No. 7,528,282, which is a continuation-in-part of application No. 11/326,277, filed on Jan. 5, 2006, now Pat. No. 7,217,838, said application No. 12/390,286 is a continuation-in-part of application No. 12/195,937, filed on Aug. 21, 2008, now abandoned.

(60) Provisional application No. 60/641,496, filed on Jan. 5, 2005, provisional application No. 60/957,082, filed on Aug. 21, 2007.

(51) Int. Cl.
| | | |
|---|---|---|
| A61K 31/16 | (2006.01) | |
| C07C 233/11 | (2006.01) | |
| A61K 31/165 | (2006.01) | |
| A61K 31/195 | (2006.01) | |
| A61K 31/44 | (2006.01) | |
| A61K 31/45 | (2006.01) | |
| A61K 31/5377 | (2006.01) | |
| C07C 233/52 | (2006.01) | |
| C07C 233/58 | (2006.01) | |
| C07C 233/63 | (2006.01) | |
| C07C 237/24 | (2006.01) | |
| C07C 311/46 | (2006.01) | |
| C07D 207/277 | (2006.01) | |
| C07D 211/78 | (2006.01) | |
| C07D 213/56 | (2006.01) | |
| C07D 231/12 | (2006.01) | |
| C07D 261/08 | (2006.01) | |
| C07D 333/24 | (2006.01) | |

(52) U.S. Cl.
CPC ............. *C07C 233/11* (2013.01); *A61K 31/165* (2013.01); *A61K 31/195* (2013.01); *A61K 31/44* (2013.01); *A61K 31/45* (2013.01); *A61K 31/5377* (2013.01); *C07C 233/52* (2013.01); *C07C 233/58* (2013.01); *C07C 233/63* (2013.01); *C07C 237/24* (2013.01); *C07C 311/46* (2013.01); *C07D 207/277* (2013.01); *C07D 211/78* (2013.01); *C07D 213/56* (2013.01); *C07D 231/12* (2013.01); *C07D 261/08* (2013.01); *C07D 333/24* (2013.01); *C07C 2101/02* (2013.01); *C07C 2101/04* (2013.01); *C07C 2101/08* (2013.01); *C07C 2101/14* (2013.01); *C07C 2103/74* (2013.01)
USPC ........................................................ 514/613

(58) Field of Classification Search
USPC ........................................................ 514/613
See application file for complete search history.

(56) References Cited

U.S. PATENT DOCUMENTS

| 4,273,704 A | 6/1981 | Mazur |
| 4,324,791 A | 4/1982 | Welstead, Jr. |

(Continued)

FOREIGN PATENT DOCUMENTS

| EP | 215297 A2 | 3/1987 |
| EP | 336356 A2 | 10/1989 |

(Continued)

OTHER PUBLICATIONS

References cited in 892 form in parent U.S. Appl. No. 12/390,286.*

(Continued)

*Primary Examiner* — Shawquia Jackson
(74) *Attorney, Agent, or Firm* — Lisa V. Mueller; Michael Best & Friedrich LLP

(57) ABSTRACT

The present invention relates to inhibitors of the 11-beta-hydroxysteroid dehydrogenase Type 1 enzyme and their use in treatment of non-insulin dependent type 2 diabetes, insulin resistance, obesity, lipid disorders, metabolic syndrome, central nervous system disorders, and diseases and conditions that are related to excessive glucocorticoids.

18 Claims, 9 Drawing Sheets

(56) References Cited

U.S. PATENT DOCUMENTS

| | | | |
|---|---|---|---|
| 4,514,332 | A | 4/1985 | Hansen, Jr. et al. |
| 4,751,292 | A | 6/1988 | Fox |
| 4,921,958 | A | 5/1990 | Abou-Gharbia et al. |
| 5,397,788 | A | 3/1995 | Horwell et al. |
| 5,622,983 | A | 4/1997 | Horwell et al. |
| 6,368,816 | B2 | 4/2002 | Walker et al. |
| 6,784,167 | B2 | 8/2004 | Wood et al. |
| 7,087,400 | B2 | 8/2006 | Walker et al. |
| 7,122,531 | B2 | 10/2006 | Walker et al. |
| 7,217,838 | B2 | 5/2007 | Rohde et al. |
| 7,435,833 | B2 | 10/2008 | Yeh et al. |
| 2004/0122033 | A1 | 6/2004 | Nargund et al. |
| 2004/0133011 | A1 | 7/2004 | Waddell et al. |
| 2005/0245534 | A1 | 11/2005 | Link et al. |
| 2005/0261302 | A1 | 11/2005 | Hoff et al. |
| 2005/0277647 | A1 | 12/2005 | Link et al. |
| 2005/0288338 | A1 | 12/2005 | Yao et al. |
| 2006/0004049 | A1 | 1/2006 | Yao et al. |
| 2006/0009471 | A1 | 1/2006 | Yao et al. |
| 2006/0009491 | A1 | 1/2006 | Yao et al. |
| 2006/0079506 | A1 | 4/2006 | Linders et al. |
| 2006/0089349 | A1 | 4/2006 | Gundertofte et al. |
| 2006/0094699 | A1 | 5/2006 | Kampen et al. |
| 2006/0100235 | A1 | 5/2006 | Andersen et al. |
| 2006/0106008 | A1 | 5/2006 | Andersen et al. |
| 2006/0106071 | A1 | 5/2006 | Lin et al. |
| 2006/0111348 | A1 | 5/2006 | Kampen et al. |
| 2006/0111366 | A1 | 5/2006 | Andersen et al. |
| 2006/0281773 | A1 | 12/2006 | Patel et al. |
| 2007/0161641 | A1 | 7/2007 | Hendrix et al. |
| 2008/0064693 | A1 | 3/2008 | Jaroskova et al. |

FOREIGN PATENT DOCUMENTS

| | | |
|---|---|---|
| EP | 405537 A1 | 1/1991 |
| EP | 564924 A2 | 10/1993 |
| EP | 697403 A1 | 2/1996 |
| EP | 1180513 A1 | 2/2002 |
| SU | 740752 | 6/1980 |
| SU | 803348 | 9/1981 |
| WO | WO-9113081 A1 | 9/1991 |
| WO | WO-9214697 A1 | 9/1992 |
| WO | WO-9428885 A1 | 12/1994 |
| WO | WO-9500146 A1 | 1/1995 |
| WO | WO-9902145 A1 | 1/1999 |
| WO | WO-0129007 A1 | 4/2001 |
| WO | WO-03059905 A1 | 7/2003 |
| WO | WO-03065983 A2 | 8/2003 |
| WO | WO-03075660 A1 | 9/2003 |
| WO | WO-2004011310 A1 | 2/2004 |
| WO | WO-2004033427 A1 | 4/2004 |
| WO | WO-2004037251 A1 | 5/2004 |
| WO | WO-2004056744 A1 | 7/2004 |
| WO | WO-2004056745 A2 | 7/2004 |
| WO | WO-2004065351 A1 | 8/2004 |
| WO | WO-2004089367 A1 | 10/2004 |
| WO | WO-2004089380 A2 | 10/2004 |
| WO | WO-2004089416 A2 | 10/2004 |
| WO | WO-2004089470 A2 | 10/2004 |
| WO | WO-2004089471 A2 | 10/2004 |
| WO | WO-2004089896 A1 | 10/2004 |
| WO | WO-2004113310 A1 | 12/2004 |
| WO | WO-2005016877 A2 | 2/2005 |
| WO | WO-2005042513 A1 | 5/2005 |
| WO | WO-2005046685 A1 | 5/2005 |
| WO | WO-2005047250 A1 | 5/2005 |
| WO | WO-2005060963 A1 | 7/2005 |
| WO | WO-2005097764 A1 | 10/2005 |
| WO | WO-2005103023 A1 | 11/2005 |
| WO | WO-2005108359 A1 | 11/2005 |
| WO | WO-2005108361 A1 | 11/2005 |
| WO | WO-2005116002 A2 | 12/2005 |
| WO | WO-2006002349 A1 | 1/2006 |
| WO | WO-2006002350 A1 | 1/2006 |
| WO | WO-2006002361 A2 | 1/2006 |
| WO | WO-2006012173 A1 | 2/2006 |
| WO | WO-2006012226 A2 | 2/2006 |
| WO | WO-2006012227 A2 | 2/2006 |
| WO | WO-2006012642 A2 | 2/2006 |
| WO | WO-2006017542 A1 | 2/2006 |
| WO | WO-2006020598 A2 | 2/2006 |
| WO | WO-2006024627 A2 | 3/2006 |
| WO | WO-2006024628 A1 | 3/2006 |
| WO | WO-2006040329 A1 | 4/2006 |
| WO | 2006048330 A1 | 5/2006 |
| WO | 2006048331 A1 | 5/2006 |
| WO | 2006048750 A2 | 5/2006 |
| WO | 2006049952 A1 | 5/2006 |
| WO | 2006050908 A1 | 5/2006 |
| WO | 2006053024 A2 | 5/2006 |
| WO | WO-2006048330 A1 | 5/2006 |
| WO | WO-2006048331 A1 | 5/2006 |
| WO | WO-2006048750 A2 | 5/2006 |
| WO | WO-2006049952 A1 | 5/2006 |
| WO | WO-2006050908 A1 | 5/2006 |
| WO | WO-2006053024 A2 | 5/2006 |
| WO | 2006066109 A2 | 6/2006 |
| WO | WO-2006066109 A2 | 6/2006 |
| WO | 2006104280 A1 | 10/2006 |
| WO | WO-2006104280 A1 | 10/2006 |

OTHER PUBLICATIONS

Cooper et al., Bone Osteoprogenitor Cells in Cell Populations Derived from Mouse and Rat Calvaria Differ in Their Response to Corticosterone, Cortisol and Cortisone 23(2): 119-125 (1998).

Albrecht S. et al., "Nonpituitary Tumors of the Sellar Region," Cushing's Disease in:Melmed S. Ed. The Pituitary, 2002, pp. 592-612, 2nd Ed.

Anstead G. M., "Steroids, Retinoids, and Wound Healing," Adv Wound Care, 1998, pp. 277-285, vol. 11.

Armaly M. F., "Dexamethasone Ocular Hypertension and Eosinopenia, and Glucose Tolderance Test," Arch Ophthalmol, 1967, pp. 193-197, vol. 78.

Baxter J. D., "Glucocorticoid Hormone Action," Pharmac Ther, 1976, pp. 605-659, vol. 2.

Beer H. D. et al., "Glucocorticoid-Regulated Gene Expression During Cutaneous Wound Repair," Vitam Horm, 2000, pp. 217-239, vol. 59.

Belanoff J. K. et al., "Corticosteroids and cognition," J. of Psych. Res, 2001, pp. 127-145, vol. 35.

Bellows C.G. et al., "Osteoprogenitor Cells in Cell Populations Derived From Mouse and Rat Calvaria Differ in Their Response to Corticosterone, Cortisol, and Cortisone," Bone, 1998, pp. 119-125, vol. 23 (2).

Bertagna X, "Pituitary Tumors Cushing's Disease," 2002, pp. 592-612, Chap. 13 Sec. 3.

Billaudel B. et al., "Direct Effect of Corticostrone upon Insuline Secretion Studied by Three Different Techniques," Horm. Metabl. Res, 1979, pp. 555-560, vol. 11.

Billaudel B., "Immediate in-vivo effect of corticosterone on glucose-induced insulin secretion in the rat," Journ of Endocrin, 1982, pp. 315-320, vol. 95.

Bland R. et al., "Characterization of 11.beta.-hydroxysteroid dehydrogenase activity and corticosteroid receptor expression in human osteosarcoma cell lines," J. of Endocrin, 1999, pp. 455-464, vol. 161.

Boscaro M. et al., "Cushing's syndrome," The Lancet, 2001, pp. 783-791, vol. 357.

Budziszewska., "Effect of antidepressant drugs on the hypothalamic-pituitary-adrenal axis activity and glucocorticoid receptor function," Polish Journal of Pharm, 2002, pp. 343-349, vol. 54.

Cooper M.S. et al., "Expression and Functional Consequences of 11.beta.-Hydroxysteroid Dehydrogenase Activity in Human Bone," Bone, 2000, pp. 375-381, vol. 27 (3).

Cooper M.S. et al., "Modulation of 11θ-Hydroxysteroid Dehydrogenase Enzymes by Proinflammatory Cytokines in Osteoblasts: An Autocrine Switch from Glucocorticoid Inactivation to Activation," J Bone Miner Res, 2001, pp. 1037-1044, vol. 16.

(56) References Cited

OTHER PUBLICATIONS

Cooper M.S. et al., "Osteoblastic 11.beta.-Hydroxysteroid Dehydrogenase Type 1 Activity Increases With Age and Glucocorticoid Exposure," J. of Bone & Mineral Res, 2002, pp. 979-986, vol. 17 (6).
Davani et al., "Type 1 11.beta.-Hydroxysteroid Dehydrogenase Mediates Glucocorticoid Activation and Insulin Release in Pancreatic Islets," Journal of Biol. Chem, 2000, pp. 34841-34844, vol. 275.
De Battista et al., "The use of mifepristone in the treatment of neuropsychiatric disorders," Trends in Endoc. Metab, 2006, pp. 117-120, vol. 17.
De Quervain, "Glucocorticoid-related genetic susceptibility for Alzheimer's Disease," Hum. Molec. Genetics, 2004, pp. 47-52, vol. 13 (1).
Gomez Sanchez et al., "Central hypertensinogenic effects of glycyrrhizic acid and carbenoxolone," AJP Endocrinology and Metabolism, 2006, pp. E1125-E1130, vol. 263 (6).
Good Man ,Gilman's., "The Pharmacological Basis of Therapeutics, seventh Edition MacMillan Publishing Company New York, NY," 1985.
Greene T.W. et al., "Protective Groups in Organic Synthesis," 1999, pp. 494-653, 3rd Ed, John Wiley & Sons.
Hammami M.M., "Regulation of 11.beta.-Hydroxysteroid Dehydrogenase Activity in Human SkinFibroblasts: enzymatic Modulation of Glucocorticoid Action," Journal of Clin endocrinology Metab, 1991, pp. 326-334, 73.
Han et al., "Properly Designed Modular Asymmetric Synthesis for Enantiopure Sulfinamise Auxiliaries from N-Sulfonyl 1,2,3-oxathiazolidine-2-oxide Agents," J. Am. Chem. Soc., 2002, pp. 7880-7881, 124.
Harris, H.J. et al., "Intracellular regeneration of glucocorticoids by 11beta-hydroxysteroid dehydrogenase (11beta-HSD)-1 plays a key role in regulation of the hypothalamic-pituitary-adrenal axis: analysis of 11beta-HSD-1-deficient mice," Endocrinology, 2001, pp. 114-120, 142 (1).
Hermanowski Vosatka A. et al., "11.beta.-HSD1 inhibition ameliorates metabolic syndrome and prevents progression of atherosclerosis in mice," J. of Exp. Med, 2005, pp. 517-527, vol. 202 (4).
Higuchi T., "Pro-drugs as Novel Delivery Systems," Bioreversible Carriers in Drug Design, 1987, vol. 14, American Pharmaceutical Association and Pergamon Press.
Hodge G. et al., "Salt-sensitive hypertension resulting from nitric oxide synthase inhibition is associated with loss of regulation of angiotensin II in the rat," Exp. Physiol, 2002, pp. 1-8, vol. 87 (1).
Hong et al., "Synthesis and biological studies of novel neurotensin (8-13) mimetics," Bioorganic & Medicinal Chemistry, 2002, pp. 3849-3858, vol. 10 (12).
International Search Report for application No. PCT/US2006/000201, Mailed on Aug. 11, 2006, 5 pages.
International Search Report for application No. PCT/US2006/000402, Mailed on Sep. 11, 2006, 6 pages.
International Search Report for application No. PCT/US2007/066125, Mailed on Sep. 21, 2007, 5 pages.
International Search Report for application No. PCT/US2008/073830, Mailed on Mar. 12, 2009, 5 pages.
Issa A.M. et al., "Hypothalamic-Pituitary-Adrenal Activity in Aged, Cognitively Impaired and Cognitively Unimpaired Rats," J. of Neurosci, 1990, pp. 3247-3254, vol. 10 (10).
Jones C.D et al., "Effects of Substituent Modification on Face Selection in Reduction," Journal Org. Chem, 1998, pp. 2758-2760, vol. 63.
Kerr D.S., "Modulation of hippocampal long-term potentiation and long-term depression by corticosteroid receptor activation," Psychobiology, 1994, pp. 123-133, vol. 22.
Kershaw E.E., "Adipocyte-Specific Glucocorticoid Inactivation Protects Against Diet-Induced Obesity," Diabetes, 2005, pp. 1023-1031, vol. 54.
Kim C. H. et al., "Effects of dexamethasone on proliferation, activity, and cytkine secretion of normal human bone marrow stromal cells: possible mechanisms of glucocorticoidinduced bone loss," Journ of Endocrin, 1999, pp. 371-379, vol. 162.
Kolocouris N. et al., "Synthesis and antiviral activity evaluation of some new aminoadamantane derivatives," Journal of Medicinal Chemistry, 1996, pp. 3307-3318, vol. 39 (17).
Kornel L., "Steroids Mechanism of the Effects of Glucocorticoids and mineralocorticoids on Vascular Smooth Muscle Contractility," 1993, pp. 580-587, vol. 58.
Kozlowski J.A. et al., "Substituted 2-0-Methyl Piperazines as Muscarinic M2 Selective Ligands," Bioorg & Medicin Chem Ltrs, 2002, pp, 791-794, vol. 12.
Lakshmi et al., "Regional Distribution of 11-beta-Hydroxysteroid Dehydrogenase in Rat Brain," Endocrinology, 1991, 128 (4), 1741-1748.
Landfield.,"Hippocampal Cell Death," Science, 1996, vol. 272, pp. 1249-1251.
Lane N., "Med Pediatr Oncol. Effect of Glucocorticoids on Bone Density," 2003, pp. 212-216, vol. 41.
Le Noble W.J. et al., "5-tert-Butyladamantan-2-one," J Org Chem, 1983, pp. 1099-1101, vol. 48.
Lupien S., "Cortisol Levels during Human aging Predict Hippocampal Atrophy and memory deficits," Nat Neurosci, 1998, pp. 69-73, vol. 1 (1).
Mason D., "Genetic variation in the stress response: susceptibility to experimental allergic encephalomyelitis and implications for human inflammatory disease," Immun, 1991, pp. 57-60, vol. 12 (2).
Masuzaki et al., "Transgenic Amplification of Glucocorticoid Action in Adipose Tissue Causes High Blood Pressure in Mice," Journal of Clin Invest, 2003, pp. 83-90, vol. 112 (1).
Masuzaki H. et al., "A Transgenic Model of Fisceral Obesity and the Metabolic Syndrome," Science, 2001, pp. 2166-2170, vol. 294.
McEwen., "Glucocorticoids, depression, and mood disorders: structural remodeling in the brain," Metab. Clin. and Exp, 2005, vol. 54,pp. 20-23.
Moisan et al., "11-beta-Hydroxysteroid Dehydrogenase Bioactivity and Messenger RNA Expression in Rat Forebrain: Localization in Hypothalamus, Hippocampus, and Cortex," Endocrinology, 1990, 127 (3), 1450-1455.
Monder et al., Vitamins and Hormones, 1983, pp. 187-271, vol. 47.
Montague C.T. et al., "The Perils of Portliness: Causes and Consequences of Fisceral Adiposity," Diabetes, 2000, pp. 883-888, vol. 49 (6).
Morton N.M. et al., "Improved Lipid and Lipoprotein Profile, Hepatic Insulin Sensitivity, and Glucose Tolerance in 11.beta.-Hydroxysteroid Dehydrogenase Type 1 Null Mice," J. of Biol. Chem, 2001, pp. 41293-41300, vol. 276 (44).
Nagasawa et al., Journal of Medicinal Chemistry, 1975, pp. 826-830, vol. 18 (8).
Norman et al., "Emerging treatments for major depression," Expert Rev. Neurotherapeutics, 2007, vol. 7, pp. 203-213.
Orth D., "Normal Hypothalamic-Pituitary-Adrenal Physiology," The New England Journal of Medicine, 1995, pp. 791-803, vol. 332 (12).
Ortsater H. et al., "Regulation of 11β-hydroxyteroid dehydrogenase type 1 and glucose-stimulated insulin secretion in pancreatic islets of Langerhans," Diabetes Metab. Res. Rev, 2005, pp. 359-366.
Parks W. G., "Gordon Research Conferences: Program for 1966," Science, 1966, pp. 1249-1251, vol. 272.
Paterson J.M. et al., "Metabolic syndrome without obesity: Hepatic overexpression of 11.beta.-hydroxysteroid dehydrogenase type 1 in transgenic mice," Proc. Natl. Acad. Sci, 2004, pp. 7088-7093, vol. 101 (18).
Pirkle et al., "Use of intercalative effects to enhance enantioselectivity chiral stationary phase design," Journal of Chromatography, 1993, pp. 11-19, vol. 641.
Pirpiris M., "Hypertension Pressor Responsiveness in Corticosteroid-Induced Hypertension in Humans," 1992, pp, 567-574, vol. 19.
Rajan et al., "11 beta-Hydroxysteroid dehydrogenase in cultured hippocampal cells reactivates inert 11-dehydrocorticosterone, potentiating neurotoxicity," Journal of Neuroscience, 1996, pp. 65-70, vol. 16.
Rauz S. et al., "Expression and Putative Role of 11.beta.-Hydroxysteroid Dehydrogenase Isozymes within the Human Eye," Invest. Ophthal. & Vis. Sci, 2001, pp. 2037-2042, vol. 42 (9).

(56) References Cited

OTHER PUBLICATIONS

Rauz S. et al., "Inhibition of 11.beta.-hydroxysteroid dehydrogenase type 1 lowers intraocular pressure in pateints with ocular hypertension," Q. J. Med, 2003, pp. 481-490, vol. 96.
Ringman J., "What the Study of Persons at Risk for Familial Alzheimer's Disease Can Tell Us about the Earliest Stages of the disorder," J Geriatr Psychiatry Neurology, 2005, pp. 228-233.
Roche E., "Bioreversible Carriers in Drug Design, American Pharmaceutical Association and Pergamon Press Table of Contents," 1987.
Rook G.A.W. et al., "Clinical Endocrinology and Metabolism Glucocorticoids and Immune Function," 1999, pp. 567-581, vol. 13 (4).
Sakai R. R. et al., "Immunocytochemical Localization of 11 Beta-Hydroxysteroid Dehydrogenase in Hippocampus and Other Brain Regions of the Rat," J Neuroendocrinol, 1992, 101-106, vol. 4.
Sandeep T., "11.beta-Hydroxysteroid Dehydrogenase Inhibition Improves Cognitive Function in Healthy Elderly Men and Type 2 Diabetes," PNAS, 2004, pp. 6734-6739, vol. 101.
Schteingart D.E., "Cushing Syndrome," in: Princ. & Prac. of Endoc. & Metab, 3rd ed., Becker KL, ed., 2001, pp. 723-728, Chap. 75.
Seckl et al., "The 11-beta hydroxysteroid dehydrogenase inhibitor glycyrrhetinic acid affects corticosteroid feedback regulation of hypothalamic corticotrophin-releasing peptides in rats," Journal of Endocrinology, 1993, pp. 471-477, vol. 136.
Seckl J.R et al., "11.beta.-Hydroxysteroid Dehydrogenase Type 1—A Tissue Specific Amplifier of Glucocorticoid Action," Endocrinology Minireview, 2001, pp. 1371-1376, vol. 142.
Small G.R. et al., "Preventing local regeneration of glucocorticoids by 11β-Hydroxysteroid dehydrogenase type 1 enhances angiogenesis," Proc. Natl. Acad. Sci, 2005, pp. 12165-12170.
Stokes J. et al., "Altered Peripheral Sensitivity to Glucocorticoids in Primary Open-Angle Glaucoma," Invest Ophthalmol Vis Sci, 2003, pp. 5163-5167, vol. 44 (12).
Strohle et al.,"Stress Responsive Neurohormones in Depression and Anxiety," Pharmacopsychiatry, 2003, vol. 36, pp. S207-S214.
Tadayyon M., "Insulin sensitization in the treatment of Type 2 diabetes," Expert Opin Investig Drugs, 2003, pp, 307-324, vol. 12 (3).
Tronche F., "Disruption of the glucocorticoid receptor gene in the nervous system results in reduced anxiety," Nature Genetics, 1999, pp. 99-103, vol. 23.
Turner R.T., "Calcif . Tissue Int. Prednisone Inhibits Formation of Cortical Bone in Sham-Operated and Ovariectomized Female Rats," 1995, pp. 311-315, vol. 56.
Vaidyanathan ., "Decarboxylation of 1-Aminocyclopropanecarboxylic Acid and Its Derivatives," J Org Chem, 1989, pp. 1810-1815, vol. 54.
Walker B.R. et al., "Carbenoxolone increases Hepatic insulin Sensitivity in Man: A Novel Role for 11-Oxosteroid Reductase in Enhancing Glucocorticoid Receptor Activation," Journal of Clin. Endocrinology and Met, 1995, pp. 3155-3159, vol. 80.
Walker B.R., "Corticosteroids and Vascular Tone: Mapping the Messenger Maze," Clinical Science, 1992, pp. 597-605, vol. 82.
Walker et al, "Preventing local regeneration of glucocorticoids by 11.sub.-hydroxysteroid dehydrogenase type 1enhances angiogenesis," PNAS, 2005, pp. 12165-12170, vol. 102 (34).
Wolkowitz O.M., "The Steroid Dementia Syndrome: An Unrecognized Complication of Glucocorticoid Treatment," Annals New York Academy of Sciences, 2004, pp. 191-194, vol. 1032.
Wooley C.S. et al., "Exposure to excess glucocorticoids alters dendritic morphology of adult hippocampal pyramidal neurons," Brain Res, 1990, pp. 225-331, vol. 531.
Yau J.L.W. et al., "Lack of tissue glucocorticoid reactivation in 11.beta.-hydroxysteroid dehydrogenase type 1 knockout mice ameliorates age-related learning impairments," Proc. Natl. Acad. Sci, 2001, pp. 4716-4721, vol. 98 (8).
Yau Jel W., "Glucocorticoids, Hippocampal Corticosteroid Receptor Gene Expression and Antidepressant Treatment: Relationship with Spatial learning in Young and Aged Rats," Neuroscience, 1995, pp. 571-581, vol. 66 (3).

Yeh et al., "Discovery of orally active butyrolactam llbeta-HSD1 inhibitors," Bioorganic & Medicinal Chemistry Letters, Oxford, GB, 2006, pp. 5555-5560, vol. 16 (21).
Yeh Vince S.C. et al., "A highly efficient synthesis of potent and selective butyrolactam inhibitors of IIbeta-HSD1," Organic Letters, 2006, pp. 3963-3966, vol. 8 (18).
Ziegler Fee., "Substitution Reactions of Specifically ortho-Metalated Piperonal Cyclohexylimine," J Org Chem, 1976, pp. 1564-1566, vol. 41 (9).
Rehman Q. and Lane N.E., "Effect of Glucocorticoids on Bone Density," Medical and Pediatric Oncology, 2003, pp. 212-216, vol. 41(3).
Le Noble W.J. et al., "5-tert-Butyladamantan-2-one," J. Org. Chem., 1983, pp. 1099-1101, vol. 48.
Lupien S., "Cortisol levels during human aging predict hippocampal atrophy and memory deficits," Nat. Neurosci., 1998, pp. 69-73, vol. 1(1).
Mason D., "Genetic variation in the stress response: susceptibility to experimental allergic encephalomyelitis and implications for human inflammatory disease," Immun. Today, 1991, pp. 57-60, vol. 12(2).
Masuzaki et al., "Transgenic amplification of glucocorticoid action in adipose tissue causes high blood pressure in mice," Journal of Clin. Invest., 2003, pp. 83-90, vol. 112(1).
McEwen, "Glucocorticoids, depression, and mood disorders: structural remodeling in the brain," Metab. Clin. and Exp., 2005, pp. 20-23, vol. 54.
Moisan et al., "11β-hydroxysteroid dehydrogenase bioactivity and messenger ma expression in rat forebrain: localization in hypothalamus, hippocampus, and cortex," Endocrinology, 1990, pp. 1450-1455, vol. 127(3).
Monder et al., "11.beta-Hydroxysteriod dehydrogenase" Vitamins and Hormones, 1983, pp. 187-271, vol. 47.
Montague C.T. et al., "The perils of portliness: causes and consequences of visceral adiposity," Diabetes, 2000, pp. 883-888, vol. 49(6).
Morton N.M. et al., "Improved lipid and lipoprotein profile, hepatic insulin sensitivity, and glucose tolerance in 11β-hydroxysteroid dehydrogenasetype 1 null mice," J. of Biol. Chem., 2001, pp. 41293-41300, vol. 276(44).
Nagasawa et al., Journal of Medicinal Chemistry, 1975, pp. 826-830, vol. 18(8).
Neurodegenerative disorder [online] retrieved from internet on Jul. 24, 2011 URL; http://ec.europa.eu/health/major_chronic_diseases/diseases/brain_neurological/index_en.htm.
Norman et al., "Emerging treatments for major depression," Expert Rev. Neurotherapeutics, 2007, pp. 203-213, vol. 7.
Orth D., "Cushing's Syndrome," The New England Journal of Medicine, 1995, pp. 791-803, vol. 332(12).
Ortsater H. et al., "Regulation of 11β-hydroxysteroid dehydrogenase type 1 and glucose-stimulated insulin secretion in pancreatic islets of langerhans," Diabetes Metab. Res. Rev, 2005, pp. 359-366.
Parks W. G., "Gordon Research Conferences: Program for 1966," Science, 1966, pp. 1249-1251, vol. 151.
Paterson J.M. et al., "Metabolic syndrome without obesity: hepatic overexpression of 11β-hydroxysteroid dehydrogenase type 1 in transgenic mice," Proc. Natl. Acad. Sci., 2004, pp. 7088-7093, vol. 101(18).
Pirkle et al., "Chiral stationary phase design. Use of intercalate effects to enhance enantioselectivity," Journal of Chromatography, 1993, pp. 11-19, vol. 641.
Pirpiris M., "Pressor Responsiveness in Corticosteroid-Induced Hypertension in Humans," Hypertension 1992, pp. 567-574, vol. 19.
Prueksaritanont, et al. Toxicology and Applied Pharmacology, 2006, pp. 143-152, vol. 217.
Rajan et al., "11β-hydroxysteroid dehydrogenase in cultured hippocampal cells reactivates inert 11-dehydrocorticosterone, potentiating neurotoxicity," Journal of Neuroscience, 1996, pp. 65-70, vol. 16.
Rauz S. et al., "Expression and putative role of 11β-hydroxysteroid dehydrogenase isozymes within the human eye," Invest. Ophthal. & Vis. Sci, 2001, pp. 2037-2042, vol. 42(9).

(56) References Cited

OTHER PUBLICATIONS

Rauz S. et al., "Inhibition if 11β-hydroxysteroid dehydrogenase type 1 lower intraocular pressure in patients with ocular hypertension," Q. J. Med, 2003, pp. 481-490, vol. 96.

Ringman J., "What the study of persons at risk for familial alzheimer's disease can tell us about the earliest stages of the disorder," J. Geriatr. Psychiatry Neurology, 2005, pp. 228-233 vol. 18.

Roche E., "Bioreversible carriers in drug design," American Pharmaceutical Association and Perqamon Press Table of Contents, 1987.

Rook G.A.W. et al., "Glucocorticoids and immune function," Bailliere's Clinical endocrinology and metabolism, 1999, pp. 567-581, vol. 13(4).

Sakai R. R. et al. Immunocytochemical localization of 11β-hydroxysteroid dehydrogenase in hippocampus and other brain regions of the rat, J Neuroendocrinol, 1992. 101-106. vol. 4.

Sandeep T., "11β-hydroxysteroid dehydrogenase inhibition improves cognitive function in healthy elderly men and type 2 diabetes," PNAS, 2004, pp. 6734-6739, vol. 101.

Schteingart D.E., "Cushing Syndrome," in: Princ. & Prac. of Endoc. & Metab, 3rd ed. Becker KL, ed., 2001, pp. 723-738, Chap. 75.

Seckl et al., "The 11β-hydroxysteroid dehydrogenase inhibitor glycyrrhetinic acid affects corticosteroid feedback regulation of hypothalamic corticotrophin-releasing peptides in rats," Journal of Endocrinology, 1993, pp. 471-477, vol. 136.

Seckl J.R et al., "Minireview: 11β-hydroxysteroid dehydrogenase type 1—a tissue-specific amplifier of glucocorticoid action," Endocrinology, 2001, pp. 1371-1376, vol. 142.

Small G.R. et al., "Preventing local regeneration of glucocorticoids by 11U-hydroxysteroid dehydrogenase type 1 enhances angiogenesis," Proc. Natl. Acad. Sci, 2005, pp. 12165-12170 vol. 102.

Stokes J. et al., "Altered peripheral sensitivity to glucocorticoids in primary open-ang glaucoma," Invest. Ophthalmol. Vis. Sci., 2003, pp. 5163-5167, vol. 44(12).

Strohle et al., "Stress responsive neurohormones in depression and anxiety," pharmacopsychiatry, 2003, vol. 36, pp. S207-S214.

Tadayyon M., "Insulin sensitization in the treatment of Type 2 diabetes," Expert Opin, Investig. Drugs., 2003, pp. 307-324, vol. 12(3).

Turner R.T., "Prednisone Inhibits Formation of Cortical Bone in Sham-Operated and Ovariectomized Female Rats," Calcif . Tissue Int., 1995, pp. 311-315, vol. 56.

Vaidyanathan , "Decarboxylation of 1-aminocyclopropanecarboxylic acid and its derivatives," J. Org. Chem., 1989, pp. 1810-1815, vol. 54.

Walker B.R. et al., "Carbenoxolone increases hepatic insulin sensitivity in man: a novel role for 11-0xosteroid reductase in enhancing glucocorticoid receptor activation," Journal of Clin. Endocrinology and Met., 1995, pp. 3155-3159, vol. 80.

Woolley C.S. et al., "Exposure to excess glucocorticoids alters dendritic morphology of adult hippocampal pyramidal neurons," Brain Res., 1990, pp. 225-331, vol. 531.

Yau Jel W., "Glucocorticoids, hippocampal corticosteroid receptor gene expression and antidepressant treatment: relationship with spatial learning in young and aged rats," Neuroscience, 1995, pp. 571-581, vol. 66(3).

Yau J.L.W. et al., "Lack of tissue glucocorticoid reactivation in 11-beta-hydroxysteroid dehydrogenase type 1 knockout miceamerliorates age-related learning impairments," Proc. Natl. Acad. Sci., 2001, pp. 4716-4721, vol. 98(8).

Yeh et al., "Discovery of orally active butyrolactam llbeta-HSD1 inhibitors," Bioorganic & Medicinal Chemistry Letters, Oxford, GB, 2006, pp. 5555-5560, vol. 16(21).

Yeh Vince S.C. et al., "A highly efficient synthesis of potent and selective butyrolactam inhibitors of IIbeta-HSD1," Organic Letters, 2006, pp. 3963-3966, vol. 8(18).

Ziegler F., "Substitution Reactions of Specifically ortho-Metalated Piperonal Cyclohexylimine," J. Org. Chem., 1976, pp. 1564-1566, vol. 41(9).

* cited by examiner

Effects of Compound MM at 30 mg/kg, po., on acetylcholine release in rat prefrontal cortex in rats transferred from home cage to novel cage and back to home cage.

Effects of Compound MM at 30 mg/kg, p.o., on acetylcholine release in rat hippocampus in rats transferred from home cage to novel cage and back to home cage.

Effects of Compound MM at 30 mg/kg, p.o., on acetylcholine release in rat prefrontal cortex and hippocampus under resting conditions Data are means ± SEM percentage change of the average of two pre-application basal levels Data means ± SEM area under curve AUC $_{0-2-10}$ minutes in arbitrary units.

INHIBITORS OF THE 11-BETA-HYDROXYSTEROID DEHYDROGENASE TYPE 1 ENZYME

This is a divisional of U.S. patent application No. 12/390,286, filed Feb. 20, 2009, now U.S. Pat. No. 8,198,331, which is a continuation-in-part of U.S. patent application No. 11/733,636, filed on Apr. 10, 2007, now U.S. Pat. No. 7,528,282, which is a continuation-in-part of U.S. patent application No. 11/326,277, filed on Jan. 5, 2006, now U.S. Pat. No. 7,217,838, which claims priority to U.S. patent application No. 60/641,496, filed on Jan. 5, 2005, the entire contents of all of which are fully incorporated herein by reference. In addition, U.S. patent application No. 12/390,286, filed on Feb. 20, 2009, now U.S. Pat. No. 8,198,331, is a continuation-in-part of U.S. patent application No. 12/195,937, filed on Aug. 21, 2008, which claims priority to U.S. patent application No. 60/957,082, filed on Aug. 21, 2007, the entire contents of all of which are fully incorporated herein by reference.

FIELD OF INVENTION

The present invention relates to compounds that are inhibitors of the 11-beta-hydroxysteroid dehydrogenase Type 1 enzyme. The present invention further relates to the use of inhibitors of 11-beta-hydroxysteroid dehydrogenase Type 1 enzyme for the treatment of non-insulin dependent type 2 diabetes, insulin resistance, obesity, lipid disorders, metabolic syndrome, disorders and deficits of the central nervous system associated with diabetes, associated with aging and neurodegeneration, comprising attention deficit disorder in general, attention deficit hyperactivity disorder (ADHD), Alzheimer's disease (AD), mild cognitive impairment, senile dementia, AIDS dementia, neurodegeneration, depression, and schizophrenia, and other diseases and conditions that are mediated by excessive glucocorticoid action.

BACKGROUND OF THE INVENTION

Insulin is a hormone that modulates glucose and lipid metabolism. Impaired action of insulin (i.e., insulin resistance) results in reduced insulin-induced glucose uptake, oxidation and storage, reduced insulin-dependent suppression of fatty acid release from adipose tissue (i.e., lipolysis) and reduced insulin-mediated suppression of hepatic glucose production and secretion. Insulin resistance frequently occurs in diseases that lead to increased and premature morbidity and mortality.

Diabetes mellitus is characterized by an elevation of plasma glucose levels (hyperglycemia) in the fasting state or after administration of glucose during a glucose tolerance test. While this disease may be caused by several underlying factors, it is generally grouped into two categories, Type 1 and Type 2 diabetes. Type 1 diabetes, also referred to as Insulin Dependent Diabetes Mellitus ("IDDM"), is caused by a reduction of production and secretion of insulin. In type 2 diabetes, also referred to as non-insulin dependent diabetes mellitus, or NIDDM, insulin resistance is a significant pathogenic factor in the development of hyperglycemia. Typically, the insulin levels in type 2 diabetes patients are elevated (i.e., hyperinsulinemia), but this compensatory increase is not sufficient to overcome the insulin resistance. Persistent or uncontrolled hyperglycemia in both type 1 and type 2 diabetes mellitus is associated with increased incidence of macrovascular and/or microvascular complications including atherosclerosis, coronary heart disease, peripheral vascular disease, stroke, nephropathy, neuropathy and retinopathy.

Insulin resistance, even in the absence of profound hyperglycemia, is a component of the metabolic syndrome. Recently, diagnostic criteria for metabolic syndrome have been established. To qualify a patient as having metabolic syndrome, three out of the five following criteria must be met: elevated blood pressure above 130/85 mmHg, fasting blood glucose above 110 mg/dl, abdominal obesity above 40" (men) or 35" (women) waist circumference and blood lipid changes as defined by an increase in triglycerides above 150 mg/dl or decreased HDL cholesterol below 40 mg/dl (men) or 50 mg/dl (women). It is currently estimated that 50 million adults, in the US alone, fulfill these criteria. That population, whether or not they develop overt diabetes mellitus, are at increased risk of developing the macrovascular and microvascular complications of type 2 diabetes listed above.

Available treatments for type 2 diabetes have recognized limitations. Diet and physical exercise can have profound beneficial effects in type 2 diabetes patients, but compliance is poor. Even in patients having good compliance, other forms of therapy may be required to further improve glucose and lipid metabolism.

One therapeutic strategy is to increase insulin levels to overcome insulin resistance. This may be achieved through direct injection of insulin or through stimulation of the endogenous insulin secretion in pancreatic beta cells. Sulfonylureas (e.g., tolbutamide and glipizide) or meglitinide are examples of drugs that stimulate insulin secretion (i.e., insulin secretagogues) thereby increasing circulating insulin concentrations high enough to stimulate insulin-resistant tissue. However, insulin and insulin secretagogues may lead to dangerously low glucose concentrations (i.e., hypoglycemia). In addition, insulin secretagogues frequently lose therapeutic potency over time.

Two biguanides, metformin and phenformin, may improve insulin sensitivity and glucose metabolism in diabetic patients. However, the mechanism of action is not well understood. Both compounds may lead to lactic acidosis and gastrointestinal side effects (e.g., nausea or diarrhea).

Alpha-glucosidase inhibitors (e.g., acarbose) may delay carbohydrate absorption from the gut after meals, which may in turn lower blood glucose levels, particularly in the postprandial period. Like biguanides, these compounds may also cause gastrointestinal side effects.

Glitazones (i.e., 5-benzylthiazolidine-2,4-diones) are a newer class of compounds used in the treatment of type 2 diabetes. These agents may reduce insulin resistance in multiple tissues, thus lowering blood glucose. The risk of hypoglycemia may also be avoided. Glitazones modify the activity of the Peroxisome Proliferator Activated Receptor ("PPAR") gamma subtype. PPAR is currently believed to be the primary therapeutic target for the main mechanism of action for the beneficial effects of these compounds. Other modulators of the PPAR family of proteins are currently in development for the treatment of type 2 diabetes and/or dyslipidemia. Marketed glitazones suffer from side effects including bodyweight gain and peripheral edema.

Additional treatments to normalize blood glucose levels in patients with diabetes mellitus are needed. Other therapeutic strategies are being explored. For example, research is being conducted concerning Glucagon-Like Peptide 1 ("GLP-1") analogues and inhibitors of Dipeptidyl Peptidase IV ("DPP-IV") that increase insulin secretion. Other examples include: Inhibitors of key enzymes involved in the hepatic glucose production and secretion (e.g., fructose-1,6-bisphosphatase inhibitors) and direct modulation of enzymes involved in insulin signaling (e.g., Protein Tyrosine Phosphatase-1B, or "PTP-1B").

Another method of treating or prophylactically treating diabetes mellitus includes using inhibitors of 11-β-hydroxysteroid dehydrogenase Type 1 (11β-HSD1). Such methods are discussed in J. R. Seckl et al., *Endocrinology*, 142: 1371-1376, 2001 and references cited therein. Glucocorticoids are steroid hormones that are potent regulators of glucose and lipid metabolism. Excessive glucocorticoid action may lead to insulin resistance, type 2 diabetes, dyslipidemia, increased abdominal obesity and hypertension. Glucocorticoids circulate in the blood in an active form (i.e., cortisol in humans) and an inactive form (i.e., cortisone in humans). 11β-HSD1, which is highly expressed in liver and adipose tissue, converts cortisone to cortisol leading to higher local concentration of cortisol. Inhibition of 11β-HSD1 prevents or decreases the tissue specific amplification of glucocorticoid action thus imparting beneficial effects on blood pressure and glucose- and lipid-metabolism.

11β-HSD-1 is a low affinity enzyme with $K_m$ for cortisone in the micromolar range that prefers NADPH/NADP$^+$ (nicotinamide adenine dinucleotide phosphate) as cofactors. 11β-HSD-1 is widely expressed and particularly high expression levels are found in liver, brain, lung, adipose tissue, and vascular smooth muscle cells. In vitro studies indicate that 11β-HSD-1 is capable of acting both as a reductase and a dehydrogenase. However, many studies have shown that it functions primarily as a reductase in vivo and in intact cells. It converts inactive 11-ketoglucocorticoids (i.e., cortisone or dehydrocorticosterone) to active 11-hydroxyglucocorticoids (i.e., cortisol or corticosterone), and thereby amplifies glucocorticoid action in a tissue-specific manner.

11β-HSD-1 is expressed in mammalian brain, and published data indicates that elevated levels of glucocorticoids may cause neuronal degeneration and dysfunction, particularly in the aged (de Quervain et al., *Hum Mol Genet.*, 13, 47-52 (2004); Belanoff et al. *J. Psychiatr Res.*, 35, 127-35, (2001)). Evidence in rodents and humans suggests that prolonged elevation of plasma glucocorticoid levels impairs cognitive function that becomes more profound with aging. (A. M. Issa et al., *J. Neurosci.*, 10, 3247-3254 (1990); S. J. Lupien et. al., *Nat. Neurosci.*, 1, 69-73 (1998); J. L. Yau et al., *Neuroscience*, 66, 571-581 (1995)). Chronic excessive cortisol levels in the brain may result in neuronal loss and neuronal dysfunction. (D. S. Kerr et al., *Psychobiology*, 22, 123-133 (1994); C. Woolley, *Brain Res.*, 531, 225-231, (1990); P. W. Landfield, *Science*, 272, 1249-1251 (1996)). Furthermore, glucocorticoid-induced acute psychosis exemplifies a more pharmacological induction of this response, and is of major concern to physicians when treating patients with these steroidal agents (Wolkowitz et al.; *Ann NY Acad Sci.*, 1032, 191-194 (2004)). It has been recently shown that 11β-HSD-1 mRNA is expressed in human hippocampus, frontal cortex and cerebellum, and that treatment of elderly diabetic individuals with the non-selective 11β-HSD-1 and 11β-HSD-2 inhibitor carbenoxolone improved verbal fluency and memory (Thekkapat et al., *Proc Natl Acad Sci USA*, 101, 6743-6749 (2004)). Excessive glucocorticoid levels also affects psychopathology, as shown in animal models, it leads to increased anxiety and aggression. Chronic elevation of cortisol has been also associated with depression in Cushing's disease (McEwen, *Metab. Clin. & Exp.*, 54, 20-23 (2005)). A number of animal and clinical studies have provided evidence for the correlation between increases in glucocorticoid levels and neuropsychiatric disorders such as major depressive disorder, psychotic depression, anxiety, panic disorder, post traumatic stress disorder, and depression in Cushing's syndrome (Budziszewska, *Polish J. of Pharmacol.*, 54, 343-349, (2002); Ströhle et al., *Pharmacopsychiatry* Vol. 36, S207-S214, 2003; DeBattista et al., *TRENDS in Endocr. Metab.*, 17, 117-120 (2006); Norman et al., *Expert Rev. Neurotherapeutics*, Vol. 7, pages 203-213 (2007)).

Thus, inhibiting 11β-HSD1 benefits patients suffering from non-insulin dependent type 2 diabetes, insulin resistance, obesity, lipid disorders, metabolic syndrome, central nervous system disorders, age-related or glucocorticoid-related declines in cognitive function such as those seen in Alzheimer's and associated dementias, major depressive disorder, psychotic depression, anxiety, panic disorder, post traumatic stress disorder, depression in Cushing's syndrome, and treatment resistant depression, and other diseases and conditions mediated by excessive glucocorticoid action.

SUMMARY OF THE INVENTION

All patents, patent applications and literature references cited in the specification are herein incorporated by reference in their entirety.

One aspect of the present invention is directed toward a compound of formula (I), or a pharmaceutically acceptable salt, prodrug, salt of a prodrug, or a combination thereof

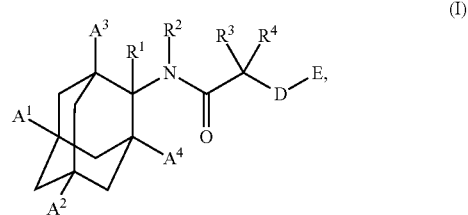

wherein
one of $A^1$, $A^2$, $A^3$ and $A^4$ is selected from the group consisting of alkyl-NH-alkyl, alkylcarbonyl, alkylsulfonyl, cycloalkyl, cycloalkylcarbonyl, cycloalkylsulfonyl, aryl carbonyl, arylsulfonyl, heteroaryl, heteroarylalkyl, heteroaryloxyalkyl, heterocyclecarbonyl, heterocyclesulfonyl, aryl$^1$, arylalkyl, aryloxyalkyl, carboxyalkyl, carboxycycloalkyl, haloalkyl, heterocyclealkyl, heterocycleoxyalkyl, —S(O)$_2$—N(R$^5$R$^6$), —NR$^7$—[C(R$^8$, R$^9$)]$_n$—C(O)—R$^{10}$, —O—[C(R$^{11}$R$^{12}$)]—C(O)—R$^{13}$, —OR$^{14a}$, —N(R$^{15}$R$^{16}$), —CO$_2$R$^{17}$, —C(O)—N(R$^{18}$R$^{19}$), —C(R$^{20}$R$^{21}$)—OR$^{22}$, —C(R$^{23}$R$^{24}$)—N(R$^{25}$R$^{26}$), and heterocycle, with the exception that 5 membered heterocycles may not contain two oxygen atoms, and the remaining members of the group consisting of $A^1$, $A^2$, $A^3$ and $A^4$ are each individually selected from the group consisting of hydrogen, alkyl, alkyl-NH-alkyl, alkylcarbonyl, alkylsulfonyl, cycloalkyl, cycloalkylcarbonyl, cycloalkylsulfonyl, arylcarbonyl, arylsulfonyl, heterocyclecarbonyl, heterocyclesulfonyl, aryl, arylalkyl, aryloxyalkyl, carboxyalkyl, carboxycycloalkyl, halogen, haloalkyl, heteroaryl, heteroarylalkyl, heteroaryloxyalkyl, heterocycle, heterocyclealkyl, heterocycleoxyalkyl, —S(O)$_2$—N(R$^5$R$^6$), —NR$^7$—[C(R$^8$R$^9$)]$_n$—C(O)—R$^{10}$, —O—[C(R$^{11}$R$^{12}$)]$_p$—C(O)—R$^{13}$, —OR$^{14b}$, —N(R$^{15}$R$^{16}$), —CO$_2$R$^{17}$, —C(O)—N(R$^{18}$R$^{19}$), —C(R$^{20}$R$^{21}$)—OR$^{22}$, and —C(R$^{23}$R$^{24}$)—. N(R$^{25}$R$^{26}$);

n is 0 or 1;
p is 0 or 1;
D is selected from the group consisting of a bond, —C(R$^{27}$R$^{28}$)—X— and —C(R$^{27}$R$^{28}$)—C(R$^{29}$R$^{30}$)—X—;
E is selected from the group consisting of a cycloalkyl, alkyl, aryl, heteroaryl and heterocycle, wherein the heteroaryl and the heterocycle are appended to the parent molecular moiety through an available carbon atom, or R$^4$ and E together with the atoms to which they are attached form a ring selected from the group consisting of cycloalkyl and heterocycle;

X is selected from the group consisting of a bond, —N($R^{31}$)—, —O—, —S—, —S(O)— and —S(O)$_2$—;

$R^1$ is selected from the group consisting of hydrogen and alkyl;

$R^2$ is selected from the group consisting of hydrogen, alkyl and cycloalkyl;

$R^3$ and $R^4$ are each independently selected from the group consisting of hydrogen, alkyl, carboxyalkyl, carboxycycloalkyl, cycloalkyl, haloalkyl, aryl, arylalkyl, heteroaryl, heteroarylalkyl, heterocycle and heterocyclealkyl, or $R^3$ and $R^4$ together with the atom to which they are attached form a ring selected from the group consisting of cycloalkyl and heterocycle;

$R^5$ and $R^6$ are each independently selected from the group consisting of hydrogen, alkoxy, alkyl, alkylcarbonyl, alkylsulfonyl, carboxy, carboxyalkyl, carboxycycloalkyl, cycloalkyl, cycloalkyloxy, cycloalkylsulfonyl, aryl, arylalkyl, arylalkylcarbonyl, arylcarbonyl, aryloxy, aryloxyalkyl, arylsulfonyl, heteroaryl, heteroarylalkyl, heteroarylalkylcarbonyl, heteroarylcarbonyl, heteroaryloxyalkyl, heteroarylsulfonyl, heterocycle, heterocyclealkyl, heterocyclealkylcarbonyl, heterocyclecarbonyl, heterocycleoxyalkyl, heterocycleoxy, heterocyclesulfonyl and hydroxy, or $R^5$ and $R^6$ together with the atom to which they are attached form a heterocycle;

$R^7$ is selected from the group consisting of hydrogen, alkyl, carboxyalkyl, cycloalkyl, carboxycycloalkyl, aryl, arylalkyl, aryloxyalkyl, hydroxy, alkoxy, heteroaryl, heteroarylalkyl, heteroaryloxyalkyl, heterocycle, heterocyclealkyl and heterocycleoxyalkyl;

$R^8$ and $R^9$ are each independently selected from the group consisting of hydrogen and alkyl, or $R^8$ and $R^9$ taken together with the atom to which they are attached form a ring selected from the group consisting of cycloalkyl and heterocycle;

$R^{10}$ is selected from the group consisting of hydrogen, alkyl, carboxyalkyl, cycloalkyl, carboxycycloalkyl, aryl, arylalkyl, aryloxy, aryloxyalkyl, hydroxy, alkoxy, cycloalkyloxy, heteroaryl, heteroarylalkyl, heteroaryloxy, heteroaryloxyalkyl, heterocycle, heterocyclealkyl, heterocycleoxy, heterocycleoxyalkyl and —N($R^{32}R^{33}$);

$R^{11}$ and $R^{12}$ are each independently selected from the group consisting of hydrogen and alkyl or $R^{11}$ and $R^{12}$ taken together with the atom to which they are attached form a ring selected from the group consisting of cycloalkyl and heterocycle;

$R^{13}$ is selected from the group consisting of hydroxy and —N($R^{34}R^{35}$);

$R^{14a}$ is selected from the group consisting of carboxyalkyl, cycloalkyl, carboxycycloalkyl, aryl, arylalkyl, aryloxyalkyl, haloalkyl, heteroaryl, heteroarylalkyl, heteroaryloxyalkyl, heterocycle, heterocyclealkyl and heterocycleoxyalkyl;

$R^{14b}$ is selected from the group consisting of hydrogen, alkyl, carboxyalkyl, cycloalkyl, carboxycycloalkyl, aryl, arylalkyl, aryloxyalkyl, haloalkyl, heteroaryl, heteroarylalkyl, heteroaryloxyalkyl, heterocycle, heterocyclealkyl and heterocycleoxyalkyl;

$R^{15}$ and $R^{16}$ are each independently selected from the group consisting of hydrogen, alkyl, alkylcarbonyl, carboxyalkyl, cycloalkyl, carboxycycloalkyl, aryl, arylalkyl, arylalkylcarbonyl, arylcarbonyl, aryloxyalkyl, heteroaryl, heteroarylalkyl, heteroarylalkylcarbonyl, heteroarylcarbonyl, heteroaryloxyalkyl, heteroarylsulfonyl, heterocycle, heterocyclealkyl, heterocyclealkylcarbonyl, heterocyclecarbonyl, heterocycleoxyalkyl, heterocyclesulfonyl, alkylsulfonyl, cycloalkylsulfonyl and arylsulfonyl, or $R^{15}$ and $R^{16}$ together with the atom to which they are attached form a heterocycle;

$R^{17}$ is selected from the group consisting of hydrogen, alkyl, carboxyalkyl, cycloalkyl, carboxycycloalkyl, aryl, arylalkyl, aryloxyalkyl, heteroaryl, heteroarylalkyl, heteroaryloxyalkyl, heterocycle, heterocyclealkyl and heterocycleoxyalkyl;

$R^{18}$ and $R^{19}$ are each independently selected from the group consisting of hydrogen, alkoxy, alkyl, alkylsulfonyl, carboxy, carboxyalkyl, carboxycycloalkyl, cycloalkyl, cycloalkyloxy, cycloalkylsulfonyl, aryl, arylalkyl, aryloxy, aryloxyalkyl, arylsulfonyl, heteroaryl, heteroarylalkyl, heteroaryloxyalkyl, heteroarylsulfonyl, heterocycle, heterocyclealkyl, heterocycleoxyalkyl, heterocycleoxy, heterocyclesulfonyl and hydroxy, or $R^{18}$ and $R^{19}$ together with the atom to which they are attached form a heterocycle;

$R^{20}$, $R^{21}$ and $R^{22}$ are each independently selected from the group consisting of hydrogen, alkyl, aryl, arylalkyl, carboxyalkyl, carboxycycloalkyl, cycloalkyl, haloalkyl, heteroaryl, heteroarylalkyl, heterocycle and heterocyclealkyl;

$R^{23}$ and $R^{24}$ are each independently selected from the group consisting of hydrogen, alkyl, alkylcarbonyl, alkylsulfonyl, aryl, arylcarbonyl, arylsulfonyl, carboxyalkyl, carboxycycloalkyl, cycloalkyl, cycloalkylcarbonyl, cycloalkylsulfonyl, heteroaryl, heteroarylcarbonyl, heteroarylsulfonyl, heterocycle, heterocyclecarbonyl and heterocyclesulfonyl;

$R^{25}$ and $R^{26}$ are each independently selected from the group consisting of hydrogen, alkoxy, alkyl, alkyl carbonyl, alkylsulfonyl, aryl, arylcarbonyl, aryloxy, arylsulfonyl, carboxyalkyl, carboxycycloalkyl, cycloalkyl, cycloalkylcarbonyl, cycloalkyloxy, cycloalkylsulfonyl, heteroaryl, heteroarylcarbonyl, heteroaryloxy, heteroarylsulfonyl, heterocycle, heterocyclecarbonyl, heterocycleoxy, heterocyclesulfonyl and hydroxy, or $R^{25}$ and $R^{26}$ together with the nitrogen to which they are attached form a ring selected from the group consisting of heteroaryl and heterocycle;

$R^{27}$ and $R^{28}$ are each independently selected from the group consisting of hydrogen, alkyl, aryl, cycloalkyl, heteroaryl and heterocycle or $R^{27}$ and $R^{28}$ together with the atom to which they are attached form a ring selected from the group consisting of cycloalkyl and heterocycle, or $R^{27}$ and $R^{29}$ together with the atoms to which they are attached form a ring selected from the group consisting of cycloalkyl and heterocycle, or $R^{28}$ and $R^4$ together with the atoms to which they are attached form a ring selected from the group consisting of cycloalkyl and heterocycle;

$R^{29}$ and $R^{30}$ are each independently selected from the group consisting of hydrogen, alkyl, alkoxy, aryl, aryloxy, cycloalkyl, cycloalkyloxy, heteroaryl, heterocycle, and —N($R^{36}R^{37}$), or $R^{29}$ and $R^{30}$ together with the atom to which they are attached form a ring selected from the group consisting of cycloalkyl and heterocycle, or $R^{29}$ and $R^4$ together with the atoms to which they are attached form a ring selected from the group consisting of cycloalkyl and heterocycle, or $R^{29}$ and E together with the atoms to which they are attached form a ring selected from the group consisting of cycloalkyl and heterocycle;

$R^{31}$ is selected from the group consisting of hydrogen, alkyl, aryl, cycloalkyl, heterocycle and heteroaryl, or $R^{31}$ and E together with the atom to which they are attached form a ring selected from the group consisting of heteroaryl and heterocycle, or $R^{31}$ and $R^4$ together with the atoms to which they are attached form a heterocycle;

$R^{32}$ and $R^{33}$ are each independently selected from the group consisting of hydrogen, alkyl, carboxy, carboxyalkyl, cycloalkyl, cycloalkyloxy, carboxycycloalkyl, aryl, arylalkyl, aryloxy, aryloxyalkyl, heterocycle, heterocyclealkyl, heterocycleoxyalkyl, heterocycleoxy, hydroxy, alkoxy, alkylsulfonyl, cycloalkylsulfonyl, arylsulfonyl, and heterocyclesulfonyl, or $R^{32}$ and $R^{33}$ together with the atom to which they are attached form a heterocycle;

$R^{34}$ and $R^{35}$ are each independently selected from the group consisting of hydrogen, alkyl, carboxy, carboxyalkyl, cycloalkyl, cycloalkyloxy, carboxycycloalkyl, aryl, arylalkyl, aryloxy, aryloxyalkyl, heterocycle, heterocyclealkyl, heterocycleoxyalkyl, heterocycleoxy, hydroxy, alkoxy, alkylsulfonyl, cycloalkylsulfonyl, arylsulfonyl, and heterocyclesulfonyl, or $R^{34}$ and $R^{35}$ together with the atom to which they are attached form a heterocycle; and $R^{36}$ and $R^{37}$ are each independently selected from the group consisting of hydrogen, alkyl and aryl.

A further aspect of the present invention encompasses the use of the compounds of formula (I) for the treatment of disorders that are mediated by 11-beta-hydroxysteroid dehydrogenase Type 1 enzyme, such as non-insulin dependent type 2 diabetes, insulin resistance, obesity, lipid disorders, metabolic syndrome and other diseases and conditions that are mediated by excessive glucocorticoid action, comprising administering a therapeutically effective amount of a compound of formula (I).

According to still another aspect, the present invention is directed to a pharmaceutical composition comprising a therapeutically effective amount of a compound of formula (I) in combination with a pharmaceutically suitable carrier.

DETAILED DESCRIPTION OF THE INVENTION

Figure 1:
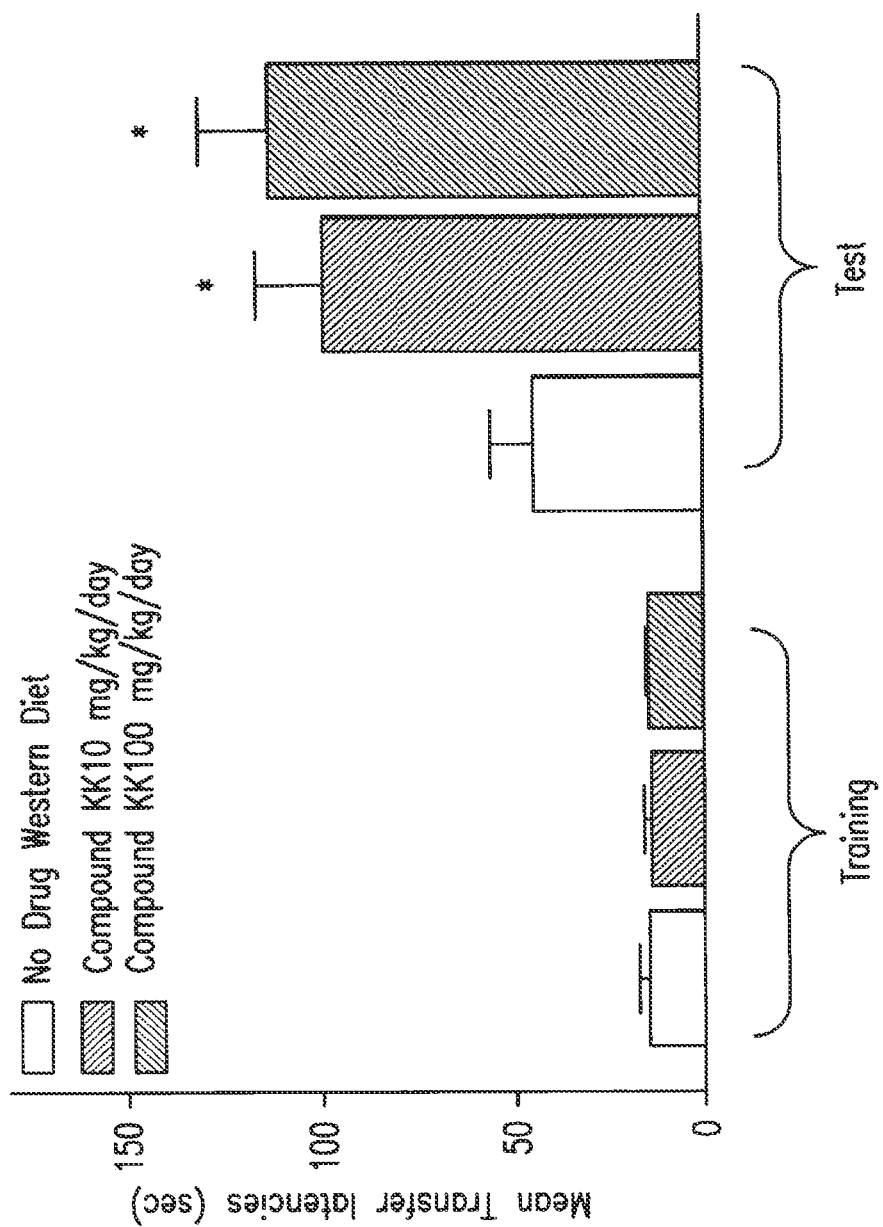
FIG. 1 shows the results of memory consolidation in treated and untreated mice measured as Mean Transfer Latency.

One aspect of the present invention is directed toward a compound of formula (I), or a pharmaceutically acceptable salt, prodrug, salt of a prodrug, or a combination thereof

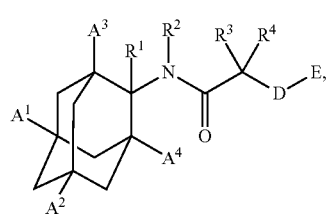

(I)

wherein one of $A^1$, $A^2$, $A^3$ and $A^4$ is selected from the group consisting of alkyl-NH-alkyl, alkylcarbonyl, alkylsulfonyl, cycloalkyl, cycloalkylcarbonyl, cycloalkylsulfonyl, arylcarbonyl, arylsulfonyl, heteroaryl, heteroarylalkyl, heteroaryloxyalkyl, heterocyclecarbonyl, heterocyclesulfonyl, aryl¹, arylalkyl, aryloxyalkyl, carboxyalkyl, carboxycycloalkyl, haloalkyl, heterocyclealkyl, heterocycleoxyalkyl, —S(O)₂—N(R⁵R⁶), —NR⁷—[C(R⁸R⁹)]ₐ—C(O)—R¹⁰, —O—[C(R¹¹R¹²)]ₚ—C(O)—R¹³, —OR¹⁴ᵃ, —N(R¹⁵R¹⁶), —CO₂R¹⁷, —C(O)—N(R¹⁸R¹⁹), —C(R²⁰R²¹)—OR²², —C(R²³R²⁴)—N(R²⁵R²⁶), and heterocycle, with the exception that 5 membered heterocycles may not contain two oxygen atoms, and the remaining members of the group consisting of $A^1$, $A^2$, $A^3$ and $A^4$ are each individually selected from the group consisting of hydrogen, alkyl, alkyl-NH-alkyl, alkylcarbonyl, alkylsulfonyl, cycloalkyl, cycloalkylcarbonyl, cycloalkylsulfonyl, arylcarbonyl, arylsulfonyl, heterocyclecarbonyl, heterocyclesulfonyl, aryl, arylalkyl, aryloxyalkyl, carboxyalkyl, carboxycycloalkyl, halogen, haloalkyl, heteroaryl, heteroarylalkyl, heteroaryloxyalkyl, heterocycle, heterocyclealkyl, heterocycleoxyalkyl, —S(O)₂—N(R⁵R⁶), —NR⁷—[C(R⁸R⁹)]ₙ—C(O)—R¹⁰, —O—[C(R¹¹R¹²)]ₚ—C(O)—R¹³, —OR¹⁴ᵇ, —N(R¹⁵R¹⁶), —CO₂R¹⁷, —C(O)—N(R¹⁸R¹⁹), —C(R²⁰R²¹)—OR²², and —C(R²³R²⁴)—N(R²⁵R²⁶);

n is 0 or 1;

p is 0 or 1;

D is selected from the group consisting of a bond, —C(R²⁷R²⁸)—X— and —C(R²⁷R²⁸)—C(R²⁹R³⁰)—X—;

E is selected from the group consisting of a cycloalkyl, alkyl, aryl, heteroaryl and heterocycle, wherein the heteroaryl and the heterocycle are appended to the parent molecular moiety through an available carbon atom, or $R^4$ and E together with the atoms to which they are attached form a ring selected from the group consisting of cycloalkyl and heterocycle;

X is selected from the group consisting of a bond, —N(R³¹)—, —O—, —S—, —S(O)— and —S(O)₂—;

$R^1$ is selected from the group consisting of hydrogen and alkyl;

$R^2$ is selected from the group consisting of hydrogen, alkyl and cycloalkyl;

$R^3$ and $R^4$ are each independently selected from the group consisting of hydrogen, alkyl, carboxyalkyl, carboxycycloalkyl, cycloalkyl, haloalkyl, aryl, arylalkyl, heteroaryl, heteroarylalkyl, heterocycle and heterocyclealkyl, or $R^3$ and $R^4$ together with the atom to which they are attached form a ring selected from the group consisting of cycloalkyl and heterocycle;

$R^5$ and $R^6$ are each independently selected from the group consisting of hydrogen, alkoxy, alkyl, alkylcarbonyl, alkylsulfonyl, carboxy, carboxyalkyl, carboxycycloalkyl, cycloalkyl, cycloalkyloxy, cycloalkylsulfonyl, aryl, arylalkyl, arylalkylcarbonyl, arylcarbonyl, aryloxy, aryloxyalkyl, arylsulfonyl, heteroaryl, heteroarylalkyl, heteroarylalkylcarbonyl, heteroarylcarbonyl, heteroaryloxyalkyl, heteroarylsulfonyl, heterocycle, heterocyclealkyl, heterocyclealkylcarbonyl, heterocyclecarbonyl, heterocycleoxyalkyl, heterocycleoxy, heterocyclesulfonyl and hydroxy, or $R^5$ and $R^6$ together with the atom to which they are attached form a heterocycle;

$R^7$ is selected from the group consisting of hydrogen, alkyl, carboxyalkyl, cycloalkyl, carboxycycloalkyl, aryl, arylalkyl, aryloxyalkyl, hydroxy, alkoxy, heteroaryl, heteroarylalkyl, heteroaryloxyalkyl, heterocycle, heterocyclealkyl and heterocycleoxyalkyl;

$R^8$ and $R^9$ are each independently selected from the group consisting of hydrogen and alkyl, or $R^8$ and $R^9$ taken together with the atom to which they are attached form a ring selected from the group consisting of cycloalkyl and heterocycle;

$R^{10}$ is selected from the group consisting of hydrogen, alkyl, carboxyalkyl, cycloalkyl, carboxycycloalkyl, aryl, arylalkyl, aryloxy, aryloxyalkyl, hydroxy, alkoxy, cycloalkyloxy, heteroaryl, heteroarylalkyl, heteroaryloxy, heteroaryloxyalkyl, heterocycle, heterocyclealkyl, heterocycleoxy, heterocycleoxyalkyl and —$N(R^{32}R^{33})$;

$R^{11}$ and $R^{12}$ are each independently selected from the group consisting of hydrogen and alkyl or $R^{11}$ and $R^{12}$ taken together with the atom to which they are attached form a ring selected from the group consisting of cycloalkyl and heterocycle;

$R^{13}$ is selected from the group consisting of hydroxy and —$N(R^{34}R^{35})$;

$R^{14a}$ is selected from the group consisting of carboxyalkyl, cycloalkyl, carboxycycloalkyl, aryl, arylalkyl, aryloxyalkyl, haloalkyl, heteroaryl, heteroarylalkyl, heteroaryloxyalkyl, heterocycle, heterocyclealkyl and heterocycleoxyalkyl;

$R^{14b}$ is selected from the group consisting of hydrogen, alkyl, carboxyalkyl, cycloalkyl, carboxycycloalkyl, aryl, arylalkyl, aryloxyalkyl, haloalkyl, heteroaryl, heteroarylalkyl, heteroaryloxyalkyl, heterocycle, heterocyclealkyl and heterocycleoxyalkyl;

$R^{15}$ and $R^{16}$ are each independently selected from the group consisting of hydrogen, alkyl, alkylcarbonyl, carboxyalkyl, cycloalkyl, carboxycycloalkyl, aryl, arylalkyl, arylalkylcarbonyl, arylcarbonyl, aryloxyalkyl, heteroaryl, heteroarylalkyl, heteroarylalkylcarbonyl, heteroarylcarbonyl, heteroaryloxyalkyl, heteroarylsulfonyl, heterocycle, heterocyclealkyl, heterocyclealkylcarbonyl, heterocyclecarbonyl, heterocycleoxyalkyl, heterocyclesulfonyl, alkylsulfonyl, cycloalkylsulfonyl and arylsulfonyl, or $R^{15}$ and $R^{16}$ together with the atom to which they are attached form a heterocycle;

$R^{17}$ is selected from the group consisting of hydrogen, alkyl, carboxyalkyl, cycloalkyl, carboxycycloalkyl, aryl, arylalkyl, aryloxyalkyl, heteroaryl, heteroarylalkyl, heteroaryloxyalkyl, heterocycle, heterocyclealkyl and heterocycleoxyalkyl;

$R^{18}$ and $R^{19}$ are each independently selected from the group consisting of hydrogen, alkoxy, alkyl, alkylsulfonyl, carboxy, carboxyalkyl, carboxycycloalkyl, cycloalkyl, cycloalkyloxy, cycloalkylsulfonyl, aryl, arylalkyl, aryloxy, aryloxyalkyl, arylsulfonyl, heteroaryl, heteroarylalkyl, heteroaryloxyalkyl, heteroarylsulfonyl, heterocycle, heterocyclealkyl, heterocycleoxyalkyl, heterocycleoxy, heterocyclesulfonyl and hydroxy, or $R^{18}$ and $R^{19}$ together with the atom to which they are attached form a heterocycle;

$R^{20}$, $R^{21}$ and $R^{22}$ are each independently selected from the group consisting of hydrogen, alkyl, aryl, arylalkyl, carboxyalkyl, carboxycycloalkyl, cycloalkyl, haloalkyl, heteroaryl, heteroarylalkyl, heterocycle and heterocyclealkyl;

$R^{23}$ and $R^{24}$ are each independently selected from the group consisting of hydrogen, alkyl, alkylcarbonyl, alkylsulfonyl, aryl, arylcarbonyl, arylsulfonyl, carboxyalkyl, carboxycycloalkyl, cycloalkyl, cycloalkylcarbonyl, cycloalkylsulfonyl, heteroaryl, heteroarylcarbonyl, heteroarylsulfonyl, heterocycle, heterocyclecarbonyl and heterocyclesulfonyl;

$R^{25}$ and $R^{26}$ are each independently selected from the group consisting of hydrogen, alkoxy, alkyl, alkylcarbonyl, alkylsulfonyl, aryl, arylcarbonyl, aryloxy, arylsulfonyl, carboxyalkyl, carboxycycloalkyl, cycloalkyl, cycloalkylcarbonyl, cycloalkyloxy, cycloalkylsulfonyl, heteroaryl, heteroarylcarbonyl, heteroaryloxy, heteroarylsulfonyl, heterocycle, heterocyclecarbonyl, heterocycleoxy, heterocyclesulfonyl and hydroxy, or $R^{25}$ and $R^{26}$ together with the nitrogen to which they are attached form a ring selected from the group consisting of heteroaryl and heterocycle;

$R^{27}$ and $R^{28}$ are each independently selected from the group consisting of hydrogen, alkyl, aryl, cycloalkyl, heteroaryl and heterocycle or $R^{27}$ and $R^{28}$ together with the atom to which they are attached form a ring selected from the group consisting of cycloalkyl and heterocycle, or $R^{27}$ and $R^{29}$ together with the atoms to which they are attached form a ring selected from the group consisting of cycloalkyl and heterocycle, or $R^{28}$ and $R^4$ together with the atoms to which they are attached form a ring selected from the group consisting of cycloalkyl and heterocycle;

$R^{29}$ and $R^{30}$ are each independently selected from the group consisting of hydrogen, alkyl, alkoxy, aryl, aryloxy, cycloalkyl, cycloalkyloxy, heteroaryl, heterocycle, and —$N(R^{36}R^{37})$, or $R^{29}$ and $R^{30}$ together with the atom to which they are attached form a ring selected from the group consisting of cycloalkyl and heterocycle, or $R^{29}$ and $R^4$ together with the atoms to which they are attached form a ring selected from the group consisting of cycloalkyl and heterocycle, or $R^{29}$ and E together with the atoms to which they are attached form a ring selected from the group consisting of cycloalkyl and heterocycle;

$R^{31}$ is selected from the group consisting of hydrogen, alkyl, aryl, cycloalkyl, heterocycle and heteroaryl, or $R^{31}$ and E together with the atom to which they are attached form a ring selected from the group consisting of heteroaryl and heterocycle, or $R^{31}$ and $R^4$ together with the atoms to which they are attached form a heterocycle;

$R^{32}$ and $R^{33}$ are each independently selected from the group consisting of hydrogen, alkyl, carboxy, carboxyalkyl, cycloalkyl, cycloalkyloxy, carboxycycloalkyl, aryl, arylalkyl, aryloxy, aryloxyalkyl, heterocycle, heterocyclealkyl, heterocycleoxyalkyl, heterocycleoxy, hydroxy, alkoxy, alkylsulfonyl, cycloalkylsulfonyl, arylsulfonyl, and heterocyclesulfonyl, or $R^{32}$ and $R^{33}$ together with the atom to which they are attached form a heterocycle;

$R^{34}$ and $R^{35}$ are each independently selected from the group consisting of hydrogen, alkyl, carboxy, carboxyalkyl, cycloalkyl, cycloalkyloxy, carboxycycloalkyl, aryl, arylalkyl, aryloxy, aryloxyalkyl, heterocycle, heterocyclealkyl, heterocycleoxyalkyl, heterocycleoxy, hydroxy, alkoxy, alkylsulfonyl, cycloalkylsulfonyl, arylsulfonyl, and heterocyclesulfonyl, or $R^{34}$ and $R^{35}$ together with the atom to which they are attached form a heterocycle; and $R^{36}$ and $R^{37}$ are each independently selected from the group consisting of hydrogen, alkyl and aryl.

Another aspect of the present invention is directed toward a compound of formula (I), or a pharmaceutically acceptable salt, prodrug, salt of a prodrug, or a combination thereof, wherein $A^2$, $A^3$ and $A^4$ are hydrogen;

$R^1$ and $R^2$ are hydrogen; and $A^1$, $R^3$, $R^4$, D and E are as described in the summary of the invention.

Another aspect of the present invention is directed toward a compound of formula (I), or a pharmaceutically acceptable salt, prodrug, salt of a prodrug, or a combination thereof, wherein $A^2$, $A^3$ and $A^4$ are hydrogen;

$R^1$ and $R^2$ are hydrogen;

D is a bond; and $A^1$, $R^3$, $R^4$ and E are as described in the summary of the invention.

Another aspect of the present invention is directed toward a compound of formula (I), or a pharmaceutically acceptable salt, prodrug, salt of a prodrug, or a combination thereof, wherein $A^2$, $A^3$ and $A^4$ are hydrogen;
$R^1$ and $R^2$ are hydrogen;
D is a bond;
E is selected from the group consisting of alkyl, aryl, and heteroaryl; and
$A^1$, $R^3$, and $R^4$ are as described in the summary of the invention.

Another aspect of the present invention is directed toward a compound of formula (I), or a pharmaceutically acceptable salt, prodrug, salt of a prodrug, or a combination thereof, wherein
$A^2$, $A^3$ and $A^4$ are hydrogen;
$R^1$ and $R^2$ are hydrogen;
D is a bond;
E is selected from the group consisting of alkyl, aryl and heteroaryl;
$R^3$ and $R^4$ are hydrogen; and
$A^1$ is selected from the group consisting of heteroaryl, —$CO_2R^{17}$, —C(O)—N($R^{18}R^{19}$), alkylsulfonyl and —S(O)$_2$—N($R^5R^6$); wherein $R^5$, $R^6$, $R^{17}$, $R^{18}$ and $R^{19}$ are as described in the summary of the invention.

Another aspect of the present invention is directed toward a compound of formula (I), or a pharmaceutically acceptable salt, prodrug, salt of a prodrug, or a combination thereof, wherein
$A^2$, $A^3$ and $A^4$ are hydrogen;
$R^1$ and $R^2$ are hydrogen;
D is a bond;
E is selected from the group consisting of alkyl, aryl and heteroaryl;
$R^3$ is hydrogen;
$R^4$ is alkyl; and
$A^1$ is selected from the group consisting of heteroaryl, —$CO_2R^{17}$, —C(O)—N($R^{18}R^{19}$), alkylsulfonyl and —S(O)$_2$—N($R^5R^6$); wherein $R^5$, $R^6$, $R^{17}$, $R^{18}$ and $R^{19}$ are as described in the summary of the invention.

Another aspect of the present invention is directed toward a compound of formula (I), or a pharmaceutically acceptable salt, prodrug, salt of a prodrug, or a combination thereof; wherein
$A^2$, $A^3$ and $A^4$ are hydrogen;
$R^1$ and $R^2$ are hydrogen;
D is a bond;
E is selected from the group consisting of alkyl, aryl and heteroaryl;
$R^3$ and $R^4$ are alkyl; and
$A^1$ is selected from the group consisting of heteroaryl, —$CO_2R^{17}$, —C(O)—N($R^{18}R^{19}$), alkylsulfonyl and —S(O)$_2$—N($R^5R^6$); wherein $R^5$, $R^6$, $R^{17}$, $R^{18}$ and $R^{19}$ are as described in the summary of the invention Another aspect of the present invention is directed toward a compound of formula (I), or a pharmaceutically acceptable salt, prodrug, salt of a prodrug, or a combination thereof, wherein
$A^2$, $A^3$ and $A^4$ are hydrogen;
$R^1$ and $R^2$ are hydrogen;
D is a bond;
E is selected from the group consisting of alkyl, aryl and heteroaryl;
$R^3$ and $R^4$ together with the atom to which they are attached form a ring selected from the group consisting of cycloalkyl and heterocycle; and $A^1$ is as described in the summary of the invention.

Another aspect of the present invention is directed toward a compound of formula (I), or a pharmaceutically acceptable salt, prodrug, salt of a prodrug, or a combination thereof;

wherein
$A^2$, $A^3$ and $A^4$ are hydrogen;
$R^1$ and $R^2$ are hydrogen;
D is a bond;
E is selected from the group consisting of alkyl, aryl and heteroaryl;
$R^3$ and $R^4$ together with the atom to which they are attached form a cycloalkyl ring; and
$A^1$ is selected from the group consisting of heteroaryl, —$CO_2R^{17}$, —C(O)—N($R^{18}R^{19}$), alkylsulfonyl and —S(O)$_2$—N($R^5R^6$); wherein $R^5$, $R^6$, $R^{17}$, $R^{18}$ and $R^{19}$ are as described in the summary of the invention.

Another aspect of the present invention is directed toward a compound of formula (I), or a pharmaceutically acceptable salt, prodrug, salt of a prodrug, or a combination thereof, wherein
$A^2$, $A^3$ and $A^4$ are hydrogen;
$R^1$ and $R^2$ are hydrogen;
D is a bond;
E is selected from the group consisting of alkyl, aryl and heteroaryl;
$R^3$ and $R^4$ together with the atom to which they are attached, form a heterocycle ring; and
$A^1$ is selected from the group consisting of heteroaryl, —$CO_2R^{17}$, —C(O)—N($R^{18}R^{19}$), alkylsulfonyl and —S(O)$_2$—N($R^5R^6$); wherein. $R^5$, $R^6$, $R^{17}$, $R^{18}$ and $R^{19}$ are as described in the summary of the invention.

Another aspect of the present invention is directed toward a compound of formula (I), or a pharmaceutically acceptable salt, prodrug, salt of a prodrug, or a combination thereof, wherein
$A^2$, $A^3$ and $A^4$ are hydrogen;
$R^1$ and $R^2$ are hydrogen;
D is a bond;
$R^4$ and E together with the atoms to which they are attached form a ring selected from the group consisting of cycloalkyl and heterocycle; and
$A^1$ is selected from the group consisting of heteroaryl, —$CO_2R^{17}$, —C(O)—N($R^{18}R^{19}$), alkylsulfonyl and —S(O)$_2$—N($R^5$, $R^6$); wherein $R^3$, $R^5$, $R^6$, $R^{17}$, $R^{18}$ and $R^{19}$ are as described in the summary of the invention.

Another aspect of the present invention is directed toward a compound of formula (II), or a pharmaceutically acceptable salt, prodrug, salt of a prodrug, or a combination thereof,

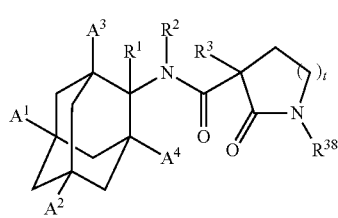

(II)

wherein
t is 1 or 2;
$A^2$, $A^3$ and $A^4$ are hydrogen;
$R^1$ and $R^2$ are hydrogen;
$R^3$ is alkyl;
$A^1$ is selected from the group consisting of heteroaryl, —$CO_2R^{17}$, —C(O)—N($R^{18}R^{19}$), alkylsulfonyl, and —S(O)$_2$—N($R^5R^6$); wherein $R^5$, $R^6$, $R^{17}$, $R^{18}$ and $R^{19}$ are as described in the summary of the invention; and
$R^{38}$ is selected from the group consisting of arylalkyl and heteroarylalkyl wherein the aryl of the arylalkyl and the heteroaryl of the heteroarylalkyl are each independently unsubstituted or substituted with 1, 2 or 3 substituents selected from the group consisting of alkyl, halogen and haloalkyl.

Another aspect of the present invention is directed toward a compound of formula (III), or a pharmaceutically acceptable salt, prodrug, salt of a prodrug, or a combination thereof,

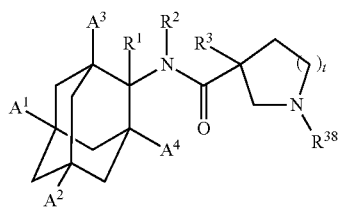

(III)

wherein
t is 1 or 2;
$A^2$, $A^3$ and $A^4$ are hydrogen;
$R^1$ and $R^2$ are hydrogen;
$R^3$ is alkyl;
$A^1$ is selected from the group consisting of heteroaryl, $-CO_2R^{17}$, $-C(O)-N(R^{18}R^{19})$, alkylsulfonyl, and $-S(O)_2-N(R^5R^6)$; wherein $R^5$, $R^6$, $R^{17}$, $R^{18}$ and $R^{19}$ are as described in the summary of the invention; and
$R^{38}$ is selected from the group consisting of arylalkyl and heteroarylalkyl wherein the aryl of the arylalkyl and the heteroaryl of the heteroarylalkyl are each independently unsubstituted or substituted with 1, 2 or 3 substituents selected from the group consisting of alkyl, halogen and haloalkyl.

Another aspect of the present invention is directed toward a compound of formula (I), or a pharmaceutically acceptable salt, prodrug, salt of a prodrug, or a combination thereof, wherein
$A^2$, $A^3$ and $A^4$ are hydrogen;
$R^1$ and $R^2$ are hydrogen;
D is selected from the group consisting of $-C(R^{27}R^{24})-X-$ and $-C(R^{27}R^{28})-C(R^{29}R^{30})-X-$; and $R^{27}$, $R^{28}$, $R^{29}$, $R^{30}$, X, $A^1$, $R^3$, $R^4$ and E are as described in the summary of the invention.

Another aspect of the present invention is directed toward a compound of formula (I), or a pharmaceutically acceptable salt, prodrug, salt of a prodrug, or a combination thereof, wherein
$A^2$, $A^3$ and $A^4$ are hydrogen;
$R^1$ and $R^2$ are hydrogen;
D is selected from the group consisting of $-C(R^{27}R^{28})-X-$ and $-C(R^{27}R^{28})-C(R^{29}R^{30})-X-$; wherein $R^{27}$, $R^{28}$, $R^{29}$, and X are as described in the summary of the invention;
E is selected from the group consisting of aryl and heteroaryl; and $A^1$, $R^3$, and $R^4$ are as described in the summary of the invention.

Another aspect of the present invention is directed toward a compound of formula (I), or a pharmaceutically acceptable salt, prodrug, salt of a prodrug, or a combination thereof, wherein
$A^2$, $A^3$ and $A^4$ are hydrogen;
$R^1$ and $R^2$ are hydrogen;
D is selected from the group consisting of $-C(R^{27}R^{28})-X-$ and $-C(R^{27}R^{28})-C(R^{29}R^{30})-X-$; wherein $R^{27}$, $R^{28}$, $R^{29}$, and $R^{30}$ are as described in the summary of the invention;
E is selected from the group consisting of aryl and heteroaryl;
X is a bond; and $A^1$, $R^3$, and $R^4$ are as described in the summary of the invention. Another aspect of the present invention is directed toward a compound of formula (I), or a pharmaceutically acceptable salt, prodrug, salt of a prodrug, or a combination thereof, wherein
$A^2$, $A^3$ and $A^4$ are hydrogen;
$R^1$ and $R^2$ are hydrogen;
D is selected from the group consisting of $-C(R^{27}R^{28})-X-$ and $-C(R^{27}R^{28})-C(R^{29}R^{30})-X-$; wherein $R^{27}$, $R^{28}$, $R^{29}$, and $R^{30}$ are each independently selected from the group consisting of hydrogen and alkyl;
E is selected from the group consisting of aryl and heteroaryl;
X is a bond;
$R^3$ and $R^4$ are hydrogen; and
$A^1$ is selected from the group consisting of heteroaryl, $-CO_2R^{17}$, $-C(O)-N(R^{18}R^{19})$, alkylsulfonyl, and $-S(O)_2-N(R^5R^6)$; wherein $R^5$, $R^6$, $R^{17}$, $R^{18}$ and $R^{19}$ are as described in the summary of the invention.

Another aspect of the present invention is directed toward a compound of formula (I), or a pharmaceutically acceptable salt, prodrug, salt of a prodrug, or a combination thereof, wherein
$A^2$, $A^3$ and $A^4$ are hydrogen;
$R^1$ and $R^2$ are hydrogen;
D is selected from the group consisting of $-C(R^{27}R^{28})-X-$ and $-C(R^{27}R^{28})-C(R^{29}R^{30})-X-$; wherein $R^{27}$, $R^{28}$, $R^{29}$, and $R^{30}$ are each independently selected from the group consisting of hydrogen and alkyl;
E is selected from the group consisting of aryl and heteroaryl;
X is a bond;
$R^3$ is hydrogen;
$R^4$ is alkyl; and
$A^1$ is selected from the group consisting of heteroaryl, $-CO_2R^{17}$, $-C(O)-N(R^{18}R^{19})$, alkylsulfonyl, and $-S(O)_2-N(R^5R^6)$; wherein $R^5$, $R^6$, $R^{17}$, $R^{18}$ and $R^{19}$ are as described in the summary of the invention.

Another aspect of the present invention is directed toward a compound of formula (I), or a pharmaceutically acceptable salt, prodrug, salt of a prodrug, or a combination thereof, wherein
$A^2$, $A^3$ and $A^4$ are hydrogen;
$R^1$ and $R^2$ are hydrogen;
D is selected from the group consisting of $-C(R^{27}R^{28})-X-$ and $-C(R^{27}R^{28})-C(R^{29}R^{30})-X-$; wherein $R^{27}$, $R^{28}$, $R^{29}$, and $R^{30}$ are each independently selected from the group consisting of hydrogen and alkyl;
E is selected from the group consisting of aryl and heteroaryl;
X is a bond;
$R^3$ and $R^4$ are alkyl; and
$A^1$ is selected from the group consisting of heteroaryl, $-CO_2R^{17}$, $-C(O)-N(R^{18}R^{19})$, alkylsulfonyl, and $-S(O)_2-N(R^5R^6)$; wherein $R^5$, $R^6$, $R^{17}$, $R^{18}$ and $R^{19}$ are as described in the summary of the invention.

Another aspect of the present invention is directed toward a compound of formula (I), or a pharmaceutically acceptable salt, prodrug, salt of a prodrug, or a combination thereof, wherein
$A^2$, $A^3$ and $A^4$ are hydrogen;
$R^1$ and $R^2$ are hydrogen;
D is selected from the group consisting of $-C(R^{27}R^{28})-X-$ and $-C(R^{27}R^{28})-C(R^{29}R^{30})-X-$; wherein $R^{27}$, $R^{28}$, $R^{29}$, and $R^{30}$ are as described in the summary of the invention;
E is selected from the group consisting of aryl and heteroaryl;
X is a bond;

$R^3$ and $R^4$ together with the atom to which they are attached form a ring selected from the group consisting of cycloalkyl and heterocycle; and $A^1$ is as described in the summary of the invention.

Another aspect of the present invention is directed toward a compound of formula (I), or a pharmaceutically acceptable salt, prodrug, salt of a prodrug, or a combination thereof, wherein $A^2$, $A^3$ and $A^4$ are hydrogen;

$R^1$ and $R^2$ are hydrogen;

D is selected from the group consisting of $-C(R^{27}R^{28})-X-$ and $-C(R^{27}R^{28})-C(R^{29}R^{30})-X-$; wherein $R^{27}$, $R^{28}$, $R^{29}$, and $R^{30}$ are each independently selected from the group consisting of hydrogen and alkyl;

E is selected from the group consisting of aryl and heteroaryl;

X is a bond;

$R^3$ and $R^4$ together with the atom to which they are attached form a cycloalkyl ring; and $A^1$ is selected from the group consisting of heteroaryl, $-CO_2R^{17}$, $-C(O)-N(R^{18}R^{19})$, alkylsulfonyl, and $-S(O)_2-N(R^5R^6)$; wherein $R^5$, $R^6$, $R^{17}$, $R^{18}$ is and $R^{19}$ are as described in the summary of the invention.

Another aspect of the present invention is directed toward a compound of formula (I), or a pharmaceutically acceptable salt, prodrug, salt of a prodrug, or a combination thereof, wherein $A^2$, $A^3$ and $A^4$ are hydrogen;

$R^1$ and $R^2$ are hydrogen;

D is selected from the group consisting of $-C(R^{27}R^{28})-X-$ and $-C(R^{27}R^{28})-C(R^{29}R^{30})-X-$; wherein $R^{27}$, $R^{28}$, $R^{29}$, and $R^{30}$ are each independently selected from the group consisting of hydrogen and alkyl;

E is selected from the group consisting of aryl and heteroaryl;

X is a bond;

$R^3$ and $R^4$ together with the atom to which they are attached form a heterocycle ring; and $A^1$ is selected from the group consisting of heteroaryl, $-CO_2R^{17}$, $-C(O)-N(R^{18}R^{19})$, alkylsulfonyl, and $-S(O)_2-N(R^5R^6)$; wherein $R^5$, $R^6$, $R^{17}$, $R^{18}$ and $R^{19}$ are as described in the summary of the invention.

Another aspect of the present invention is directed toward a compound of formula (I), or a pharmaceutically acceptable salt, prodrug, salt of a prodrug, or a combination thereof, wherein $A^2$, $A^3$ and $A^4$ are hydrogen;

$R^1$ and $R^2$ are hydrogen;

D is selected from the group consisting of $-C(R^{27}R^{28})-X-$ and $-C(R^{27}R^{28})-C(R^{29}R^{30})-X-$; wherein $R^{27}$, $R^{28}$, $R^{29}$, and $R^{30}$ are as described in the summary of the invention;

E is selected from the group consisting of aryl and heteroaryl;

X is selected from the group consisting of $-N(R^{31})-$ and $-O-$; and $A^1$, $R^3$, and $R^4$ are as described in the summary of the invention.

Another aspect of the present invention is directed toward a compound of formula (I), or a pharmaceutically acceptable salt, prodrug, salt of a prodrug, or a combination thereof, wherein $A^2$, $A^3$ and $A^4$ are hydrogen;

$R^1$ and $R^2$ are hydrogen;

D is selected from the group consisting of $-C(R^{27}R^{28})-X-$ and $-C(R^{27}R^{28})-C(R^{29}R^{30})-X-$; wherein $R^{27}$, $R^{28}$, $R^{29}$, and $R^{30}$ are each independently selected from the group consisting of hydrogen and alkyl;

E is selected from the group consisting of aryl and heteroaryl;

X is selected from the group consisting of $-N(R^{31})-$ and $-O-$;

$R^3$ and $R^4$ are hydrogen; and $A^1$ is selected from the group consisting of heteroaryl, $-CO_2R^{17}$, $-C(O)-N(R^{18}R^{19})$, alkylsulfonyl, and $-S(O)_2-N(R^5R^6)$; wherein $R^5$, $R^6$, $R^{17}$, $R^{18}$ and $R^{19}$ are as described in the summary of the invention.

Another aspect of the present invention is directed toward a compound of formula (I), or a pharmaceutically acceptable salt, prodrug, salt of a prodrug, or a combination thereof, wherein $A^2$, $A^3$ and $A^4$ are hydrogen;

$R^1$ and $R^2$ are hydrogen;

D is selected from the group consisting of $-C(R^{27}R^{28})-X-$ and $-C(R^{27}R^{28})-C(R^{29}R^{30})-X-$; wherein $R^{27}$, $R^{28}$, $R^{29}$, and $R^{30}$ are each independently selected from the group consisting of hydrogen and alkyl;

E is selected from the group consisting of aryl and heteroaryl;

X is selected from the group consisting of $-N(R^{31})-$ and $-O-$;

$R^3$ is hydrogen;

$R^4$ is alkyl; and $A^1$ is selected from the group consisting of heteroaryl, $-CO_2R^{17}$, $-C(O)-N(R^{18}R^{19})$, alkylsulfonyl, and $-S(O)_2-N(R^5R^6)$; wherein $R^5$, $R^6$, $R^{17}$, $R^{18}$ and $R^{19}$ are as described in the summary of the invention.

Another aspect of the present invention is directed toward a compound of formula (I), or a pharmaceutically acceptable salt, prodrug, salt of a prodrug, or a combination thereof, wherein $A^2$, $A^3$ and $A^4$ are hydrogen;

$R^1$ and $R^2$ are hydrogen;

D is selected from the group consisting of $-C(R^{27}R^{28})-X-$ and $-C(R^{27}R^{28})-C(R^{29}R^{30})-X-$; wherein $R^{27}$, $R^{28}$, $R^{29}$, and $R^{30}$ are each independently selected from the group consisting of hydrogen and alkyl;

E is selected from the group consisting of aryl and heteroaryl;

X is selected from the group consisting of $-N(R^{31})-$ and $-O-$;

$R^3$ and $R^4$ are alkyl; and $A^1$ is selected from the group consisting of heteroaryl, $-CO_2R^{17}$, $-C(O)-N(R^{18}R^{19})$, alkylsulfonyl, and $-S(O)_2-N(R^5R^6)$; wherein $R^5$, $R^6$, $R^{17}$, $R^{18}$ and $R^{19}$ are as described in the summary of the invention.

Another aspect of the present invention is directed toward a compound of formula (I), or a pharmaceutically acceptable salt, prodrug, salt of a prodrug, or a combination thereof, wherein $A^2$, $A^3$ and $A^4$ are hydrogen;

$R^1$ and $R^2$ are hydrogen;

D is selected from the group consisting of $-C(R^{27}R^{28})-X-$ and $-C(R^{27}R^{28})-C(R^{29}R^{30})-X-$; wherein $R^{27}$, $R^{28}$, $R^{29}$, and $R^{30}$ are each independently selected from the group consisting of hydrogen and alkyl;

E is selected from the group consisting of aryl and heteroaryl;

X is selected from the group consisting of $-N(R^{31})-$ and $-O-$;

$R^3$ and $R^4$ together with the atom to which they are attached form a ring selected from the group consisting of cycloalkyl and heterocycle; and A¹ is selected from the group consisting of heteroaryl, —CO₂R¹⁷, —C(O)—N(R¹⁸R¹⁹), alkylsulfonyl, and —S(O)₂—N(R⁵R⁶); wherein R⁵, R⁶, R¹⁷, R¹⁸ and R¹⁹ are as described in the summary of the invention.

Another aspect of the present invention is directed toward a compound of formula (I), or a pharmaceutically acceptable salt, prodrug, salt of a prodrug, or a combination thereof, wherein A², A³ and A⁴ are hydrogen;

R¹ and R² are hydrogen;

D is selected from the group consisting of —C(R²⁷R²⁸)—X— and —C(R²⁷R²⁸)—C(R²⁹R³⁰)—X—; wherein R²⁷, R²⁸, R²⁹, and R³⁰ are each independently selected from the group consisting of hydrogen and allyl;

E is selected from the group consisting of aryl and heteroaryl;

X is selected from the group consisting of —N(R³¹)— and —O—;

R³ and R⁴ together with the atom to which they are attached form a cycloalkyl ring; and A¹ is selected from the group consisting of heteroaryl, —CO₂R¹⁷, —C(O)—N(R¹⁸R¹⁹), alkylsulfonyl, and —S(O)₂—N(R⁵R⁶); wherein R⁵, R⁶, R¹⁷, R¹⁸ and R¹⁹ are as described in the summary of the invention.

Another aspect of the present invention is directed toward a compound of formula (I), or a pharmaceutically acceptable salt, prodrug, salt of a prodrug, or a combination thereof, wherein A², A³ and A⁴ are hydrogen;

R¹ and R² are hydrogen;

D is selected from the group consisting of —C(R²⁷R²⁸)—X— and —C(R²⁷R²⁸)—C(R²⁹R³⁰)—X—; wherein R²⁷, R²⁸, and R³⁰ are each independently selected from the group consisting of hydrogen and alkyl;

E is selected from the group consisting of aryl and heteroaryl;

X is selected from the group consisting of —N(R³¹)— and —O—;

R³ and R⁴ together with the atom to which they are attached form a heterocycle ring; and A¹ is selected from the group consisting of heteroaryl, —CO₂R¹⁷, —C(O)—N(R¹⁸R¹⁹), alkylsulfonyl, and —S(O)₂—N(R⁵R⁶); wherein R⁵, R⁶, R¹⁷, R¹⁸ and R¹⁹ are as described in the summary of the invention.

Exemplary compounds of the present invention having formula (I) include, but are not limited to, E-4-{[(1-(4-Chloro-phenyl)-cyclobutanecarbonyl]-amino}-adamantane-1-carboxylic acid;

E-4-[(1-Phenyl-cyclopropanecarbonyl)-amino]-adamantane-1-carboxylic acid;

E-4-(2-Methyl-2-phenyl-propionylamino)-adamantane-1-carboxylic acid;

E-4-({[1-(4-Chloro-phenyl)-cyclobutanecarbonyl]-amino}-adamantane-1-carboxylic acid amide;

E-4-[(1-Phenyl-cyclopropanecarbonyl)-amino]-adamantane-1-carboxylic acid amide;

E-4-(2-Methyl-2-phenyl-propionylamino)-adamantane-1-carboxylic acid amide;

E-4-({[1-(4-chlorophenyl)cyclohexyl]carbonyl}amino)adamantane-1-carboxamide;

E-4-({[1-(4-chlorophenyl)cyclopropyl]carbonyl)amino}adamantane-1-carboxamide;

E-4-({[1-(4-chlorophenyl)cyclopentyl]carbonyl}amino)adamantane-1-carboxamide;

E-4-{[2-(4-chlorophenyl)-2-methylpropanoyl]amino}adamantane-1-carboxamide;

E-4-({[(1-phenylcyclopentyl)carbonyl]amino}adamantane-1-carboxamide;

E-4-({[1-(3-fluorophenyl)cyclopentyl]carbonyl}amino)adamantane-1-carboxamide;

E-4-({[1-(2-chloro-4-fluorophenyl)cyclopentyl]carbonyl}amino)adamantane-1-carboxamide;

E-4-({[1-(4-fluorophenyl)cyclopentyl]carbonyl}amino)adamantane-1-carboxamide;

E-4-({[1-(2-fluorophenyl)cyclopentyl]carbonyl}amino)adamantane-1-carboxamide;

E-4-{[(1-methylcyclohexyl)carbonyl]amino}adamantane-1-carboxamide;

E-4-({[1-(2,4-dichlorophenyl)cyclopropyl]carbonyl}amino)adamantane-1-carboxamide;

E-4-({[1-(4-methoxyphenyl)cyclopropyl]carbonyl}amino)adamantane-1-carboxamide;

E-4-({[1-(4-methylphenyl)cyclopropyl]carbonyl}amino)adamantane-1-carboxamide;

E-4-{[2-methyl-2-(4-pyridin-4-ylphenyl)propanoyl]amino}adamantane-1-carboxamide;

E-4-[(2-methyl-2-thien-2-ylpropanoyl)amino]adamantane-1-carboxamide;

E-4-[(2-methyl-2-thien-3-ylpropanoyl)amino]adamantane-1-carboxamide;

E-4-({2-methyl-2-[5-(trifluoromethyl)pyridin-2-yl]propanoyl}amino)adamantane-1-carboxamide;

E-4-[(2-methyl-2-{4-[5-(trifluoromethyl)pyridin-2-yl]phenyl}propanoyl)amino]adamantane-1-carboxamide;

E-4-({[1-(4-methoxyphenyl)cyclopentyl]carbonyl}amino)adamantane-1-carboxamide;

E-4-{[2-(4-bromophenyl)-2-methylpropanoyl]amino}adamantane-1-carboxamide;

E-4-[5-(aminocarbonyl)-2-adamantyl]-3-methyl-1-(2-methylbenzyl)-2-oxopiperidine-3-carboxamide;

E-4-(aminocarbonyl)-2-adamantyl]-1-benzyl-3-methyl-2-oxopyrrolidine-3-carboxamide;

E-4-(aminocarbonyl)-2-adamantyl]-3-methyl-1-(2-methylbenzyl)-2-oxopyrrolidine-3-carboxamide;

E-4-(aminocarbonyl)-2-adamantyl]-1-(2-chlorobenzyl)-3-methyl-2-oxopyrrolidine-3-carboxamide;

E-4-(aminocarbonyl)-2-adamantyl]-1-(3-chlorobenzyl)-3-methyl-2-oxopyrrolidine-3-carboxamide;

E-4-({2-methyl-2-[4-(1-methyl-1-pyrazol-4-yl)phenyl]propanoyl}amino)adamantane-1-carboxamide;

E-4-{[2-(3-bromophenyl)-2-methylpropanoyl]amino}adamantane-1-carboxamide;

E-4-({2-[4-(3,5-dimethylisoxazol-4-yl)phenyl]-2-methylpropanoyl}amino)adamantane-1-carboxamide;

E-4-{[2-methyl-2-(4-pyridin-3-ylphenyl)propanoyl]amino}adamantane-1-carboxamide;

4-{[({(E)-4-[(2-methyl-2-thien-2-ylpropanoyl)amino]-1-adamantyl}carbonyl)amino]methyl}benzoic acid;

E-4-({2-methyl-2-[4-(1H-pyrazol-4-yl)phenyl]propanoyl}amino)adamantane-1-carboxamide;

E-4-(aminocarbonyl)-2-adamantyl]-3-methyl-1-(1-methyl-1-phenylethyl)-2-oxopyrrolidine-3-carboxamide;

E-4-(aminocarbonyl)-2-adamantyl]-3-methyl-2-oxo-1-[(1R)-1-phenylethyl]pyrrolidine-3-carboxamide;

E-4-(aminocarbonyl)-2-adamantyl]-3-methyl-2-oxo-1-[(1S)-1-phenylethyl]pyrrolidine-3-carboxamide;

E-4-{[2-methyl-2-(1,3-thiazol-2-yl)propanoyl]amino}adamantane-1-carboxamide;

E-4-(aminocarbonyl)-2-adamantyl]-1-(4-chlorobenzyl)-3-methylpiperidine-3-carboxamide;

E-4-{[2-(4-hydroxyphenyl)-2-methylpropanoyl]amino}adamantane-1-carboxamide;

E-4-(aminocarbonyl)-2-adamantyl]-1-benzyl-3-methyl-2-oxopiperidine-3-carboxamide;
E-4-{[2-methyl-2-(4-phenoxyphenyl)propanoyl]amino}adamantane-1-carboxamide;
E-4-{[2-(1-benzothien-3-yl)-2-methylpropanoyl]amino}adamantane-1-carboxamide;
E-4-{[2-(5-fluoropyridin-2-yl)-2-methylpropanoyl]amino}adamantane-1-carboxamide;
E-4-[(2-methyl-2-quinoxalin-2-ylpropanoyl)amino]adamantane-1-carboxamide;
(E)-4-[(2-methyl-2-pyrazin-2-ylpropanoyl)amino]adamantane-1-carboxamide;
N-[(E)-5-(aminocarbonyl)-2-adamantyl]-3-methyl-2-oxo-1-(2-pyridin-2-ylethyl)pyrrolidine-3-carboxamide;
methyl(E)-4-[(2-methyl-2-phenylpropanoyl)amino]adamantane-1-carboxylate;
(E)-4-({2-methyl-2-[3-(1,3-thiazol-4-ylmethoxy)phenyl]propanoyl}amino)adamantane-1-carboxamide;
(E)-4-({2-methyl-2-[6-(methylamino)pyridin-3-yl]propanoyl}amino)adamantane-1-carboxamide;
(E)-4-({2-methyl-2-[3-(morpholin-4-ylmethyl)phenyl]propanoyl}amino)adamantane-1-carboxamide;
(E)-4-({2-methyl-2-[4-(trifluoromethyl)pyridin-2-yl]propanoyl}amino)adamantane-1-carboxamide;
(E)-4-[(2-{3-[2-(1H-imidazol-1-yl)ethoxy]phenyl}-2-methylpropanoyl)amino]adamantane-1-carboxamide;
methyl(E)-4-{[(1-phenylcyclopropyl)carbonyl]amino}adamantane-1-carboxylate;
(E)-4-{[2-(6-fluoropyridin-3-yl)-2-methylpropanoyl]amino}adamantane-1-carboxamide;
(E)-N-[3-(aminocarbonyl)benzyl]-4-[(2-methyl-2-phenylpropanoyl)amino]adamantane-1-carboxamide;
N-[(E)-5-(aminocarbonyl)-2-adamantyl]-1-(2-chlorobenzyl)-3-methyl-2-oxopiperidine-3-carboxamide;
N-[(E)-5-(aminocarbonyl)-2-adamantyl]-3-methyl-2-oxo-1-(pyridin-4-ylmethyl)pyrrolidine-3-carboxamide;
(E)-4-{[2-methyl-2-(4-phenoxyphenyl)propanoyl]amino}adamantane-1-carboxylic acid;
N-[(E)-5-(aminosulfonyl)-2-adamantyl]-1-phenylcyclopropanecarboxamide;
(E)-4-({3-[(5-cyanopyridin-2-yl)oxy]-2,2-dimethylpropanoyl}amino)adamantane-1-carboxamide;
N-[(E)-5-(aminocarbonyl)-2-adamantyl]-3-methyl-2-oxo-1-(1-pyridin-2-ylethyl)pyrrolidine-3-carboxamide;
(E)-4-[(2-methyl-3-phenylpropanoyl)amino]adamantane-1-carboxamide;
(E)-4-{[2-methyl-2-(6-morpholin-4-ylpyridin-3-yl)propanoyl]amino}adamantane-1-carboxamide;
methyl(E)-4-({[1-(4-chlorophenyl)cyclobutyl]carbonyl}amino)adamantane-1-carboxylate;
N-[(E)-5-(aminocarbonyl)-2-adamantyl]-3-methyl-2-oxo-1-(pyridin-3-ylmethyl)pyrrolidine-3-carboxamide;
(E)-4-[(2-methyl-2-{6-[(2-morpholin-4-ylethyl)amino]pyridin-3-yl}propanoyl)amino]adamantane-1-carboxamide;
(E)-4-[(2-methyl-2-{4-[(E)-2-pyridin-4-ylvinyl]phenyl}propanoyl)amino]adamantane-1-carboxamide;
N-[(E)-5-(aminosulfonyl)-2-adamantyl]-2-(4-chlorophenyl)-2-methylpropanamide;
(E)-4-({2-methyl-2-[3-(2-morpholin-4-ylethoxy)phenyl]propanoyl}amino)adamantane-1-carboxamide;
(E)-4-{[2-(3-cyanopyridin-2-yl)-2-methylpropanoyl]amino}adamantane-1-carboxamide;
(E)-4-({2-methyl-2-[6-(4-methylpiperazin-1-yl)pyridin-3-yl]propanoyl}amino)adamantane-1-carboxamide;
N-[(E)-5-(aminocarbonyl)-2-adamantyl]-3-methyl-2-oxo-1-(pyridin-2-ylmethyl)pyrrolidine-3-carboxamide;
(E)-N-[4-(aminosulfonyl)benzyl]-4-[(2-methyl-2-phenylpropanoyl)amino]adamantane-1-carboxamide;
(E)-4-({2-methyl-2-[4-(pentyloxy)phenyl]propanoyl}amino)adamantane-1-carboxylic acid;
(E)-4-({2-methyl-2-[4-(1,3-thiazol-4-ylmethoxy)phenyl]propanoyl}amino)adamantane-1-carboxylic acid;
(E)-4-[(2-methyl-2-phenylpropanoyl)amino]-N-(1,3-thiazol-5-ylmethyl)adamantane-1-carboxamide;
(E)-4-({2-[4-(benzyloxy)phenyl]-2-methylpropanoyl}amino)adamantane-1-carboxylic acid;
(E)-4-{[2-(5-cyanopyridin-2-yl)-2-methylpropanoyl]amino}adamantane-1-carboxamide;
(E)-4-{[2-(4-chlorophenyl)-2-methylpropanoyl]amino}adamantane-1-carboxylic acid;
4-[({[(E)-4-({2-methyl-2-[5-(trifluoromethyl)pyridin-2-yl]propanoyl}amino)-1-adamantyl]carbonyl}amino)methyl]benzoic acid;
4-{[({(E)-4-[(2-methyl-2-phenylpropanoyl)amino]-1-adamantyl}carbonyl)amino]methyl}benzoic acid;
3-{[({(E)-4-[(2-methyl-2-phenylpropanoyl)amino]-1-adamantyl}carbonyl)amino]methyl}benzoic acid;
(E)-4-({[1-(4-methylphenyl)cyclopropyl]carbonyl}amino)adamantane-1-carboxylic acid;
(E)-4-[(2-methyl-2-phenylpropanoyl)amino]-N-(pyridin-4-ylmethyl)adamantane-1-carboxamide;
(E)-4-({[1-(2,4-dichlorophenyl)cyclopropyl]carbonyl}amino)adamantane-1-carboxylic acid;
(E)-N-(2-furylmethyl)-4-[(2-methyl-2-phenylpropanoyl)amino]adamantane-1-carboxamide;
3-[(E)-4-({2-methyl-2-[5-(trifluoromethyl)pyridin-2-yl]propanoyl}amino)-1-adamantyl]-1H-pyrazole-5-carboxamide;
(E)-4-[(2-methyl-2-phenylpropanoyl)amino]-N-(pyridin-3-ylmethyl)adamantane-1-carboxamide;
(E)-4-[(2-methyl-2-phenylpropanoyl)amino]-N-(pyridin-2-ylmethyl)adamantane-1-carboxamide;
(E)-4-({2-[4-(cyclohexylmethoxy)phenyl]-2-methylpropanoyl}amino)adamantane-1-carboxylic acid;
(E)-4-[(2-methyl-2-{4-[5-(trifluoromethyl)pyridin-2-yl]phenyl}propanoyl)amino]adamantane-1-carboxylic acid; and
N-[(E)-5-(aminosulfonyl)-2-adamantyl]-1-(2-chlorobenzyl)-3-methyl-2-oxopyrrolidine-3-carboxamide.

Another embodiment of the present invention discloses a method of inhibiting 11-beta-hydroxysteroid dehydrogenase Type I enzyme, comprising administering to a mammal, a therapeutically effective amount of the compound of formula (I).

Another embodiment of the present invention discloses a method of treating disorders in a mammal by inhibiting 11-beta-hydroxysteroid dehydrogenase Type I enzyme, comprising administering to a mammal, a therapeutically effective amount of the compound of formula (I).

Another embodiment of the present invention discloses a method of treating non-insulin dependent type 2 diabetes in a mammal by inhibiting 11-beta-hydroxysteroid dehydrogenase Type I enzyme comprising administering to a mammal, a therapeutically effective amount of the compound of formula (I).

Another embodiment of the present invention discloses a method of treating insulin resistance in a mammal by inhibiting 11-beta-hydroxysteroid dehydrogenase Type I enzyme comprising administering to a mammal, a therapeutically effective amount of the compound of formula (I).

Another embodiment of the present invention discloses a method of treating obesity in a mammal by inhibiting 11-beta-hydroxysteroid dehydrogenase Type I enzyme comprising administering to a mammal, a therapeutically effective amount of the compound of formula (I).

Another embodiment of the present invention discloses a method of treating lipid disorders in a mammal by inhibiting 11-beta-hydroxysteroid dehydrogenase Type I enzyme comprising administering to a mammal, a therapeutically effective amount of the compound of formula (I).

Another embodiment of the present invention discloses a method of treating metabolic syndrome in a mammal by inhibiting 11-beta-hydroxysteroid dehydrogenase Type I enzyme comprising administering to a mammal, a therapeutically effective amount of the compound of formula (I).

Another embodiment of the present invention discloses a method of treating diseases and conditions that are mediated by excessive glucocorticoid action in a mammal by inhibiting 11-beta-hydroxysteroid dehydrogenase Type I enzyme comprising administering to a mammal, a therapeutically effective amount of the compound of formula (I).

Another embodiment of the present invention discloses a pharmaceutical composition comprising a therapeutically effective amount of the compound of formula (I) in combination with a pharmaceutically suitable carrier.

DEFINITION OF TERMS

The term "alkenyl" as used herein, refers to a straight or branched chain hydrocarbon containing from 2 to 10 carbons and containing at least one carbon-carbon double bond formed by the removal of two hydrogens. Representative examples of alkenyl include, but are not limited to, ethenyl, 2-propenyl, 2-methyl-2-propenyl, 3-butenyl, 4-pentenyl, 5-hexenyl, 2-heptenyl, 2-methyl-1-heptenyl, and 3-decenyl.

The term "alkoxy" as used herein, refers to an alkyl group, as defined herein, appended to the parent molecular moiety through an oxygen atom. Representative examples of alkoxy include, but are not limited to, methoxy, ethoxy, propoxy, 2-propoxy, butoxy, tert-butoxy, pentyloxy and hexyloxy.

The term "alkoxyalkyl" as used herein, refers to an alkoxy group, as defined herein, appended to the parent molecular moiety through an alkyl group, as defined herein. Representative examples of alkoxyalkyl include, but are not limited to, tert-butoxymethyl, 2-ethoxyethyl, 2-methoxyethyl and methoxymethyl.

The term "alkoxycarbonyl" as used herein, refers to an alkoxy group, as defined herein, appended to the parent molecular moiety through a carbonyl group, as defined herein. Representative examples of alkoxycarbonyl include, but are not limited to, methoxycarbonyl, ethoxycarbonyl and tert-butoxycarbonyl.

The term "alkyl" as used herein, refers to a straight or branched chain hydrocarbon containing from 1 to 10 carbon atoms. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl and n-decyl.

The term "alkylcarbonyl," as used herein, refers to an alkyl group, as defined herein, appended to the parent molecular moiety through a carbonyl group, as defined herein. Representative examples of alkylcarbonyl include, but are not limited to, acetyl, 1-oxopropyl, 2,2-dimethyl-1-oxopropyl, 1-oxobutyl and 1-oxopentyl.

The term "alkylsulfonyl" as used herein, refers to an alkyl group, as defined herein, appended to the parent molecular moiety through a sulfonyl group, as defined herein. Representative examples of alkylsulfonyl include, but are not limited to, methylsulfonyl and ethylsulfonyl.

The term "alkyl-NH" as used herein, refers to an alkyl group, as defined herein, appended to the parent molecular moiety through a nitrogen atom.

The term "alkyl-NH-alkyl" as used herein, refers to an alkyl-NH group, as defined herein, appended to the parent molecular moiety through an alkyl group, as defined herein.

The term "aryl" as used herein, means a phenyl group, or a bicyclic or a tricyclic fused ring system. Bicyclic fused ring systems are exemplified by a phenyl group appended to the parent molecular moiety and fused to a monocyclic cycloalkyl group, as defined herein, a phenyl group, a monocyclic heteroaryl group, as defined herein, or a monocyclic heterocycle, as defined herein. Tricyclic fused ring systems are exemplified by an aryl bicyclic fused ring system, as defined herein and fused to a monocyclic cycloalkyl group, as defined herein, a phenyl group, a monocyclic heteroaryl group, as defined herein, or a monocyclic heterocycle, as defined herein. Representative examples of aryl include, but are not limited to, anthracenyl, azulenyl, fluorenyl, indanyl, indenyl, naphthyl, phenyl and tetrahydronaphthyl.

The aryl groups of this invention may be optionally substituted with 1, 2, 3, 4 or 5 substituents independently selected from alkenyl, alkoxy, alkoxyalkoxy, alkoxyalkyl, alkoxycarbonyl, alkoxycarbonylalkyl, alkyl, alkylcarbonyl, alkynyl, aryl, arylalkenyl, arylalkyl, arylalkoxy, arylcarbonyl, aryloxy, arylsulfonyl, carboxy, carboxyalkyl, cyano, cyanoalkyl, cycloalkylalkoxy, ethylenedioxy, formyl, haloalkoxy, haloalkyl, halogen, heteroaryl, heteroarylalkenyl, heteroarylalkyl, heteroarylalkoxy, heteroarylcarbonyl, heterocycle, heterocyclealkyl, heterocyclealkoxy, heterocyclecarbonyl, heterocycleoxy, hydroxy, hydroxyalkyl, nitro, $R_fR_gN-$, $R_fR_gNalkyl$, $R_fR_gNcarbonyl$ and $R_fR_gNsulfonyl$, wherein $R_f$ and $R_g$ are independently selected from the group consisting of hydrogen, alkyl, alkoxyalkyl, alkylcarbonyl, alkylsulfonyl, cycloalkyl, heterocyclealkyl and cycloalkylalkyl and wherein the cycloalkyl, the heterocycle of heterocyclealkyl and the cycloalkyl of cycloalkylalkyl as represented by $R_f$ and $R_g$ are each independently unsubstituted or substituted with 1, 2 or 3 substituent selected from the group consisting of alkyl, haloalkyl and halogen. The substituent aryl, the aryl of arylalkyl, the aryl of arylalkenyl, the aryl of arylalkoxy, the aryl of arylcarbonyl, the aryl of aryloxy, the aryl of arylsulfonyl, the cycloalkyl of cycloalkylalkoxy, the substituent heteroaryl, the heteroaryl of heteroarylalkyl, the heteroaryl of heteroarylalkenyl, the heteroaryl of heteroarylalkoxy, the heteroaryl of heteroarylcarbonyl, the substituent heterocycle, the heterocycle of heterocyclealkyl, the heterocycle of heterocyclealkoxy, the heterocycle of heterocyclecarbonyl, the heterocycle of heterocycleoxy, the heterocycle of heterocyclesulfonyl may be optionally substituted with 1, 2 or 3 substituents independently selected from the group consisting of alkoxy, alkoxyalkyl, alkoxycarbonyl, alkyl, alkylcarbonyl, alkynyl, carboxy, carboxyalkyl, cyano, haloalkyl, halogen, hydroxy, hydroxyalkyl, nitro, $R_fR_gN-$, $R_fR_gNalkyl$, $R_fR_gNcarbonyl$ and $R_fR_gNsulfonyl$.

The term "aryl$^1$" as used herein, refers to a substituted phenyl group wherein the substituent is a member selected from the group consisting of alkenyl, alkoxy, alkoxyalkoxy, alkoxyalkyl, alkoxycarbonyl, alkoxycarbonylalkyl, alkyl, alkylcarbonyl, alkynyl, aryl, aryl carbonyl, aryloxy, arylsulfonyl, carboxy, carboxyalkyl, cyano, cyanoalkyl, ethylenedioxy, formyl, haloalkoxy, haloalkyl, halogen, heteroaryl, heteroaryl alkyl, heteroaryl carbonyl, heterocycle, heterocyclecarbonyl, heterocycleoxy, hydroxy, hydroxyalkyl and nitro, or a bicyclic or a tricyclic fused ring system. Bicyclic fused ring systems are exemplified by a phenyl group appended to the parent molecular moiety, which is fused to a cycloalkyl group, as defined herein, a phenyl group, a heteroaryl, as defined herein, or a heterocycle as defined herein. Tricyclic fused ring systems are exemplified by an aryl bicyclic fused ring system fused to a cycloalkyl group, as defined herein, a phenyl group, a heteroaryl, as defined herein, or a heterocycle as defined herein. Bicyclic and tricyclic fused ring systems of this invention may be optionally substituted with 1, 2, 3, 4 or 5 substituents independently selected from alkenyl, alkoxy, alkoxyalkoxy, alkoxyalkyl, alkoxycarbonyl, alkoxycarbonylalkyl, alkyl, alkylcarbonyl, alkynyl, aryl, arylcarbonyl, aryloxy, arylsulfonyl, carboxy, carboxyalkyl, cyano, cyanoalkyl, ethylenedioxy, formyl, haloalkoxy, haloalkyl, halogen, heteroaryl, heteroarylalkyl, heteroarylcarbonyl, heterocycle, heterocyclecarbonyl, heterocycleoxy, hydroxy, hydroxyalkyl, nitro, $R_fR_gN-$, $R_fR_gN$alkyl, $R_fR_gN$-carbonyl and $R_fR_gN$sulfonyl, wherein $R_f$ and $R_g$ are as described herein. Representative examples of aryl include, but are not limited to, anisole, aniline, anthracenyl, azulenyl, fluorenyl, naphthyl, and tetrahydronaphthyl.

The term "arylalkenyl" as used herein, refers to an aryl group, as defined herein, appended to the parent molecular moiety through an alkenyl group, as defined herein.

The term "arylalkyl" as used herein, refers to an aryl group, as defined herein, appended to the parent molecular moiety through an alkyl group, as defined herein. Representative examples of arylalkyl include, but are not limited to, benzyl, 2-phenylethyl, 3-phenylpropyl and 2-naphth-2-ylethyl.

The term "arylalkoxy" as used herein, refers to an aryl group, as defined herein, appended to the parent molecular moiety through an alkoxy group, as defined herein.

The term "arylcarbonyl" as used herein, refers to an aryl group, as defined herein, appended to the parent molecular moiety through a carbonyl group, as defined herein. Representative examples of arylcarbonyl include, but are not limited to, benzoyl and naphthoyl.

The term "aryl-NH—" as used herein, refers to an aryl group, as defined herein, appended to the parent molecular moiety through a nitrogen atom.

The term "aryl-NH-alkyl" as used herein, refers to an aryl-NH— group, as defined herein, appended to the parent molecular moiety through an alkyl group, as defined herein.

The term "aryloxy," as used herein, refers to an aryl group, as defined herein, appended to the parent molecular moiety through an oxy moiety, as defined herein. Representative examples of aryloxy include, but are not limited to phenoxy, naphthyloxy, 3-bromophenoxy, 4-chlorophenoxy, 4-methylphenoxy and 3,5-dimethoxyphenoxy.

The term "aryloxyalkyl" as used herein, refers to an aryloxy group, as defined herein, appended to the parent molecular moiety through an alkyl group, as defined herein.

The term "arylsulfonyl" as used herein, refers to an aryl group, as defined herein, appended to the parent molecular moiety through a sulfonyl group, as defined herein. Representative examples of arylsulfonyl include, but are not limited to, phenylsulfonyl, 4-bromophenylsulfonyl, and naphthylsulfonyl.

The term "carbonyl" as used herein refers to a —C(O)— group.

The term "carboxy" as used herein refers to a —C(O)—OH group.

The term "carboxyalkyl" as used herein refers to a carboxy group as defined herein, appended to the parent molecular moiety through an alkyl group as defined herein.

The term "carboxycycloalkyl" as used herein refers to a carboxy group as defined herein, appended to the parent molecular moiety through an cycloalkyl group as defined herein.

The term "cycloalkyl" as used herein, refers to a monocyclic, bicyclic, or tricyclic ring system. Monocyclic ring systems are exemplified by a saturated cyclic hydrocarbon group containing from 3 to 8 carbon atoms. Examples of monocyclic ring systems include cyclopropyl, cyclobutyl, cyclopentyl, cyclohexyl, cycloheptyl and cyclooctyl. Bicyclic fused ring systems are exemplified by a cycloalkyl group appended to the parent molecular moiety, which is fused to an additional cycloalkyl group, as defined herein, a phenyl group, a heteroaryl, as defined herein, or a heterocycle as defined herein. Tricyclic fused ring systems are exemplified by a cycloalkyl bicyclic fused ring system fused to an additional cycloalkyl group, as defined herein, a phenyl group, a heteroaryl, as defined herein, or a heterocycle as defined herein. Bicyclic ring systems are also exemplified by a bridged monocyclic ring system in which two non-adjacent carbon atoms of the monocyclic ring are linked by an alkylene bridge of between one and three additional carbon atoms. Representative examples of bicyclic ring systems include, but are not limited to, bicyclo[3.1.1]heptane, bicyclo[2.2.1]heptane, bicyclo[2.2.2]octane, bicyclo[3.2.2]nonane, bicyclo[3.3.1]nonane and bicyclo[4.2.1]nonane. Tricyclic ring systems are also exemplified by a bicyclic ring system in which two non-adjacent carbon atoms of the bicyclic ring are linked by a bond or an alkylene bridge of between one and three carbon atoms. Representative examples of tricyclic-ring systems include, but are not limited to, tricyclo[3.3.1.0$^{3,7}$]nonane and tricyclo[3.3.1.1$^{3,7}$]decane (adamantane). The cycloalkyl groups of this invention may be substituted with 1, 2, 3, 4 or 5 substituents independently selected from alkenyl, alkoxy, alkoxyalkoxy, alkoxyalkyl, alkoxycarbonyl, alkoxycarbonylalkyl, alkyl, alkylcarbonyl, alkynyl, aryl, arylalkyl, arylcarbonyl, aryloxy, arylsulfonyl, carboxy, carboxyalkyl, cyano, cyanoalkyl, cycloalkyl, ethylenedioxy, formyl, haloalkoxy, haloalkyl, halogen, heteroaryl, heteroarylalkyl, heteroarylcarbonyl, heterocycle, heterocyclealkyl, heterocyclecarbonyl, heterocycleoxy, hydroxy, hydroxyalkyl, nitro, $R_fR_gN-$, $R_fR_gN$allyl, $R_fR_gN$carbonyl and $R_fR_gN$sulfonyl, wherein $R_f$ and $R_g$ are independently selected from the group consisting of hydrogen, alkyl, alkoxyalkyl, alkylcarbonyl, alkylsulfonyl, cycloalkyl and cycloalkylalkyl. The substituent aryl, the aryl of arylalkyl, the aryl of arylcarbonyl, the aryl of aryloxy, the aryl of arylsulfonyl, the substituent heteroaryl, the heteroaryl of heteroarylalkyl, the heteroaryl of heteroarylcarbonyl, the substituent heterocycle, the heterocycle of heterocyclealkyl, the heterocycle of heterocyclecarbonyl, the heterocycle of heterocycleoxy, the heterocycle of heterocyclesulfonyl may be optionally substituted with 0, 1, 2 or 3 substituents independently selected from the group consisting of alkoxy, alkoxyalkyl, alkoxycarbonyl, alkyl, alkylcarbonyl, alkynyl, carboxy, carboxyalkyl, cyano, haloalkyl, halogen, hydroxy, hydroxyalkyl, nitro, $R_fR_gN-$, $R_fR_gN$alkyl, $R_fR_gN$carbonyl and $R_fR_gN$sulfonyl.

The term "cycloalkylalkyl" as used herein, refers to a cycloalkyl group, as defined herein, appended to the parent molecular moiety through an alkyl group, as defined herein. Representative examples of cycloalkylalkyl include, but are not limited to, cyclopropylmethyl, 2-cyclobutylethyl, cyclopentylmethyl, cyclohexylmethyl and 4-cycloheptylbutyl.

The term "cycloalkylalkoxy" as used herein, refers to a cycloalkyl group, as defined herein, appended to the parent molecular moiety through an alkoxy group, as defined herein.

The term "cycloalkylcarbonyl" as used herein, refers to cycloalkyl group, as defined herein, appended to the parent molecular moiety through a carbonyl group, as defined herein. Representative examples of cycloalkylcarbonyl include, but are not limited to, cyclopropylcarbonyl, 2-cyclobutylcarbonyl and cyclohexylcarbonyl.

The term "cycloalkyloxy," as used herein, refers to cycloalkyl group, as defined herein, appended to the parent molecular moiety through an oxy group, as defined herein.

The term "cycloalkylsulfonyl," as used herein, refers to cycloalkyl group, as defined herein, appended to the parent molecular moiety through a sulfonyl group, as defined herein. Representative examples of cycloalkylsulfonyl include, but are not limited to, cyclohexylsulfonyl and cyclobutylsulfonyl.

The term "halo" or "halogen," as used herein, refers to —Cl, —Br, —I or —F.

The term "haloalkyl," as used herein, refers to at least one halogen, as defined herein, appended to the parent molecular moiety through an alkyl group, as defined herein. Representative examples of haloalkyl include, but are not limited to, chloromethyl, 2-fluoroethyl, trifluoromethyl, pentafluoroethyl and 2-chloro-3-fluoropentyl.

The term "heteroaryl," as used herein, refers to an aromatic monocyclic ring or an aromatic bicyclic ring system. The aromatic monocyclic rings are five or six membered rings containing at least one heteroatom independently selected from the group consisting of N, O and S. The five membered aromatic monocyclic rings have two double bonds and the six membered aromatic monocyclic rings have three double bonds. The bicyclic heteroaryl groups are exemplified by a monocyclic heteroaryl ring appended to the parent molecular moiety and fused to a monocyclic cycloalkyl group, as defined herein, a monocyclic aryl group, as defined herein, a monocyclic heteroaryl group, as defined herein, or a monocyclic heterocycle, as defined herein. Representative examples of heteroaryl include, but are not limited to, benzimidazolyl, benzofuranyl, benzothiazolyl, benzothienyl, benzoxazolyl, furyl, imidazolyl, indazolyl, indolyl, indolizinyl, isobenzofuranyl, isoindolyl, isoxazolyl, isoquinolinyl, isothiazolyl, naphthyridinyl, oxadiazolyl, oxazolyl, phthalazinyl, pyridinyl, pyridazinyl, pyrimidinyl, pyrazinyl, pyrazolyl, pyrrolyl, quinolinyl, quinolizinyl, quinoxalinyl, quinazolinyl, tetrazolyl, thiadiazolyl, thiazolyl, thienyl, triazolyl and triazinyl.

The heteroaryls of this invention may be optionally substituted with 1, 2 or 3 substituents independently selected from alkenyl, alkoxy, alkoxyalkoxy, alkoxyalkyl, alkoxycarbonyl, alkoxycarbonylalkyl, alkyl, alkylcarbonyl, alkynyl, aryl, arylalkenyl, arylalkyl, arylcarbonyl, aryloxy, arylsulfonyl, carboxy, carboxyalkyl, cyano, cyanoalkyl, cycloalkyl, ethylenedioxy, formyl, haloalkoxy, haloalkyl, halogen, heteroaryl, heteroarylalkenyl, heteroarylalkyl, heterocycle, heterocyclealkyl, heterocyclecarbonyl, heterocycleoxy, hydroxy, hydroxyalkyl, nitro, $R_fR_gN$—, $R_fR_g$Nalkyl, $R_fR_g$Ncarbonyl and $R_fR_g$Nsulfonyl, wherein $R_f$ and $R_g$ are as described herein. The substituent aryl, the aryl of arylalkyl, the aryl of arylalkenyl, the aryl of arylcarbonyl, the aryl of aryloxy, the aryl of arylsulfonyl, the substituent heteroaryl, the heteroaryl of heteroarylalkyl, the heteroaryl of heteroarylalkenyl, the substituent heterocycle, the heterocycle of heterocyclealkyl, the heterocycle of heterocyclecarbonyl, the heterocycle of heterocycleoxy, may be optionally substituted with 1, 2 or 3 substituents independently selected from the group consisting of alkoxy, alkoxyalkyl, alkoxycarbonyl, alkyl, alkylcarbonyl, alkynyl, carboxy, carboxyalkyl, cyano, haloalkyl, halogen, hydroxy, hydroxyalkyl, nitro, $R_fR_gN$—, $R_fR_g$Nalkyl, $R_fR_g$Ncarbonyl and $R_fR_g$Nsulfonyl.

The term "heteroarylalkenyl" as used herein, refers to a heteroaryl, as defined herein, appended to the parent molecular moiety through an alkenyl group, as defined herein.

The term "heteroarylalkyl" as used herein, refers to a heteroaryl, as defined herein, appended to the parent molecular moiety through an alkyl group, as defined herein.

The term "heteroarylalkoxy" as used herein, refers to a heteroaryl, as defined herein, appended to the parent molecular moiety through an alkoxy group, as defined herein.

The term "heteroaryloxy" as used herein, refers to a heteroaryl, as defined herein, appended to the parent molecular moiety through an oxy group, as defined herein.

The term "heteroaryloxyalkyl" as used herein, refers to a heteroaryloxy, as defined herein, appended to the parent molecular moiety through an alkyl group, as defined herein.

The term "heterocycle" as used herein, refers to a non-aromatic monocyclic ring or a non-aromatic bicyclic ring. The non-aromatic monocyclic ring is a three, four, five, six, seven, or eight membered ring containing at least one heteroatom, independently selected from the group consisting of N, O and S. Representative examples of monocyclic ring systems include, but are not limited to, azetidinyl, aziridinyl, diazepinyl, dithianyl, imidazolinyl, imidazolidinyl, isothiazolinyl, isoxazolinyl, isoxazolidinyl, morpholinyl, oxazolinyl, oxazolidinyl, piperazinyl, piperidinyl, pyranyl, pyrazolinyl, pyrazolidinyl, pyrrolinyl, pyrrolidinyl, tetrahydrofuranyl, tetrahydro-2H-pyranyl, tetrahydro-2H-pyran-2-yl, tetrahydro-2H-pyran-4-yl, tetrahydrothienyl, thiazolinyl, thiazolidinyl, thiomorpholinyl, 1,1-dioxidothiomorpholinyl (thiomorpholine sulfone) and thiopyranyl. The bicyclic heterocycles are exemplified by a monocyclic heterocycle appended to the parent molecular moiety and fused to a monocyclic cycloalkyl group, as defined herein, a monocyclic aryl group, a monocyclic heteroaryl group, as defined herein, or a monocyclic heterocycle, as defined herein. Bicyclic ring systems are also exemplified by a bridged monocyclic ring system in which two non-adjacent atoms of the monocyclic ring are linked by a bridge of between one and three atoms selected from the group consisting of carbon, nitrogen and oxygen. Representative examples of bicyclic ring systems include but are not limited to, for example, benzopyranyl, benzothiopyranyl, benzodioxinyl, 1,3-benzodioxolyl, cinnolinyl, 1,5-diazocanyl, 3,9-diaza-bicyclo[4.2.1]non-9-yl, 3,7-diazabicyclo[3.3.1]nonane, octahydro-pyrrolo[3,4-c]pyrrole, indolinyl, isoindolinyl, 2,3,4,5-tetrahydro-1H-benzo[c]azepine, 2,3,4,5-tetrahydro-1H-benzo[b]azepine, 2,3,4,5-tetrahydro-1H-benzo[d]azepine, tetrahydroisoquinolinyl and tetrahydroquinolinyl.

The heterocycles of this invention may be optionally substituted with 1, 2 or 3 substituents independently selected from oxo, alkenyl, alkoxy, alkoxyalkoxy, alkoxyalkyl, alkoxycarbonyl, alkoxycarbonylalkyl, alkyl, alkylcarbonyl, alkynyl, aryl, arylalkyl, arylcarbonyl, aryloxy, arylsulfonyl, carboxy, carboxyalkyl, cyano, cyanoalkyl, ethylenedioxy, formyl, haloalkoxy, haloalkyl, halogen, heteroaryl, heteroarylalkyl, heterocycle, heterocyclealkyl, heterocyclecarbonyl, heterocycleoxy, hydroxy, hydroxyalkyl, nitro, $R_fR_gN$—, $R_fR_g$Nalkyl, $R_fR_g$Ncarbonyl and $R_fR_g$Nsulfonyl, wherein $R_f$ and $R_g$ are as described herein.

The substituent aryl, the aryl of arylalkyl, the aryl of arylcarbonyl, the aryl of aryloxy, the aryl of arylsulfonyl, the heteroaryl, the heteroaryl of heteroarylalkyl, the substituent heterocycle, the heterocycle of heterocyclealkyl, the heterocycle of heterocyclecarbonyl, the heterocycle of heterocycleoxy, may be optionally substituted with 1, 2 or 3 substituents independently selected from the group consisting of alkoxy, alkoxyallyl, alkoxycarbonyl, alkyl, alkylcarbonyl, alkynyl, carboxy, carboxyalkyl, cyano, haloalkyl, halogen, hydroxy, hydroxyalkyl, nitro, $R_fR_gN$—, $R_fR_g$Nalkyl, $R_fR_g$Ncarbonyl and $R_fR_g$Nsulfonyl.

The term "heterocyclealkyl" as used herein, refers to a heterocycle, as defined herein, appended to the parent molecular moiety through an alkyl group, as defined herein. Representative examples of heterocyclealkyl include, but are not limited to, pyridin-3-ylmethyl and 2-pyrimidin-2-ylpropyl.

The term "heterocyclealkylcarbonyl" as used herein, refers to a heterocyclealkyl, as defined herein, appended to the parent molecular moiety through a carbonyl group, as defined herein.

The term "heterocyclealkoxy" as used herein, refers to a heterocycle, as defined herein, appended to the parent molecular moiety through an alkoxy group, as defined herein.

The term "heterocycleoxy" as used herein, refers to a heterocycle, as defined herein, appended to the parent molecular moiety through an oxy group, as defined herein.

The term "heterocycleoxyalkyl" as used herein, refers to a heterocycleoxy, as defined herein, appended to the parent molecular moiety through an alkyl group, as defined herein.

The term "heterocycle-NH—" as used herein, refers to a heterocycle, as defined herein, appended to the parent molecular moiety through a nitrogen atom.

The term "heterocycle-NH-alkyl" as used herein, refers to a heterocycle-NH—, as defined herein, appended to the parent molecular moiety through an alkyl group, as defined herein.

The term "heterocyclecarbonyl" as used herein, refers to a heterocycle, as defined herein, appended to the parent molecular moiety through a carbonyl group, as defined herein. Representative examples of heterocyclecarbonyl include, but are not limited to, 1-piperidinylcarbonyl, 4-morpholinylcarbonyl, pyridin-3-ylcarbonyl and quinolin-3-ylcarbonyl.

The term "heterocyclesulfonyl" as used herein, refers to a heterocycle, as defined herein, appended to the parent molecular moiety through a sulfonyl group, as defined herein. Representative examples of heterocyclesulfonyl include, but are not limited to, 1-piperidinylsulfonyl, 4-morpholinylsulfonyl, pyridin-3-ylsulfonyl and quinolin-3-ylsulfonyl.

The term "hydroxy" as used herein, refers to an —OH group.

The term "hydroxyalkyl" as used herein, refers to a hydroxy group, as defined herein, appended to the parent molecular moiety through an alkyl group, as defined herein. Representative examples of hydroxyalkyl include, but are not limited to, hydroxymethyl, 2-hydroxyethyl, 3-hydroxypropyl and 2-ethyl-4-hydroxyheptyl.

The term "oxo" as used herein, refers to a =O group.

The term "oxy" as used herein, refers to a —O— group.

The term "sulfonyl" as used herein, refers to a —S(O)$_2$— group.

The present compounds may exist as therapeutically suitable salts. The term "therapeutically suitable salt," refers to salts or zwitterions of the compounds which are water or oil-soluble or dispersible, suitable for treatment of disorders without undue toxicity, irritation and allergic response, commensurate with a reasonable benefit/risk ratio and effective for their intended use. The salts may be prepared during the final isolation and purification of the compounds or separately by reacting an amino group of the compounds with a suitable acid. For example, a compound may be dissolved in a suitable solvent, such as but not limited to methanol and water and treated with at least one equivalent of an acid, like hydrochloric acid. The resulting salt may precipitate out and be isolated by filtration and dried under reduced pressure. Alternatively, the solvent and excess acid may be removed under reduced pressure to provide the salt. Representative salts include acetate, adipate, alginate, citrate, aspartate, benzoate, benzenesulfonate, bisulfate, butyrate, camphorate, camphorsulfonate, digluconate, glycerophosphate, hemisulfate, heptanoate, hexanoate, formate, isethionate, fumarate, lactate, maleate, methanesulfonate, naphthylenesulfonate, nicotinate, oxalate, pamoate, pectinate, persulfate, 3-phenylpropionate, picrate, oxalate, maleate, pivalate, propionate, succinate, tartrate, trichloroacetate, trifluoroacetate, glutamate, para-toluenesulfonate, undecanoate, hydrochloric, hydrobromic, sulfuric, phosphoric and the like. The amino groups of the compounds may also be quaternized with alkyl chlorides, bromides and iodides such as methyl, ethyl, propyl, isopropyl, butyl, lauryl, myristyl, stearyl and the like.

Basic addition salts may be prepared during the final isolation and purification of the present compounds by reaction of a carboxyl group with a suitable base such as the hydroxide, carbonate, or bicarbonate of a metal cation such as lithium, sodium, potassium, calcium, magnesium, or aluminum, or an organic primary, secondary, or tertiary amine. Quaternary amine salts derived from methylamine, dimethylamine, trimethylamine, triethylamine, diethylamine, ethylamine, tributylamine, pyridine, N,N-dimethylaniline, N-methylpiperidine, N-methylmorpholine, dicyclohexylamine, procaine, dibenzylamine, N,N-dibenzylphenethylamine, 1-ephenamine and N,N'-dibenzylethylenediamine, ethylenediamine, ethanolamine, diethanolamine, piperidine, piperazine and the like, are contemplated as being within the scope of the present invention.

The present compounds may also exist as therapeutically suitable prodrugs. The term "therapeutically suitable prodrug," refers to those prodrugs or zwitterions which are suitable for use in contact with the tissues of patients without undue toxicity, irritation and allergic response, are commensurate with a reasonable benefit/risk ratio and are effective for their intended use. The term "prodrug," refers to compounds that are rapidly transformed in vivo to the parent compounds of formula (I-IXc) for example, by hydrolysis in blood. The term "prodrug," refers to compounds that contain, but are not limited to, substituents known as "therapeutically suitable esters." The term "therapeutically suitable ester," refers to alkoxycarbonyl groups appended to the parent molecule on an available carbon atom. More specifically, a "therapeutically suitable ester," refers to alkoxycarbonyl groups appended to the parent molecule on one or more available aryl, cycloalkyl and/or heterocycle groups as defined herein. Compounds containing therapeutically suitable esters are an example, but are not intended to limit the scope of compounds considered to be prodrugs. Examples of prodrug ester groups include pivaloyloxymethyl, acetoxymethyl, phthalidyl, indanyl and methoxymethyl, as well as other such groups known in the art. Other examples of prodrug ester groups are found in T. Higuchi and V. Stella, Pro-drugs as Novel Delivery Systems, Vol. 14 of the A.C.S. Symposium Series and in Edward B. Roche, ed., Bioreversible Carriers in Drug Design, American Pharmaceutical Association and Pergamon Press, 1987, both of which are incorporated herein by reference.

Asymmetric centers may exist in the present compounds. Individual stereoisomers of the compounds are prepared by synthesis from chiral starting materials or by preparation of racemic mixtures and separation by conversion to a mixture of diastereomers followed by separation or recrystallization, chromatographic techniques, or direct separation of the enantiomers on chiral chromatographic columns. Starting materials of particular stereochemistry are either commercially available or are made by the methods described hereinbelow and resolved by techniques well known in the art.

Geometric isomers may exist in the present compounds. The invention contemplates the various geometric isomers and mixtures thereof resulting from the disposal of substituents around a carbon-carbon double bond, a cycloalkyl group, or a heterocycloalkyl group. Substituents around a carbon-carbon double bond are designated as being of Z or E configuration and substituents around a cycloalkyl or heterocycloalkyl are designated as being of cis or trans configuration. Furthermore, the invention contemplates the various isomers and mixtures thereof resulting from the disposal of substituents around an adamantane ring system. Two substituents around a single ring within an adamantane ring system are designated as being of Z or E relative configuration. For examples, see C. D. Jones, M. Kaselj, R. N. Salvatore, W. J. le Noble J. Org. Chem. 63: 2758-2760, 1998.

Preparation of Compounds of the Invention

The compounds and processes of the present invention will be better understood in connection with the following synthetic schemes and Experimentals that illustrate a means by which the compounds of the invention can be prepared.

The compounds of this invention can be prepared by a variety of procedures and synthetic routes. Representative procedures and synthetic routes are shown in, but are not limited to, Schemes 1-17.

Abbreviations which have been used in the descriptions of the Schemes and the Examples that follow are: AcCl for acetyl chloride; DCM for dichloromethane; AIBN for 2,2′-azobis(2-methylpropionitrile); DMA for N,N-dimethylacetamide; DIEA or Hunig's base for N,N-diisopropylethylamine; DMAP for dimethylaminopyridine; DMF for N,N-dimethylformamide; DMSO for dimethylsulfoxide; DMPU for 1,3-dimethyl-3,4,5,6-tetrahydro-2(1H)-pyrimidinone; EDCI or EDAC for (3-dimethylaminopropyl)-3-ethylcarbodiimide hydrochloride; EtOAc for ethyl acetate; EtOH for ethanol; Et$_2$O for diethyl ether; HATU for O-(7-azabenzotriazol-1-yl)-N,N, N′,N′-tetramethyluronium hexafluorophosphate; HOBt for hydroxybenzotriazole hydrate; KOTMS for potassium trimethylsilanolate; MeOH for methanol; MeCN for acetonitrile; MTBE for methyl t-butyl ether; NMO for N-methylmorpholine N-oxide; TBTU for O-benzotriazol-1-yl-N,N,N′,N′-tetramethyluronium tetrafluoroborate; THF for tetrahydrofuran; and, triflate for trifluoromethane sulfonyl Scheme 1

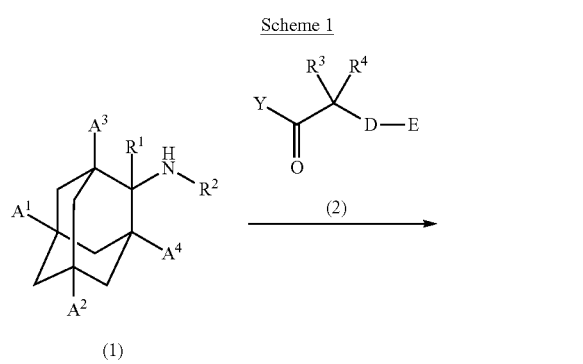

(1)

(2)

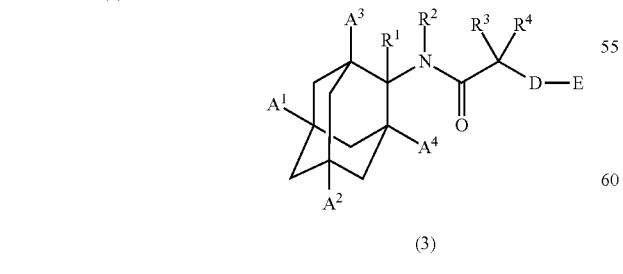

(3)

Substituted adamantanes of general formula (3), wherein $A^1$, $A^2$, $A^3$, $A^4$, $R^1$, $R^2$, $R^3$, $R^4$, D and E are as defined in formula I, may be prepared as in Scheme 1. Substituted adamantamines of general formula (I), purchased, prepared as described herein, or prepared using methodology known to those in the art, may be treated with an acylating agents of general formula (2), wherein Y is chloro, bromo, or fluoro and $R^3$, $R^4$, D and E are defined as in formula I, in the presence of a base such as diisopropylethylamine to provide amides of general formula (3). Alternatively, acids of general formula (2) wherein Y=OH can be coupled to substituted adamantamines of general formula (I) with reagents such as EDCT and HOBt to provide amides of general formula (3). In some examples, $A^1$, $A^2$, $A^3$ and/or $A^4$ in amines of formula (I) and D and E in the reagents of formula (2) may exist as or contain a group further substituted with a protecting group such as a carboxylic acid protected as the methyl ester. Examples containing a protected functional group may be required due to the synthetic schemes and the reactivity of said groups and could be later removed to provide the desired compound. Such protecting groups can be removed using methodology known to those skilled in the art or as described in T. W. Greene, P. G. M. Wuts "Protective Groups in Organic Synthesis" 3$^{rd}$ ed. 1999, Wiley & Sons, Inc.

Scheme 2

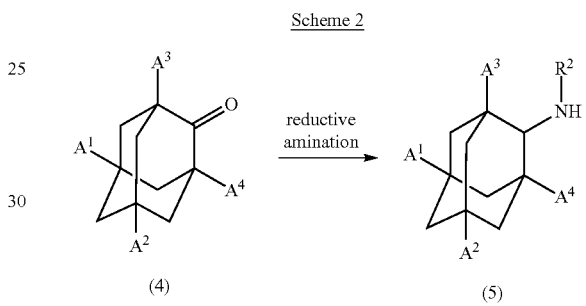

(4)                           (5)

Substituted adamantane amines of general formula (5), wherein $A^1$, $A^2$, $A^3$, $A^4$ and $R^2$ are as defined in formula I, may be prepared as in Scheme 2. Substituted adamantane ketones of general formula (4) can be purchased, prepared as described herein, or prepared using methodology known to those skilled in the art. Ketones of general formula (4) can be treated with ammonia or primary amines ($R^2NH_2$) followed by reduction with reagents such as sodium borohydride or $H_2$ over Pd/C in a solvent like methanol to provide amines of general formula (5). In some examples, $A^1$, $A^2$, $A^3$ and/or $A^4$ in ketones of formula (4) may be a substituent with a functional group containing a protecting group such as a carboxylic acid protected as the methyl ester. Such esters can be hydrolyzed and other protecting groups removed here to provide compounds of general formula (5) or in compounds subsequently prepared from (5) using methodology known to those skilled in the art.

Scheme 3

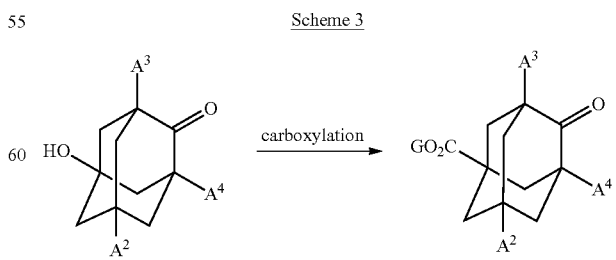

(6)                           (7)

Substituted adamantanes of general formula (7), wherein $A^2$, $A^3$ and $A^4$ are as defined in formula I and G is alkyl, cycloalkyl, arylalkyl, or aryl, as defined in the definition of terms, or G is hydrogen or an acid protecting group, may be prepared as in Scheme 3. Substituted adamantanes of general formula (6) can be purchased or prepared using methodology known to those in the art. Tertiary alcohols of general formula (6) can be treated with oleum and formic acid followed by water or an alcohol GOH to provide polycycles of general formula (7). In some examples, G in formula (7) may be a protecting group such as methyl. Such ester protecting groups can be removed from polycycles of general formula (7) or from compounds subsequently prepared from (7).

Scheme 4

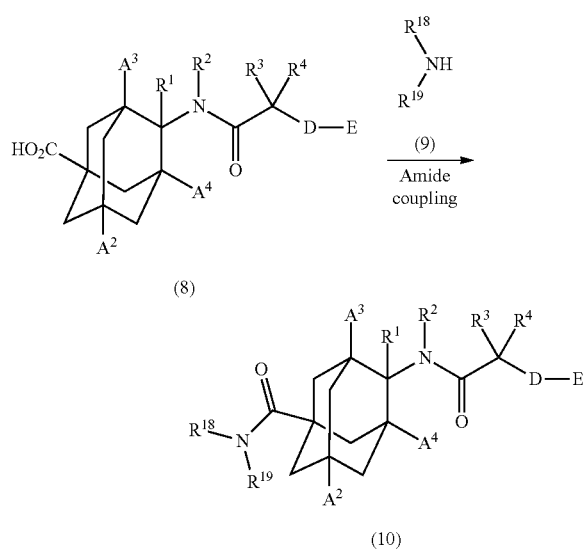

(8)

(10)

Substituted adamantanes of general formula (10), wherein $A^2, A^3, A^4, R^1, R^2, R^3, R^4, D, E, R^{18}$ and $R^{19}$ are as defined in formula I, may be prepared as in Scheme 4. Adamantane acids of general formula (8) may be prepared as described herein or using methodology known to those in the art. The acids of general formula (8) may be coupled with amines of general formula (9) (wherein $R^{18}$ and $R^{19}$ are defined as in formula I) with reagents such as O-(benzotrialzol-1-yl)-1,1,3,3-tetramethyluronium tetrafluoroborate (TBTU) to provide amides of general formula (10). In some examples, $R^{18}$ and/or $R^{19}$ in amides of formula (10) may be a substituent with a functional group containing a protecting group, such as a carboxylic acid protected as the methyl ester. Such esters can be hydrolyzed and other protecting groups removed using methodology known to those skilled in the art.

Scheme 5

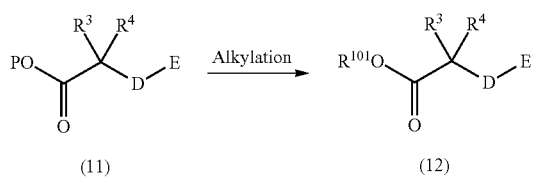

(11)    (12)

Acids of general formula (12), wherein $R^{101}$ is hydrogen, and $R^3$, $R^4$, D and E are as defined in formula (I) can be prepared as shown in Scheme 5.

Esters of general formula (11) wherein P is an acid protecting group such as, but not limited to, $C_1$-$C_6$ alkyl, unsubstituted or substituted aryl (for example, phenyl) or unsubstituted or substituted arylalkyl (for example, benzyl), $R^3$ and $R^4$ are hydrogen, or one of $R^3$ and $R^4$ is hydrogen and the other is as defined in formula (I), can be purchased, prepared as described herein, or prepared using methodologies known to those skilled in the art. Esters of general formula (11) can be mono-alkylated or bis-alkylated to provide esters of general formula (12) wherein $R^{101}$ is the acid protecting group, P, as described above. The bis-alkylation can be conducted either sequentially or in a one pot reaction.

Mono or bis-alkylation of esters of general formula (11) can be achieved in the presence of a base such as, but not limited to, sodium hydride, and an alkylating agent such as, but not limited to, alkyl halides (for example, methyl iodide, allyl bromide and the like). The reaction is generally performed in a solvent such as, but not limited to, anhydrous N,N-dimethylformamide, at a temperature from about 0° C. to about 23° C.

Removal of the protecting group P can be achieved using methodologies known to those skilled in the art or as described in T. W. Greene, P. G. M. Wuts "Protective Groups in Organic Synthesis" $3^{rd}$ ed. 1999, Wiley & Sons, Inc., to provide compounds of formula (12) wherein $R^{101}$ is hydrogen. Typically, such transformation can be achieved by stirring with an acid (for example, hydrochloric acid and the like) or a base (for example, lithium hydroxide, sodium hydroxide and the like) in a solvent such as, but not limited to, dioxane, tetrahydrofuran, ethanol, and mixtures thereof, at ambient temperature or at elevated temperature (typically at about 50° C. to about 70° C.). In cases where P is unsubstituted or substituted arylalkyl (for example, benzyl), hydrogenation can be employed to cleave the acid protecting group.

Scheme 6

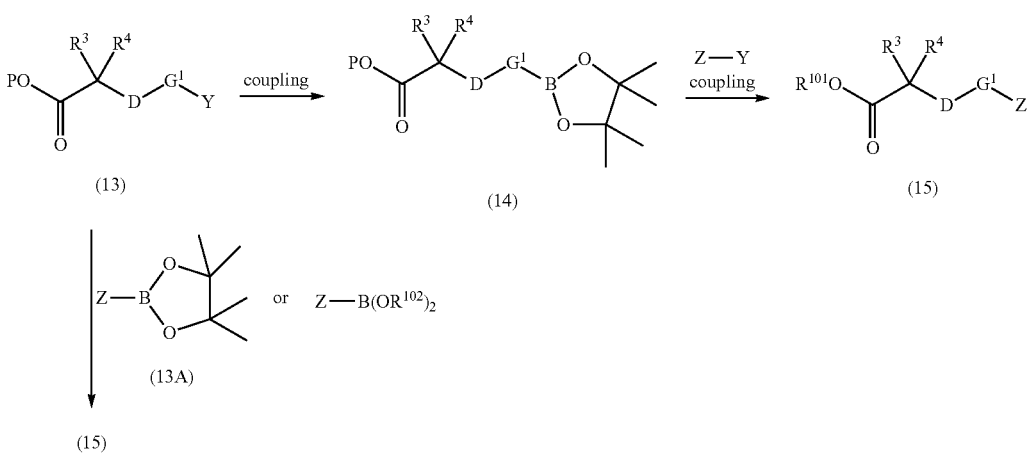

(13)    (14)    (15)

(13A)

(15)

Synthesis of acids of general formula (15), wherein $R^{101}$ is hydrogen, $R^3$, $R^4$, and D are as defined in formula (I), and $G^1$ and Z are independently aryl or heteroaryl, is outlined in Scheme 6.

Esters of formula (13), wherein P is $C_1$-$C_6$ alkyl, unsubstituted or substituted aryl (for example, phenyl) or unsubstituted or substituted arylalkyl (for example, benzyl); and Y is Cl, Br, I, or triflate can be purchased, prepared as described herein, or prepared using methodologies known to those skilled in the art. Esters of formula (13) can be converted to boronic esters of formula (14) when treated with a boron source like bis(pinacolato)diboron, a catalyst such as 1,1'-bis(diphenylphosphino)ferrocenedichloropalladium (H), and a base like potassium acetate. The conversion is facilitated in a solvent such as, but not limited to, dimethyl sulfoxide, N,N-dimethylformamide or toluene, at a temperature of about 80° C. to about 100° C. Boronic esters of general formula (14) may be coupled with reagents of formula Z—Y, wherein Z is aryl or heteroaryl and Y is Cl, Br, I, or triflate, a catalyst such as 1,1'-bis(diphenylphosphino)ferrocenedichloropalladium (II), and a base like sodium carbonate, to provide compounds of formula (15) wherein $R^{101}$ is an acid protecting group, P. The reaction can be performed in a solvent system like N,N-dimethylformamide and water at a temperature of about 80° C. to 90° C.

Alternatively, compounds of formula (13) wherein Y is Cl, Br, I, or triflate can be treated with a boronic acid or ester of formula (13A) or Z—B(OR$^{102}$)$_2$, wherein $R^{102}$ is hydrogen or alkyl, in the presence of a catalyst, such as but not limited to, bis(triphenylphospine)palladium (II) chloride or dichlorobis(tri-o-tolylphosphine)palladium (II), and a base such as triethylamine or sodium carbonate, to provide compounds of formula (15) wherein $R^{101}$ is an acid protecting group, P. The reaction can be effected by heating at a temperature from about 50° C. to about 180° C. in solvents such as isopropanol, ethanol, dimethoxyethane, water or dioxane.

Conversion of compounds of formula (15) wherein $R^{101}$ is an acid protecting group, P, to compounds of formula (15) wherein $R^{101}$ is hydrogen can be prepared using reaction conditions as described in Scheme 5.

Scheme 7

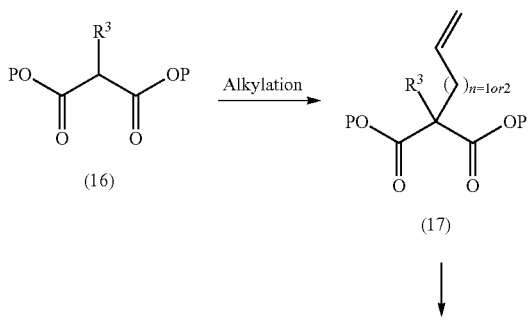

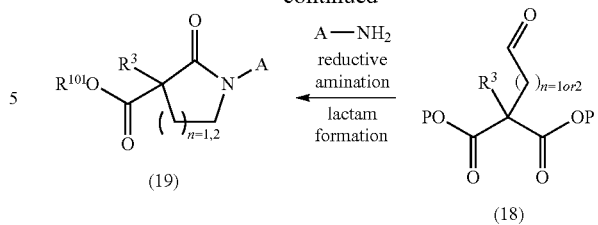

Acids of general formula (19), wherein $R^{101}$ is hydrogen, $R^3$ is as defined in formula (I) and A is a substituent of heterocycle as defined in the definition of terms, can be prepared from malonic acid di-ester of formula (16) wherein P is $C_1$-$C_6$ alkyl or benzyl as shown in Scheme 7.

Malonic acid di-esters of general formula (16) wherein P is an acid protecting group such as $C_1$-$C_6$ alkyl, unsubstituted or substituted aryl (for example, phenyl) or unsubstituted or substituted arylalkyl (for example, benzyl), can be purchased or prepared using methodologies known to those skilled in the art. Malonic acid di-esters of general formula (16) can be treated with one molar equivalent of allyl bromide or 4-bromo-1-butene, using mono alkylation conditions for the conversion of (11) to (12) in Scheme 5, to provide compounds of formula (17). Ozonolysis of the terminal olefin of di-ester (17) may be achieved in a solvent system like dichloromethane and methanol at a low temperature of about −78° C., by bubbling ozone through the solution, followed by purging the solution with nitrogen gas, and reduction of the intermediate ozonide with dimethyl sulfide to provide aldehyde di-esters of the general formula (18). Treatment of aldehyde di-ester (18) with a primary amine of formula A-NH$_2$, wherein A is a substituent of heterocycle as defined in the definition of terms, a reducing agent like resin bound MP-triacetoxy borohydride, and in a solvent like tetrahydrofuran at a temperature around 23° C., provides esters of general formula (19) wherein $R^{101}$ is an acid protecting group, P. Removal of P using reaction conditions as outlined in Scheme 5 converts (19) wherein $R^{101}$ is an acid protecting group, P, to compounds of formula (19) wherein $R^{101}$ is hydrogen.

Scheme 8

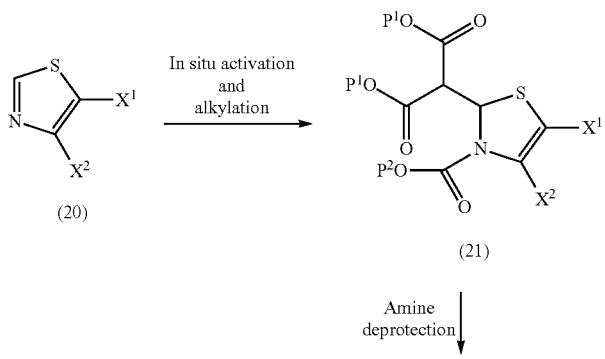

Amine deprotection

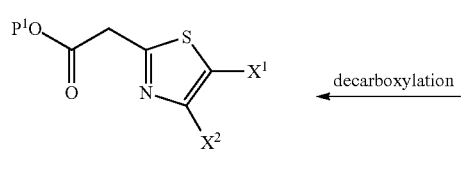

(23)

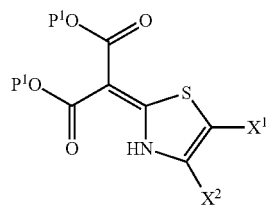

(22)

Scheme 8 outlines the synthesis of esters of general formula (23), wherein $P^1$ is an acid protecting group such as, but not limited to, $C_1$-$C_6$ alkyl, and $X^1$ and $X^2$ are substituents of heteroaryl as defined in the definition of terms, from thiazoles of formula (20).

Thiazoles of formula (20) can be purchased or prepared using methodologies known to those skilled in the art. Thiazoles of formula (20) may be alkylated by in situ activation with a chloroformate such as, but not limited to, ethyl chloroformate, followed by treatment of a nucleophile such as lithio diethylmalonate (prepared from a malonic acid di-ester in a solution such as tetrahydrofuran with a base such as lithium bis(trimethylsilyl)amide), to afford compounds of formula (21) wherein $P^1$ and $P^2$ are $C_1$-$C_6$ alkyl. The former can be conducted in a solvent such as, but not limited to, tetrahydrofuran, at a temperature around 0° C. Treatment with the nucleophile can be effected in a solvent such as tetrahydrofuran and at a temperature around 23° C. The lithio diethylmalonate may be formed in a solvent such as tetrahydrofuran. The N-protected malonic acid di-ester adduct of general formula (21) may be oxidized with an agent such as tetrachloro-1,2-benzoquinone in a solvent such as dichloromethane at a temperature around 0° C. to afford the di-ester of general formula (22). Mono-decarboxylation of di-ester (22) may be achieved by heating in a solvent system such as water and dimethyl sulfoxide with a salt such as sodium chloride at a temperature near 180° C. to provide esters of general formula (23).

Scheme 9

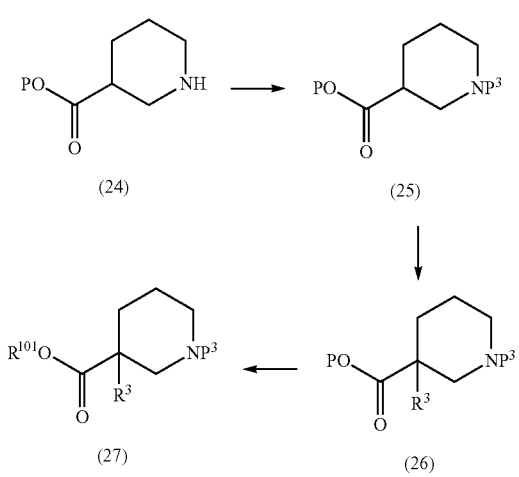

Acids of formula (27) wherein $R^{101}$ is hydrogen, $P^3$ is —C(O)OCH$_2$C$_6$H$_5$, and $R^3$ is as defined in formula (I) can be prepared from compounds of formula (24) where P is an acid protecting group such as, $C_1$-$C_6$ alkyl, unsubstituted or substituted aryl (for example, phenyl) or unsubstituted or substituted arylalkyl (for example, benzyl), as shown in Scheme 9.

Compounds of formula (24) can be purchased or prepared using methodologies known to those skilled in the art. Treatment of compounds of formula (24) with benzyl chloroformate and a base such as, but not limited to, sodium bicarbonate in water, provides compounds of formula (25) wherein $P^3$ is —C(O)OCH$_2$C$_6$H$_5$. Mono alkylation of compounds of formula (25) with halides of formula $R^3$—$X^3$ wherein $X^3$ is Cl, Br or I, using reaction conditions as described in Scheme 5 provides compounds of formula (26).

Conversion of compounds of formula (26) to compounds of formula (27) wherein $R^{101}$ is hydrogen can be achieved using reaction conditions as described in Scheme 5 for removal of a protecting group, P.

Scheme 10

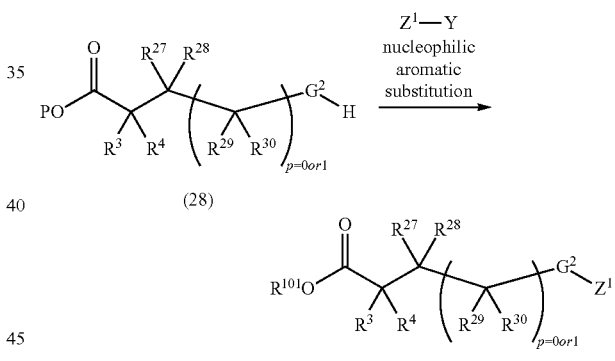

Compounds of general formula (29), wherein $R^3$, $R^4$, $R^{27}$, $R^{28}$, $R^{29}$, $R^{30}$, and $R^{31}$ are as defined in formula I; $G^2$ is —N($R^{31}$)—, —O— or —S—; $Z^1$ is aryl or heteroaryl; $R^{101}$ is hydrogen or is an acid protecting group, P, such as, but not limited to, $C_1$-$C_6$ alkyl, unsubstituted or unsubstituted aryl (for example, phenyl) or unsubstituted or substituted arylalkyl (for example benzyl), can be prepared as shown in Scheme 10.

Compounds of formula (28) can be purchased, prepared as described herein, or prepared using methodologies known to those skilled in the art. Compounds of formula (28) wherein P is an acid protecting group can be reacted with compounds of formula $Z^1$—Y, wherein Y is Cl, Br, I, or triflate such as 6-chloronicotinonitrile, with a base such as sodium hydride, and in an anhydrous solvent system such as tetrahydrofuran and 1,3-dimethyl-3,4,5,6-tetrahydro-2(1H)-pyrimidinone (DMPU) at a temperature ranging from 0° C. to 23° C. to provide esters of general formula (29), wherein $R^{101}$ is a protecting group, P.

Conversion of compounds of formula (29) wherein $R^{101}$ is P to compounds of formula (29) wherein $R^{101}$ is hydrogen can be achieved using reaction conditions as described in Scheme 5 for removal of a protecting group, P.

Scheme 11

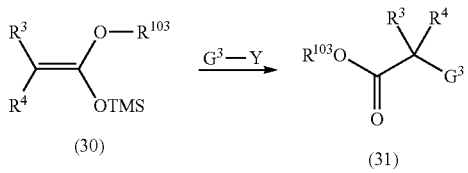

(30)     (31)

Compounds of general formula (31), wherein $R^3$ and $R^4$ are as defined in formula (I), $G^3$ is aryl or heteroaryl, and $R^{103}$ is hydrogen, potassium, sodium, lithium, or $C_1$-$C_6$ alkyl, can be prepared as shown in Scheme 11.

Compounds of formula $G^3$-Y wherein $G^3$ is aryl or heteroaryl and Y is Cl, Br, I or triflate can be purchased or prepared using methodologies known to those skilled in the art, as well as, alkyl trimethylsilyl ketene acetals of formula (30) wherein $R^{103}$ is $C_1$-$C_6$ alkyl. Compounds of formula $G^3$-Y such as, but not limited to, 2-chloro-5-(trifluoro-methyl)pyridine can be reacted with an alkyl trimethylsilyl ketene acetal of formula (30) wherein $R^{103}$ is $C_1$-$C_6$ alkyl such as, but not limited to, methyl or ethyl; a salt such as zinc fluoride; a catalyst such as tris(dibenzylideneacetone)dipalladium (0); a ligand such as tri-t-butylphosphine; and, in a solvent such as N,N-dimethylformamide at a temperature of about 90° C. to provide esters of general formula (31) wherein $R^{103}$ is $C_1$-$C_6$ alkyl.

Numerous methodologies for the conversion of compounds of formula (31) wherein $R^{103}$ is $C_1$-$C_6$ alkyl to compounds of formula (31) wherein $R^{103}$ is hydrogen are described in "Protective Groups in Organic Synthesis" 3$^{rd}$ edition, 1999, Wiley & Sons, Inc. Additionally, one can obtain a salt of compounds of formula (31) where $R^{101}$ is potassium, sodium, or lithium by stirring compounds of formula (31) wherein $R^{103}$ is $C_1$-$C_6$ alkyl with a base such as, but not limited to, potassium trimethylsilanolate in a solvent such as, but not limited to, tetrahydrofuran, at ambient temperature.

Scheme 12

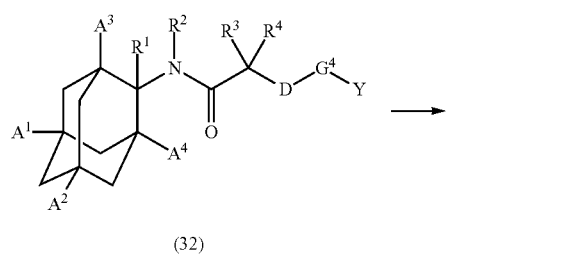

(32)

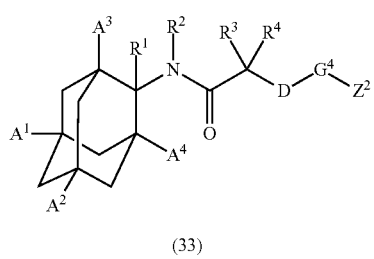

(33)

Compounds of formula (32) wherein Y is Cl, Br, I or triflate, $G^4$ is aryl or heteroaryl as defined in the definition of terms, and $A^1$, $A^2$, $A^3$, $A^4$, $R^2$, $R^3$, $R^4$ and D are as defined in formula (I) can be prepared as described herein or prepared using methodologies known to those skilled in the art. Conversion of compounds of formula (32) to compounds of formula (33), depicted in Scheme 12, wherein $Z^2$ is aryl or heteroaryl can be achieved using the series of reaction conditions as described in Scheme 6 for the transformation of (13) to (15).

Scheme 13

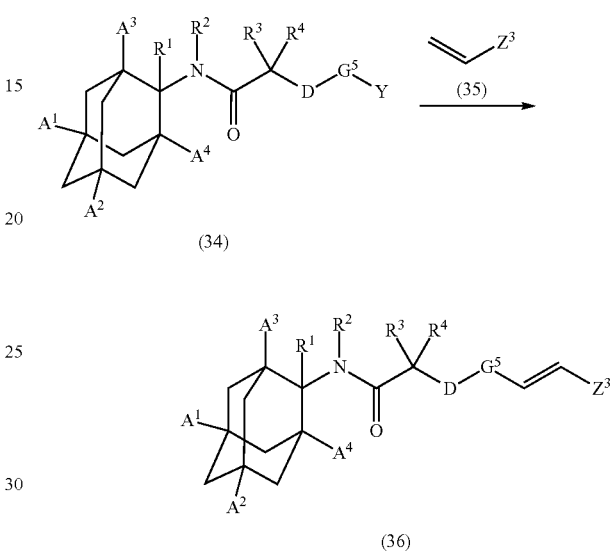

(34)

(36)

Adamantanes of general formula (36), wherein $A^1$, $A^2$, $A^3$, $A^4$, $R^1$, $R^2$, $R^3$, $R^4$ and D are as defined in formula (I), and $G^5$ and $Z^3$ are independently either aryl or heteroaryl as defined in the definition of terms, can be prepared as shown in Scheme 13.

Adamantanes of general formula (34) wherein Y is Cl, Br or I, can be prepared as described herein or prepared using methodologies known to those skilled in the art. Olefins of general formula (35) wherein $Z^3$ is either aryl or heteroaryl can be purchased or prepared using methodologies known to those skilled in the art. Adamantanes of general formula (34) can be reacted with olefins of general formula (35), such as, but not limited to, 4-vinylpyridine; a catalyst such as, but not limited to, bis(triphenylphosphine)palladium (II) dichloride; a base such as, but not limited to, triethylamine; and, in a solvent system such as N,N-dimethylformamide at a temperature of near 150° C. to provide adamantanes of general formula (36).

Scheme 14

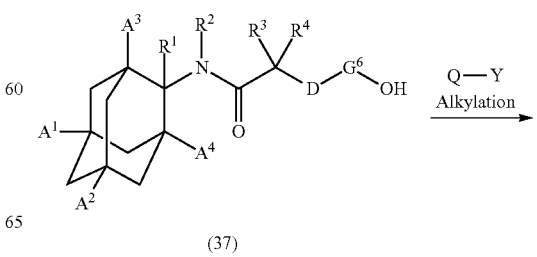

(37)

-continued

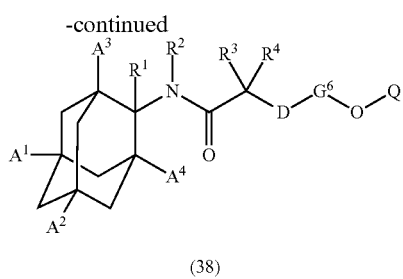

(38)

Substituted adamantanes of general formula (38), wherein $A^1, A^2, A^3, A^4, R^1, R^2, R^3, R^4$, and D are as defined in formula (I); $G^6$ is aryl or heteroaryl; and, Q is alkyl, arylalkyl, heteroarylalkyl, heterocycle alkyl, or cycloalkylalkyl, can be prepared as shown in Scheme 14.

Substituted adamantanes of general formula (37) can be prepared as described herein or prepared using methodologies known to those skilled in the art. Substituted adamantanes of general formula (37) can be alkylated with alkylating agents Q-Y, wherein Q is alkyl, arylalkyl, heteroarylalkyl, heterocycle alkyl, or cycloalkylalkyl and Y is a leaving group like I, Br, Cl, or triflate, in the presence of a base like potassium carbonate and in a solvent like N,N-dimethylformamide to yield substituted adamantanes of general formula (38).

Scheme 15

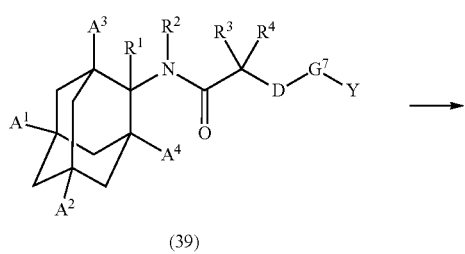

(39)

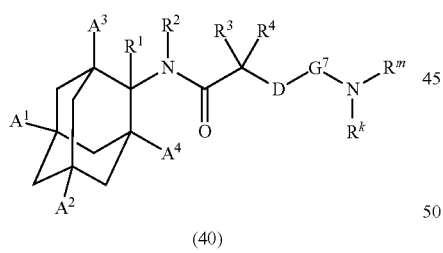

(40)

Substituted adamantanes of general formula (40), wherein $A^1, A^2, A^3, A^4, R^2, R^3, R^4$, and D are as defined in formula I; $G^7$ is aryl or heteroaryl; and, $R^k$ and $R^m$ are independently hydrogen, alkyl, or heterocyclealkyl, or $R^k$ and $R^m$ together with the nitrogen to which they are attached form a heterocycle ring, can be prepared as shown in Scheme 15.

Substituted adamantanes of general formula (39), wherein Y is F, Cl, Br, or I, can be prepared as described herein or prepared using methodologies known to those skilled in the art. Substituted adamantanes of general formula (39) can be condensed with amines of general formula $R^kR^mNH$, to provide compounds of formula (40). The reaction can be conducted neat in a microwave synthesizer at a temperature near 150° C. for a period of about 40 minutes.

Scheme 16

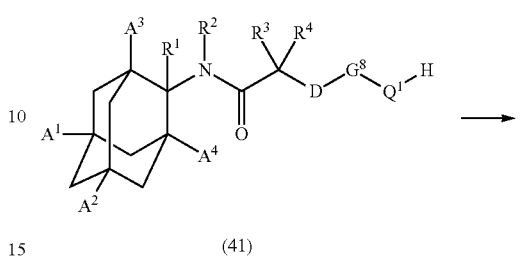

(41)

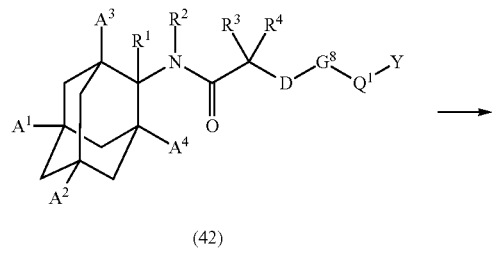

(42)

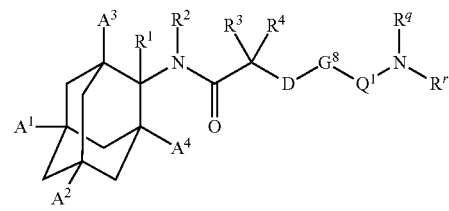

(43)

Substituted adamantanes of general formula (43), wherein $A^1, A^2, A^3, A^4, R^1, R^2, R^3, R^4$, and D are as defined in formula I; $G^8$ is aryl or heteroaryl as defined in the definition of terms; $Q^1$ is $C_1$-$C_3$ alkyl; and, $R^q$ and $R^r$ are independently hydrogen, alkyl, or heterocyclealkyl, or $R^q$ and $R^r$ together with the nitrogen to which they are attached form a heterocycle ring, can be prepared as shown in Scheme 16.

Substituted adamantanes of general formula (41) can be prepared as described herein or prepared using methodologies known to those skilled in the art. Substituted adamantanes of general formula (41) can be halogenated with a reagent like N-halosuccinimde (for example, N-chlorosuccinimide and the like) in the presence of a radical initiator like AIBN and in a solvent like carbon tetrachloride at a temperature near 80° C. to yield substituted adamantanes of general formula (42), wherein Y is Cl, Br, or I. Substituted adamantanes of general formula (42) when treated with amines of general formula $R^qR^rNH$ in a solvent like dichloromethane at a temperature between 23° C. and 40° C. provide substituted adamantanes of general formula (43).

Scheme 17

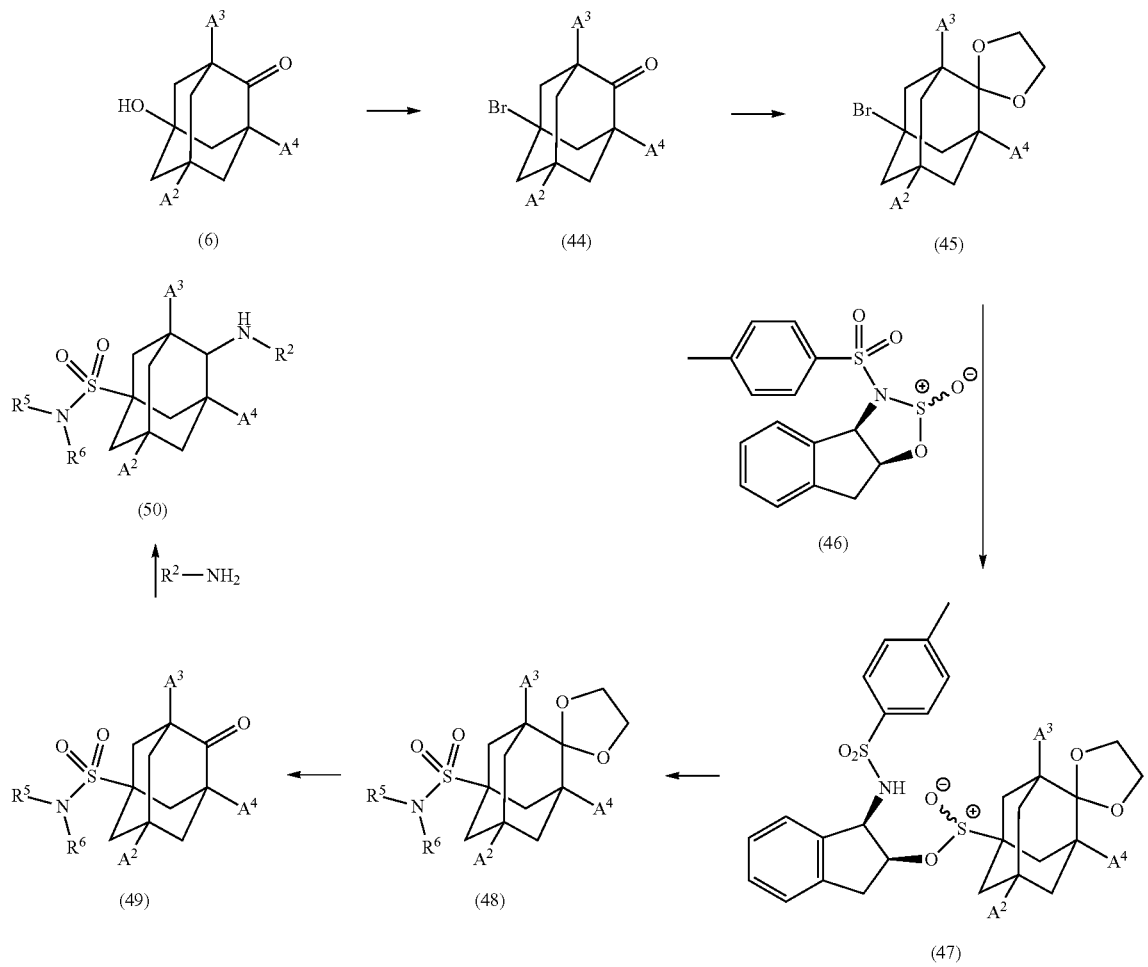

Substituted adamantanes of general formula (50), wherein $A^2$, $A^3$, $A^4$, $R^2$, $R^5$ and $R^6$ are as defined in formula I, can be prepared as shown in Scheme 17.

Substituted adamantanes of general formula (6) can be purchased or prepared using methodology known to those in the art. Substituted adamantanes of general formula (6) can be brominated with a reagent like hydrobromic acid in a solvent like water to provide bromides of general formula (44). Adamantanes of general formula (44) when treated with ethylene glycol and a catalytic amount of an acid like p-toluenesulfonic acid in a solvent like benzene provide adamantanes of general formula (45). Bromides of general formula (45) can be (a) treated with Rieke zinc in a solvent like tetrahydrofuran; and (b) followed by treatment with reagent (46) (prepared as described in Han, Z.; Krishnamurthy, D.; Grover, P.; Fang, Q. K.; Senanayake, C. H. *J. Am. Chem. Soc.* 2002, 124, 7880-7881) in a solvent like tetrahydrofuran to provide adamantanes of general formula (47). Adamantanes of general formula (47) may be treated with lithium amide of formula $LiNHR^5R^6$ (prepared in situ by reacting ammonia with lithium or amines of formula $R^5R^6NH$ wherein $R^5$ and $R^6$ are other than hydrogen, with t-butyl lithium) in a solvent like tetrahydrofuran. The resulting sulfinamides can be oxidized with a reagent like osmium tetroxide with a catalyst oxidant like NMO in a solvent like tetrahydrofuran to provide sulfonamides of general formula (48). Adamantanes of general formula (48) can be deketalized with reagents like hydrochloric acid in a solvent mixture like water and tetrahydrofuran to provide ketones of formula (49). Ketones of formula (49) can be treated with amines of formula $R^2NH_2$ followed by reduction with reducing reagents such as, but not limited to, sodium borohydride or hydrogen over Pd/C in a solvent like methanol to provide amines of general formula (50). In some examples, $A^2$, $A^3$, $A^4$, $R^2$, $R^5$ and $R^6$ in amines of formula (50) may be a substituent with a functional group containing a protecting group such as a carboxylic acid protected as the methyl ester. Such esters can be hydrolyzed and other protecting groups removed here or in compounds subsequently prepared from (50) using methodology known to those skilled in the art.

It is understood that the schemes described herein are for illustrative purposes and that routine experimentation, including appropriate manipulation of the sequence of the synthetic route, protection of any chemical functionality that are not compatible with the reaction conditions and deprotection are included in the scope of the invention. Protection and Deprotection of carboxylic acids and amines are known to one skilled in the art and references can be found in "Protective Groups in Organic Synthesis", T. W. Greene, P. G. M. Wuts, 3rd edition, 1999, Wiley & Sons, Inc.

The compounds and processes of the present invention will be better understood by reference to the following Examples, which are intended as an illustration of and not a limitation upon the scope of the invention. Further, all citations herein are incorporated by reference.

Compounds of the invention were named by ACD/ChemSketch version 5.01 (developed by Advanced Chemistry Development, Inc., Toronto, ON, Canada) or were given names consistent with ACD nomenclature. Adamantane ring system isomers were named according to common conventions. Two substituents around a single ring within an adamantane ring system are designated as being of Z or E relative configuration (for examples see C. D. Jones, M. Kaselj, R. N. Salvatore, W. J. le Noble J. Org. Chem. 63: 2758-2760, 1998).

Example 1

E-4-{[1-(4-Chloro-phenyl)-cyclobutanecarbonyl]-amino}-adamantane-1-carboxylic acid Example 1A 4-oxo-adamantane-1-carboxylic acid A 5 L 4-neck flask equipped with $N_2$ inlet/bubbler with $H_2O$ trap, overhead stirring, and an addition funnel was charged with 30% oleum (~10.5 volumes, 2.2 L, 8×500 g bottles+100 mL), and heated to 50° C. under a slight $N_2$ flow. 5-Hydroxy-2-adamantanone (220 g, 81 wt % purity, 1.07 mol) was dissolved in 5 volumes $HCO_2H$ (~98%, 1.10 L) and added drop-wise to the warm oleum solution over 5 hours. The addition rate was adjusted to maintain the internal temperature between 70-90° C. After stirring an additional 2 hours at 70° C. The reaction solution was cooled to 10° C. in an ice bath. 20 volumes of 10% NaCl aq (4 L) were cooled to <10° C., the crude reaction mixture was quenched into the brine solution in batches, maintaining an internal temperature <70° C. The quenched reaction solution was combined with a second identical reaction mixture for isolation. The combined product solutions were extracted 3×5 volumes with $CH_2Cl_2$ (3×2.2 L) and the combined $CH_2Cl_2$ layers were then washed 1×2 volumes with 10% NaCl (1 L). The $CH_2Cl_2$ solution was then extracted 3×5 volumes with 10% $Na_2CO_3$ (3×2.2 L). The combined $Na_2CO_3$ extracts were washed with 1×2 volumes with $CH_2Cl_2$ (1 L). The $Na_2CO_3$ layer was then adjusted to pH 1-2 with concentrated HCl(~2 volumes, product precipitates out of solution). The acidic solution was then extracted 3×5 volumes with $CH_2Cl_2$ (3×2.2 L), and the organic layer was washed 1×2 volumes with 10% NaCl. The organic solution was then dried over $Na_2SO_4$, filtered, concentrated to ~¼ volume, then chase distilled with 2 volumes EtOAc (1 L). Nucleation occurred during this distillation. The suspension was then chase distilled 2×5 volumes (2×2 L) with heptane and cooled to room temperature. The suspension was then filtered, and the liquors were recirculated 2× to wash the wet cake. The resultant material was dried overnight at 50° C., 20 mm Hg to afford the title compound.

Example 1B

E- and Z-4-amino-adamantane-1-carboxylic acid

To 1.0 g (10 wt %) of 5% Pd/C is added 10.0 g of the product from Example 1A followed by 200 mL (20 volumes) of 7M $NH_3$ in MeOH. The reaction mixture is stirred under an atmosphere of $H_2$ at RT for 16-24 hours. 200 mL of water is added and the catalyst is removed by filtration. The catalyst is washed with MeOH. Solvent is removed by distillation at a bath temperature of 35° C. until solvent stops coming over. Approximately 150 mL of a slurry remains. 300 ml of MeCN is added to the slurry, which is then stirred for three hours at RT. The slurry is filtered and washed once with 100 mL MeCN. The wet cake is dried at 50° C. and 20 mm Hg under $N_2$ to afford the title compound with a 13.1:1.0 E:Z ratio by $^1$H-NMR ($D_2O$).

Example 1C

E-4-amino-adamantane-1-carboxylic acid methyl ester hydrochloride

Methanol (10 volumes, 85 mL) was cooled to 0° C. AcCl was added dropwise (5.0 equiv., 15.5 mL), and the solution was warmed to ambient temperature for 15-20 minutes. The product from Example 1B (8.53 g, 43.7 mmol, 1.0 equiv.) was added and the reaction solution was heated to 45° C. for 16 hours (overnight). Consumption of the starting aminoacid was monitored by LC/MS (APCI). The reaction solution was then cooled to room temperature, 10 volumes McCN (85 mL) was added, distilled to ~¼ volume (heterogeneous), and chase distilled 2×10 volumes with MeCN (2×85 mL). The resulting suspension was cooled to room temperature, filtered, and the filtrate was recirculated twice to wash the wet cake. The product was dried at 50° C., 20 mm Hg overnight to afford the title compound.

Example 1D

E-4-{[1-(4-Chloro-phenyl)-cyclobutanecarbonyl]-amino}-adamantane-1-carboxylic acid Step A A solution of the product from Example 1C (50 mg, 0.20 mmol), 1-(4-chlorophenyl)-1-cyclobutanecarboxylic acid (39 mg, 0.19 mmol), and O-benzotriazol-1-yl-N,N,N',N'-tetramethyluronium tetrafluoroborate (TBTU) (65 mg, 0.20 mmol) in N,N-dimethylacetamide (DMA) (2 mL) and DIEA (80 μL, 0.46 mmol) was stirred for 16 hours at 23° C. The reaction mixture was analyzed by LC/MS and determined to be near completion. The reaction mixture was concentrated under reduced pressure. The residue was taken up in methylene chloride and washed with 1 N HCl (2×), saturated $NaHCO_3$ (2×), water, and brine before drying over $Na_2SO_4$, filtering, and concentrating under reduced pressure. The resultant solid was triturated with ethyl acetate, dried under reduced pressure to provide the methyl ester of the titled compound.

Step B

The methyl ester of the titled compound obtained from step A (50 mg, 0.12 mmol) was dissolved in 3 N HCl (1 mL), dioxane (0.25 mL), and 4 N HCl (1 mL). The homogenous acid solution was heated to 60° C. for 24 hours, was cooled to 23° C., and was then concentrated under reduced pressure to provide the title compound. $^1$H NMR (300 MHz, DMSO-$d_6$) δ 12.02 (s, 1H), 7.40 (m, 4H), 6.87 (d, J=6.6 Hz, 1H), 3.68 (m, 1H), 2.71 (m, 2H), 2.36 (m, 2H), 1.75 (m, 13H), 1.34 (m, 2H); MS (ESI+) m/z 389 (M+H)$^+$.

Example 2

E-4-[(1-Phenyl-cyclopropanecarbonyl)-amino]-adamantane-1-carboxylic acid

Step A

The methyl ester of the titled compound was prepared according to the method of step A of Example 1D substituting 1-phenyl-1-cyclopropanecarboxylic acid for 1-(4-chlorophenyl)-1-cyclobutanecarboxylic acid, and the crude methyl ester was purified by chromatography on flash silica gel with an eluant gradient of 20-40% ethyl acetate/hexanes.

Step B

The methyl ester obtained from step A (47 mg, 0.13 mmol) was dissolved in 3 N HCl (1 mL), dioxane (0.25 mL), and 4 N HCl (1 mL), heated to 60° C. for 24 hours, was cooled to 23° C., and was then concentrated under reduced pressure to provide the title compound. NMR (300 MHz, DMSO-$d_6$) δ 12.05 (s, 1H), 7.43 (m, 4H), 7.36 (m, 1H), 5.80 (d, J=7.8 Hz, 1H), 3.72 (m, 1H), 1.79 (m, 6H), 1.71 (m, 3H), 1.40 (m, 1H), 1.35 (m, 3H), 1.20 (m, 2H), 1.02 (m, 2H); MS (ESI+) m/z 341 (M+H)$^+$.

Example 3

E-4-(2-Methyl-2-phenyl-propionylamino)-adamantane-1-carboxylic acid

Step A

The methyl ester of the titled compound was prepared according to the method of step A of Example 1D substituting 2-methyl-2-phenyl propionic acid for 1-(4-chlorophenyl)-1-cyclobutanecarboxylic acid, and the crude methyl ester was purified by chromatography on flash silica gel with an eluant gradient of 20-40% ethyl acetate/hexanes.

Step B

The methyl ester obtained from step A (49 mg, 0.14 mmol) was dissolved in 3 N HCl (1 mL) and dioxane (0.25 mL), heated to 60° C. for 24 hours, was cooled to 23° C., and was then concentrated under reduced pressure to provide the title compound. NMR (300 MHz, DMSO-$d_6$) δ 12.04 (s, 1H), 7.34 (m, 4H), 7.24 (m, 1H), 6.26 (d, J=6.9 Hz, 1H), 3.74 (m, 1H), 1.87 (m, 2H), 1.81 (m, 4H), 1.74 (m, 3H), 1.55 (m, 2H), 1.49 (s, 6H), 1.35 (m, 2H); MS (ESI+) m/z 343 (M+H)$^+$.

Example 4

E-4-{[1-(4-Chloro-phenyl)-cyclobutanecarbonyl]-amino}-adamantane-1-carboxylic acid amide A solution of the product from step B of Example 1D (24 mg, 0.062 mmol) in DCM (2 mL) was treated with HOBt (12 mg, 0.090 mmol) and EDCI (20 mg, 0.10 mmol) and stirred at room temperature for 1 hour. Excess of aqueous (35%) ammonia (1 mL) was added and the reaction was stirred for 16 hours. The layers were separated and the aqueous extracted twice more with methylene chloride (2×2 mL). The combined organic extracts were dried over Na$_2$SO$_4$, filtered, and concentrated under reduced pressure. The residue was dissolved in DMSO/MeOH (1:1, 1.5 mL) and purified by preparative HPLC on a Waters Symmetry C8 column (25 mm×100 mm, 7 um particle size) using a gradient of 10% to 100% acetonitrile:aqueous ammonium acetate (10 mM) over 8 minutes (10 minute run time) at a flow rate of 40 mL/minute on reverse phase HPLC to afford the title compound upon concentration under reduced pressure. $^1$H NMR (300 MHz, DMSO-$d_6$) δ 7.40 (m, 4H), 6.94 (s, 1H), 6.84 (d, J=6.6 Hz, 1H), 6.68 (s, 1H), 3.69 (m, 1H), 2.71 (m, 2H), 2.35 (m, 2H), 1.76 (m, 13H), 1.32 (m, 2H); MS (ESI+) m/z 388 (M+H)$^+$.

Example 5

E-4-[(1-Phenyl-cyclopropanecarbonyl)-amino]-adamantane-1-carboxylic acid amide

The title compound was prepared according to the method of Example 4 substituting the product from step B of Example 2 for the product from step B of Example 1D. $^1$H NMR (300 MHz, DMSO-$d_6$) δ 7.42 (m, 4H), 7.36 (m, 1H), 6.94 (s, 1H), 6.68 (s, 1H), 6.78 (d, J=7.8 Hz, 1H), 3.73 (m, 1H), 1.75 (m, 7H), 1.65 (m, 2H), 1.35 (m, 4H), 1.18 (m, 2H), 1.02 (m, 2H); MS (ESI+) m/z 340 (M+H)$^+$.

Example 6

E-4-(2-Methyl-2-phenylpropionylamino)-adamantane-1-carboxylic acid amide

The title compound was prepared according to the method of Example 4 substituting the product from step B of Example 3 for the product from step B of Example 1D. $^1$H NMR (300 MHz, DMSO-$d_6$) δ 7.35 (m, 4H), 7.25 (m, 1H), 6.96 (s, 1H), 6.69 (s, 1H), 6.23 (d, J=7.2 Hz, 1H), 3.74 (m, 1H), 1.85 (m, 2H), 1.75 (m, 5H), 1.69 (m, 2H), 1.53 (m, 2H), 1.49 (s, 6H), 1.32 (m, 2H); MS (ESI+) m/z 342 (M+H)$^+$.

Example 7

N-2-adamantyl-2-methyl-2-phenylpropanamide

A solution of 2-adamantanamine hydrochloride (38 mg, 0.20 mmol), 2-phenylisobutyric acid (30 mg, 0.19 mmol), and O-benzotriazol-1-yl-N,N,N',N'-tetramethyluronium tetrafluoroborate (TBTU) (65 mg, 0.20 mmol) in N,N-dimethylacetamide (DMA) (2 mL) and DIEA (80 μL, 0.46 mmol) was stirred for 16 hours at 23° C. The reaction mixture was analyzed by LC/MS and determined to be near completion. The reaction mixture was concentrated under reduced pressure. The residue was dissolved in DMSO/MeOH (1:1, 1.5 mL) and purified by preparative HPLC on a Waters Symmetry C8 column (25 mm×100 mm, 7 um particle size) using a gradient of 10% to 100% acetonitrile:aqueous ammonium acetate (10 mM) over 8 minutes (10 minute run time) at a flow rate of 40 mL/minute on reverse phase HPLC to afford the title compound upon concentration under reduced pressure. $^1$H NMR (300 MHz, DMSO-$d_6$) δ 7.35 (m, 4H), 7.24 (m, 1H), 6.16 (d, J=6.9 Hz, 1H), 3.78 (m, 1H), 1.74 (m, 7H), 1.64 (m, 3H), 1.55 (m, 2H), 1.48 (s, 6H), 1.41 (m, 2H); MS (DCI+) m/z 298 (M+H)$^+$.

Example 8

N-2-adamantyl-1-phenylcyclopropanecarboxamide

The titled compound was prepared according to the method of Example 7 substituting 1-phenyl cyclopropanecarboxylic acid for 2-phenylisobutyric acid. $^1$H NMR (300 MHz, DMSO-$d_6$) δ 7.43 (m, 4H), 7.37 (m, 1H), 5.77 (d, J=7.8 Hz, 1H), 3.76 (m, 1H), 1.68 (m, 10H), 1.42 (m, 2H), 1.35 (m, 2H), 1.21 (m, 2H), 1.01 (m, 2H); MS (DCI+) m/z 296 (M+H)$^+$.

Example 9

E-4-({[1-(4-chlorophenyl)cyclohexyl]carbonyl}amino)adamantane-1-carboxamide

Example 9A

E-4-({[1-(4-chlorophenyl)cyclohexyl]carbonyl}amino)adamantane-1-carboxylic acid

Step A

The methyl ester of the title compound was prepared according to the method as described in step A of Example 1D, substituting 1-(4-chlorophenyl)-1-cyclohexanecarboxylic acid for 1-(4-chlorophenyl)-1-cyclobutanecarboxylic acid, and with the exceptions that the methyl ester was purified by reverse phase chromatography. Upon work up, the residue was dissolved in DMSO/MeOH (1:1, 1.5 mL) and purified by preparative HPLC on a Waters Symmetry C8 column (25 mm×100 mm, 7 um particle size) using a gradient of 10% to 100% acetonitrile:aqueous ammonium acetate (10 mM) over 8 min (10 min run time) at a flow rate of 40 mL/min.

Step B

The methyl ester obtained from step A (47 mg, 0.11 mmol) was dissolved in 5 N aqueous HCl (1 mL) and 4 N HCl in dioxane (2 mL), heated to 60° C. for 24 hours, was cooled to 23° C., and was then concentrated under reduced pressure to provide the title compound.

Example 9B

E-4-({[1-(4-chlorophenyl)cyclohexyl]carbonyl}amino)adamantane-1-carboxamide

The title compound was prepared according to the method as described in Example 4 substituting the product of step B of Example 9A for the product of step B of Example 1D, and with the exception that the crude title compound was purified by normal phase flash chromatography with MeOH/DCM (5:95) as eluant. $^1$H NMR (500 MHz, DMSO-$d_6$) δ ppm 7.36-7.42 (m, 4H), 6.95-6.96 (bs, 1H), 6.69-6.70 (bs, 1H), 6.57 (d, J=6.56 Hz, 1H), 3.72-3.76 (m, 1H), 2.36-2.44 (m, 2H), 1.84-1.86 (m, 2H), 1.73-1.82 (m, 5H), 1.64-1.73 (m, 6H), 1.49-1.56 (m, 3H), 1.36-1.51 (m, 2H), 1.32-1.36 (m, 2H), 1.23-1.30 (m, 1H); MS (ESI+) m/z 415 (M+H)$^+$.

Example 10

E-4-({[1-(4-chlorophenyl)cyclopropyl]carbonyl}amino)adamantane-1-carboxamide

Example 10A

E-4-({[1-(4-chlorophenyl)cyclopropyl]carbonyl}amino)adamantane-1-carboxylic acid Step A The methyl ester of the title compound was prepared according to the method as described in step A of Example 1D, substituting 1-(4-chlorophenyl)-1-cyclopropanecarboxylic acid for 1-(4-chlorophenyl)-1-cyclobutanecarboxylic acid, and with the exceptions that the methyl ester was purified by reverse phase chromatography. Upon work up, the residue was dissolved in DMSO/MeOH (1:1, 1.5 mL) and purified by preparative HPLC on a Waters Symmetry C8 column (25 mm×100 mm, 7 um particle size) using a gradient of 10% to 100% acetonitrile:aqueous ammonium acetate (10 mM) over 8 min (10 min run time) at a flow rate of 40 mL/min.

Step B

The methyl ester obtained from step A (51 mg, 0.13 mmol) was dissolved in 5 N aqueous HCl (1 mL) and 4 N HCl in dioxane (2 mL), heated to 60° C. for 24 hours, was cooled to 23° C., and was then concentrated under reduced pressure to provide the title compound.

Example 10B

E-4-({[1-(4-chlorophenyl)cyclopropyl]carbonyl}amino)adamantane-1-carboxamide

The title compound was prepared according to the method as described in Example 4, substituting the product of step B of Example 10A for the product of step B of Example 1D and with the exception that title compound was purified by normal phase flash chromatography with MeOH/DCM (5:95) as eluant. $^1$H NMR (500 MHz, DMSO-$d_6$) δ ppm 7.43-7.48 (m, 4H), 6.95-6.97 (bs, 1H), 6.69-6.70 (bs, 1H), 5.98 (d, J=7.30 Hz, 1H), 3.71-3.76 (m, 1H), 1.79-1.82 (m, 2H), 1.73-1.78 (m, 5H), 1.67-1.69 (m, 2H), 1.29-1.41 (m, 6H), 0.99-1.03 (m, 2H); MS (ESI+) m/z 373 (M+H)$^+$.

Example 11

E-4-({[1-(4-chlorophenyl)cyclopentyl]carbonyl}amino)adamantane-1-carboxamide

Example 11A

E-4-({[1-(4-chlorophenyl)cyclopentyl]carbonyl}amino)adamantane-1-carboxylic acid Step A The methyl ester of the title compound was prepared according to the method as described in step A of Example 1D, substituting 1-(4-chlorophenyl)-1-cyclopentanecarboxylic acid for 1-(4-chlorophenyl)-1-cyclobutanecarboxylic acid, and with the exceptions that the methyl ester was purified by reverse phase chromatography. Upon work up, the residue was dissolved in DMSO/MeOH (1:1, 1.5 mL) and purified by preparative HPLC on a Waters Symmetry C8 column (25 mm×100 mm, 7 um particle size) using a gradient of 10% to 100% acetonitrile:aqueous ammonium acetate (10 mM) over 8 min (10 min run time) at a flow rate of 40 mL/min.

Step B

The methyl ester obtained from step A (30 mg, 0.072 mmol) was dissolved in 5 N aqueous HCl (0.5 mL) and 4 N HCl in dioxane (1 mL), heated to 60° C. for 24 hours, was cooled to 23° C., and was then concentrated under reduced pressure to provide the title compound.

Example 11B

E-4-({[1-(4-chlorophenyl)cyclopentyl]carbonyl}amino)adamantane-1-carboxamide

The title compound was prepared according to the method as described in Example 4, substituting the product of step B of Example 11A for the product of step B of Example 1D, and with the exception that title compound was purified by normal phase flash chromatography with MeOH/DCM (5:95) as eluant. $^1$H NMR (500 MHz, DMSO-$d_6$) δ ppm 7.35-7.41 (m, 4H), 6.94-6.96 (bs, 1H), 6.68-6.70 (bs, 1H), 6.58 (d, J=6.59 Hz, 1H), 3.66-3.70 (m, 1H), 2.51-2.60 (m, 2H), 1.77-1.86 (m, 5H), 1.73-1.77 (m, 4H), 1.68-1.69 (m, 2H), 1.58-1.66 (m, 6H), 1.30-1.34 (m, 2H); MS (ESI+) m/z 401 (M+H)$^+$.

Example 12

E-4-{[2-(4-chlorophenyl)-2-methylpropanoyl]amino}adamantane-1-carboxamide

Example 12A

E-4-{[2-(4-chlorophenyl)-2-methylpropanoyl]amino}adamantane-1-carboxylic acid

Step A

The methyl ester of the title compound was prepared according to the method as described in step A of Example 1D, substituting 2-methyl-2-(4-chlorophenyl) propionic acid for 1-(4-chlorophenyl)-1-cyclobutanecarboxylic acid, and with the exceptions that the methyl ester was purified by reverse phase chromatography. Upon work up, the residue was dissolved in DMSO/MeOH (1:1, 1.5 mL) and purified by preparative HPLC on a Waters Symmetry C8 column (25 mm×100 mm, 7 um particle size) using a gradient of 10% to 100% acetonitrile:aqueous ammonium acetate (10 mM) over 8 min (10 min run time) at a flow rate of 40 m L/min.
Step B The methyl ester obtained from step A (50 mg, 0.13 mmol) was dissolved in 5 N aqueous HCl (1 mL) and 4 N HCl in dioxane (2 mL), heated to 60° C. for 24 hours, was cooled to 23° C., and was then concentrated under reduced pressure to provide the title compound.

Example 12B

E-4-{[2-(4-chlorophenyl)-2-methylpropanoyl]amino}adamantane-1-carboxamide

The title compound was prepared according to the method as described in Example 4, substituting the product of step B of Example 12A for the product of step B of Example 1D, and with the exception that title compound was purified by normal phase flash chromatography with MeOH/DCM (5:95) as eluant. $^1$H NMR (500 MHz, DMSO-$d_6$) δ ppm 7.34-7.40 (m, 4H), 6.95-6.97 (bs, 1H), 6.69-6.71 (bs, 1H), 6.44 (d, J=6.72 Hz, 1H), 3.73-3.77 (m, 1H), 1.86-1.89 (m, 2H), 1.69-1.81 (m, 5H), 1.67-1.73 (m, 2H), 1.61-1.66 (m, 2H), 1.47 (s, 6H), 1.32-1.36 (m, 2H); MS (ESI+) m/z 375 (M+H)$^+$.

Example 13

E-4-{[(1-phenylcyclopentyl)carbonyl]amino}adamantane-1-carboxamide

Example 13A

E-4-{[(1-phenylcyclopentyl)carbonyl]amino}adamantane-1-carboxylic acid

Step A
The methyl ester of the title compound was prepared according to the method as described in step A of Example 1D, substituting 1-phenyl-1-cyclopentanecarboxylic acid for 1-(4-chlorophenyl)-1-cyclobutanecarboxylic acid, and with the exceptions that the methyl ester was purified by reverse phase chromatography. Upon work up, the residue was dissolved in DMSO/MeOH (1:1, 1.5 mL) and purified by preparative HPLC on a Waters Symmetry C8 column (25 mm×100 mm, 7 um particle size) using a gradient of 10% to 100% acetonitrile:aqueous ammonium acetate (10 mM) over 8 min (10 min run time) at a flow rate of 40 mL/min.
Step B The methyl ester obtained from step A (20 mg, 0.052 mmol) was dissolved in 5 N aqueous HCl (0.5 mL) and 4 N HCl in dioxane (1 mL), heated to 60° C. for 24 hours, was cooled to 23° C., and was then concentrated under reduced pressure to provide the title compound.

Example 13B

E-4-{[(1-phenylcyclopentyl)carbonyl]amino}adamantane-1-carboxamide

The title compound was prepared according to the method as described in Example 4, substituting the product of step B of Example 13A for the product of step B of Example 1D, and with the exception that title compound was purified by normal phase flash chromatography with MeOH/DCM (5:95) as eluant. $^1$H NMR (500 MHz, DMSO-$d_6$) δ ppm 7.38-7.40 (m, 2H), 7.30-7.34 (m, 2H), 7.20-7.24 (m, 1H), 6.93-6.95 (bs, 1H), 6.68-6.69 (bs, 1H), 6.38 (d, J=6.80 Hz, 1H), 3.65-3.69 (m, 1H), 2.51-2.58 (m, 2H), 1.78-1.90 (m, 4H), 1.71-1.78 (m, 5H), 1.65-1.69 (m, 2H), 1.60-1.64 (m, 4H), 1.51-1.56 (m, 2H), 1.28-1.32 (m, 2H); MS (ESI+) m/z 367 (M+H)$^+$.

Example 14

E-4-({[1-(3-fluorophenyl)cyclopentyl]carbonyl}amino)adamantane-1-carboxamide

Example 14A

E-4-({[1-(3-fluorophenyl)cyclopentyl]carbonyl}amino)adamantane-1-carboxylic acid Step A
The methyl ester of the title compound was prepared according to the method as described in step A of Example 1D, substituting 1-(3-fluorophenyl)-1-cyclopentanecarboxylic acid for 1-(4-chlorophenyl)-1-cyclobutanecarboxylic acid, and with the exceptions that the methyl ester was purified by reverse phase chromatography. Upon work up, the residue was dissolved in DMSO/MeOH (1:1, 1.5 mL) and purified by preparative HPLC on a Waters Symmetry C8 column (25 mm×100 mm, 7 um particle size) using a gradient of 10% to 100% acetonitrile:aqueous ammonium acetate (10 mM) over 8 min (10 min run time) at a flow rate of 40 mL/min.
Step B The methyl ester obtained from step A (41 mg, 0.10 mmol) was dissolved in 5 N aqueous HCl (0.5 mL) and 4 N HCl in dioxane (1 mL), heated to 60° C. for 24 hours, was cooled to 23° C., and was then concentrated under reduced pressure to provide the title compound.

Example 14B

E-4-({[1-(3-fluorophenyl)cyclopentyl]carbonyl}amino)adamantane-1-carboxamide

The title compound was prepared according to the method as described in Example 4, substituting the product of step B of Example 14A for the product of step B of Example 1D. $^1$H NMR (300 MHz, DMSO-$d_6$) δ ppm 7.31-7.40 (m, 1H), 7.18-7.24 (m, 2H), 7.01-7.09 (m, 1H), 6.93-6.96 (bs, 1H), 6.68-6.70 (bs, 1H), 6.60 (d, J=6.55 Hz, 1H), 3.64-3.71 (m, 1H), 2.48-2.66 (m, 2H), 1.71-1.88 (m, 9H), 1.58-1.71 (m, 8H), 1.29-1.35 (m, 2H); MS (ESI+) m/z 385 (M+H)$^+$.

Example 15

E-4-({[1-(2-chloro-4-fluorophenyl)cyclopentyl]carbonyl}amino)adamantane-1-carboxamide Example 15A E-4-({[1-(2-chloro-4-fluorophenyl)cyclopentyl]carbonyl}amino)adamantane-1-carboxylic acid Step A
The methyl ester of the title compound was prepared according to the method as described in step A of Example 1D, substituting 1-(2-chloro-4-fluorophenyl)-1-cyclopentanecarboxylic acid for 1-(4-chlorophenyl)-1-cyclobutanecarboxylic acid, and with the exceptions that the methyl ester was purified by reverse phase chromatography. Upon work up, the residue was dissolved in DMSO/MeOH (1:1, 1.5 mL) and purified by preparative HPLC on a Waters Symmetry C8 column (25 mm×100 mm, 7 um particle size) using a gradient of 10% to 100% acetonitrile:aqueous ammonium acetate (10 mM) over 8 min (10 min run time) at a flow rate of 40 mL/min.
Step B
The methyl ester obtained from step A (66 mg, 0.15 mmol) was dissolved in 5 N aqueous HCl (0.5 mL) and 4 N HCl in dioxane (2 mL), heated to 60° C. for 24 hours, was cooled to 23° C., and was then concentrated under reduced pressure to provide the title compound.

Example 15B

E-4-({[1-(2-chloro-4-fluorophenyl)cyclopentyl]carbonyl}amino)adamantane-1-carboxamide The title compound was prepared according to the method as described in Example 4, substituting the product of step B of Example 15A for the product of step B of Example 1D. $^1$H NMR (300 MHz, DMSO-$d_6$) δ ppm 7.61 (dd, J=8.86, 6.18 Hz, 1H), 7.43 (dd, J=8.66, 2.77 Hz, 1H), 7.24 (ddd, J=8.81, 8.11, 2.80 Hz, 1H), 6.94-6.96 (m, 1H), 6.68-6.71 (bs, 1H), 5.84 (d, J=6.96 Hz, 1H), 3.69-3.77 (m, 1H), 2.35-2.51 (m, 2H), 1.92-2.08 (m, 2H), 1.53-1.89 (m, 13H), 1.28-1.45 (m, 4H); MS (ESI+) m/z 419 (M+H)$^+$.

Example 16

E-4-({[1-(4-fluorophenyl)cyclopentyl]carbonyl}amino)adamantane-1-carboxamide

Example 16A

E-4-({[1-(4-fluorophenyl)cyclopentyl]carbonyl}amino)adamantane-1-carboxylic acid Step A
The methyl ester of the title compound was prepared according to the method as described in step A of Example 1D, substituting 1-(4-fluorophenyl)-1-cyclopentanecarboxylic acid for 1-(4-chlorophenyl)-1-cyclobutanecarboxylic acid, and with the exceptions that the methyl ester was purified by reverse phase chromatography. Upon work up, the residue was dissolved in DMSO/MeOH (1:1, 1.5 mL) and purified by preparative HPLC on a Waters Symmetry C8 column (25 mm×100 mm, 7 um particle size) using a gradient of 10% to 100% acetonitrile:aqueous ammonium acetate (10 mM) over 8 min (10 min run time) at a flow rate of 40 mL/min.
Step B
The methyl ester obtained from step A (58 mg, 0.15 mmol) was dissolved in 5 N aqueous HCl (0.5 mL) and 4 N HCl in dioxane (2 mL), heated to 60° C. for 24 hours, was cooled to 23° C., and was then concentrated under reduced pressure to provide the title compound.

Example 16B

E-4-({[1-(4-fluorophenyl)cyclopentyl]carbonyl}amino)adamantane-1-carboxamide

The title compound was prepared according to the method as described in Example 4, substituting the product of step B of Example 16A for the product of step B of Example 1D. $^1$H NMR (300 MHz, DMSO-$d_6$) δ ppm 7.37-7.45 (m, 2H), 7.10-7.17 (m, 2H), 6.93-6.96 (bs, 1H), 6.67-6.70 (bs, 1H), 6.50 (d, J=6.65 Hz, 1H), 3.64-3.70 (m, 1H), 2.51-2.61 (m, 2H), 1.54-1.86 (m, 17H), 1.27-1.37 (m, 2H); MS (ESI+) m/z 385 (M+H)$^+$.

Example 17

E-4-({[1-(2-fluorophenyl)cyclopentyl]carbonyl}amino)adamantane-1-carboxamide

Example 17A

E-4-({[1-(2-fluorophenyl)cyclopentyl]carbonyl}amino)adamantane-1-carboxylic acid Step A
The methyl ester of the title compound was prepared according to the method as described in step A of Example 1D, substituting 1-(2-fluorophenyl)-1-cyclopentanecarboxylic acid for 1-(4-chlorophenyl)-1-cyclobutanecarboxylic acid, and with the exceptions that the methyl ester was purified by reverse phase chromatography. Upon work up, the residue was dissolved in DMSO/MeOH (1:1, 1.5 mL) and purified by preparative HPLC on a Waters Symmetry C8 column (25 mm×100 mm, 7 um particle size) using a gradient of 10% to 100% acetonitrile:aqueous ammonium acetate (10 mM) over 8 min (10 min run time) at a flow rate of 40 mL/min.
Step B
The methyl ester obtained from step A (56 mg, 0.14 mmol) was dissolved in 5 N aqueous HCl (0.5 mL) and 4 N HCl in dioxane (2 mL), heated to 60° C. for 24 hours, was cooled to 23° C., and was then concentrated under reduced pressure to provide the title compound.

Example 17B

E-4-({[1-(2-fluorophenyl)cyclopentyl]carbonyl}amino)adamantane-1-carboxamide

The title compound was prepared according to the method as described in Example 4, substituting the product of step B of Example 17A for the product of step B of Example 1D. $^1$H NMR (300 MHz, DMSO-$d_6$) δ ppm 7.49 (td, J=7.94, 1.80 Hz, 1H), 7.29-7.37 (m, 1H), 7.11-7.24 (m, 2H), 6.94-6.96 (bs, 1H), 6.68-6.70 (bs, 1H), 6.02 (d, J=6.93 Hz, 1H), 3.67-3.74 (m, 1H), 2.34-2.53 (m, 2H), 1.85-2.01 (m, 2H), 1.57-1.86 (m, 13H), 1.28-1.43 (m, 4H); MS (ESI+) m/z 385 (M+H)$^+$.

Example 18

E-4-{[1-methylcyclohexyl)carbonyl]amino}adamantane-1-carboxamide

Example 18A

E-4-{[(1-methylcyclohexyl)carbonyl]amino}adamantane-1-carboxylic acid

Step A
The methyl ester of the title compound was prepared according to the method as described in step A of Example 1D, substituting 1-methyl-1-cyclohexanecarboxylic acid for 1-(4-chlorophenyl)-1-cyclobutanecarboxylic acid, and with the exceptions that the methyl ester was purified by reverse phase chromatography. Upon work up, the residue was dissolved in DMSO/MeOH (1:1, 1.5 mL) and purified by preparative HPLC on a Waters Symmetry C8 column (25 mm×100 mm, 7 um particle size) using a gradient of 10% to 100% acetonitrile:aqueous ammonium acetate (10 mM) over 8 min (10 min run time) at a flow rate of 40 mL/min.
Step B The methyl ester obtained from step A (33 mg, 0.10 mmol) was dissolved in 5 N aqueous HCl (0.5 mL) and 4 N HCl in dioxane (1 mL), heated to 60° C. for 24 hours, was cooled to 23° C., and was then concentrated under reduced pressure to provide the title compound.

Example 18B

E-4-{[(1-methylcyclohexyl)carbonyl]amino}adamantane-1-carboxamide

The title compound was prepared according to the method as described in Example 4, substituting the product of step B of Example 18A for the product of step B of Example 1D. $^1$H NMR (300 MHz, DMSO-$d_6$) δ ppm 6.96-6.99 (bs, 1H), 6.66-6.72 (m, 2H), 3.74-3.80 (m, 1H), 1.82-2.08 (m, 7H), 1.79-1.82 (m, 4H), 1.72-1.75 (m, 2H), 1.12-1.55 (m, 10H), 1.07 (s, 3H); MS (ESI+) m/z 319 (M+H)$^+$.

Example 19

E-4-({[1-(2,4-dichlorophenyl)cyclopropyl]carbonyl}amino)adamantane-1-carboxamide Example 19A E-4-({[1-(2,4-dichlorophenyl)cyclopronyl]carbonyl}amino)adamantane-1-carboxylic acid Step A The methyl ester of the title compound was prepared according to the method as described in step A of Example 1D, substituting 1-(2,4-dichlorophenyl)-1-cyclopropanecarboxylic acid for 1-(4-chlorophenyl)-1-cyclobutanecarboxylic acid and with the exceptions that the methyl ester was purified by reverse phase chromatography. Upon work up, the residue was dissolved in DMSO/MeOH (1:1, 1.5 mL) and purified by preparative HPLC on a Waters Symmetry C8 column (25 mm×100 mm, 7 um particle size) using a gradient of 10% to 100% acetonitrile:aqueous ammonium acetate (10 mM) over 8 min (10 min run time) at a flow rate of 40 mL/min.
Step B The methyl ester obtained from step A (47 mg, 0.11 mmol) was dissolved in 5 N aqueous HCl (0.5 mL) and 4 N HCl in dioxane (2 mL), heated to 60° C. for 24 hours, was cooled to 23° C., and was then concentrated under reduced pressure to provide the title compound.

Example 19B

E-4-({[1-(2,4-dichlorophenyl)cyclopropyl]carbonyl}amino)adamantane-1-carboxamide The title compound was prepared according to the method as described in Example 4, substituting the product of step B of Example 19A for the product of step B of Example 1D. $^1$H NMR (300 MHz, DMSO-$d_6$) δ ppm 7.73 (d, J=2.10 Hz, 1H), 7.56 (d, J=8.25 Hz, 1H), 7.49 (dd, J=8.27, 2.12 Hz, 1H), 6.94-6.97 (bs, 1H), 6.68-6.71 (bs, 1H), 5.66 (d, J=7.12 Hz, 1H), 3.70-3.77 (m, 1H), 1.80-1.84 (m, 2H), 1.71-1.78 (m, 5H), 1.68 (d, J=3.09 Hz, 2H), 1.43-1.53 (m, 2H), 1.27-1.42 (m, 4H), 1.02-1.12 (m, 2H); MS (ESI+) m/z 407 (M+H)$^+$.

Example 20

E-4-({[1-(4-methoxyphenyl)cyclopropyl]carbonyl}amino)adamantane-1-carboxamide

Example 20A

E-4-({[1-(4-methoxyphenyl)cyclopropyl]carbonyl}amino)adamantane-1-carboxylic acid Step A The methyl ester of the title compound was prepared according to the method as described in step A of Example 1D, substituting 1-(4-methoxyphenyl)-1-cyclopropanecarboxylic acid for 1-(4-chlorophenyl)-1-cyclobutanecarboxylic acid and with the exceptions that the methyl ester was purified by reverse phase chromatography. Upon work up, the residue was dissolved in DMSO/MeOH (1:1, 1.5 mL) and purified by preparative HPLC on a Waters Symmetry C8 column (25 mm×100 mm, 7 um particle size) using a gradient of 10% to 100% acetonitrile:aqueous ammonium acetate (10 mM) over 8 min (10 min run time) at a flow rate of 40 mL/min.
Step B The methyl ester obtained from step A (43 mg, 0.11 mmol) was dissolved in 5 N aqueous HCl (0.5 mL) and 4 N HCl in dioxane (1 mL), heated to 60° C. for 24 hours, was cooled to 23° C., and was then concentrated under reduced pressure to provide the title compound.

Example 20B

E-4-({[1-(4-methoxyphenyl)cyclopropyl]carbonyl}amino)adamantane-1-carboxamide

The title compound was prepared according to the method as described in Example 4, substituting the product of step B of Example 20A for the product of step B of Example 1D. $^1$H NMR (300 MHz, DMSO-$d_6$) δ ppm 7.34-7.38 (m, 2H), 6.95-7.00 (m, 3H), 6.68-6.71 (bs, 1H), 5.78 (d, J=7.66 Hz, 1H), 3.76 (s, 3H), 3.69-3.75 (m, 1H), 1.72-1.77 (m, 7H), 1.66-1.69 (m, 2H), 1.27-1.43 (m, 4H), 1.17-1.24 (m, 2H), 0.93-1.03 (m, 2H); MS (ESI+) m/z 369 (M+H)$^+$.

Example 21

E-4-({[1-(4-methylphenyl)cyclopropyl]carbonyl}amino)adamantane-1-carboxamide

Example 21A

E-4-{[1-(4-methylphenyl)cyclopropyl]carbonyl}amino)adamantane-1-carboxylic acid

Step A

The methyl ester of the title compound was prepared according to the method as described in step A of Example 1D, substituting 1-(4-methylphenyl)-1-cyclopropanecarboxylic acid for 1-(4-chlorophenyl)-1-cyclobutanecarboxylic acid and with the exceptions that the methyl ester was purified by reverse phase chromatography. Upon work up, the residue was dissolved in DMSO/MeOH (1:1, 1.5 mL) and purified by preparative HPLC on a Waters Symmetry C8 column (25 mm×100 mm, 7 um particle size) using a gradient of 10% to 100% acetonitrile:aqueous ammonium acetate (10 mM) over 8 min (10 min run time) at a flow rate of 40 mL/min.
Step B The methyl ester obtained from step A (39 mg, 0.11 mmol) was dissolved in 5 N aqueous HCl (0.5 mL) and 4 N HCl in dioxane (1 mL), heated to 60° C. for 24 hours, was cooled to 23° C., and was then concentrated under reduced pressure to provide the title compound.

Example 21B

E-4-({[1-(4-methylphenyl)cyclopropyl]carbonyl}amino)adamantane-1-carboxamide

The title compound was prepared according to the method as described in Example 4, substituting the product of step B of Example 21A for the product of step B of Example 1D. $^1$H NMR (300 MHz, DMSO-$d_6$) δ ppm 7.30-7.34 (m, 2H), 7.20-7.25 (m, 2H), 6.94-6.97 (bs, 1H), 6.68-6.70 (bs, 1H), 5.80 (d, J=7.62 Hz, 1H), 3.69-3.76 (m, 1H), 2.31 (s, 3H), 1.71-1.81 (m, 7H), 1.66-1.68 (m, 2H), 1.31-1.39 (m, 4H), 1.17-1.23 (m, 2H), 0.96-0.99 (m, 2H); MS (ESI+) m/z 353 (M+H)$^+$.

Example 22

E-4-{[2-methyl-2-(4-pyridin-4-ylphenyl)propanoyl]amino}adamantane-1-carboxamide

Example 22A

Ethyl 2-(4-bromophenyl)-2-methylpropanoate

A 60% suspension of sodium hydride in mineral oil (3.3 g, 82.3 mmoles) was added to N,N-dimethylformamide (60.0 ml) under a nitrogen atmosphere and the mixture was cooled to about −10° C. Iodomethane (5.1 ml, 82.3 mmoles) and subsequently ethyl 4-bromophenylacetate (5.0 g, 20.6 mmoles) were added over a period of about 30 min and the reaction mixture was then stirred for about 16 hours while being allowed to warm to room temperature. This suspension was then poured onto a mixture of ice and 2N hydrochloric acid (30.0 ml) and was extracted four times with ethyl acetate. The combined organic extracts were washed with water and brine, dried over MgSO$_4$ and filtered. The filtrate was concentrated under reduced pressure and the crude product was purified by flash column chromatography on silica gel using hexanes/ethyl acetate (2:1) as the mobile phase to provide the title compound.

Example 22B 2-(4-bromophenyl)-2-methylpronanoic acid

To a solution of the product of Example 22A (3.7 g, 13.6 mmoles) in tetrahydrofuran (110.0 ml) and methanol (37.0 ml) was added 2 N sodium hydroxide (19.0 ml) and the solution was stirred at ambient temperature for about 16 hours. The reaction mixture was concentrated in vacuum down to the water layer, was cooled with an ice bath, and was acidified by addition of 2N hydrochloric acid. The precipitate was filtered off and was dried in vacuum to provide the title compound.

Example 22C

E-4-[2-(4-Bromo-phenyl)-2-methyl-propionylamino]-adamantane-1-carboxylic acid methyl ester A solution of the product of Example 22B (3.3 g, 13.5 mmoles), the product of Example 1C (3.3 g, 13.5 mmoles), O-benzotriazol-1-yl-N,N,N',N'-tetramethyluronium tetrafluoroborate (8.6 g, 26.9 mmoles) and N,N-diisopropylethylamine (9.4 ml, 53.8 mmoles) in N,N-dimethylformamide (150.0 ml) was stirred at room temperature for about 16 hours under a nitrogen atmosphere. The solvent was evaporated in vacuum and the residue was purified by flash column chromatography on silica gel using hexanes/ethyl acetate (2:1) as the mobile phase to provide the title compound.

Example 22D

E-4-[2-Methyl-2-(4-pyridin-4-yl-phenyl)-propionylamino]-adamantane-1-carboxylic acid methyl ester To a solution of the product of Example 22C (300 mg, 0.7 mmoles) in 1,2-dimethoxyethane (6.0 ml) was added a solution of pyridine-4-boronic acid (127 mg, 1.0 mmoles) in ethanol (1.0 ml), dichlorobis(tri-o-tolylphosphine)palladium (II) (28 mg, 0.04 mmoles) and a 2M aqueous solution of sodium carbonate (1.7 ml, 3.5 mmoles) and the mixture was stirred under nitrogen in a heavy walled process vial in a microwave synthesizer (Personal Chemistry Smith Synthesizer) at about 140° C. for about 10 min. The reaction mixture was concentrated in vacuum and the crude product was purified by flash column chromatography on silica gel using hexanes/ethyl acetate (2:1) as the mobile phase to provide the title compound.

Example 22E

E-4-[2-Methyl-2-(4-pyridin-4-yl-phenyl)-propionylamino]-adamantane-1-carboxylic acid To a solution of the product of Example 22D (125 mg, 0.29 mmoles) in dioxane (4.0 ml) was added 2N aqueous hydrochloric acid (4.0 ml) and the mixture was heated to about 60° C. for about 18 hours. The mixture was cooled, concentrated to dryness and the residue was purified by preparative HPLC on a Waters Symmetry C8 column (25 mm×100 mm, 7 μm particle size) using a gradient of 10% to 100% acetonitrile: 0.1% aqueous TFA over 8 min (10 min run time) at a flow rate of 40 mL/min to provide the title compound.

Example 22F

E-4-[2-Methyl-2-(4-pyridin-4-yl-phenyl)-propionylamino]-adamantane-1-carboxylic acid amide A solution of the product of Example 22E (60 mg, 0.14 mmoles), N-(3-dimethylaminopropyl)-N'-ethylcarbodiimide hydrochloride (110 mg, 0.57 mmoles) and 1-hydroxybenzotriazole hydrate (44 mg, 0.32 mmoles) in dichloromethane (4.0 ml) was stirred at ambient temperature under a nitrogen atmosphere for about 1 hour. A 0.5 M solution of ammonia in dioxane (2.9 ml, 1.43 mmoles) was added and stirring was continued for about 16 hours. The mixture was evaporated to dryness and the residue was purified by preparative HPLC on a Waters Symmetry C8 column (25 mm×100 mm, 7 μm particle size) using a gradient of 10% to 100% acetonitrile: 0.1% aqueous TFA over 8 min (10 min run time) at a flow rate of 40 mL/min to provide the title compound as the trifluoroacetic acid salt. $^1$H NMR (500 MHz, DMSO-$d_6$) δ ppm 8.84-8.86 (m, 2H), 8.17-8.19 (m, 2H), 7.94-7.97 (m, 2H), 7.54-7.56 (m, 2H), 6.96-6.98 (bs, 1H), 6.70-6.72 (bs, 1H), 6.57 (d, J=6.64 Hz, 1H), 3.76-3.80 (m, 1H), 1.90-1.92 (m, 2H), 1.75-

1.84 (m, 5H), 1.64-1.75 (m, 4H), 1.55 (s, 6H), 1.33-1.37 (m, 2H); MS (ESI+) m/z 418 (M+H)+.

Example 23

E-4-[(2-methyl-2-thien-2-ylpropanoyl)amino]adamantane-1-carboxamide

Example 23A

Ethyl 2-methyl-2-(thiophen-2-yl)propanoate

The title compound was prepared according to the method of Example 22A, substituting ethyl 2-(thiophen-2-yl)acetate for ethyl 4-bromophenylacetate.

Example 23B

2-Methyl-2-(thiophen-2-yl)propanoic acid

The title compound was prepared according to the method of Example 22B, substituting the product of Example 23A for the product of Example 22A.

Example 23C

E-4-(2-Methyl-2-thiophen-2-yl-propionylamino)-adamantane-1-carboxylic acid methyl ester The title compound was prepared according to the method of Example 22C, substituting the product of Example 23B for the product of Example 22B.

Example 23D

E-4-(2-Methyl-2-thiophen-2-yl-propionylamino)-adamantane-1-carboxylic acid

To a solution of the product of Example 23C (250 mg, 0.69 mmoles) in dioxane (9.0 ml) was added 2N hydrochloric acid (9.0 ml) and the mixture was heated to about 60° C. for about 18 hours. The mixture was cooled, concentrated down to the water layer, the precipitate was filtered off and was dried in vacuum to give the title compound.

Example 23E

E-4-(2-Methyl-2-thiophen-2-yl-propionylamino)-adamantane-1-carboxylic acid amide The title compound was prepared according to the method of Example 22F, substituting the product of Example 23D for the product of Example 22E. $^1$H NMR (500 MHz, DMSO-d$_6$) δ ppm 7.46 (dd, J=5.10, 1.20 Hz, 1H), 7.10 (dd, J=3.52, 1.21 Hz, 1H), 7.02 (dd, J=5.09, 3.52 Hz, 1H), 6.95-6.97 (bs, 1H), 6.69-6.71 (bs, 1H), 6.24 (d, J=7.11 Hz, 1H), 3.68-3.72 (m, 1H), 1.82-1.84 (m, 2H), 1.72-1.81 (m, 5H), 1.66-1.72 (m, 2H), 1.56 (s, 6H), 1.48-1.52 (m, 2H), 1.34-1.38 (m, 2H); MS (ESI+) m/z 347 (M+H)+.

Example 24

E-4-[(2-methyl-2-thien-3-ylpropanoyl)amino]adamantane-1-carboxamide

Example 24A

Ethyl 2-methyl-2-(thiophen-3-yl)propanoate

The title compound was prepared according to the method of Example 22A substituting ethyl 2-(thiophen-3-yl)acetate for 4-bromophenylacetate.

Example 24B

2-Methyl-2-(thiophen-3-yl)propanoic acid

The title compound was prepared according to the method of Example 22B, substituting the product of Example 24A for the product of Example 22A.

Example 24C

E-4-(2-Methyl-2-thiophen-3-yl-propionylamino)-adamantane-1-carboxylic acid methyl ester The title compound was prepared according to the method of Example 22C, substituting the product of Example 24B for the product of Example 22B.

Example 24D

E-4-(2-Methyl-2-thiophen-3-yl-propionylamino)-adamantane-1-carboxylic acid

The title compound was prepared according to the method of Example 23D, substituting the product of Example 24C for the product of Example 23C.

Example 24E

E-4-(2-Methyl-2-thiophen-3-yl-propionylamino)-adamantane-1-carboxylic acid amide The title compound was prepared according to the method of Example 22F, substituting the product of Example 24D for the product of Example 22E. $^1$H NMR (500 MHz, DMSO-d$_6$) δ ppm 7.54 (dd, J=5.03, 2.90 Hz, 1H), 7.41 (dd, J=2.89, 1.44 Hz, 1H), 7.12 (dd, J=5.00, 1.40 Hz, 1H), 6.95-6.97 (bs, 1H), 6.69-6.70 (bs, 1H), 6.01-6.07 (m, 1H), 3.68-3.72 (m, 1H), 1.76-1.82 (m, 7H), 1.69 (d, J=3.14 Hz, 2H), 1.51 (s, 6H), 1.43-1.48 (m, 2H), 1.33-1.37 (m, 2H); MS (ESI+) m/z 347 (M+H)+.

Example 25

E-4-({2-methyl-2-[5-(trifluoromethyl)pyridin-2-yl]propanoyl}amino)adamantane-1-carboxamide

Example 25A

Potassium; 2-methyl-2-(5-trifluoromethyl-pyridin-2-yl)-propionate

A solution of 2-chloro-5-(trifluoro-methyl)pyridine (328 mg, 1.8 mmol), methyl trimethylsilyl dimethylketene acetal (0.378 mg, 2.17 mmol), zinc fluoride (112 mg, 1.08 mmol), tris(dibenzylideneacetone)dipalladium(0) (20 mg, 0.021 mmol) and tri-t-butylphosphine-10 wt % in hexane (172 mg, 0.084 mmol) in Argon degassed DMF (1.5 mL) was stirred at 90° C. for 12 hours. The reaction was taken up in EtOAc (25 mL) and washed with water (15 mL) followed by brine (15 mL). The organic layer was dried with MgSO$_4$, filtered, and evaporated in vacuo. The crude product was purified by flash chromatography (hexane/EtOAc 100:0 to 80:20) to give the methyl ester of the title compound. A solution of the methyl ester of the title compound (180 mg, 0.73 mmol), potassium trimethylsilanolate (KOTMS) (140 mg, 1.1 mmol) in THF (2 mL) was stirred for 12 hours at 23° C. Methyl t-butyl ether (MTBE) 8 mL was added to the solution and the title compound was isolated by filtration.

Example 25B

E-4-[2-Methyl-2-(5-trifluoromethyl-pyridin-2-yl)-propionylamino]-adamantane-1-carboxylic acid methyl ester A solution of the product of Example 25A (50 mg, 0.184 mmol), the product of Example 1C (54 mg, 0.22 mmol), TBTU (94 mg, 0.294 mmol) and DIEA (58 mg, 0.46 mmol) in DMF (1.2 mL) was stirred for 3 hrs at 23° C. The reaction was diluted with EtOAc (10 mL) and washed twice with water (6 mL) and brine (6 mL). The organic layer was dried with MgSO$_4$, filtered and evaporated in vacuo to afford the title compound. The product was carried to the next step without further purification.

Example 25C

E-4-({2-methyl-2-[5-(trifluoromethyl)pyridin-2-yl]propanoyl}amino)adamantane-1-carboxamide A solution of Example 25B (30 mg, 0.071 mmol), KOTMS (14 mg, 0.11 mmol) in THF (1 mL) was stirred for 12 hours at 23° C. The solvent was evaporated in vacuo to collect a solid. To the solid was added TBTU (40 mg, 0.12 mmol), DIEA (22 mg, 0.17 mmol) and DMF (0.5 mL) and stirred for 2 hours at 23° C. Ammonium hydroxide-30% by weight (2 mL) was added and stirred at 23° C. for a further 30 minutes. The reaction was partitioned between EtOAc (8 mL) and water (3 mL). The organic layer was washed with water (3 mL), dried with MgSO$_4$, filtered, and evaporated in vacuo. The crude reaction mixture was purified by preparative reverse phase HPLC on a Waters Symmetry C8 column (25 mm×100 mm, 7 um particle size) using a gradient of 20% to 100% acetonitrile:water (0.1% TFA) over 18 min at a flow rate of 40 mL/min. to provide the title compound as the trifluoroacetic acid salt. $^1$H NMR (500 MHz, Chloroform-d$_1$) δ ppm 8.86-8.87 (m, 1H), 7.94 (dd, J=8.38, 2.40 Hz, 1H), 7.59 (d, J=8.33 Hz, 1H), 7.41 (d, J=7.48 Hz, 1H), 6.13-6.18 (bs, 1H), 5.80-5.84 (bs, 1H), 3.93-3.97 (m, 1H), 1.99-2.03 (m, 3H), 1.93-1.99 (m, 4H), 1.87-1.89 (m, 2H), 1.69 (s, 6H), 1.63-1.68 (m, 2H), 1.56-1.60 (m, 2H); MS (APCI+) m/z 410 (M+H)$^+$.

Example 26

E-4-[(2-methyl-2-{4-[5-(trifluoro methyl)pyridin-2 yl]phenyl}propanoyl)amino]adamantane-1-carboxamide Example 26A Ethyl 2-methyl-2-(4-(4,4,5,5-tetramethyl-1,3,2-dioxaborolan-2-yl)phenyl)propanoate A mixture of the product of Example 22A (500 mg, 1.84 mmoles), bis(pinacolato)diboron (735 mg, 2.90 mmoles), 1,1'-bis(diphenylphosphino)ferrocenedichloropalladium (II) (90 mg, 0.11 mmoles) and potassium acetate (903 mg, 9.20 mmoles) in dimethyl sulfoxide (11.0 ml) was heated to about 80° C. under a nitrogen atmosphere for about two days. The mixture was cooled, diluted with benzene (28.0 ml) and was washed three times with water (18.0 ml each). The organic layer was dried over MgSO$_4$ and filtered. The filtrate was concentrated under reduced pressure and the crude product was purified by flash column chromatography on silica gel using hexanes/ethyl acetate (2:1) as the mobile phase to provide the title compound.

Example 26B

Ethyl 2-methyl-2-(4-(5-(trifluoromethyl)pyridin-2-yl)phenyl)propanoate

To a solution of the product of Example 26A (370 mg, 1.16 mmoles) and 2-bromo-5-(trifluoromethyl)pyridine (341 mg, 1.51 mmoles) in N,N-dimethylformamide (10.0 ml) were added 1,1'-bis(diphenylphosphino)ferrocenedichloropalladium (II) (28 mg, 0.04 mmoles) and a 2M aqueous solution of sodium carbonate (1.7 ml, 3.48 mmoles) and the reaction mixture was heated under a nitrogen atmosphere to about 80° C. for about 1 hour. Another portion of 1,1'-bis(diphenylphosphino)ferrocenedichloropalladium (II) (28 mg, 0.04 mmoles) was added and the mixture was heated to about 90° C. for about 2 hours. The solvent was evaporated in high vacuum, the residue was taken up in water (20.0 ml) and diethyl ether (20.0 ml), and was filtered through Celite. The layers were separated and the aqueous layer was extracted with diethyl ether. The combined organic extracts were dried over MgSO$_4$ and filtered. The filtrate was concentrated under reduced pressure and the crude product was purified by flash column chromatography on silica gel using hexanes/ethyl acetate (2:1) as the mobile phase to provide the title compound.

Example 26C

2-Methyl-2-(4-(5-(trifluoromethyl)pyridin-2-yl)phenyl)propanoic acid

The title compound was prepared according to the method of Example 22B, substituting the product of Example 26B for the product of Example 22A.

Example 26D

E-4-{2-Methyl-2-[4-(5-trifluoromethyl-pyridin-2-yl)-phenyl]-propionylamino}-adamantane-1-carboxylic acid methyl ester The title compound was prepared according to the method of Example 22C substituting the product of Example 26C for the product of Example 22B.

Example 26E

E-4-{2-Methyl-2-[4-(5-trifluoromethyl-pyridin-2-yl)-phenyl]-propionylamino}-adamantane-1-carboxylic acid The title compound was prepared according to the method of Example 22E substituting the product of Example 26D for the product of Example 22D.

Example 26F

E-4-{2-Methyl-2-[4-(5-trifluoromethyl-pyridin-2-yl)-phenyl]-propionylamino}-adamantane-1-carboxylic acid amide The trifluoroacetic acid salt of the title compound was prepared according to the method of Example 22F substituting the product of Example 26E for the product of Example 22E. $^1$H NMR (500 MHz, DMSO-$d_6$) δ ppm 9.03-9.05 (m, 1H), 8.27 (dd, J=8.46, 2.42 Hz, 1H), 8.20 (d, J=8.38 Hz, 1H), 8.13-8.16 (m, 2H), 7.50-7.53 (m, 2H), 6.96-6.98 (bs, 1H), 6.69-6.71 (bs, 1H), 6.48 (d, J=6.75 Hz, 1H), 3.76-3.81 (m, 1H), 1.88-1.91 (m, 2H), 1.74-1.84 (m, 5H), 1.60-1.74 (m, 4H), 1.54 (s, 6H), 1.32-1.36 (m, 2H); MS (ESI+) m/z 486 (M+H)$^+$.

Example 27

E-4-({[1-(4-methoxyphenyl)cyclopentyl]carbonyl}amino)adamantane-1-carboxamide

Example 27A

E-4-{[1-(4-Methoxy-phenyl)-cyclopentanecarbonyl]-amino}-adamantane-1-carboxylic acid methyl etser A solution of the product of Example 1C (110 mg, 0.45 mmol), 1-(4-methoxyphenyl)-1-cyclopentanecarboxylic acid (100 mg, 0.45 mmol), and O-benzotriazol-1-yl-N,N,N',N'-tetramethyluronium tetrafluoroborate (TBTU) (219 mg, 0.68 mmol) in N,N-dimethylformamide (DMF) (2 mL) was stirred ten minutes at room temperature, and then, diisopropylethylamine (240 µL, 1.4 mmol) was added. Reaction stirred for 16 hours at room temperature. The reaction was diluted with ethyl acetate and washed successively with water, saturated sodium bicarbonate, 1N phosphoric acid, and brine, dried over Na$_2$SO$_4$, filtered, and concentrated under reduced pressure. The residue was purified by flash chromatography on silica gel eluting with 20-30% ethyl acetate/hexane to provide the title compound.

Example 27B

E-4-{[1-(4-Methoxy-phenyl)-cyclopentanecarbonyl]-amino}-adamantane-1-carboxylic acid A solution of the product of Example 27A (160 mg, 0.39 mmol) in THF (3 mL) was treated with aqueous 4N sodium hydroxide (1.00 mL, 3.9 mmol) and methanol (1 mL), and reaction stirred 16 hours at room temperature. The reaction mixture was concentrated under reduced pressure, and the residue was taken up in water. The solution was acidified to pH 3 by the addition of aqueous 1N phosphoric acid, and the product was extracted with chloroform (3×). The combined extracts were dried (Na$_2$SO$_4$), filtered, and concentrated under reduced pressure to provide the title compound.

Example 27C

E-4-{[1-(4-Methoxy-phenyl)-cyclopentanecarbonyl]-amino}-adamantane-1-carboxylic acid amide A solution of the product of Example 27B (130 mg, 0.330 mmol), 1-hydroxybenzotriazole (54 mg, 0.40 mmol), and N-(3-dimethylaminopropyl)-N'-ethylcarbodiimide hydrochloride (EDAC) (76 mg, 0.40 mmol) in dimethylformamide (5 mL) was stirred two hours at room temperature. The reaction was treated with concentrated ammonium hydroxide (1 mL) and stirred 16 hours at room temperature. Reaction diluted with ethyl acetate and washed successively with water, saturated sodium bicarbonate, 1N phosphoric acid, and brine before drying over Na$_2$SO$_4$, filtering, and concentrating under reduced pressure. Residue purified by flash chromatography on silica gel eluting with 5% methanol/ethyl acetate to provide the title compound. $^1$H NMR (500 MHz, DMSO-$d_6$) δ ppm 7.29-7.31 (m, 2H), 6.94-6.95 (bs, 1H), 6.86-6.89 (m, 2H), 6.68-6.69 (bs, 1H), 6.32 (d, J=6.82 Hz, 1H), 3.73 (s, 3H), 3.64-3.70 (m, 1H), 2.46-2.51 (m, 2H), 1.74-1.85 (m, 9H), 1.68 (d, J=3.12 Hz, 2H), 1.53-1.62 (m, 6H), 1.30-1.34 (m, 2H); MS (ESI+) m/z 397 (M+H)$^+$.

Example 28

E-4-{[2-(4-bromophenyl)-2-methylpropanoyl]amino}adamantane-1-carboxamide

Example 28A

E-4-[2-(4-Bromo-phenyl)-2-methyl-propionylamino]-adamantane-1-carboxylic acid

The title compound was prepared according to the method of Example 23D substituting the product of Example 22C for the product of Example 23C.

Example 28B

E-4-[2-(4-Bromo-phenyl)-2-methyl-propionylamino]-adamantane-1-carboxylic acid amide The title compound was prepared according to the method of Example 22F substituting the product of Example 28A for the product of Example 22E. NMR (400 MHz, DMSO-$d_6$) δ ppm 7.50-7.53 (m, 2H), 7.27-7.30 (m, 2H), 6.93-6.95 (bs, 1H), 6.65-6.68 (bs, 1H), 6.43 (d, J=6.73 Hz, 1H), 3.72-3.76 (m, 1H), 1.86-1.89 (m, 2H), 1.77-1.79 (m, 5H), 1.61-1.73 (m, 4H), 1.47 (s, 6H), 1.32-1.37 (m, 2H); MS (DCI) m/z 419, 421 (M+H)$^+$.

Example 30

E-4-[5-(amino carbonyl)-2-adamantyl]-3-methyl-1-(2-methylbenzyl)-2-oxopiperidine-3-carboxamide

Example 30A

2-But-3-enyl-2-methyl-malonic acid dimethyl ester

A stirred solution of NaH-60% by weight (0.517 gm, 12.94 mmol) in DMF (5 mL) was cooled to 0° C. and dimethyl methyl malonate (1.26 gm, 8.63 mmol) in 3 mL of DMF was added dropwise. The reaction was warmed to ambient and stirred for 15 minutes. A solution of 4-bromo-1-butene (1.28 gm, 9.49 mmol) in 1.5 mL of DMF was added to the reaction mixture and stirred for 12 hours at 23° C. The reaction was partitioned between 10% NH$_4$Cl (20 mL) and 30 mL of EtOAc. The organic layer was washed with water (20 mL), brine (20 mL), dried with MgSO$_4$, filtered and evaporated in vacuo. The crude product was purified by flash chromatography (hexane/EtOAc 100:0 to 85:15) to provide Example 30A as an oil.

Example 30B

2-Methyl-2-(3-oxo-propyl)-malonic acid dimethyl ester

A solution of the product of Example 30A (1.0 gm, 5 mmol) was dissolved in CH$_2$Cl$_2$/MeOH 10:1 (15 mL) and cooled to −78° C. To the solution was bubbled O$_3$ over 20 minutes. The reaction solution was purged with N$_2$ for a further 10 minutes and dimethyl sulfide (DMS) (3.1 gm, 50 mmol) was added and the reaction warmed to ambient temperature and stirred for a further 2 hours. The solvent was evaporated in vacuo and product purified by flash column chromatography (hexane/EtOAc 100:0 to 70:30) to collect Example 30B as an oil.

Example 30C

Potassium; 3-Methyl-1-(2-methyl-benzyl)-2-oxo-piperidine-3-carboxylate

A solution of the product of Example 30B (0.075 gm, 0.37 mmol), 2-methyl-benzylamine (53 mg, 0.44 mmol) and MP-triacetoxy borohydride (420 mg, 0.92 mmol) in THF (2 mL) was stirred for 12 hours at 23° C. The solution was filtered and evaporated in vacuo. The resulting oil was taken up in THF (1.2 mL) and stirred with KOTMS (71 mg, 0.55 mmol) at 23° C. for 12 hours. The solvent was evaporated in vacuo to provide the title compound as a white solid.

Example 30D

E-[4-(aminocarbonyl)-2-adamantyl]-3-methyl-1-(2-methylbenzyl)-2-oxopiperidine-3-carboxamide A solution of the product of Example 30 C (50 mg, 0.167 mmol), the product of Example 1C (49 mg, 0.2 mmol), TBTU (85 mg, 0.26 mmol) and DIEA (53 mg, 0.42 mmol) in DMF (1.2 mL) was stirred for 2 hours at 23° C. The reaction was partitioned between EtOAc (8 ml) and water (4 ml). The organic layer was separated and washed twice with water (4 mL each), dried with MgSO$_4$, filtered and evaporated in vacuo. The resulting oil was taken in THF (1 mL) and stirred with KOTMS (32 mg, 0.25 mmol) at 23° C. for 12 hours. The solvent was evaporated in vacuo. The resulting solid was taken in DMF (1 mL) and stirred with TBTU (96 mg, 0.3 mmol) and DIEA (53 mg, 0.42 mmol) for 2 hours at 23° C. Ammonium hydroxide-30% by weight (2 mL) was added and stirred for a further 30 minutes at 23° C. The reaction was partitioned between EtOAc (8 mL) and water (3 mL). The organic layer was washed with water (3 mL), dried with MgSO$_4$ and evaporated in vacuo. The crude reaction mixture was purified by preparative reverse phase HPLC on a Waters Symmetry C8 column (25 mm×100 mm, 7 um particle size) using a gradient of 20% to 100% acetonitrile:water (0.1% TFA) over 18 min at a flow rate of 40 mL/min. to provide the title compound. $^1$H NMR (500 MHz, CDCl$_3$) δ ppm 8.25 (d, J=8.1 Hz, 1H), 7.19 (m, 2H), 7.13 (m, 1H), 7.02 (d, J=7.5 Hz, 1H), 6.6 (bs, 1H), 5.82 (bs, 1H), 4.93 (d, J=15.3, 1H), 4.38 (d, J=15.3, 1H), 4.01 (m, 1H), 3.22 (m, 2H), 2.67 (m, 1H), 2.28 (s, 3H), 2.1 (m, 1H), 1.99 (m, 6H), 1.81 (m, 5H), 1.57 (m, 2H), 1.56 (s, 3H); MS (APCI) m/z 438 (M+H)

Example 31

E-4-(aminocarbonyl)-2-adamantyl]-1-benzyl-3-methyl-2-oxopyrrolidine-3-carboxamide

Example 31A

2-Allyl-2-methyl-malonic acid dimethyl ester

A stirred solution of NaH-60% by weight (0.493 gm, 12.34 mmol) in DMF (5 mL) was cooled to 0° C. and dimethyl methyl malonate (1.2 gm, 8.23 mmol) in 3 mL of DMF was added dropwise. The reaction was warmed to ambient temperature and stirred for 15 minutes. A solution of allyl bromide (1.18 gm, 9.86 mmol) in 1.5 nit of DMF was added to the reaction mixture and stirred for 12 hours at 23° C. The reaction was partitioned between 10% NH$_4$Cl (20 mL) and 30 mL of EtOAc. The organic layer was washed with water (20 mL), brine (20 mL), dried with MgSO$_4$, filtered and evaporated in vacuo. The crude product was purified by flash chromatography (hexane/EtOAC 100:0 to 85:15) to provide the title compound as an oil.

Example 31B

2-Methyl-2-(2-oxo-ethyl)-malonic acid dimethyl ester

A solution of the product of Example 31A (1.1 gm, 5.9 mmol) was dissolved in CH$_2$Cl$_2$/MeOH 10:1 (15 mL) and cooled to −78° C. To the solution was bubbled O$_3$ over 20 minutes. The reaction solution was purged with N$_2$ for a further 10 minutes and dimethyl sulfide (DMS) (3.6 gm, 59 mmol) was added and the reaction warmed to ambient temperature and stirred for a further 2 hours. The solvent was evaporated in vacuo and product purified by flash column chromatography (hexane/EtOAc 100:0 to 70:30) to collect Example 31B as an oil.

Example 31C

Potassium; 1-benzyl-3-methyl-2-oxo-pyrrolidine-3-carboxylate

A solution of the product of Example 31B (0.075 gm, 0.4 mmol), benzylamine (51 mg, 0.47 mmol) and MP-triacetoxy borohydride (431 mg, 1 mmol) in THF (2 mL) was stirred for 12 hours at 23° C. The solution was filtered and evaporated in vacuo. The resulting oil was taken up in THF (1.2 mL) and stirred with KOTMS (77 mg, 0.6 mmol) for 12 hours at 23° C. The solvent was evaporated in vacuo to provide Example 31C.

Example 31D

E-4-(aminocarbonyl)-2-adamantyl]-1-benzyl-3-methyl-2-oxopyrrolidine-3-carboxamide A solution of the product of Example 31C (50 mg, 0.18 mmol), the product of Example 1C (54 mg, 0.22 mmol), TBTU (92 mg, 0.29 mmol) and DIEA (57 mg, 0.45 mmol) in DMF (1.2 mL) was stirred for 2 hours at 23° C. The reaction was partitioned between EtOAc (8 ml) and water (4 ml). The organic layer was separated and washed twice with water (4 mL each), dried with MgSO$_4$, filtered and evaporated in vacuo. The resulting oil was taken in THF (1 mL) and stirred with KOTMS (34 mg, 0.27 mmol) for 12 hours at 23° C. The solvent was evaporated in vacuo. The resulting solid was taken in DMF (1 mL) and stirred with TBTU (104 mg, 0.32 mmol) and DIEA (57 mg, 0.45 mmol) for 2 hours at 23° C. Ammonium hydroxide-30% by weight (2 mL) was added and stirred for a further 30 minutes. The reaction was partitioned between EtOAc (8 mL) and water (3 mL). The organic layer was washed with water (3 mL), dried with $MgSO_4$ and evaporated in vacuo. The crude reaction mixture was purified by preparative reverse phase HPLC on a Waters Symmetry C8 column (25 mm×100 mm, 7 um particle size) using a gradient of 20% to 100% acetonitrile:water (0.1% TFA) over 18 min at a flow rate of 40 mL/min. to provide the title compound. $^1$H NMR (400 MHz, Chloroform-$d_1$) δ ppm 8.18-8.23 (m, 1H), 7.29-7.35 (m, 3H), 7.19-7.21 (m, 2H), 5.48-5.70 (m, 2H), 4.51 (d, J=14.73 Hz, 1H), 4.43 (d, J=14.58 Hz, 1H), 3.99-4.05 (m, 1H), 3.14-3.21 (m, 2H), 2.60-2.68 (m, 1H), 2.09-2.15 (m, 1H), 2.01-2.09 (m, 2H), 1.87-2.00 (m, 8H), 1.84-1.86 (m, 1H), 1.57-1.66 (m, 2H), 1.48 (s, 3H); MS (APCI) m/z 410 (M+H)

Example 32

E-4-(aminocarbonyl)-2-adamantyl]-3-methyl-1-(2-methylbenzyl)-2-oxopyrrolidine-3-carboxamide Example 32A Potassium; 3-methyl-1-(2-methyl-benzyl)-2-oxo-pyrrolidine-3-carboxylate A solution of the product of Example 31B (0.075 gm, 0.4 mmol), 2-methyl-benzylamine (58 mg, 0.47 mmol) and MP-triacetoxy borohydride (431 mg, 1 mmol) in THF (2 mL) was stirred for 12 hours at 23° C. The solution was filtered and evaporated in vacuo. The resulting oil was taken up in THF (1.2 mL) and stirred with KOTMS (77 mg, 0.6 mmol) for 12 hours at 23° C. The solvent was evaporated in vacuo to provide Example 32A.

Example 32B

E-4-(aminocarbonyl)-2-adamantyl]-3-methyl-1-(2-methylbenzyl)-2-oxopyrrolidine-3-carboxamide A solution of Example 32A (50 mg, 0.17 mmol), the product of Example 1C (52 mg, 0.21 mmol), TBTU (87 mg, 0.27 mmol) and DIEA (54 mg, 0.42 mmol) in DMF (1.2 mL) was stirred for 2 hours at 23° C. The reaction was partitioned between EtOAc (8 ml) and water (4 ml). The organic layer was separated and washed twice with water (4 mL each), dried with $MgSO_4$, filtered and evaporated in vacuo. The resulting oil was taken in THF (1 mL) and stirred with KOTMS (33 mg, 0.25 mmol) for 12 hours at 23° C. The solvent was evaporated in vacuo. The resulting solid was taken in DMF (1 mL) and stirred with TBTU (98 mg, 0.31 mmol) and DIEA (54 mg, 0.42 mmol) for 2 hours. Ammonium hydroxide-30% by weight (2 mL) was added and stirred for a further 30 minutes at 23° C. The reaction was partitioned between EtOAc (8 mL) and water (3mL). The organic layer was washed with water (3 mL), dried with $MgSO_4$ and evaporated in vacuo. The crude reaction mixture was purified by preparative reverse phase HPLC on a Waters Symmetry C8 column (25 mm×100 mm, 7 um particle size) using a gradient of 20% to 100% acetonitrile:water (0.1% TFA) over 18 min at a flow rate of 40 mL/min. to provide the title compound. $^1$H NMR (400 MHz, Chloroform-$d_1$) δ ppm 8.17-8.22 (m, 1H), 7.12-7.24 (m, 3H), 7.08-7.11 (m, 1H), 5.56-5.66 (m, 1H), 5.34-5.43 (m, 1H), 4.50-4.51 (m, 2H), 3.99-4.05 (m, 1H), 3.07-3.17 (m, 2H), 2.65 (ddd, J=13.33, 8.70, 7.16 Hz, 1H), 2.28 (s, 3H), 2.08-2.15 (m, 1H), 1.81-2.07 (m, 1H), 1.53-1.68 (m, 2H), 1.49 (s, 3H); MS (APCI) m/z 424 (M+H)

Example 33

E-4-(aminocarbonyl)-2-adamantyl]-1-(2-chlorobenzyl)-3-methyl-2-oxo-pyrrolidine-3-carboxamide Example 33A Potassium; 1-(2-chloro-benzyl)-methyl-2-oxo-pyrrolidine-3-carboxylate A solution of the product of 31B (0.075 gm, 0.4 mmol), 2-chloro-benzylamine (68 mg, 0.47 mmol) and MP-triacetoxy borohydride (431 mg, 1 mmol) in THF (2 mL) was stirred for 12 hours at 23° C. The solution was filtered and evaporated in vacuo. The resulting oil was taken up in THF (1.2 mL) and stirred with KOTMS (77 mg, 0.6 mmol) for 12 hours at 23° C. The solvent was evaporated in vacuo to provide Example 33A.

Example 33B

E-4-(aminocarbonyl)-2-adamantyl]-1-(2-chlorobenzyl)-3-methyl-2-oxopyrrolidine-3-carboxamide A solution of the product of Example 33A (50 mg, 0.16 mmol), the product of Example 1C (48 mg, 0.19 mmol), TBTU (82 mg, 0.25 mmol) and DIEA (51 mg, 0.4 mmol) in DMF (1.2 mL) was stirred for 2 hours at 23° C. The reaction was partitioned between EtOAc (8 ml) and water (4 ml). The organic layer was separated and washed twice with water (4 mL each), dried with $MgSO_4$, filtered and evaporated in vacuo. The resulting oil was taken in THF (1 mL) and stirred with KOTMS (31 mg, 0.24 mmol) for 12 hours at 23° C. The solvent was evaporated in vacuo. The resulting solid was taken in DMF (1 mL) and stirred with TBTU (92 mg, 0.29 mmol) and DIEA (51 mg, 0.4 mmol) for 2 hours at 23° C. Ammonium hydroxide-30% by weight (2 mL) was added and stirred at 23° C. for a further 30 minutes. The reaction was partitioned between EtOAc (8 mL) and water (3 mL). The organic layer was washed with water (3 mL), dried with $MgSO_4$ and evaporated in vacuo. The crude reaction mixture was purified by preparative reverse phase HPLC on a Waters Symmetry C8 column (25 mm×100 mm, 7 um particle size) using a gradient of 20% to 100% acetonitrile:water (0.1% TFA) over 18 min at a flow rate of 40 mL/min. to provide the title compound. $^1$H NMR (400 MHz, Chloroform-$d_1$) δ ppm 8.13-8.19 (m, 1H), 7.34-7.41 (m, 1H), 7.19-7.28 (m, 3H), 5.60-5.65 (bs, 1H), 5.54-5.60 (bs, 1H), 4.62-4.64 (m, 2H), 3.99-4.05 (m, 1H), 3.15-3.30 (m, 2H), 2.63-2.73 (m, 1H), 2.09-2.15 (m, 1H), 1.80-2.08 (m, 11H), 1.53-1.66 (m, 2H), 1.49 (s, 3H); MS (PCI) m/z 444 (M+H).

Example 34

E-4-(aminocarbonyl)-2-adamantyl]-1-(3-chlorobenzyl)-3-methyl-2-oxopyrrolidine-3-carboxamide Example 34A Potassium; 1-(3-chloro-benzyl)-3-methyl-2-oxo-pyrrolidine-3-carboxylate A solution of the product of Example 31B (0.075 gm, 0.4 mmol), 3-chloro-benzylamine (68 mg, 0.47 mmol) and MP-triacetoxy borohydride (431 mg, 1 mmol) in THF (2 mL) was stirred for 12 hours at 23° C. The solution was filtered and evaporated in vacuo. The resulting oil was taken up in THF (1.2 mL) and stirred with KOTMS (77 mg, 0.6 mmol) at 23° C. for 12 hours. The solvent was evaporated in vacuo to provide Example 34A.

Example 34B

E-4-(aminocarbonyl)-2-adamantyl]-1-(3-chlorobenzyl)-3-methyl-2-oxopyrrolidine-3-carboxamide A solution of the product of Example 34A (50 mg, 0.16 mmol), the product of Example 1C (48 mg, 0.19 mmol), TBTU (82 mg, 0.25 mmol) and DIEA (51 mg, 0.4 mmol) in DMF (1.2 mL) was stirred for 2 hours at 23° C. The reaction was partitioned between EtOAc (8 ml) and water (4 ml). The organic layer was separated and washed twice with water (4 mL each), dried with $MgSO_4$, filtered and evaporated in vacuo. The resulting oil was taken in THF (1 mL) and stirred with KOTMS (31 mg, 0.24 mmol) at 23° C. for 12 hours. The solvent was evaporated in vacuo. The resulting solid was taken in DMF (1 mL) and stirred with TBTU (92 mg, 0.29 mmol) and DIEA (51 mg, 0.4 mmol) for 2 hours at 23° C. Ammonium hydroxide-30% by weight (2 mL) was added and stirred at 23° C. for a further 30 minutes. The reaction was partitioned between. EtOAc (8 mL) and water (3 mL). The organic layer was washed with water (3 mL), dried with $MgSO_4$ and evaporated in vacuo. The crude reaction mixture was purified by preparative reverse phase HPLC on a Waters Symmetry C8 column (25 mm×100 mm, 7 um particle size) using a gradient of 20% to 100% acetonitrile:water (0.1% TFA) over 18 min at a flow rate of 40 mL/min. to provide the title compound. $^1$H NMR (400 MHz, Chloroform-$d_1$) δ ppm 8.11 (d, J=7.93 Hz, 1H), 7.26-7.29 (m, 2H), 7.18-7.20 (m, 1H), 7.07-7.10 (m, 1H), 5.64-5.79 (m, 2H), 4.44 (s, 2H), 3.99-4.04 (m, 1H), 3.18-3.23 (m, 2H), 2.68 (ddd, J=15.66, 8.55, 7.17 Hz, 1H), 2.02-2.15 (m, 3H), 1.88-2.02 (m, 8H), 1.81-1.88 (m, 1H), 1.58-1.66 (m, 2H), 1.49 (s, 3H); MS (APCI) m/z 444.

Example 35

E-4-({2-methyl-2-[4-(1-methyl-1H-pyrazol-4-yl) phenyl]propanoyl}amino)adamantane-1-carboxamide

Example 35A

E-4-{2-Methyl-2-[4-(1-methyl-1H-pyrazol-4-yl)-phenyl]-propionylamino}-adamantane-1-carboxylic acid methyl ester The title compound was prepared according to the method of Example 22D substituting 1-methyl-4-(4,4,5,5-tetramethyl-1,3,2-dioxaborolan-2-yl)-1H-pyrazole for pyridine-4-boronic acid.

Example 35B

E-4-{2-Methyl-2-[4-(1-methyl-1H-pyrazol-4-yl)-phenyl]-propionylamino}-adamantane-1-carboxylic acid The title compound was prepared according to the method of Example 23D, substituting the product of Example 35A for the product of Example 23C.

Example 35C

E-4-{2-Methyl-2-[4-(1-methyl-1H-pyrazol-4-yl)-phenyl]-propionylamino}-adamantane-1-carboxylic acid amide A solution of the product of Example 35B (240 mg, 0.55 mmoles), N-(3-dimethylaminopropyl)-N'-ethylcarbodiimide hydrochloride (421 mg, 2.2 mmoles) and 1-hydroxybenzotriazole hydrate (167 mg, 1.24 mmoles) in dichloromethane (19 ml) was stirred at ambient temperature under a nitrogen atmosphere for about 1 hour. A 0.5 M solution of ammonia in dioxane (11.0 ml, 5.50 mmoles) was added and stirring was continued for about 2 hours. Ammonium hydroxide (9.5 ml) was added to the reaction mixture and stirring was continued for about 2 hours. The mixture was diluted with dichloromethane (60 ml), the layers were separated, the organic layer was dried ($MgSO_4$), filtered and the filtrate was evaporated in vacuum. The residue was purified by flash column chromatography on silica gel using dichloromethane/methanol (15:1) as the mobile phase to provide the title compound. $^1$H NMR (500 MHz, DMSO-$d_6$) δ ppm 8.11 (s, 1H), 7.83 (s, 1H), 7.51-7.53 (m, 2H), 7.31-7.33 (m, 2H), 6.95-6.97 (bs, 1H), 6.69-6.71 (bs, 1H), 6.28 (d, J=6.87 Hz, 1H), 3.85 (s, 3H), 3.74-3.78 (m, 1H), 1.84-1.89 (m, 2H), 1.73-1.82 (m, 5H), 1.67-1.70 (m, 2H), 1.54-1.60 (m, 2H), 1.49 (s, 6H), 1.31-1.37 (m, 2H); MS (ESI+) m/z 421 (M+H)$^+$.

Example 36

E-4-{[2-(3-bromophenyl)-2-methylpropanoyl] amino}adamantane-1-carboxamide

Example 36A

(3-Bromophenyl)-acetic acid methyl ester

A solution of 3-bromophenylacetic acid (2.0 g, 9.3 mmol) and 4-dimethylamino pyridine (1.1 g, 9.3 mmol) in methanol (20 mL) was treated with N-(3-dimethylaminopropyl)-N'-ethylcarbodiimide hydrochloride (EDAC) (2.1 g, 11 mmol). Reaction stirred for 16 hours at room temperature. The reaction mixture was concentrated under reduced pressure. The residue was taken up in ethyl acetate and washed with water, saturated sodium bicarbonate, 1N phosphoric acid, and brine before drying over $Na_2SO_4$, filtering, and concentrating under reduced pressure to provide the title compound.

Example 36B

2-(3-Bromophenyl)-2-methylpropionic acid methyl ester

A 0° C. solution of the product of Example 36A (2.1 g, 9.3 mmol) in anhydrous dimethylformamide (20 mL) was treated portion-wise with 60% sodium hydride (890 mg, 22 mmol) in mineral oil. The reaction mixture was stirred for twenty minutes at 0° C., and methyl iodide (1.4 mL, 22 mmol) was then added. Ice bath was removed, and reaction mixture stirred 16 hours at room temperature. Reaction mixture quenched with saturated ammonium chloride, and product extracted with ethyl acetate (2×). The combined extracts were washed with water and brine, dried ($Na_2SO_4$), filtered, and concentrated under reduced pressure. Residue purified by normal phase HPLC on silica gel eluting with 10% ethyl acetate/hexane to provide the title compound.

Example 36C

2-(3-Bromophenyl)-2-methylpropionic acid

The title compound was prepared according to the method as described in Example 27B, substituting the product of Example 36B for the product of Example 27A.

Example 36D

E-4-[2-(3-Bromophenyl)-2-methylpropionylamino]-adamantane-1-carboxylic acid methly ester The title compound was prepared according to the method as described in Example 27A, substituting the product of Example 36C for 1-(4-methoxyphenyl)-1-cyclopentanecarboxylic acid.

Example 36E

E-4-[2-(3-Bromophenyl)-2-methylpropionylamino]-adamantane-1-carboxylic acid The title compound was prepared according to the method as described in Example 27B, substituting the product of Example 36D for the product of Example 27A.

Example 36F

E-4-[2-(3-Bromophenyl)-2-methylpropionylamino]-adamantane-1-carboxylic acid amide The title compound was prepared according to the method as described in Example 27C, substituting the product of Example 36E for the product of Example 27B. $^1$H NMR (400 MHz, DMSO-$d_6$) δ 7.48 (m, 1H), 7.42 (m, 1H), 7.20 (m, 2H), 6.95 (bs, 1H), 6.66 (bs, 1H), 6.32 (d, J=6 Hz, 1H), 3.77 (m, 1H), 1.95-1.60 (m, 11H), 1.47 (s, 6H), 1.33 (m, 2H); MS (ESI+) m/z 419 (M+H)$^+$.

Example 37

E-4-({2-[4-(3,5-dimethylisoxazol-4-yl)phenyl]-2-methylpropanoyl}amino)adamantane-1-carboxamide

Example 37A

E-4-{2-[4-(3,5-Dimethyl-isoxazol-4-yl)-phenyl]-2-methyl-propionylamino}-adamantane-1-carboxylic acid methyl ester The title compound was prepared according to the method of Example 22D, substituting 3,5-dimethyl-4-(4,4,5,5-tetramethyl-1,3,2-dioxaborolane-2-yl)isoxazole for pyridine-4-boronic acid.

Example 37B

E-4-{2-[4-(3,5-Dimethyl-isoxazol-4-yl)-phenyl]-2-methyl-propionylamino}-adamantane-1-carboxylic acid The title compound was prepared according to the method of Example 23D, substituting the product of Example 37A for the product of Example 23C.

Example 37C

E-4-{2-[1-(3,5-Dimethyl-isoxazol-4-yl)-phenyl]-2-methyl-propionylamino}-adamantane-1-carboxylic acid amide The title compound was prepared according to the method of 35C, substituting the product of Example 37B for the product of Example 35B. The crude product was purified by preparative HPLC on a Waters Symmetry C8 column (25 mm×100 mm, 7 gm particle size) using a gradient of 10% to 100% acetonitrile:0.1% aqueous TFA over 8 min (10 min run time) at a flow rate of 40 mL/min. $^1$H NMR (500 MHz, DMSO-$d_6$) δ ppm 7.44-7.46 (m, 2H), 7.35-7.37 (m, 2H), 6.95-6.97 (bs, 1H), 6.69-6.71 (bs, 1H), 6.35 (d, J=6.87 Hz, 1H), 3.74-3.78 (m, 1H), 2.38 (s, 3H), 2.21 (s, 3H), 1.87-1.89 (m, 2H), 1.73-1.83 (m, 5H), 1.67-1.73 (m, 2H), 1.56-1.60 (m, 2H), 1.53 (s, 6H), 1.32-1.36 (m, 2H); MS (ESI+) m/z 436 (M+H)$^+$.

Example 38

E-4-{[2-methyl-2-(4-pyridin-3-ylphenyl)propanoyl]amino}adamantane-1-carboxamide

Example 38A

E-4-[2-Methyl-2-(4-pyridin-3-yl-phenyl)-propionylamino]-adamantane-1-carboxylic acid methyl ester The title compound was prepared according to the method of Example 22D, substituting pyridine-3-boronic acid for pyridine-4-boronic acid.

Example 38B

E-4-[2-Methyl-2-(4-pyridin-3-yl-phenyl)-propionylamino]-adamantane-1-carboxylic acid The title compound was prepared according to the method of Example 22E substituting the product of Example 38A for the product of Example 22D.

Example 38C

E-4-[2-Methyl-2-(4-pyridin-3-yl-phenyl)-propionylamino]-adamantane-1-carboxylic acid amide The trifluoroacetic acid salt of the title compound was prepared according to the method of Example 35C, substituting the product of Example 38B for the product of Example 35B, and with the exception that the crude product was purified by preparative HPLC on a Waters Symmetry C8 column (25 mm×100 mm, 7 μm particle size) using a gradient of 10% to 100% acetonitrile:0.1% aqueous TFA over 8 min (10 min run time) at a flow rate of 40 ml/min. $^1$H NMR (400 MHz, DMSO-$d_6$) δ ppm 9.07-9.08 (bs, 1H), 8.72 (d, J=5.06 Hz, 1H), 8.47 (d, J=8.03 Hz, 1H), 7.77-7.83 (m, 3H), 7.50-7.53 (m, 2H), 6.94-6.96 (bs, 1H), 6.66-6.69 (bs, 1H), 6.48 (d, J=6.68 Hz, 1H), 3.76-3.81 (m, 1H), 1.89-1.92 (m, 2H), 1.78-1.84 (m, 5H), 1.65-1.71 (m, 4H), 1.54 (s, 6H), 1.33-1.38 (m, 2H); MS (ESI+) m/z 418 (M+H)$^+$.

Example 39

4-{[({(E)-4-[(2-methyl-2-thien-2-ylpropanoyl)amino]-1-adamantyl}carbonyl)amino]methyl}benzoic acid

Example 39A

E-4-({[4-(2-Methyl-2-thiophen-2-yl-propionylamino)-adamantane-1-carbonyl]-amino}-methyl)-benzoic acid methyl ester The title compound was prepared according to the method of Example 22C, substituting the product of Example 23D for Example 22B and substituting methyl 4-(aminomethyl)-benzoate hydrochloride for the product of Example 1C.

Example 39B

E-4-({[4-(2-Methyl-2-thiophen-2-yl-propionylamino)-adamantane-1-carbonyl]-amino}-methyl)-benzoic acid The title compound was prepared according to the method of Example 22B, substituting the product of Example 39A for the product of Example 22A. $^1$H NMR (400 MHz, DMSO-$d_6$) δ ppm 12.70-12.94 (bs, 1H), 8.04-8.09 (m, 1H), 7.85-7.88 (m, 2H), 7.46 (dd, J=5.06, 1.22 Hz, 1H), 7.28-7.36 (m, 2H), 7.10 (dd, J=3.52, 1.23 Hz, 1H), 7.02 (dd, J=5.08, 3.54 Hz, 1H), 6.25 (d, J=7.10 Hz, 1H), 4.30 (d, J=5.87 Hz, 2H), 3.71-3.76 (m, 1H), 1.75-1.86 (m, 9H), 1.57 (s, 6H), 1.48-1.55 (m, 2H), 1.37-1.42 (m, 2H); MS (ESI+) m/z 481 (M+H)$^+$.

Example 40

E-4-({2-methyl-2-[4-(1H-pyrazol-4-yl)phenyl]propanoyl}amino)adamantane-1-carboxamide

Example 40A

E-4-{2-Methyl-2-[1H-pyrazol-4-yl)-phenyl]-propionylamino}-adamantane-1-carboxylic acid methyl ester The title compound was prepared according to the method of Example 22D substituting 1-tert-butoxycarbonyl-4-(4,4,5,5-tetramethyl-1,3,2-dioxaborolan-2-yl)pyrazole for pyridine-4-boronic acid.

Example 40B

E-4-{2-Methyl-2-[4-(1H-pyrazol-4-yl)-phenyl]-propionylamino}-adamantane-1-carboxylic acid The title compound was prepared according to the method of Example 22E substituting the product of Example 40A for the product of Example 22D.

Example 40C

E-4-{2-Methyl-2-[4-(1H-pyrazol-4-yl)-phenyl]-propionylamino}-adamantane-1-carboxylic acid amide The title compound was prepared according to the method of Example 35C substituting the product of Example 40B for the product of Example 35B. $^1$H NMR (400 MHz, DMSO-$d_6$) δ ppm 8.03 (s, 2H), 7.55-7.58 (m, 2H), 7.31-7.34 (m, 2H), 6.92-6.96 (bs, 1H), 6.65-6.68 (bs, 1H), 6.25 (d, J=6.95 Hz, 1H), 5.15-5.94 (bs, 1H), 3.73-3.78 (m, 1H), 1.85-1.88 (m, 2H), 1.73-1.83 (m, 5H), 1.68-1.70 (m, 2H), 1.55-1.60 (m, 2H), 1.49 (s, 6H), 1.31-1.36 (m, 2H); MS (ESI+) m/z 407 (M+H)$^+$.

Example 41

E-4-(aminocarbonyl)-2-adamantyl]-3-methyl-1-(1-methyl-1-phenylethyl)-2-oxopyrrolidine-3-carboxamide

Example 41A

Potassium; 3-methyl-1-(1-methyl-1-phenyl-ethyl)-2-oxo-pyrrolidine-3-carboxylate

A solution of the product of Example 31B (0.075 gm, 0.4 mmol), 1-methyl-1-phenylethylamine (65 mg, 0.47 mmol) and MP-triacetoxy borohydride (431 mg, 1 mmol) in THF (2 mL) was stirred for 12 hours at 23° C. The solution was filtered and evaporated in vacuo. The resulting oil was taken up in toluene (1.5 mL) and heated at 100° C. for 5 hours. The solvent was evaporated in vacuo and the residue taken in THF (1.2 mL) and stirred with KOTMS (77 mg, 0.6 mmol) for 12 hours at 23° C. The solvent was evaporated in vacuo to provide Example 41A.

Example 41B

E-4-(aminocarbonyl)-2-adamantyl]-3-methyl-1-(1-methyl-1-phenylethyl)-2-oxopyrrolidine-3-carboxamide A solution of the product of Example 41A (50 mg, 0.16 mmol), the product of Example IC (48 mg, 0.19 mmol), TBTU (82 mg, 0.25 mmol) and DIEA (51 mg, 0.4 mmol) in DMF (1.2 mL) was stirred for 2 hours at 23° C. The reaction was partitioned between EtOAc (8 ml) and water (4 ml). The organic layer was separated and washed twice with water (4 mL each), dried with MgSO$_4$, filtered and evaporated in vacuo. The resulting oil was taken in THF (1 mL) and stirred with KOTMS (31 mg, 0.24 mmol) for 12 hours at 23° C. The solvent was evaporated in vacuo. The resulting solid was taken in DMF (1 mL) and stirred with TBTU (92 mg, 0.29 mmol) and DIEA (51 mg, 0.4 mmol) for 2 hours at 23° C. Ammonium hydroxide-30% by weight (2 mL) was added and stirred for a further 30 minutes. The reaction was partitioned between EtOAc (8 mL) and water (3 mL). The organic layer was washed with water (3 mL), dried with MgSO$_4$ and evaporated in vacuo. The crude reaction mixture was purified by preparative reverse phase HPLC on a Waters Symmetry C8 column (25 mm×100 mm, 7 um particle size) using a gradient of 20% to 100% acetonitrile:water (0.1% TFA) over 18 min at a flow rate of 40 mL/min. to provide the title compound. $^1$H NMR (500 MHz, Chloroform-$d_1$) δ ppm 7.94 (d, J=7.78 Hz, 1H), 7.27-7.34 (m, 4H), 7.21-7.25 (m, 1H), 5.98-6.02 (bs, 1H), 5.69-5.73 (bs, 1H), 3.95-4.00 (m, 1H), 3.39-3.47 (m, 2H), 2.69 (ddd, J=13.17, 8.02, 6.58 Hz, 1H), 2.03-2.06 (m, 1H), 1.94-2.01 (m, 6H), 1.91 (ddd, J=13.24, 7.44, 5.76 Hz, 1H), 1.86-1.88 (m, 2H), 1.76-1.81 (m, 1H), 1.75 (s, 3H), 1.72 (s, 3H), 1.64-1.69 (m, 1H), 1.47-1.56 (m, 2H), 1.43 (s, 3H); MS (APCI) m/z 438 (M+H).

Example 42

E-4-(aminocarbonyl)-2-adamantyl]-3-methyl-2-oxo-
1-[(1R)-1-phenylethyl]pyrrolidine-3-carboxamide

Example 42A

Potassium; 3-methyl-2-oxo-1-((1R)-1-phenylethyl)
pyrrolidine-3-carboxylate

A solution of the product of Example 31B (0.075 gm, 0.4 mmol), (R)-1-phenylethylamine (58 mg, 0.47 mmol) and MP-triacetoxy borohydride (431 mg, 1 mmol) in THF (2 mL) was stirred for 12 hours at 23° C. The solution was filtered and evaporated in vacuo. The resulting oil was taken up in toluene (1.5 mL) and heated at 100° C. for 5 hours. The solvent was evaporated in vacuo and the residue taken in THF (1.2 mL) and stirred with KOTMS (77 mg, 0.6 mmol) for 12 hours at 23° C. The solvent was evaporated in vacuo to provide Example 42A as 1:1 mixture of diastereomers.

Example 42B

E-4-(aminocarbonyl)-2-adamantyl]-3-methyl-2-oxo-
1-[(1R)-1-phenylethyl]pyrrolidine-3-carboxamide A solution of the product of Example 42A (50 mg, 0.17 mmol), the product of Example IC (52 mg, 0.21 mmol), TBTU (87 mg, 0.27 mmol) and DIEA (51 mg, 0.4 mmol) in DMF (1.2 mL) was stirred for 2 hours at 23° C. The reaction was partitioned between EtOAc (8 ml) and water (4 ml). The organic layer was separated and washed twice with water (4 mL each), dried with MgSO$_4$, filtered and evaporated in vacuo. The resulting oil was taken in THF (1 mL) and stirred with KOTMS (32 mg, 0.25 mmol) for 12 hours at 23° C. The solvent was evaporated in vacuo. The resulting solid was taken in DMF (1 mL) and stirred with TBTU (98 mg, 0.31 mmol) and DIEA (51 mg, 0.4 mmol) for 2 hours at 23° C. Ammonium hydroxide-30% by weight (2 mL) was added and stirred for a further 30 minutes. The reaction was partitioned between EtOAc (8 mL) and water (3 mL). The organic layer was washed with water (3 mL), dried with MgSO$_4$, filtered and evaporated in vacuo. The crude reaction mixture was purified by preparative reverse phase HPLC on a Waters Symmetry C8 column (25 mm×100 mm, 7 um particle size) using a gradient of 20% to 100% acetonitrile:water (0.1% TFA) over 18 min at a flow rate of 40 mL/min. to provide the title compound as a 1:1 mixture of diastereomers. $^1$H NMR (500 MHz, Chloroform-d$_1$) δ ppm 8.3 (m, 2H), 7.38-7.22 (m, 10H), 6.34-6.18 (bs, 2H), 5.83-5.68 (bs, 2H), 5.52-5.41 (m, 2H), 4.06-3.95 (m, 2H), 3.31-3.18 (m, 2H), 3.01-2.78 (m, 2H), 2.62-2.44 (m, 4H), 2.1-1.87 (m, 24H), 1.56-1.53 (m, 6H), 1.47-1.43 (m, 6H); MS (APCI) m/z 424 (M+H).

Example 43

E-4-(aminocarbonyl)-2-adamantyl]-3-methyl-2-oxo-
1-[(1S)-1-phenyl ethyl]pyrrolidine-3-carboxamide

Example 43A

Potassium; 3-methyl-2-oxo-1-((1S)-1-phenylethyl)
pyrrolidine-3-carboxylate

A solution of the product of Example 31B (0.075 gm, 0.4 mmol), (S)-1-phenylethylamine (58 mg, 0.47 mmol) and MP-triacetoxy borohydride (431 mg, 1 mmol) in THF (2 mL) was stirred for 12 hours at 23° C. The solution was filtered and evaporated in vacuo. The resulting oil was taken up in toluene (1.5 mL) and heated at 100° C. for 5 hours. The solvent was evaporated in vacuo and the residue taken in THF (1.2 mL) and stirred with KOTMS (77 mg, 0.6 mmol) at 23° C. for 12 hours. The solvent was evaporated in vacuo to provide Example 43A as a 1:1 mixture of diastereomers.

Example 43B

E-4-(aminocarbonyl)-2-adamantyl]-3-methyl-2-oxo-
1-[(1S)-1-phenylethyl]pyrrolidine-3-carboxamide A solution of the product of Example 43A (50 mg, 0.17 mmol), the product of Example 1C (52 mg, 0.21 mmol), TBTU (87 mg, 0.27 mmol) and DTEA (51 mg, 0.4 mmol) in DMF (1.2 mL) was stirred at 23° C. for 2 hours. The reaction was partitioned between EtOAc (8 ml) and water (4 ml). The organic layer was separated and washed twice with water (4 mL each), dried with MgSO$_4$, filtered and evaporated in vacuo. The resulting oil was taken in THF (1 mL) and stirred with KOTMS (32 mg, 0.25 mmol) at 23° C. for 12 hours. The solvent was evaporated in vacuo. The resulting solid was taken in DMF (1 mL) and stirred with TBTU (98 mg, 0.31 mmol) and DTEA (51 mg, 0.4 mmol) at 23° C. for 2 hours. Ammonium hydroxide-30% by weight (2 mL) was added and stirred for a further 30 minutes. The reaction was partitioned between EtOAc (8 mL) and water (3 mL). The organic layer was washed with water (3 mL), dried with MgSO$_4$, filtered, and evaporated in vacuo. The crude reaction mixture was purified by preparative reverse phase HPLC on a Waters Symmetry C8 column (25 mm×100 mm, 7 um particle size) using a gradient of 20% to 100% acetonitrile:water (0.1% TFA) over 18 min at a flow rate of 40 mL/min. to provide the title compound as a 1:1 mixture of diastereomers. $^1$H NMR (500 MHz, Chloroform-d$_1$) δ ppm 8.29 (m, 2H), 7.34-7.18 (m, 10H), 6.30-6.14 (bs, 2H), 5.79-5.66 (bs, 2H), 5.48-5.37 (m, 2H), 4.06-3.95 (m, 2H), 3.31-3.18 (m, 2H), 3.01-2.78 (m, 2H), 2.62-2.44 (m, 4H), 2.1-1.87 (m, 24H), 1.56-1.53 (m, 6H), 1.47-1.43 (m, 6H); MS (APCI) m/z 424 (M+H).

Example 44

E-4-{[2-methyl-2-(1,3-thiazol-2-yl)propanoyl]
amino}adamantane-1-carboxamide

Example 44A

Diethyl 2-(3-(ethoxycarbonyl)-2,3-dihydrothiazol-2-
yl)malonate

Ethyl chloroformate (6.46 ml, 67.8 mmoles) was added dropwise to a stirred solution of thiazole (5.0 g, 58.7 mmoles) in tetrahydrofuran (113.0 ml) at about 0° C. under a nitrogen atmosphere. After about 1 hour, a freshly prepared solution of lithio diethylmalonate (To a solution of diethylmalonate (10.3 ml, 67.8 mmoles) in tetrahydrofuran (17.0 ml) was added dropwise a 1 M solution of lithium bis(trimethylsilyl)amide in tetrahydrofuran (67.8 ml, 67.8 mmoles) and the mixture was stirred at 23° C. for about 10 min) was added via cannula and the mixture was stirred at room temperature for about 18 hours. The mixture was diluted with diethyl ether (60.0 ml), was washed with saturated aqueous ammonium chloride (140.0 ml) and brine (120.0 ml). The organic layer was dried over MgSO$_4$, filtered, concentrated in vacuum and the crude product was purified by flash column chromatography on silica gel using hexanes/ethyl acetate (2:1) as the mobile phase to provide the title compound.

Example 44B

Diethyl 2-(thiazol-2(3H)-ylidene)malonate

To a solution of the product of Example 44A (12.9 g, 40.7 mmoles) in dichloromethane (100.0 ml) was added tetrachloro-1,2-benzoquinone (10.0 g, 40.7 mmoles) in portions at about 0° C., such that the mixture always had time to decolorize to a yellow-orange color. The mixture was then stirred for about 1 hour at 0° C. and was then washed with saturated aqueous sodium bicarbonate solution (200.0 ml) and brine (100.0 ml). The organic layer was dried over $MgSO_4$, filtered, concentrated in vacuum and the crude product was purified by flash column chromatography on silica gel using hexanes/ethyl acetate (2:1) as the mobile phase to provide the title compound.

Example 44C

Ethyl 2-(thiazol-2-yl)acetate

A solution of the product of Example 44B (2.8 g, 11.5 mmoles), sodium chloride (1.3 g, 22.9 mmoles) and water (0.4 ml, 22.9 mmoles) in dimethyl sulfoxide (48.0 ml) was stirred at about 180° C. for about 30 min. The mixture was cooled, diluted with water (100.0 ml) and was extracted twice with (1:1) ethyl acetate/diethyl ether (80.0 ml each). The combined organic extracts were washed with brine, dried over $MgSO_4$, filtered and concentrated in vacuum. The crude product was purified by flash column chromatography on silica gel using hexanes/ethyl acetate (2:1) as the mobile phase to provide the title compound.

Example 44D

Ethyl 2-methyl-2-(thiazol-2-yl)propanoate

The title compound was prepared according to the method of Example 22A substituting the product of Example 44C for ethyl 4-bromophenylacetate.

Example 44E

2-Methyl-2-(thiazol-2-yl)propanoic acid

The title compound was prepared according to the method of Example 22B substituting the product of Example 44D for the product of Example 22A.

Example 44F

E-4-(2-Methyl-2-thiazol-2-yl-propionylamino)-adamantane-1-carboxylic acid methyl ester The title compound was prepared according to the method of Example 22C substituting the product of Example 44E for the product of Example 22B.

Example 44G

E-4-(2-Methyl-2-thiazol-2-yl-propionylamino)-adamantane-1-carboxylic acid

The title compound was prepared according to the method of Example 23D substituting the product of Example 44F for the product of Example 23C.

Example 44H

E-4-(2-Methyl-2-thiazol-2-yl-propionylamino)-adamantane-1-carboxylic acid amide

The title compound was prepared according to the method of Example 35C substituting the product of Example 44G for the product of Example 35B. $^1$H NMR (400 MHz, DMSO-$d_6$) δ ppm 7.86 (d, J=3.30 Hz, 1H), 7.71 (d, J=3.29 Hz, 1H), 7.42 (d, J=7.26 Hz, 1H), 6.94-6.97 (bs, 1H), 6.67-6.69 (bs, 1H), 3.72-3.77 (m, 1H), 1.82-1.88 (m, 3H), 1.75-1.82 (m, 4H), 1.71-1.74 (m, 2H), 1.62 (s, 6H), 1.57-1.64 (m, 2H), 1.39-1.47 (m, 2H); MS (ESI+) m/z 348 (M+H)$^+$.

Example 45

E-4-(aminocarbonyl)-2-adamantyl]-1-(4-chlorobenzyl)-3-methylpiperidine-3-carboxamide

Example 45A

Piperidine-1,3-dicarboxylic acid 1-benzyl ester 3-ethyl ester

To a room temperature solution of 4.05 g (25.8 mmoles) of ethyl nipecotate and 4.33 g (51.5 mmoles) of $NaHCO_3$ in water (26 mL) was added benzyl chloroformate (4.1 mL, 28.3 mmol). The reaction mixture was stirred at 23° C. under an atmosphere of $N_2$ overnight. The crude products were diluted with water, extracted with $Et_2O$, washed with brine, dried over $Na_2SO_4$, filtered, and concentrated in vacuo. The crude product was purified by silica gel chromatography employing a solvent gradient (hexane→70:30 hexane:EtOAc) to yield the title compound as a clear colorless oil.

Example 45B

3-Methyl-piperidine-1,3-dicarboxylic acid 1-benzyl ester

To a −78° C. solution of the product of Example 45A (6.0 g, 20.6 mmoles) in THF (50 mL) was added a solution of lithium bis(trimethylsilyl)amide (1.0 M in THF, 22.7 mmoles). After 35 min, iodomethane (1.4 mL, 22.7 mmoles) was added and the reaction was slowly warmed to room temperature and stirred overnight. The reaction was quenched with aqueous sat. ammonium chloride and extracted with $Et_2O$. The organic layer was then rinsed with brine, dried over $Na_2SO_4$, filtered, and concentrated in vacuo. The crude product was purified by silica gel chromatography employing a solvent gradient (hexane→65:35 hexane:EtOAc). The resulting ester was hydrolyzed overnight at room temperature in THF (15 mL), $H_2O$ (10 mL), and EtOH (15 mL) with NaOH (2.5 g). The solution was concentrated under vacuum; the residue was dissolved in saturated ammonium chloride; and, the solution was extracted with ethyl acetate (3×). The combined ethyl acetate extracts were dried over sodium sulfate, filtered, and concentrated under vacuum to yield the title compound as a white solid.

Example 45C

N-[E-4-(carbomethoxy)-2-adamantyl]-1-(4-benzyloxycarbonyl)-3-methylpiperidine-3-carboxamide The title compound was prepared according to the procedure outlined in Example 7, substituting the product of Example 45B for 2-phenylisobutyric acid and substituting the product of Example 1C for 2-adamantanamine hydrochloride.

Example 45D

N-[E-4-(carbomethoxy)-2-adamantyl]-1-3-methylpiperidine-3-carboxamide

A solution of the product of Example 45C (0.62 g, 1.32 mmoles) and 10% palladium on carbon (60 mg) in EtOAc (20 mL) was exposed to hydrogen (60 psi) at room temperature for 6 hours. The reaction was incomplete so EtOH was added and the reaction continued for an additional 8 h. The crude product was then filtered away from the catalyst using methanol and isolated after concentration in vacuo to provide the title compound.

Example 45E

E-4-(carbomethoxy)-2-adamantyl]-1-(4-chlorobenzyl)-3-methylpiperidine-3-carboxamide To a solution of the product of Example 45D (100 mg, 0.3 mmoles) and 4-chlorobenzaldehyde in dichloroethane (0.75 mL) and acetic acid (0.07 mL, 1.2 mmoles) was added sodium triacetoxyborohydride (127 mg, 0.6 mmoles). The resulting reaction mixture was stirred at room temperature overnight. The reaction was quenched with sat. aqueous $NH_4Cl$ and extracted with EtOAc. The organic layer was then rinsed with brine, dried over $Na_2SO_4$, filtered, and concentrated in vacuo to provide a crude sample of the title compound.

Example 45F

E-4-(aminocarbonyl)-2-adamantyl]-1-(4-chlorobenzyl)-3-methylpiperidine-3-carboxamide The crude product from Example 45E was hydrolyzed with an excess of NaOH at room temperature in a solution of water, EtOH, and tetrahydrofuran for 16 hours. The reaction was quenched with sat. aqueous $NH_4Cl$ and extracted with EtOAc. The organic layer was then rinsed with brine, dried over $Na_2SO_4$, filtered, and concentrated in vacuo. The residue, EDCI (80 mg, 0.42 mmoles), and 1-hydroxybenzotriazole hydrate (56.5 mg, 0.42 mmoles) were dissolved in DMF (0.75 mL) and stirred for 30 min at room temperature. Concentrated $NH_4OH$ (0.75 mL) was then added and stirring was continued overnight. The reaction was quenched with sat. aqueous $NH_4Cl$ and extracted with EtOAc. The organic layer was then washed with water (2×), rinsed with brine, dried over $Na_2SO_4$, filtered, and concentrated in vacuo. The product was purified by reverse phase preparative HPLC (acetonitrile: 10 mM $NH_4OAc$ in $H_2O$ on a YMC prep ODS-A column) to provide the title compound. $^1H$ NMR (500 MHz, Chloroform-$d_1$) δ ppm 8.74-8.79 (m, 1H), 7.28-7.32 (m, 2H), 7.18-7.21 (m, 2H), 5.65-5.69 (bs, 1H), 5.55-5.59 (bs, 1H), 4.04-4.07 (m, 1H), 3.56 (d, J=12.82 Hz, 1H), 3.43 (d, J=12.82 Hz, 1H), 3.00-3.05 (m, 1H), 2.93-2.98 (m, 1H), 2.08-2.13 (m, 1H), 2.00-2.05 (m, 1H), 1.93-2.00 (m, 6H), 1.90-1.94 (m, 2H), 1.83-1.90 (m, 1H), 1.76-1.82 (m, 1H), 1.69-1.74 (m, 1H), 1.61-1.69 (m, 1H), 1.52-1.63 (m, 4H), 1.12 (s, 3H), 1.06-1.15 (m, 1H); MS (ESI+) m/z 444 (M+H)$^+$.

Example 46

E-4-{[2-(4-hydroxyphenyl)-2-methylpropanoyl]amino}adamantane-1-carboxamide

Example 46A 2-(4-Hydroxyphenyl)-proprionic acid methyl ester

The title compound was prepared according to the method as described in Example 36A substituting 2-(4-hydroxyphenyl)-proprionic acid for 3-bromophenylacetic acid.

Example 46B 2-(4-Allyloxyphenyl)-proprionic acid methyl ester

A solution of the product of Example 46A (2.6 g, 12 mmol) in anhydrous dimethylformamide (20 mL) was treated with potassium carbonate (3.3 g, 24 mmol) and allyl bromide (1.2 mL, 13 mmol), and reaction heated for 16 hours at 80° C. Reaction mixture cooled and diluted with ethyl acetate. Mixture washed with water and brine, dried ($Na_2SO_4$), filtered, and concentrated under reduced pressure. Residue purified by normal phase HPLC on silica gel eluting with 3% ethyl acetate/hexane to provide the title compound.

Example 46C 2-(4-Allyloxyphenyl)-2-methylproprionic acid methyl ester

A 0° C. solution of the product of Example 46B (1.9 g, 8.6 mmol) in anhydrous dimethylformamide (10 mL) was treated portion-wise with 60% sodium hydride (410 mg, 10 mmol) in mineral oil. The reaction mixture was stirred twenty minutes at 0° C., and methyl iodide (1.4 mL, 22 mmol) was then added. Ice bath was removed, and reaction mixture stirred 16 hours at room temperature. Reaction mixture quenched with saturated ammonium chloride, and product extracted with ethyl acetate (2×). The combined extracts were washed with water and brine, dried ($Na_2SO_4$), filtered, and concentrated under reduced pressure. Residue purified by normal phase HPLC on silica gel eluting with 3% ethyl acetate/hexane to provide the title compound.

Example 46D 2-(4-Allyloxyphenyl)-2-methylproprionic acid

The title compound was prepared according to the method as described in Example 27B, substituting the product of Example 46C for the product of Example 27A.

Example 46E

E-4-[2-(4-Allyloxyphenyl)-2-methylpropionylamino]-adamantane-1-carboxylic acid methyl ester The title compound was prepared according to the method as described in Example 27A, substituting the product of Example 46D for 1-(4-methoxyphenyl)-1-cyclopentanecarboxylic acid.

Example 46F

E-4-[2-(4-Hydroxyphenyl)-2-methylpropionylamino]-adamantane-1-carboxylic acid methyl ester A 0° C. solution of the product of Example 46E (1.4 g, 3.4 mmol) and tetrakis(triphenylphosphine)palladium (390 mg, 0.34 mmol) in anhydrous methylene chloride (10 mL) was treated with phenyl silane (0.84 mL, 6.8 mmol). Reaction stirred ten minutes at 0° C. and two hours at room temperature. Reaction diluted with methylene chloride, washed with brine, dried ($Na_2SO_4$), filtered, and concentrated under reduced pressure. Residue purified by normal phase HPLC on silica gel eluting with 30-40% ethyl acetate/hexane to provide the title compound.

Example 46G

E-4-[2-(4-Hydroxyphenyl)-2-methylpropionylamino]-adamantane-1-carboxylic acid

The title compound was prepared according to the method as described in Example 27B substituting the product of Example 46F for the product of Example 27A.

Example 46H

E-4-[2-(4-Hydroxyphenyl)-2-methylpropionylamino]-adamantane-1-carboxylic acid amide The title compound was prepared according to the method as described in Example 27C, substituting the product of Example 46G for the product of Example 27B. $^1$H NMR (500 MHz, DMSO-$d_6$) δ ppm 9.24-9.38 (bs, 1H), 7.15-7.17 (m, 2H), 6.95-6.97 (bs, 1H), 6.69-6.74 (m, 3H), 6.69-6.70 (m, 1H), 6.03 (d, J=7.16 Hz, 1H), 3.69-3.73 (m, 1H), 1.80-1.83 (m, 2H), 1.73-1.79 (m, 4H), 1.67-1.69 (m, 2H), 1.44-1.50 (m, 2H), 1.43 (s, 6H), 1.30-1.36 (m, 2H); MS (ESI+) m/z 357 (M+H)$^+$.

Example 47

E-4-(aminocarbonyl)-2-adamantyl]-1-benzyl-3-methyl-2-oxopiperidine-3-carboxamide

Example 47A

Potassium;
1-benzyl-3-methyl-2-oxo-piperidine-3-carboxylate

A solution of the product of Example 30B (0.075 gm, 0.37 mmol), benzylamine (47 mg, 0.44 mmol) and MP-triacetoxy borohydride (420 mg, 0.92 mmol) in THF (2 mL) was stirred for 12 hours at 23° C. The solution was filtered and evaporated in vacuo. The resulting oil was taken up in THF (1.2 mL) and stirred with KOTMS (71 mg, 0.55 mmol) for 12 hours at 23° C. The solvent was evaporated in vacuo to provide Example 47A.

Example 47B

E-4-(aminocarbonyl)-2-adamantyl]-1-benzyl-3-methyl-2-oxopiperidine-3-carboxamide A solution of the product of Example 47A (50 mg, 0.17 mmol), the product of Example 1C (49 mg, 0.2 mmol), TBTU (87 mg, 0.27 mmol) and DIEA (54 mg, 0.42 mmol) in DMF (1.2 mL) was stirred for 2 hours at 23° C. The reaction was partitioned between EtOAc (8 ml) and water (4 ml). The organic layer was separated and washed twice with water (4 mL each), dried with $MgSO_4$, filtered and evaporated in vacuo. The resulting oil was taken in THF (1 mL) and stirred with KOTMS (32 mg, 0.25 mmol) for 12 hours at 23° C. The solvent was evaporated in vacuo. The resulting solid was taken in DMF (1 mL) and stirred with TBTU (96 mg, 0.3 mmol) and DIEA (53 mg, 0.42 mmol) at 23° C. for 2 hours. Ammonium hydroxide-30% by weight (2 mL) was added and stirred for a further 30 minutes. The reaction was partitioned between EtOAc (8 mL) and water (3 mL). The organic layer was washed with water (3 mL), dried with MgSO4 and evaporated in vacuo. The crude reaction mixture was purified by preparative reverse phase HPLC on a Waters Symmetry C8 column (25 mm×100 mm, 7 um particle size) using a gradient of 20% to 100% acetonitrile:water (0.1% TFA) over 18 min at a flow rate of 40 mL/min. to provide the title compound. $^1$H NMR (500 MHz, Chloroform-$d_1$) δ ppm 8.17 (d, J=7.93 Hz, 1H), 7.27-7.34 (m, 3H), 7.21-7.24 (m, 2H), 6.12-6.17 (bs, 1H), 5.68-5.83 (m, 1H), 4.95 (d, J=14.58 Hz, 1H), 4.29 (d, J=14.59 Hz, 1H), 3.97-4.02 (m, 1H), 3.24-3.35 (m, 2H), 2.65 (ddd, J=13.31, 5.72, 2.61 Hz, 1H), 2.09-2.11 (m, 1H), 1.96-2.05 (m, 6H), 1.85-1.90 (m, 3H), 1.64-1.83 (m, 4H), 1.55-1.63 (m, 2H), 1.54 (s, 3H); MS (APCI) m/z 424 (M+H).

Example 48

E-4-{[2-methyl-2-(4-phenoxyphenyl)propanoyl] amino}adamantane-1-carboxamide

Example 48A

Methyl 2-(4-phenoxyphenyl)acetate

To a solution of 4-phenoxyphenylacetic acid (1.0 g, 4.38 mmoles) in methanol (5.0 ml) was added concentrated sulfuric acid (0.05 ml, 0.88 mmoles) and the mixture was heated to reflux for about 5 hours. The mixture was cooled and concentrated under reduced pressure. To the residue was added a saturated aqueous solution of sodium bicarbonate (20.0 ml) and the mixture was extracted with ethyl acetate. The combined organic extracts were washed with water and brine, dried over $MgSO_4$, filtered and evaporated to dryness to afford the title compound.

Example 48B

Methyl 2-methyl-2-(4-phenoxyphenyl)propanoate

The title compound was prepared according to the method of Example 22A substituting the product of Example 48A for ethyl-4-bromophenyl acetate.

Example 48C

2-Methyl-2-(4-phenoxyphenyl)propanoic acid

The title compound was prepared according to the method of Example 22B, substituting the product of Example 48B for the product of Example 22A.

Example 48D

E-4-[2-Methyl-2-(4-phenoxy-phenyl)-propionylamino]-adamantane-1-carboxylic acid methyl ester The title compound was prepared according to the method of Example 22C, substituting the product of Example 48C for the product of Example 22B.

Example 48E

E-4-[2-Methyl-2-(4-phenoxy-phenyl)-proniony-lamino]-adamantane-1-carboxylic acid The title compound was prepared according to the method of Example 23D, substituting the product of Example 48D for the product of Example 23C.

Example 48F

E-4-[2-Methyl-2-(4-phenoxy-phenyl)-propionylamino]-adamantane-1-carboxylic acid amide The title compound was prepared according to the method of Example 35C, substituting the product of Example 48E for the product of Example 35B. $^1$H NMR (400 MHz, DMSO-$d_6$) δ ppm 7.34-7.41 (m, 4H), 7.10-7.15 (m, 1H), 6.93-7.01 (m, 5H), 6.66-6.68 (bs, 1H), 6.22 (d, J=6.94 Hz, 1H), 3.72-3.77 (m, 1H), 1.85-1.88 (m, 2H), 1.73-1.84 (m, 5H), 1.70-1.71 (m, 2H), 1.53-1.59 (m, 2H), 1.49 (s, 6H), 1.33-1.38 (m, 2H); MS (ESI+) m/z 433 (M+H)$^+$.

Example 49

E-4-{[2-(1-benzothien-3-yl)-2-methylpropanoyl]amino}adamantine-1-carboxamide

Example 49A

Methyl 2-(benzo[b]thiophen-3-yl)acetate

The title compound was prepared according to the method of Example 48A substituting benzo[b]thiophene-3-acetic acid for 4-phenoxyphenylacetic acid.

Example 49B

Methyl 2-(benzo[b]thiophen-3-yl)-2-methylpropanoate

The title compound was prepared according to the method of Example 22A substituting the product of Example 48A for ethyl-4-bromophenylacetate.

Example 49C 2-(Benzo[b]thiophen-3-yl)-2-methylpropanoic acid

The title compound was prepared according to the method of Example 22B substituting the product of Example 49B for the product of Example 22A.

Example 49D 4-(2-Benzo[b]thiophen-3-yl-2-methyl-propionylamino)-adamantane-1-carboxylic acid methyl ester The title compound was prepared according to the method of Example 22C, substituting the product of Example 49C for the product of Example 22B.

Example 49E 4-(2-Benzo[b]thiophen-3-yl-2-methyl-propionylamino)-adamantane-1-carboxylic acid The title compound was prepared according to the method of Example 23D substituting the product of Example 49D for the product of Example 23C.

Example 49F 4-(2-Benzo[b]thiophen-3-yl-2-methyl-propionylamino)-adamantane-1-carboxylic acid amide The title compound was prepared according to the method of Example 35C substituting the product of Example 49E for the product of Example 35B. $^1$H NMR (400 MHz, DMSO-$d_6$) δ ppm 7.97 (s, 1H), 7.64-7.66 (m, 2H), 7.31-7.36 (m, 2H), 6.89-6.92 (bs, 1H), 6.63-6.66 (bs, 1H), 6.13 (d, J=7.21 Hz, 1H), 3.71-3.76 (m, 1H), 1.66-1.79 (m, 1.60 (s, 6H), 1.55-1.63 (m, 3H), 1.07-1.18 (m, 4H); MS (ESI+) m/z 397 (M+H)$^+$.

Example 50

E-4-{[2-(5-fluoropyridin-2-yl)-2-methylpropanoyl]amino}adamantane-1-carboxamide

Example 50A

Potassium; 2-(5-fluoro-pyridin-2-yl)-2-methyl-propionate

A solution of 2-bromo-5-fluoropyridine (315 mg, 1.8 mmol), methyl trimethylsilyl dimethylketene acetal (0.378 mg, 2.17 mmol), zinc fluoride (112 mg, 1.08 mmol), tris(dibenzylideneacetone)dipalladium(0) (20 mg, 0.021 mmol) and tri-t-butylphosphine-10 wt % in hexane (172 mg, 0.084 mmol) in Argon degassed DMF (1.5 mL) was stirred at 90° C. for 12 hours. The reaction was taken up in EtOAc (25 mL) and washed with water (15 mL) followed by brine (15 mL). The organic layer was dried with MgSO$_4$, filtered, and evaporated in vacuo. The crude product was purified by flash chromatography (hexane/EtOAc 100:0 to 80:20) to give the methyl ester of Example 50A. A solution of the corresponding methyl ester (144 mg, 0.73 mmol), potassium trimethylsilanolate (KOTMS) (140 mg, 1.1 mmol) in THF (2 mL) was stirred for 12 hours at 23° C. Methyl t-butyl ether (MTBE) 8 mL was added to the solution and Example 50A was isolated by filtration.

Example 50B

E-4-{[2-(5-fluoropyridin-2-yl)-2-methylpropanoyl]amino}adamantane-1-carboxamide A solution of the product of Example 50A (30 mg, 0.15 mmol), the product of Example 1C (45 mg, 0.18 mmol), TBTU (77 mg, 0.24 mmol) and DIEA (47 mg, 0.37 mmol) in DMF (1.2 mL) was stirred at 23° C. for 3 hrs. The reaction was diluted with EtOAc (10 mL) and washed twice with water (6 mL) and brine (6 mL). The organic layer was dried with $MgSO_4$, filtered, and evaporated in vacuo. The residue was taken in THF (1 mL) and stirred with KOTMS (29 mg, 0.22 mmol) for 12 hours at 23° C. The solvent was evaporated in vacuo. The residue solid was taken in DMF (1 mL) and added TBTU (86 mg, 0.27 mmol), DIEA (47 mg, 0.37 mmol) and stirred at 23° C. for 2 hours. Ammonium hydroxide-30% by weight (2 mL) was added and stirred for a further 30 minutes. The reaction was partitioned between EtOAc (8 mL) and water (3 mL). The organic layer was washed with water (3 mL), dried with $MgSO_4$, filtered and evaporated in vacuo. The crude reaction mixture was purified by preparative reverse phase HPLC on a Waters Symmetry C8 column (25 mm×100 mm, 7 um particle size) using a gradient of 20% to 100% acetonitrile:water (0.1% TFA) over 18 min at a flow rate of 40 mL/min. to provide the title compound as the trifluoroacetic acid salt. $^1H$ NMR (500 MHz, Chloroform-$d_1$) δ ppm 8.51-8.55 (m, 1H), 7.58-7.64 (m, 1H), 7.50-7.55 (m, 2H), 7.42-7.48 (bs, 1H), 6.83-7.12 (bs, 1H), 6.00-6.07 (bs, 1H), 3.93-3.98 (m, 1H), 2.02-2.07 (m, 3H), 1.94-1.97 (m, 4H), 1.87-1.90 (m, 2H), 1.70 (s, 6H), 1.66-1.72 (m, 2H), 1.56-1.62 (m, 2H); MS (APCI) m/z 360 (M+H).

Example 51

E-4-[(2-methyl-2-quinoxalin-2-ylpropanoyl)amino]adamantane-1-carboxamide

Example 51A

Potassium; 2-methyl-2-quinoxalin-2-yl-propionate

A solution of 2-chloroquinoxaline (295 mg, 1.8 mmol), methyl trimethylsilyl dimethylketene acetal (0.378 mg, 2.17 mmol), zinc fluoride (112 mg, 1.08 mmol), tris(dibenzylideneacetone)dipalladium(0) (20 mg, 0.021 mmol) and tri-t-butylphosphine-10 wt % in hexane (172 mg, 0.084 mmol) in Argon degassed DMF (1.5 mL) was stirred at 90° C. for 12 hours. The reaction was taken up in EtOAc (25 mL) and washed with water (15 mL) followed by brine (15 mL). The organic layer was dried with $MgSO_4$, filtered and evaporated in vacuo. The crude product was purified by flash chromatography (hexane/EtOAc 100:0 to 80:20) to give the methyl ester of Example 51A. A solution of the corresponding methyl ester (168 mg, 0.73 mmol), potassium trimethylsilanolate (KOTMS) (140 mg, 1.1 mmol) in THF (2 mL) was stirred at 23° C. for 12 hours. Methyl t-butyl ether (MTBE) 8 mL was added to the solution and Example 51A was isolated by filtration.

Example 51B

E-4-[(2-methyl-2-quinoxalin-2-ylpropanoyl)amino]adamantane-1-carboxamide

A solution of the product of Example 51A (30 mg, 0.12 mmol), the product of Example 1C (35 mg, 0.14 mmol), TBTU (61 mg, 0.19 mmol) and DIEA (38 mg, 0.3 mmol) in DMF (1.2 mL) was stirred at 23° C. for 3 hrs. The reaction was diluted with EtOAc (10 mL) and washed twice with water (6 mL) and brine (6 mL). The organic layer was dried with $MgSO_4$, filtered and evaporated in vacuo. The residue was taken in THF (1 mL) and stirred with KOTMS (23 mg, 0.18 mmol) at 23° C. for 12 hours. The solvent was evaporated in vacuo. The residue solid was taken in DMF (1 mL) and added TBTU (69 mg, 0.22 mmol), DIEA (38 mg, 0.3 mmol) and stirred at 23° C. for 2 hours. Ammonium hydroxide-30% by weight (2 mL) was added and stirred for a further 30 minutes. The reaction was partitioned between EtOAc (8 mL) and water (3 mL). The organic layer was washed with water (3 mL), dried with $MgSO_4$, filtered, and evaporated in vacuo. The crude reaction mixture was purified by preparative reverse phase HPLC on a Waters Symmetry C8 column (25 mm×100 mm, 7 um particle size) using a gradient of 20% to 100% acetonitrile:water (0.1% TFA) over 18 min at a flow rate of 40 mL/min. to provide the title compound as the trifluoroacetic acid salt. NMR (400 MHz, Chloroform-$d_1$) δ ppm 9.03 (s, 1H), 8.12-8.16 (m, 1H), 8.04-8.08 (m, 1H), 7.76-7.85 (m, 2H), 7.33-7.38 (m, 1H), 6.28-6.41 (m, 1H), 5.69-5.82 (m, 1H), 3.91-4.05 (m, 1H), 1.96-2.04 (m, 4H), 1.89-1.97 (m, 4H), 1.84-1.88 (m, 2H), 1.83 (s, 6H), 1.62-1.69 (m, 2H), 1.52-1.59 (m, 2H); MS (APCI) m/z 393 (M+H).

Biological Data

Measurement of Inhibition Constants:

The ability of test compounds to inhibit human 11β-HSD-1 enzymatic activity in vitro was evaluated in a Scintillation Proximity Assay (SPA). Tritiated-cortisone substrate, NADPH cofactor and titrated compound were incubated with truncated human 11β-HSD-1 enzyme (24-287AA) at room temperature to allow the conversion to cortisol to occur. The reaction was stopped by adding a non-specific 11β-HSD inhibitor, 18β-glycyrrhetinic acid. The tritiated cortisol was captured by a mixture of an anti-cortisol monoclonal antibody and SPA beads coated with anti-mouse antibodies. The reaction plate was shaken at room temperature and the radioactivity bound to SPA beads was then measured on a β-scintillation counter. The 11-βHSD-1 assay was carried out in 96-well microtiter plates in a total volume of 220 μl. To start the assay, 188 μl of master mix which contained 17.5 nM $^3$H-cortisone, 157.5 nM cortisone and 181 mM NADPH was added to the wells. In order to drive the reaction in the forward direction, 1 mM G-6-P was also added. Solid compound was dissolved in DMSO to make a 10 mM stock followed by a subsequent 10-fold dilution with 3% DMSO in Tris/EDTA buffer (pH 7.4). 22 μl of titrated compounds was then added in triplicate to the substrate. Reactions were initiated by the addition of 10 μl of 0.1 mg/ml *E. coli* lysates overexpressing 11β-HSD-1 enzyme. After shaking and incubating plates for 30 minutes at room temperature, reactions were stopped by adding 10 μl of 1 mM glycyrrhetinic acid. The product, tritiated cortisol, was captured by adding 10 μl of 1 mM monoclonal anti-cortisol antibodies and 100 μl SPA beads coated with anti-mouse antibodies. After shaking for 30 minutes, plates were read on a liquid scintillation counter Topcount. Percent inhibition was calculated based on the background and the maximal signal. Wells that contained substrate without compound or enzyme were used as the background, while the wells that contained substrate and enzyme without any compound were considered as maximal signal. Percent of inhibition of each compound was calculated relative to the maximal signal and $IC_{50}$ curves were generated. This assay was applied to 11β-HSD-2 as well, whereby tritiated cortisol and NAD⁺ were used as substrate and cofactor, respectively.

Compounds of the present invention are active in the 11-βHSD-1 assay described above and show selectivity for human 11-β-HSD-1 over human 11-β-HSD-2, as indicated in Table 1.

TABLE 1

11-β-HSD-1 and 11-β-HSD-2 activity for representative compounds.

| Compound | 11-β-HSD-1 IC$_{50}$ (nM) | 11-β-HSD-2 IC$_{50}$ (nM) |
|---|---|---|
| A (Example 1) | 43 | >10,000 |
| B (Example 2) | 102 | |
| C (Example 3) | 82 | >10,000 |
| D (Example 4) | 24 | |
| G (Example 9) | 59 | 7,400 |
| H (Example 10) | 33 | >30,000 |
| I (Example 11) | 35 | 12,000 |
| J (Example 12) | 33 | 30,000 |
| K (Example 13) | 43 | 16,000 |
| L (Example 14) | 25 | 16,000 |
| M (Example 15) | 30 | >30,000 |
| N (Example 16) | 31 | >30,000 |
| O (Example 17) | 38 | 16,000 |
| P (Example 18) | 38 | >30,000 |
| Q (Example 19) | 36 | 16,000 |
| R (Example 20) | 27 | 21,000 |
| S (Example 21) | 37 | 15,000 |
| T (Example 22) | 31 | >30,000 |
| U (Example 23) | 16 | 12,000 |
| V (Example 24) | 19 | 15,000 |
| W (Example 25) | 23 | >30,000 |
| X (Example 26) | 104 | >30,000 |
| Y (Example 27) | 18 | 13,000 |
| Z (Example 28) | 21 | 23,000 |
| AA (Example 30) | 15 | 15,000 |
| BB (Example 31) | 26 | 30,000 |
| CC (Example 32) | 23 | 12,000 |
| DD (Example 33) | 23 | 6,300 |
| EE (Example 34) | 29 | 10,000 |
| FF (Example 35) | 28 | >100,000 |
| GG (Example 36) | 17 | 9,300 |
| HH (Example 37) | 44 | 40,000 |
| II (Example 38) | 62 | 44,000 |
| JJ (Example 39) | 95 | 60,000 |

The data in Table 1 demonstrates that compounds of formula (I) are active in the human 11β-HSD-1 enzymatic SPA assay described above and the tested compounds show selectivity for 11β-HSD-1 over 11β-HSD-2. The 11β-HSD-1 inhibitors of this invention generally have an inhibition constant IC$_{50}$ of less than 600 nM and preferably less than 50 nM. The compounds preferably are selective, having an inhibition constant IC$_{50}$ against 11β-HSD-2 greater than 1000 nM and preferably greater than 10,000 nM. Generally, the IC$_{50}$ ratio for 11β-HSD-2 to 11β-HSD-1 of a compound is at least 10 or greater and preferably 100 or greater.

Metabolic Stability
Incubation Conditions:

Metabolic stability screen: each substrate (10 μM) was incubated with microsomal protein (0.1-0.5 mg/ml) in 50 mM potassium phosphate buffer (pH 7.4) in 48-Well plate. The enzyme reaction was initiated by the addition of 1 mM NADPH, then incubated at 37° C. in a Form a Scientific incubator (Marietta, Ohio, USA) with gentle shaking. The reactions were quenched by the addition of 800 μl of ACN/MeOH (1:1, v/v), containing 0.5 μM of internal standard (IS), after 30 min incubation. Samples were then filtered by using Captiva 96-Well Filtration (Varian, Lake Forest, Calif., USA) and analyzed by LC/MS (mass spectrometry). Liver microsomal incubations were conducted in duplicate.

LC/MS Analysis:

The parent remaining in the incubation mixture was determined by LC/MS. The LC/MS system consisted of an Agilent 1100 series (Agilent Technologies, Waldbronn, Germany) and API 2000 (MDS SCIEX, Ontario, Canada). A Luna C8(2) (50×2.0 mm, particle size 3 μm, Phenomenex, Torrance, Calif., USA) was used to quantify each compound at ambient temperature. The mobile phase consisted of (A): 10 mM NH$_4$AC (pH 3.3) and (B): 100% ACN and was delivered at a flow rate of 0.2 ml/min. Elution was achieved using a linear gradient of 0-100% B over 3 min, then held 100% B for 4 min and returned to 100% A in 1 min. The column was equilibrated for 7 min before the next injection.

The peak area ratios (each substrate over IS) at each incubation time were expressed as the percentage of the ratios (each substrate over IS) of the control samples (0 min incubation). The parent remaining in the incubation mixture was expressed as the percentage of the values at 0 min incubation. The percentage turnover is calculated using the following equation (% turnover=100% turnover–% parent remaining) and is recorded as the percentage turnover in the Table 2.

TABLE 2

Microsomal metabolic stability.

| Compound | Human Liver Microsomal Turnover (%) | Mouse Liver Microsomal Turnover (%) |
|---|---|---|
| A | 5 | 5 |
| B | 2 | 0 |
| C | 0 | 0 |
| D | 10 | |
| E | 83 | |
| F | 62 | |

Compounds A, B, C and D contain a substituted adamantane, whereas the adamantane ring of Compounds E and F is unsubstituted. The microsomal, metabolic, stability data in Table 2 demonstrates that substituted adamantane compounds of the present invention may exhibit an increase in metabolic stability compared to unsubstituted adamantane compounds which may lead to longer in vivo half lives and pharmacokinetic advantages over unsubstituted adamantanes.

Selective 11β-HSD1 Inhibitors Enhance Memory Consolidation in Mice After 2-Week Food-in-Diet Dosing Episodic memory is a type of long-term memory that requires one exposure for memory formation to occur. Patients with Alzheimer's disease suffer from episodic memory dysfunction, among other cognitive deficits. In addition, studies indicate that patients with a genetic risk for Alzheimer's disease have early deficits in episodic memory and executive function (Ringman, J. Geriatr. Psychiatry Neurology, 2005, 18:228-233).

The 24-hour inhibitory avoidance task in mice is a measure of one-trial learning and memory consolidation in response to a discrete aversive event (foot-shock). Mice are first placed in an illuminated compartment of a two-compartment apparatus. Mice will naturally step through into an adjoining dark compartment, which they prefer. When the mice enter the dark they receive a mild foot-shock. To assess memory, mice are tested 24 hours later and the length of time the animal refrains from entering the dark compartment is recorded (higher latencies indicate improved memory for the aversive event).

Male CD-1 mice were obtained from Charles River, Wilmington, Mass. Mice were group-housed 10 per cage. The body weight upon arrival was 20-25 g. Food and water were available ad libitum except during experiments. Animals were acclimated to the animal facilities for a period of at least one week prior to commencement of experiments. Animals were tested in the light phase of a 12-hour light: 12-hour dark schedule (lights on 0600 hours).

Compound KK ([2-(2-Chloro-4-fluorophenoxy)-2-methyl-N-[(E)-5-(methylsulfonyl)-2-adamantyl]propanamide]) was synthesized at Abbott Laboratories. Compound KK was administered via a drug-in-diet administration (100 mg/kg/day in Western diet) or (10 mg/kg/day in Western diet).

On the first day of testing (17 days after drug-in-diet was presented) mice were removed from the colony room in their home cage, brought to the testing room, and left undisturbed for 2 hours prior to testing initiation. Following this habituation period, drug-in-diet mice were tested. Upon testing initiation, mice were placed one at a time into the light (safe) compartment of a two-chambered apparatus (Gemini apparatus, San Diego Instruments, San Diego, Calif.), during which time the retractable door was closed. After 30 sec at the completion of the acclimation period the door between the light and dark compartments was opened. Measurement of the training latency commenced at this point. This measure (training) provides some indication of general locomotor activity. If a mouse has not crossed within 60 s the animal's data is excluded from the analysis. After the mouse crossed into the dark chamber the door was lowered and inescapable footshock (0.13 mA, 1 sec duration) was presented to the mouse after it completely entered the chamber and the door closed. The mouse was immediately removed from the chamber and returned to the home cage. 24-hours later the mouse was tested using methods identical to those on the training day, except without being dosed and without shock presentation. The latency to enter the dark chamber was recorded and was the dependent variable measured for assessing memory retention (latency is defined as entry of the whole mouse; all 4 paws on the grids in the dark side, plus the tail in the chamber for 5 sec; 180 sec is maximum latency). Data were analyzed using Mann Whitney U comparisons. $P<0.05$ was regarded as significant. As illustrated in FIG. 1, there was a significant improvement in memory retention following the administration of Compound KK at both doses compared to the response of vehicle control mice.

A Selective 11β-HSD1 Inhibitor Enhances Phosphorylated CREB, a Biochemical Marker of Cognitive Enhancement, in Mice After 2-Week Food-in-Diet Dosing In vivo signaling studies were conducted to examine the biochemical pathways that may be mechanistically involved in the cognitive efficacy associated with Compound KK. An important signaling process that serves as a biochemical correlate of synaptic plasticity underlying learning and memory is the phosphorylation of CREB (c-AMP-response element binding protein), a transcription factor critical to long-term memory. To investigate the effects of Compound KK on CREB phosphorylation, CD1 mice treated and tested (data presented in FIG. 1) were given a 24-hour rest after testing before immunohistochemical procedures commenced.

Male CD-1 mice were obtained from Charles River, Wilmington, Mass. Mice were group-housed 10 per cage. The body weight upon arrival was 20-25 g. Food and water were available ad libitum except during experiments. Animals were acclimated to the animal facilities for a period of at least one week prior to commencement of experiments. Animals were tested in the light phase of a 12-hour light: 12-hour dark schedule (lights on 0600 hours).

Figure 2:
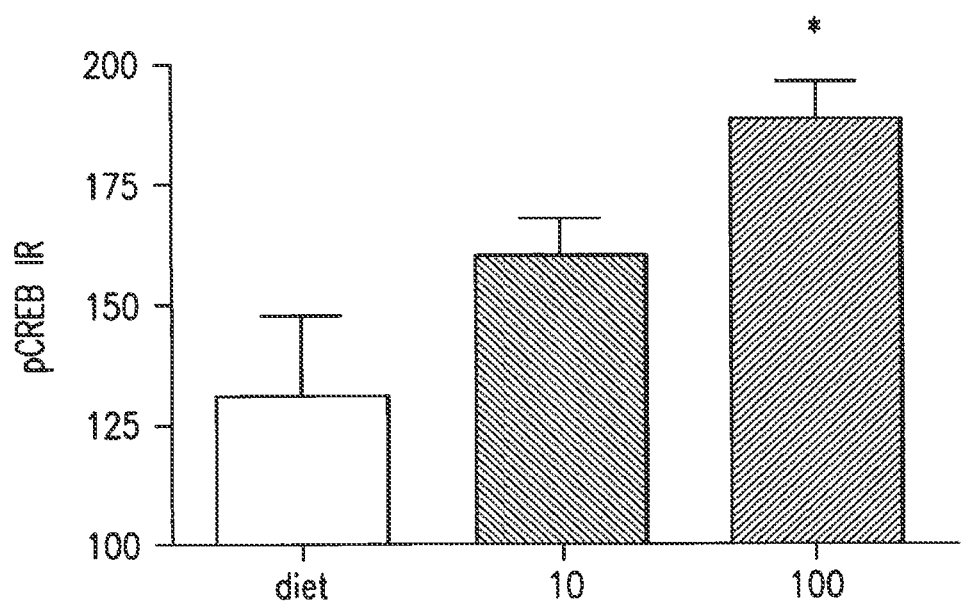
FIG. 2 depicts amount of phosphorylation of CREB in treated and untreated mice.

Compound KK was administered via a drug-in-diet administration (100 mg/kg/day in Western diet) or (10 mg/kg/day in Western diet). 18-days after receiving Compound KK food-in-diet (10 and 100 mg/kg/day) rats were anesthetized and perfused through the aorta with normal saline followed by 10% formalin. Following perfusion, brains were removed and postfixed in 20% sucrose-PBS (phosphate buffered saline) overnight and subsequently cut on a cryostat (40 μm coronal sections) and collected as free-floating sections in PBS. Sections were then immunostained for Fos protein using a 3-step ABC-peroxidase technique beginning with a 30-min incubation with blocking serum. Sections were next incubated with anti-phsopho-CREB (rabbit IgG, 1:1000, Cell signaling) antibodies for 48 hrs at 4 degrees C., washed with PBS and incubated for 1-hr with either biotinylated secondary anti-sheep or anti-mouse antibody (Ab) solution (1:200). Finally, sections were washed in PBS, incubated with ABC reagent (Vector) and then developed in a peroxidase substrate solution. The sections were mounted, coverslipped and examined and photographed with a light microscope (Leica, DMRB). Immuno-reactivity (IR) was quantified using an image analysis system (Leica, Quantimet 500) that determined number and/or area of peroxidase substrate-positive stained neurons from digitized photomicrographs according to a pixel gray level empirically determined prior to analysis. Overall statistical significance was determined using a one-way ANOVA, with Dunnett's post hoc analyses used to determine significance ($p<0.05$ was considered significant). FIG. 2 shows the increase in phosphorylated CREB following the administration of Compound KK mg/kg/day.

Selective 11β-HSD1 Inhibitors Enhance Memory Consolidation in Mice After Subchronic Dosing The 24-hour inhibitory avoidance model in mice was used to evaluate the effects of Compound KK and Compound LL ([N-{(E)-5-[(Z)-Amino(hydroxyimino)methyl]-2-adamantyl}-2-(4-chlorophenoxy)-2-methylpropanamide]) following a subchronic (3 administration) dosing regimen.

Male CD-1 mice were obtained from Charles River, Wilmington, Mass. Mice were group-housed 10 per cage. The body weight upon arrival was 20-25 g. Food and water were available ad libitum except during experiments. Animals were acclimated to the animal facilities for a period of at least one week prior to commencement of experiments. Animals were tested in the light phase of a 12-hour light: 12-hour dark schedule (lights on 0600 hours).

Compound KK and Compound LL were synthesized at Abbott Laboratories. Compounds AA and BB were solubilized in a solution of 5% Tween80/water. Compound KK was administered in a cloudy, fine suspension, while Compound LL was administered in a solution.

Mice were weighed and dosed BID (≈8 AM and 3 PM) PO with Compound AA (30 mg/kg), or Compound LL (30 mg/kg) or vehicle the day before training. On training day, mice were injected with Compound KK, Compound LL or vehicle one-hour PO before training. One hour following injection (start of training) mice were subjected to a training session in which they were placed in a lighted compartment of a two-compartment chamber (Gemini apparatus, San Diego Instruments, San Diego, Calif.) with a manually operated gate separating the compartments. Following a 30 second habituation period in the lighted compartment, the door to the adjacent dark compartment was opened. Once the mouse had completely transferred, the door was closed and a 0.13 mA current was applied to the grid floor for 1 s. The mouse was then immediately removed and returned to the home cage. Twenty-four hours later mice were again tested in the same apparatus, except without shock, and the transfer latency from the lighted to the dark compartment recorded and used as an index of memory for the punished response 24 hours earlier. The electric shock parameters of this test were established such that vehicle treated mice would only have minimal retention of the conditioning trial, thus allowing a large window for improvement of the memory following drug treatment. Data were analyzed using Mann Whitney U comparisons. P<0.05 was regarded as significant.

Figure 3:
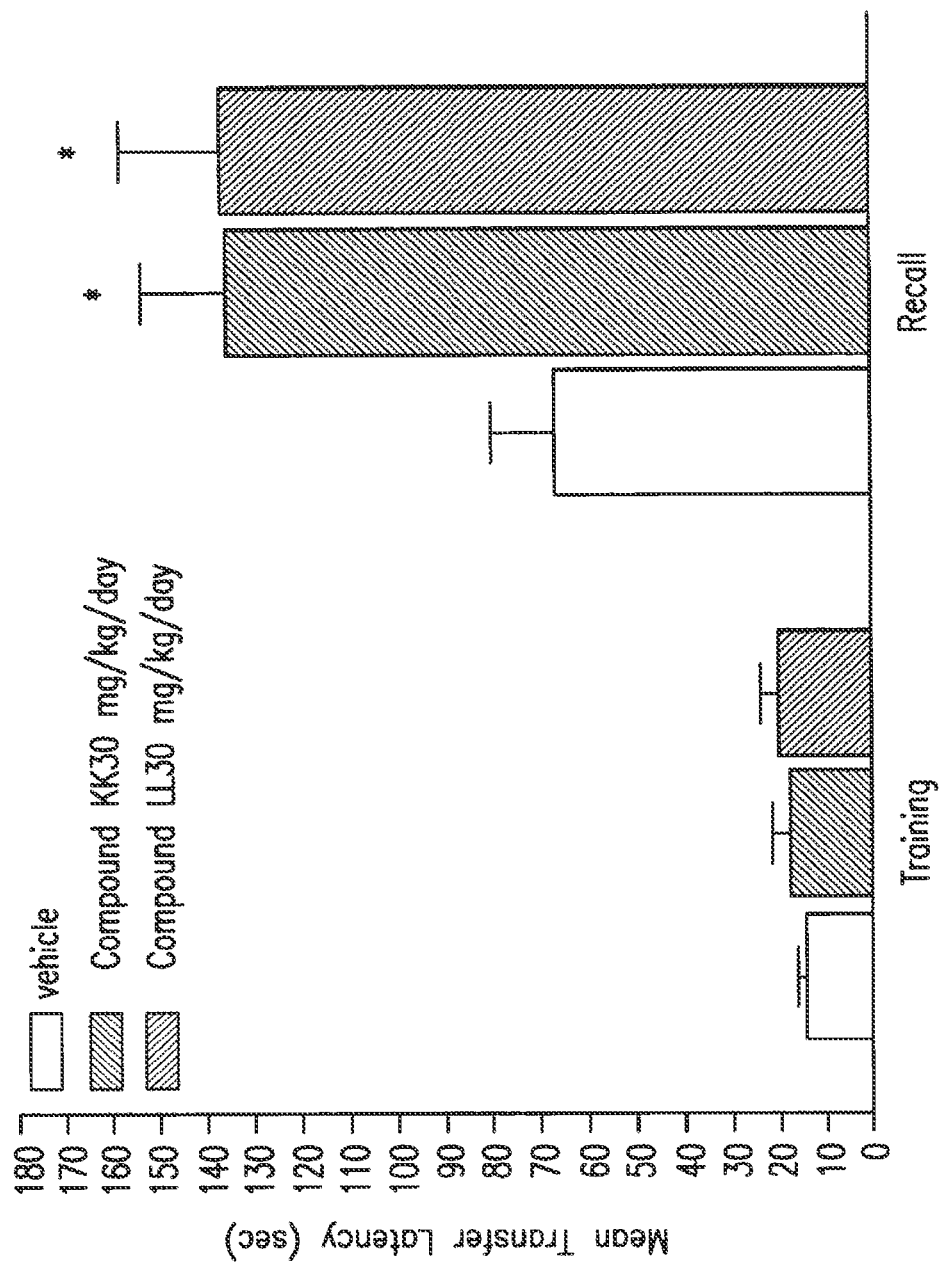
FIG. 3 shows the results of memory consolidation in treated and untreated mice measured as Mean Transfer Latency.

As illustrated in FIG. 3, there was a significant improvement in memory retention following the administration of both Compounds AA and BB compared to the response of vehicle control mice.

A Selective 11β-HSD1 Inhibitor Enhances Short-Term Memory in Rats After Subchronic Dosing Social memory and social cognition are impaired in disorders such as Alzheimer's disease and schizophrenia. One of the more commonly used preclinical models of social recognition memory is short-term social recognition in the rat, a model of short-term memory based on the recognition of a juvenile rat by an adult rat. When adult rats are allowed to interact with a juvenile rat for 5 min, the adult exhibits behaviors such as close following, grooming or sniffing the juvenile for as much as 40-50% of the duration of a 5 min trial. The juvenile rat is then removed and reintroduced 120 min later, and interactive behavior of the adult rat is again monitored. If memory has been lost over the interval between trials 1 and 2, the extent of interaction is equal (expressed as a ratio of investigation time of T1/T2) and the ratio will be close to 1. However, if the adult remembers the juvenile, the investigation ratio declines. To test for non-specific effects, a novel juvenile is introduced at 120 minutes instead of the familiar juvenile. If the ratio is less than 1, this indicates the drug is having effects that may not be specific to cognition.

Male Sprague Dawley rats from Charles Rivers (Portage, Mich., USA) were used. Adults weighed 370-500 g, and juveniles weighed 70-120 g at the time of testing. All animals were housed in a quiet room under conditions of 12 h lights on/12 h lights off (on at 06:00 am) in groups of four with food and water available ad libitum. Studies were conducted between 08:00 h and 16:00 h, and treatment groups were arranged for equal representation of time of day. Compound MM ([N-[(E)-5-Hydroxy-2-adamantyl]-2-{-4-[5-(trifluoromethyl)pyridin-2-yl]piperazin-1-yl}acetamide], 30 mg/kg) was dissolved in PEG 400 using a warm sonicator bath. Compound was administered in solution in a volume of 1 mL/1 g body weight, p.o.

Rats were pre-dosed po at 24, 18 and 1 hour before first juvenile rat exposure with vehicle, or Compound MM (30 mg/kg). During testing, the adult rat was placed into the test cage. After 30 min, a juvenile rat was placed into the test cage with the adult rat for 5 min. The time the adult spent exploring (sniffing, grooming, close following) the juvenile during this test session was recorded, and defined as the first investigation duration. The juvenile was then removed from the test cage, and placed into its home cage. Following a further 90 min, the adult was placed back into the same test chamber, for a second 30-min habituation. Following this second habituation the same juvenile (familiar) was again placed into the test cage for a 5-min test session; the time spent exploring the juvenile during this test session was defined as the second investigation duration. Vehicle treated rats do not remember the familiar juvenile following this two hr delay. Data were analyzed using a one-way analysis of variance. If there was a significant effect, subsequent post hoc significance was determined using Dunnett's multiple comparison testing (p<0.05 was regarded as significant).

Figure 4:
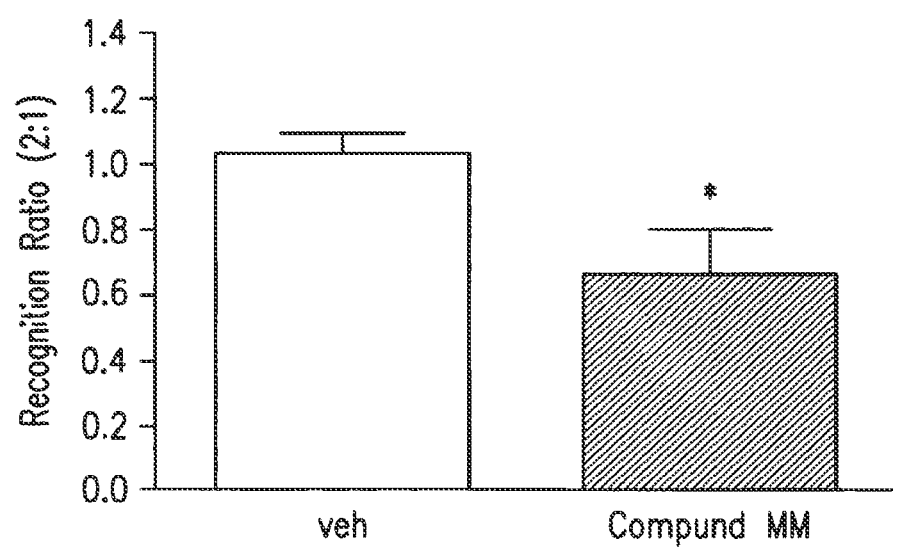
FIG. 4 shows the results of short memory retention in treated and untreated mice measured as Mean Transfer Latency.

As shown in FIG. 4, there was a significant improvement in short-term memory retention following the administration of Compound MM compared to the response of vehicle control rats.

Figure 5A:
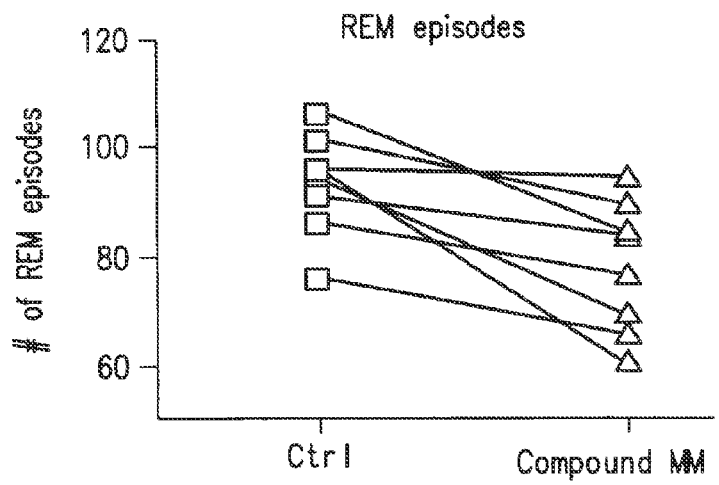
FIGS. 5a-5c show REM episodes, time and latency to first episode, respectively, on rat treated with an exemplary 11β-HSD-1 inhibitor.
Figure 5B:
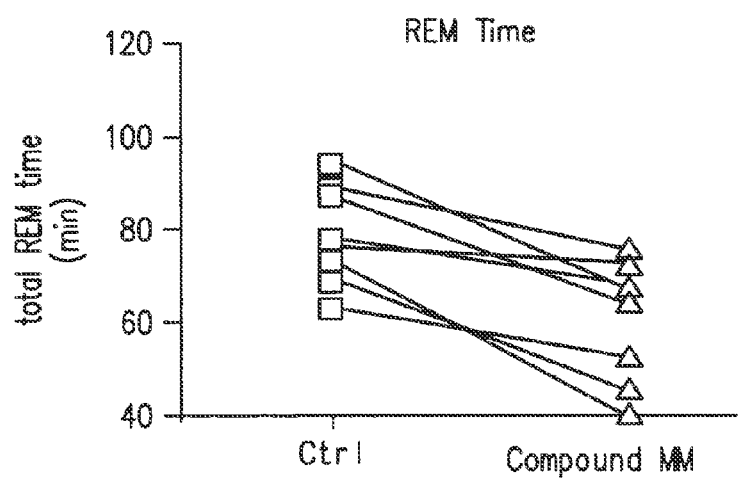
Figure 5C:
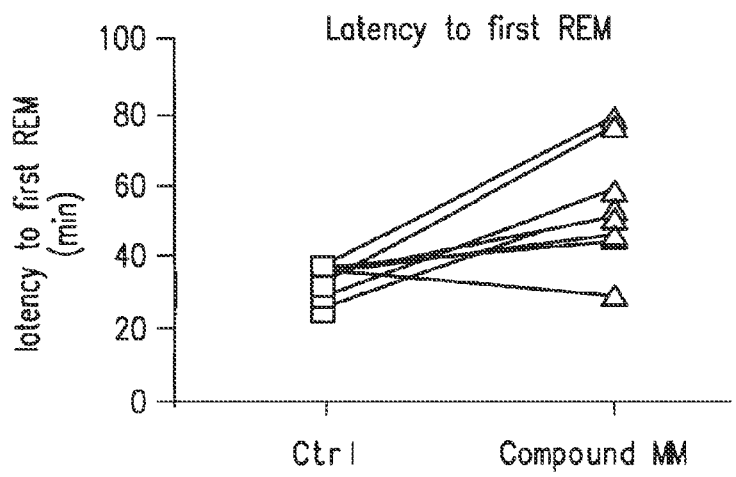

Effects of 11βHSD-1 Inhibitor on Rat Wake EEG Power Spektrum and REM Sleep Parameter EEG of Fisher rats (n=8/group) with chronically implanted supracortical EEG-electrodes were analyzed for an 8 h period. Intraindividual drug-induced changes of power spectra were analyzed. For REM sleep the number of REM episodes, latency to first REM, and total REM time was analyzed. Compound MM (30 mg/kg; 3 times at 24, 26, and 0.1 hours before measurement) significantly reduced the number of REM sleep episodes by 16% (total sleep time by 10%); the corresponding REM time was reduced by 23%. The latency to first REM significantly increased by 62% (See FIGS. 5a, 5b and 5c, respectively).

The observed effects on REM were in line with the effects of antidepressants like SSRIs and TCAs. These effects differ from the procognitive effects induced by inhibitors of AChesteras like donepezil and physostigmine.

Modulation of Cortical/Hippocampal Acetylcholine Serotonin Release by 11β-HSD1 Inhibition Microdialysis studies (resting or challenging conditions) in freely moving, male Sprague Dawley rats (Janvier, 295-315 g, n=5-8/treatment group) were performed using stereotactically instrumented microdialysis probes (CMA/12-14-2): mPFC, hippocampus. Aliquots of the same microdialysate fractions (6 before, and 9-12 after compound administration) were analyzed either for acetylcholine or for serotonin by HPLC and electrochemical detection.

Microdialysate Acetylcholine Levels

Figure 6A:
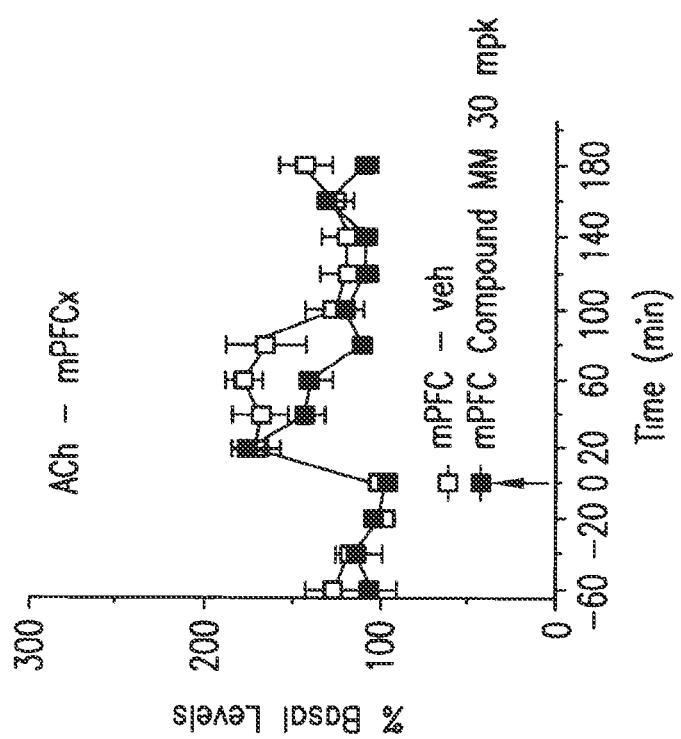
FIGS. 6a, 6b and 6c show the effects of an exemplary 11β-HSD-1 inhibitor on cortical and hippocampal Ach release.
Figure 6B:
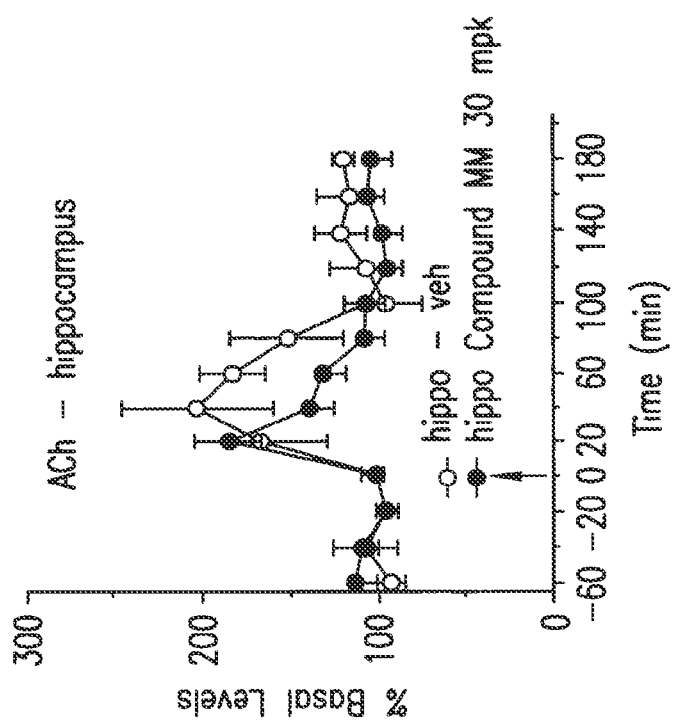
Figure 6C:
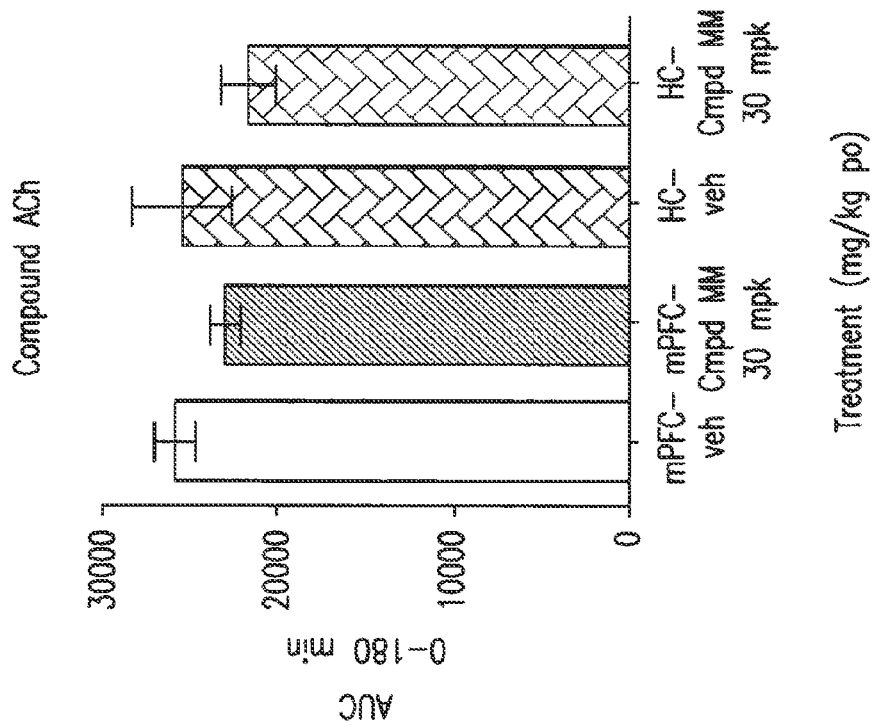
Figure 7A:
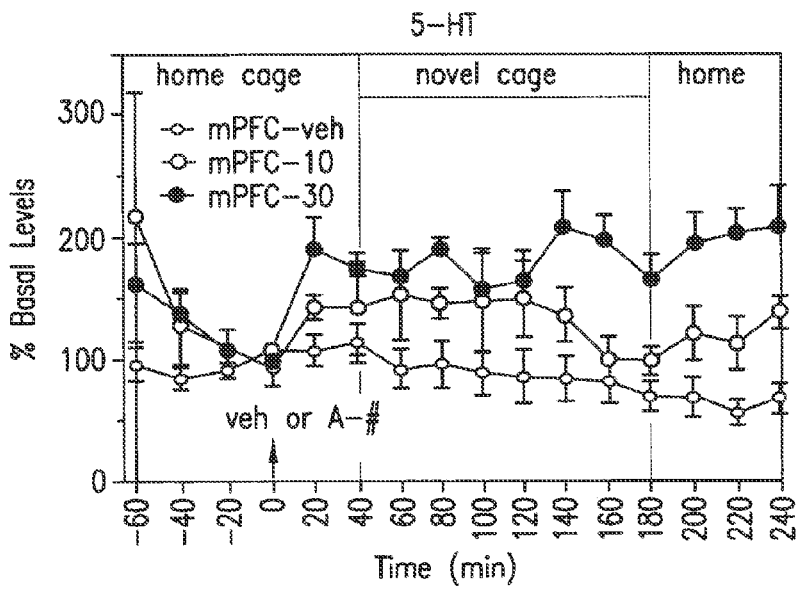
FIGS. 7a and 7b show the effects of an exemplary 11β-HSD-1 inhibitor on cortical and hippocampal 5-HT release.
Figure 7B:
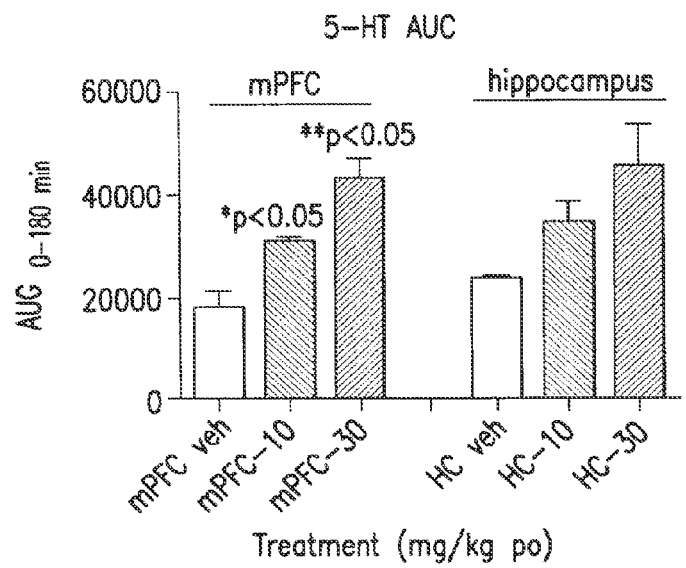

Acute, single administration of Compound MM (30 mg/kg, p.o.) did not change ACh release under resting conditions. Challenging conditions as the transfer from home cage to novel cage, and back to home cage resulted in stimulation of ACh release (see FIGS. 6a, 6b and 6c). Single administration of Compound MM did not induce any further stimulation of ACh release, neither in the cortex nor in the hippocampus.

Microdialysate Serotonin Levels

Single administration of Compound MM (30 mg/kg, p.o.) resulted in a long-lasting increase of serotonin (5-HT) levels in the medial prefrontal cortex and in the hippocampus. This is a feature shared by marketed anti-depressive drugs and might indicate the potential use for 11β-HSD1 inhibitors as antidepressants/anxiolytic drugs. These findings remain to be confirmed by (i) investigating 11β-HSD1 inhibitors from different chemotype(s) in selected microdialysis studies and/or (ii) in animal models of depression/anxiety. Additionally, these results differentiate 11β-HSD-1 inhibition from acetylcholine esterase inhibition, the current therapeutic principle for symptomatic treatment of Alzheimer's disease.

Effects of HSD-1 Inhibitors on Monkey Ex Vivo HSD1 Activity

Compound KK demonstrated potent ex vivo inhibition of monkey brain, fat and liver 2.5 and 16 hours following a single oral 10 mg/kg dose. Harvested tissues (approximately 150 mg) were minced into small, 2 mm pieces in the presence of 5× volume of incubation buffer. Cortisone at final concentrations of 0, 3, 10 or 30 μM was added to each well. Cell culture plates with tissues were incubated at 37° C. for three hours. Two-hundred μL of tissue culture supernatant was then removed and spun at 1000 rpm in an Eppindorf tube, and then 100 μL of resulting supernatant was aliquotted into two tubes for LCMS analysis of cortisol. Results are indicated as & vehicle control activity in the table below:

TABLE 3

HSD-1 Ex Vivo Activity in Cynomolgus Monkeys Following a Single 10 mg/kg Oral Dose of Compound KK

| Tissue | Time | Mean % Veh Control |
|---|---|---|
| Liver | 2.5 hours | 38% |
| Mesenteric Fat | 2.5 hours | 90% |
| Liver | 16 hours | 9% |
| Mesenteric Fat | 16 hours | 50% |
| Cerebral Cortex | 16 hours | 30% |
| Hippocampus | 16 hours | 42% |

N = 3/group

Biochemical Mechanism

Glucocorticoids are steroid hormones that play an important role in regulating multiple physiological processes in a wide range of tissues and organs. For example, glucocorticoids are potent regulators of glucose and lipid metabolism. Excess glucocorticoid action may lead to insulin resistance, type 2 diabetes, dyslipidemia, visceral obesity and hypertension. Cortisol is the major active and cortisone is the major inactive form of glucocorticoids in humans, while corticosterone and dehydrocorticosterone are the major active and inactive forms in rodents.

Previously, the main determinants of glucocorticoid action were thought to be the circulating hormone concentration and the density of glucocorticoid receptors in the target tissues. In the last decade, it was discovered that tissue glucocorticoid levels may also be controlled by 11β-hydroxysteroid dehydrogenases enzymes (11β-HSDs). There are two 11β-HSD isozymes which have different substrate affinities and cofactors. The 11β-hydroxysteroid dehydrogenases type 1 enzyme (11β-HSD-1) is a low affinity enzyme with $K_m$ for cortisone in the micromolar range that prefers NADPH/NADP$^+$ (nicotinamide adenine dinucleotide) as cofactors. 11β-HSD-1 is widely expressed and particularly high expression levels are found in liver, brain, lung, adipose tissue and vascular smooth muscle cells. In vitro studies indicate that 11β-HSD-1 is capable of acting both as a reductase and a dehydrogenase. However, many studies have shown that it is predominantly a reductase in vivo and in intact cells. It converts inactive 11-ketoglucocorticoids (i.e., cortisone or dehydrocorticosterone) to active 11-hydroxyglucocorticoids (i.e., cortisol or corticosterone) and therefore amplifies the glucocorticoid action in a tissue-specific manner.

With only 20% homology to 11β-HSD-1, the 11β-hydroxysteroid dehydrogenases type 2 enzyme (11β-HSD-2) is a NAD$^+$-dependent, high affinity dehydrogenase with a $K_m$ for cortisol in the nanomolar range. 11β-HSD-2 is found primarily in mineralocorticoid target tissues, such as kidney, colon and placenta. Glucocorticoid action is mediated by the binding of glucocorticoids to receptors, such as mineralocorticoid receptors and glucocorticoid receptors. Through binding to its receptor, the main mineralocorticoid aldosterone controls the water and salts balance in the body. However, the mineralocorticoid receptors have a high affinity for both cortisol and aldosterone. 11β-HSD-2 converts cortisol to inactive cortisone, therefore preventing the non-selective mineralocorticoid receptors from being exposed to high levels of cortisol. Mutations in the gene encoding 11β-HSD-2 cause Apparent Mineralocorticoid Excess Syndrome (AME), which is a congenital syndrome resulting in hypokaleamia and severe hypertension. AME Patients have elevated cortisol levels in mineralocorticoid target tissues due to reduced 11β-HSD-2 activity. The AME symptoms may also be induced by administration of 11β-HSD-2 inhibitor, glycyrrhetinic acid. The activity of 11β-HSD-2 in placenta is probably important for protecting the fetus from excess exposure to maternal glucocorticoids, which may result in hypertension, glucose intolerance and growth retardation. Due to the potential side effects resulting from 11β-HSD-2 inhibition, the present invention describes selective 11β-HSD-1 inhibitors.

Glucocorticoid levels and/or activity may contribute to numerous disorders, including Type II diabetes, obesity, dyslipidemia, insulin resistance and hypertension. Administration of the compounds of the present invention decreases the level of cortisol and other 11β-hydroxysteroids in target tissues, thereby reducing the effects of glucucocrticoid activity in key target tissues. The present invention could be used for the treatment, control, amelioration, prevention, delaying the onset of or reducing the risk of developing the diseases and conditions that are described herein.

Since glucocorticoids are potent regulators of glucose and lipid metabolism, glucocorticoid action may contribute or lead to insulin resistance, type 2 diabetes, dyslipidemia, visceral obesity and hypertension. For example, cortisol antagonizes the insulin effect in liver resulting in reduced insulin sensitivity and increased gluconeogenesis. Therefore, patients who already have impaired glucose tolerance have a greater probability of developing type 2 diabetes in the presence of abnormally high levels of cortisol. Previous studies (B. R. Walker et al., *J. of Clin. Endocrinology and Met.*, 80: 3155-3159, 1995) have demonstrated that administration of non-selective 11β-HSD-1 inhibitor, carbenoxolone, improves insulin sensitivity in humans. Therefore, administration of a therapeutically effective amount of an 11β-HSD-1 inhibitor may treat, control, ameliorate, delay, or prevent the onset of type 2 diabetes.

Administration of glucocorticoids in vivo has been shown to reduce insulin secretion in rats (B. Billaudel et al., Horm. Metab. Res. 11: 555-560, 1979). It has also been reported that conversion of dehydrocorticosterone to corticosterone by 11β-HSD-1 inhibits insulin secretion from isolated murine pancreatic β cells. (B. Davani et al., J. Biol. Chem., 275: 34841-34844, 2000), and that incubation of isolated islets with an 11β-HSD-1 inhibitor improves glucose-stimulated insulin secretion (H Orstater et al., Diabetes Metab. Res. Rev. 21: 359-366, 2005). Therefore, administration of a therapeutically effective amount of an 11β-HSD-1 inhibitor may treat, control, ameliorate, delay, or prevent the onset of type 2 diabetes by improving glucose-stimulated insulin secretion in the pancreas.

Abdominal obesity is closely associated with glucose intolerance (C. T. Montague et al., Diabetes, 49: 883-888, 2000), hyperinsulinemia, hypertriglyceridemia and other factors of metabolic syndrome (also known as syndrome X), such as high blood pressure, elevated VLDL and reduced HDL. Animal data supporting the role of 11β-HSD-1 in the pathogenesis of the metabolic syndrome is extensive (Masuzaki, et al. *Science*. 294: 2166-2170, 2001; Paterson, J. M., et al.; *Proc Natl. Acad. Sci. USA*. 101: 7088-93, 2004; Montague and O'Rahilly. *Diabetes*. 49: 883-888, 2000). Therefore, administration of a therapeutically effective amount of an 11β-HSD-1 inhibitor may treat, control, ameliorate, delay, or prevent the onset of obesity. Long-term treatment with an 11β-HSD-1 inhibitor may also be useful in delaying the onset of obesity, or perhaps preventing it entirely if the patients use an 11β-HSD-1 inhibitor in combination with controlled diet, exercise, or in combination or sequence with other pharmacological approaches.

By reducing insulin resistance and/or maintaining serum glucose at normal concentrations and/or reducing obesity compounds of the present invention also have utility in the treatment and prevention of conditions that accompany Type 2 diabetes and insulin resistance, including the metabolic syndrome or syndrome X, obesity, reactive hypoglycemia, and diabetic dyslipidemia.

11β-HSD-1 is present in multiple tissues, including vascular smooth muscle, where local glucocorticoid levels that are thought to increase insulin resistance, leading to reductions in nitric oxide production, and potentiation of the vasoconstrictive effects of both catecholamines and angiotensin II (M. Pirpiris et al., *Hypertension,* 19:567-574, 1992, C. Kornel et al., Steroids, 58: 580-587, 1993, B. R. Walker and B. C. Williams, Clin. Sci. 82:597-605, 1992; Hodge, G. et al *Exp. Physiol* 87: 1-8, 2002). High levels of cortisol in tissues where the mineralocorticoid receptor is present may lead to hypertension, as observed in Cushing's patients (See, D. N. Orth, N. Engl. J. Med. 332:791-803, 1995, M. Boscaro, et al., Lancet, 357: 783-791, 2001, X. Bertagna, et al, Cushing's Disease. In: Melmed. S., Ed. The Pituitary. $2^{nd}$ ed. Malden, M A: Blackwell; 592-612, 2002). Transgenic mice overexpressing 11β-HSD-1 in liver and fat are also hypertensive, a phenotype believed to result from glucocorticoid activation of the renin angiotensin system (Paterson, J. M. et al, PNAS. 101: 7088-93, 2004; Masuzaki, H. et al, J. Clin. Invest. 112: 83-90, 2003). Therefore, administration of a therapeutically effective dose of an 11β-HSD-1 inhibitor may treat, control, ameliorate, delay, or prevent the onset of hypertension.

Cushing's syndrome is a life-threatening metabolic disorder characterized by sustained and elevated glucocorticoid levels caused by the endogenous and excessive production of cortisol from the adrenal glands. Typical Cushingoid characteristics include central obesity, diabetes and/or insulin resistance, moon face, buffalo hump, skin thinning, dyslipidemia, osteoporosis, reduced cognitive capacity, dementia, hypertension, sleep deprivation, and atherosclerosis among others (Principles and Practice of Endocrinology and Metabolism. Edited by Kenneth Becker, Lippincott Williams and Wilkins Publishers, Philadelphia, 2001; pg 723-8). The same characteristics can also arise from the exogenous administration of high doses of exogenous glucocorticoids, such as prednisone or dexamethasone, as part of an anti-inflammatory treatment regimen. Endogenous Cushings typically evolves from pituitary hyperplasia, some other ectopic source of ACTH, or from an adrenal carcinoma or nodular hyperplasia. Administration of a therapeutically effective dose of an 11β-HSD-1 inhibitor may reduce local glucocorticoid concentrations and therefore treat, control, ameliorate, delay, or prevent the onset of Cushing's disease and/or similar symptoms arising from glucocorticoid treatment.

11β-HSD-1 is expressed in mammalian brain, and published data indicates that glucocorticoids may cause neuronal degeneration and dysfunction, particularly in the aged (de Quervain et al.; *Hum Mol. Genet.* 13: 47-52, 2004; Belanoff et al. *J. Psychiatr Res.* 35: 127-35, 2001). Evidence in rodents and humans suggests that prolonged elevation of plasma glucocorticoid levels impairs cognitive function that becomes more profound with aging. (Issa, A. M. et al. *J. Neurosci.* 10: 3247-54, 1990; Lupien, S. J et al. *Nat. Neurosci.* 1: 69-73, 1998; Yau, J. L. W. et al *Proc Natl Acad Sci USA.* 98: 4716-4712, 2001). Thekkapat et al has recently shown that 11β-HSD-1 mRNA is expressed in human hippocampus, frontal cortex and cerebellum, and that treatment of elderly diabetic individuals with the non-selective HSD1/2 inhibitor carbenoxolone improved verbal fluency and memory (*Proc Natl Acad Sci USA.* 101: 6743-9, 2004). Additional CNS effects of glucocorticoids include glucocorticoid-induced acute psychosis which is of major concern to physicians when treating patients with these steroidal agents (Wolkowitz et al.; *Ann NY Acad. Sci.* 1032: 191-4, 2004). Conditional mutagenesis studies of the glucocorticoid receptor in mice have also provided genetic evidence that reduced glucocorticoid signaling in the brain results in decreased anxiety (Tronche, F. et al. (1999) Nature Genetics 23: 99-103). Therefore, it is expected that potent, selective 11β-HSD-1 inhibitors would treat, control, ameliorate, delay, or prevent the onset of cognitive decline, dementia, steroid-induced acute psychosis, depression, and/or anxiety.

In Cushing's patients, excess cortisol levels contributes to the development of hypertension, dyslipidemia, insulin resistance, and obesity, conditions characteristic of metabolic syndrome (Orth, D. N. et al N. Engl. J. Med. 332:791-803, 1995; Boscaro, M. et al., Lancet, 357: 783-791, 2001, Bertagna, X. et al, Cushing's Disease. In: Melmed S., Ed. The Pituitary. $2^{nd}$ ed. Malden, M A: Blackwell; 592-612, 2002). Hypertension and dyslipidemia are also associated with development of atherosclerosis. 11β-HSD-1 knockout mice are resistant to the dyslipidemic effects of a high fat diet and have an improved lipid profile vs wild type controls (Morton N. M. et al, JBC, 276: 41293-41300, 2001), and mice which overexpress 11β-HSD-1 in fat exhibit the dyslipidemic phenotype characteristic of metabolic syndrome, including elevated circulating free fatty acids, and triglycerides (Masuzaki, H., et al Science. 294: 2166-2170, 2001). Administration of a selective 11β-HSD-1 inhibitor has also been shown to reduce elevated plasma triglycerides and free fatty acids in mice on a high fat diet, and significantly reduce aortic content of cholesterol esters, and reduce progression of atherosclerotic plaques in mice (Hermanowski-Vosatka, A. et al. J. Exp. Med. 202: 517-27, 2005). The administration of a therapeutically effective amount of an 11β-HSD-1 inhibitor would therefore be expected to treat, control, ameliorate, delay, or prevent the onset of dyslipidemia and/or atherosclerosis.

Glucocorticoids are known to cause a variety of skin related side effects including skin thinning, and impairment of wound healing (Anstead, G. *Adv Wound Care.* 11: 277-85, 1998; Beer, et al.; *Vitam Horm.* 59: 217-39, 2000). 11β-HSD-1 is expressed in human skin fibroblasts, and it has been shown that the topical treatment with the non-selective HSD1/2 inhibitor glycerrhetinic acid increases the potency of topically applied hydrocortisone in a skin vasoconstrictor assay (Hammami, M M, and Siiteri, P K. *J. Clin. Endocrinol. Metab.* 73: 326-34, 1991). Advantageous effects of selective 11β-HSD-1 inhibitors such as BVT.2733 on wound healing have also been reported (WO 2004/11310). High levels of glucocorticoids inhibit blood flow and formation of new blood vessels to healing tissues. In vitro and in vivo models of angiogenesis have shown that systemic antagonism with the glucocorticoid receptor RU-486 enhances angiogenesis in subcutaneous sponges as well as in mouse myocardium following coronary artery ligation (Walker, et al, PNAS, 102: 12165-70, 2005). 11β-HSD-1 knockout mice also showed enhanced angiogenesis in vitro and in vivo within sponges, wounds, and infracted myocardium. It is therefore expected that potent, selective 11β-HSD-1 inhibitors would treat, control, ameliorate, delay, or prevent the onset of skin thinning and/or promote wound healing and/or angiogenesis.

Although cortisol is an important and well-recognized anti-inflammatory agent (J. Baxer, Pharmac. Ther., 2:605-659, 1976), if present in large amount it also has detrimental effects. In certain disease states, such as tuberculosis, psoriasis and stress in general, high glucocorticoid activity shifts the immune response to a humoral response, when in fact a cell based response may be more beneficial to patients. Inhibition of 11β-HSD-1 activity may reduce glucocorticoid levels, thereby shifting the immuno response to a cell based response. (D. Mason, Immunology Today, 12: 57-60, 1991, G. A. W. Rook, Baillier's Clin. Endocrinol. Metab. 13: 576-581, 1999). Therefore, administration of 11β-HSD-1 specific inhibitors could treat, control, ameliorate, delay, or prevent the onset of tuberculosis, psoriasis, stress, and diseases or conditions where high glucocorticoid activity shifts the immune response to a humoral response.

One of the more significant side effects associated with topical and systemic glucocorticoid therapy is glaucoma, resulting in serious increases in intraocular pressure, with the potential to result in blindness (Armaly et al.; Arch Ophthalmol. 78: 193-7, 1967; Stokes et al.; Invest Ophthalmol Vis Sci. 44: 5163-7, 2003;). The cells that produce the majority of aqueous humor in the eye are the nonpigmented epithelial cells (NPE). These cells have been demonstrated to express 11β-HSD-1, and consistent with the expression of 11β-HSD-1, is the finding of elevated ratios of cortisol:cortisone in the aqueous humor (Rauz et al. Invest Ophthalmol V is Sci. 42: 2037-2042, 2001). Furthermore, it has been shown that patients who have glaucoma, but who are not taking exogenous steroids, have elevated levels of cortisol vs. cortisone in their aqueous humor (Rauz et al. QJM. 96: 481-490, 2003.) Treatment of patients with the nonselective HSD1/2 inhibitor carbenoxolone for 4 or 7 days significantly lowered intraocular pressure and local cortisol generation within the eye (Rauz et al.; QJM. 96: 481-490, 2003.). It is therefore expected that potent, selective 11β-HSD-1 inhibitors would treat, control, ameliorate, delay, or prevent the onset of glaucoma.

Glucocorticoids (GCs) are known to increase bone resorption and reduce bone formation in mammals (Turner et al. Calcif Tissue Int. 54: 311-5, 1995; Lane, N E et al. Med Pediatr Oncol. 41: 212-6, 2003). 11β-HSD-1 mRNA expression and reductase activity have been demonstrated in primary cultures of human osteoblasts in homogenates of human bone (Bland et al.; J. Endocrinol. 161: 455-464, 1999; Cooper et al.; Bone, 23: 119-125, 2000). In surgical explants obtained from orthopedic operations, 11β-HSD-1 expression in primary cultures of osteoblasts was found to be increased approximately 3-fold between young and old donors (Cooper et al.; J. Bone Miner Res. 17: 979-986, 2002). Glucocorticoids, such as prednisone and dexamethasone, are also commonly used to treat a variety of inflammatory conditions including arthritis, inflammatory bowl disease, and asthma. These steroidal agents have been shown to increase expression of 11β-HSD-1 mRNA and activity in human osteoblasts (Cooper et al.; J. Bone Miner Res. 17: 979-986, 2002). These studies suggest that 11β-HSD-1 plays a potentially important role in the development of bone-related adverse events as a result of excessive glucocorticoid levels or activity. Bone samples taken from healthy human volunteers orally dosed with the non-selective HSD1/2 inhibitor carbenoxolone showed a significant decrease in markers of bone resorption (Cooper et al.; Bone. 27: 375-81, 2000). It is therefore expected that potent, selective 11β-HSD-1 inhibitors would treat, control, ameliorate, delay, or prevent the onset of conditions of glucocorticoid-induced or age-dependent osteoporosis The following diseases, disorders and conditions can be treated, controlled, prevented or delayed, by treatment with the compounds of this invention: (1) hyperglycemia, (2) low glucose tolerance, (3) insulin resistance, (4) lipid disorders, (5) hyperlipidemia, (6) hypertriglyceridemia, (9) hypercholesterolemia, (10) low HDL levels, (11) high LDL levels, (12), atherosclerosis and its sequelae, (13) vascular restensosis, (14) pancreatitis, (15) obdominal obesity, (16) neurodegenerative disease, (17) retinopathy, (18) nephropather, (19), neuropathy, (20) hypertension and other disorders where insulin resistance is a component, and (21) other diseases, disorders, and conditions that can benefit from reduced local glucocorticoid levels.

Neuronal Effects of 11β-HSD Inhibitors

Studies have shown that in homogenates of hippocampus, both dehydrogenation and reduction occur (V. Lakshmi, et al., Endocrinol., 128, 1741-1748, 1991) and that 11β-HSD-1 is expressed in mammalian brain, and published data indicates that glucocorticoids may cause neuronal degeneration and dysfunction (de Quervain et al., Hum Mol. Genet. 13: 47-52, 2004; Belanoff et al., J. Psychiatr Res., 35: 127-35, 2001). Several studies have demonstrated 11β-HSD activity, immunoreactivity and mRNA expression in hippocampal neurons (M-P Moisan, et al., Endocrinol 127, 1450-1455, 1990; V. Lakshmi, et al., Endocrinol., 128, 1741-1748, 1991; R R Sakai, et al., J Neuroendocrinol., 4, 101-106, 1992). Administration of 11β-HSD inhibitors alters functional activity in the hippocampus in vivo (J R Seckl, et al., J Endocrinol 136, 471-477, 1993). Evidence in rodents and humans suggests that prolonged elevation of plasma glucocorticoid levels impairs cognitive function that becomes more profound with aging (A. M. Issa et al., 0.1. Neurosci., 10: 3247-3254, 1990, S. J. Lupien, et. al., Nat. Neurosci., 1:69-73 1998, J. L. Yau et al., Neuroscience, 66: 571-581, 1995). Chronic excessive cortisol levels in the brain may result in neuronal loss and neuronal dysfunction. (See, D. S. Kerr et al., Psychobiology 22: 123-133, 1994, C. Woolley, Brain Res. 531: 225-231, 1990, P. W. Landfield, Science, 272: 1249-1251, 1996). Furthermore, glucocorticoid-induced acute psychosis exemplifies a more pharmacological induction of this response, and is of major concern to physicians when treating patients with these steroidal agents (Wolkowitz et al., Ann NY Acad. Sci. 1032: 191-4, 2004). Thekkapat et al have recently shown that 11β-HSD-1 mRNA is expressed in human hippocampus, frontal cortex and cerebellum, and that treatment of elderly diabetic individuals with the non-selective 11β-HSD-1 and 11β-HSD-2 inhibitor carbenoxolone improved verbal fluency and memory (Proc Natl Acad Sci USA. 101: 6743-9, 2004). In addition, Walker et al have examined 11β-HSD activity and its function in primary cultures of fetal hippocampus cells (U.S. Pat. No. 7,122,531; U.S. Pat. No. 7,087,400; Rajan V, et al., J. Neurosci., 16, 65-70 (1996)), the contents of which are incorporated herein by reference.

Therefore, the CNS diseases, disorders and conditions can be treated, controlled, prevented or delayed, by treatment with the compounds of this invention. Administration of a therapeutic dose of an 11β-HSD-1 inhibitor may reduce, ameliorate, control and/or prevent disorders such as the cognitive impairment associated with aging, neuronal dysfunction, dementia, steroid-induced acute psychosis, decline in cognitive function in Alzheimer's and associated dementias, cognitive deficits associated with aging and neurodegeneration, dementia, senile dementia, AIDS dementia, depression, major depressive disorder, psychotic depression, treatment resistant depression, anxiety, panic disorder, post traumatic stress disorder, depression in Cushing's syndrome, steroid-induced acute psychosis, cognitive deficits associated with diabetes, attention deficit disorder in general, attention deficit hyperactivity disorder (ADHD), mild cognitive impairment, and schizophrenia.

HSD-1 related disorders include, but are not limited to, non-insulin dependent type 2 diabetes, insulin resistance, obesity, lipid disorders, metabolic syndrome, hyperglycemia, low glucose tolerance, hyperlipidemia, hypertriglyceridemia, hypercholesterolemia, low HDL levels, high LDL levels, atherosclerosis and its sequelae, vascular restensosis, pancreatitis, abdominal obesity, retinopathy, nephropather, neuropathy, hypertension, other disorders where insulin resistance is a component, cognitive impairment associated with aging, neuronal dysfunction, dementia, steroid-induced acute psychosis, decline in cognitive function in Alzheimer's disease and associated dementias, cognitive deficits associated with aging and neurodegeneration, dementia, senile dementia, AIDS dementia, anxiety, panic disorder, post traumatic stress disorder, steroid-induced acute psychosis, cognitive deficits associated with diabetes, attention deficit disorder in general, attention deficit hyperactivity disorder (ADHD), mild cognitive impairment, schizophrenia, and depression including major depressive disorder, psychotic depression, depression in Cushing's syndrome, and treatment resistant depression.

Accordingly, an embodiment is a method of inhibiting 11-beta-hydroxysteroid dehydrogenase Type I enzyme, comprising administering to a mammal, a therapeutically effective amount of a compound of formula (I). Another embodiment is treating or prophylactically treating the above disorders in a mammal. The disorders may be mediated by excessive glucocorticoid action in a mammal.

Therapeutic Compositions-Administration-Dose Ranges

Therapeutic compositions of the present compounds comprise an effective amount of the same formulated with one or more therapeutically suitable excipients. The term "therapeutically suitable excipient," as used herein, generally refers to pharmaceutically suitable, solid, semi-solid or liquid fillers, diluents, encapsulating material, formulation auxiliary and the like. Examples of therapeutically suitable excipients include, but are not limited to, sugars, cellulose and derivatives thereof, oils, glycols, solutions, buffers, colorants, releasing agents, coating agents, sweetening agents, flavoring agents, perfuming agents and the like. Such therapeutic compositions may be administered parenterally, intracisternally, orally, rectally, intraperitoneally or by other dosage forms known in the art.

Liquid dosage forms for oral administration include, but are not limited to, emulsions, microemulsions, solutions, suspensions, syrups and elixirs. Liquid dosage forms may also contain diluents, solubilizing agents, emulsifying agents, inert diluents, wetting agents, emulsifiers, sweeteners, flavorants, perfuming agents and the like.

Injectable preparations include, but are not limited to, sterile, injectable, aqueous, oleaginous solutions, suspensions, emulsions and the like. Such preparations may also be formulated to include, but are not limited to, parenterally suitable diluents, dispersing agents, wetting agents, suspending agents and the like. Such injectable preparations may be sterilized by filtration through a bacterial-retaining filter. Such preparations may also be formulated with sterilizing agents that dissolve or disperse in the injectable media or other methods known in the art.

The absorption of the compounds of the present invention may be delayed using a liquid suspension of crystalline or amorphous material having poor water solubility. The rate of absorption of the compounds generally depends upon the rate of dissolution and crystallinity. Delayed absorption of a parenterally administered compound may also be accomplished by dissolving or suspending the compound in oil. Injectable depot dosage forms may also be prepared by microencapsulating the same in biodegradable polymers. The rate of drug release may also be controlled by adjusting the ratio of compound to polymer and the nature of the polymer employed. Depot injectable formulations may also prepared by encapsulating the compounds in liposomes or microemulsions compatible with body tissues.

Solid dosage forms for oral administration include, but are not limited to, capsules, tablets, gels, pills, powders, granules and the like. The drug compound is generally combined with at least one therapeutically suitable excipient, such as carriers, fillers, extenders, disintegrating agents, solution retarding agents, wetting agents, absorbents, lubricants and the like. Capsules, tablets and pills may also contain buffering agents. Suppositories for rectal administration may be prepared by mixing the compounds with a suitable non-irritating excipient that is solid at ordinary temperature but fluid in the rectum.

The present drug compounds may also be microencapsulated with one or more excipients. Tablets, dragees, capsules, pills and granules may also be prepared using coatings and shells, such as enteric and release or rate controlling polymeric and nonpolymeric materials. For example, the compounds may be mixed with one or more inert diluents. Tableting may further include lubricants and other processing aids. Similarly, capsules may contain opacifying agents that delay release of the compounds in the intestinal tract.

Transdermal patches have the added advantage of providing controlled delivery of the present compounds to the body. Such dosage forms are prepared by dissolving or dispensing the compounds in suitable medium. Absorption enhancers may also be used to increase the flux of the compounds across the skin. The rate of absorption may be controlled by employing a rate controlling membrane. The compounds may also be incorporated into a polymer matrix or gel.

For a given dosage form, disorders of the present invention may be treated, prophylatically treated, or have their onset delayed in a patient by administering to the patient a therapeutically effective amount of compound of the present invention in accordance with a suitable dosing regimen. In other words, a therapeutically effective amount of any one of compounds of formulas (I) is administered to a patient to treat and/or prophylatically treat disorders modulated by the 11-beta-hydroxysteroid dehydrogenase type 1 enzyme. The specific therapeutically effective dose level for a given patient population may depend upon a variety of factors including, but not limited to, the specific disorder being treated, the severity of the disorder; the activity of the compound, the specific composition or dosage form, age, body weight, general health, sex, diet of the patient, the time of administration, route of administration, rate of excretion, duration of the treatment, drugs used in combination, coincidental therapy and other factors known in the art.

The present invention also includes therapeutically suitable metabolites formed by in vivo biotransformation of any of the compounds of formula (I). The term "therapeutically suitable metabolite", as used herein, generally refers to a pharmaceutically active compound formed by the in vivo biotransformation of compounds of formula (I). For example, pharmaceutically active metabolites include, but are not limited to, compounds made by adamantane hydroxylation or polyhydroxylation of any of the compounds of formulas (I). A discussion of biotransformation is found in Goodman and Gilman's, The Pharmacological Basis of Therapeutics, seventh edition, MacMillan Publishing Company, New York, N.Y., (1985).

The total daily dose (single or multiple) of the drug compounds of the present invention necessary to effectively inhibit the action of 11-beta-hydroxysteroid dehydrogenase type 1 enzyme may range from about 0.01 mg/kg/day to about 50 mg/kg/day of body weight and more preferably about 0.1 mg/kg/day to about 25 mg/kg/day of body weight. Treatment regimens generally include administering from about 10 mg to about 1000 mg of the compounds per day in single or multiple doses.

It is understood that the foregoing detailed description and accompanying examples are merely illustrative and are not to be taken as limitations upon the scope of the invention, which is defined solely by the appended claims and their equivalents. Various changes and modifications to the disclosed aspects will be apparent to those skilled in the art. Such changes and modifications, including without limitation those relating to the chemical structures, substituents, derivatives, intermediates, syntheses, formulations and/or methods of use of the invention, may be made without departing from the spirit and scope thereof.

What is claimed is:

1. A method for treating a patient suffering from a disorder selected from the group consisting of neuropathy, neuronal dysfunction, decline in cognitive function in Alzheimer's disease and associated dementias, attention deficit disorder in general, attention deficit hyperactivity disorder (ADHD), mild cognitive impairment, steroid-induced acute psychosis, schizophrenia, and combinations thereof, comprising administering to the patient an effective amount of a compound of formula (I), or a pharmaceutically acceptable salt, or a combination thereof,

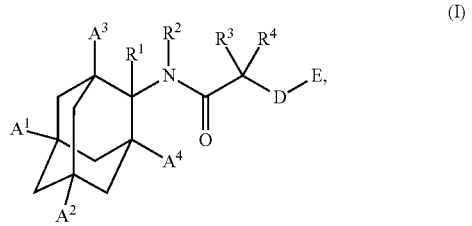

(I)

wherein one of $A^1$, $A^2$, $A^3$ and $A^4$ is selected from the group consisting of alkyl-NH-alkyl, alkylcarbonyl, alkylsulfonyl, cycloalkyl, cycloalkylcarbonyl, cycloalkylsulfonyl, arylcarbonyl, arylsulfonyl, heteroaryl, heteroarylalkyl, heteroaryloxyalkyl, heterocyclecarbonyl, heterocyclesulfonyl, aryl, arylalkyl, aryloxyalkyl, carboxyalkyl, carboxycycloalkyl, haloalkyl, heterocyclealkyl, heterocycleoxyalkyl, $—S(O)_2—N(R^5R^6)$, $—NR^7—[C(R^8R^9)]_n—C(O)—R^{10}$, $—O—[C(R^{11}R^{12})]_p—C(O)—R^{13}$, $—OR^{14a}$, $—N(R^{15}R^{16})$, $—CO_2R^{17}$, $—C(O)—N(R^{18}R^{19})$, $—C(R^{20}R^{21})—OR^{22}$, $—C(R^{23}R^{24})—N(R^{25}R^{26})$, and heterocycle, with the exception that 5 membered heterocycles may not contain two oxygen atoms, and the remaining members of the group consisting of $A^1$, $A^2$, $A^3$ and $A^4$ are each individually selected from the group consisting of hydrogen, alkyl, alkyl-NH-alkyl, alkylcarbonyl, alkylsulfonyl, cycloalkyl, cycloalkylcarbonyl, cycloalkylsulfonyl, arylcarbonyl, arylsulfonyl, heterocyclecarbonyl, heterocyclesulfonyl, aryl, arylalkyl, aryloxyalkyl, carboxyalkyl, carboxycycloalkyl, halogen, haloalkyl, heteroaryl, heteroarylalkyl, heteroaryloxyalkyl, heterocycle, heterocyclealkyl, heterocycleoxyalkyl, $—S(O)_2—N(R^5R^6)$, $—NR^7—[C(R^8R^9)]_n—C(O)—R^{10}$, $—O—[C(R^{11}R^{12})]_p—C(O)—R^{13}$, $—OR^{14b}$, $—N(R^{15}R^{16})$, $—CO_2R^{17}$, $—C(O)—N(R^{18}R^{19})$, $—C(R^{20}R^{21})—OR^{22}$ and $—C(R^{23}R^{24})—N(R^{25}R^{26})$;

n is 0 or 1;

p is 0 or 1;

D is selected from the group consisting of a bond, $—C(R^{27}R^{28})—X—$ and $—C(R^{27}R^{28})—C(R^{29}R^3)—X—$;

E is selected from the group consisting of cycloalkyl, alkyl, aryl, heteroaryl and heterocycle, wherein the heteroaryl is appended to the parent molecular moiety through an available carbon atom, or $R^4$ and E together with the atoms to which they are attached form a ring selected from the group consisting of cycloalkyl and heterocycle;

X is selected from the group consisting of a bond, $—N(R^{31})—$, $—O—$, $—S—$, $—S(O)—$ and $—S(O)_2—$;

$R^1$ is selected from the group consisting of hydrogen and alkyl;

$R^2$ is selected from the group consisting of hydrogen, alkyl and cycloalkyl;

$R^3$ and $R^4$ are each independently selected from the group consisting of hydrogen, alkyl, carboxyalkyl, carboxycycloalkyl, cycloalkyl, haloalkyl, aryl, arylalkyl, heteroaryl, heteroarylalkyl, heterocycle and heterocyclealkyl, or $R^3$ and $R^4$ together with the atom to which they are attached form a ring selected from the group consisting of cycloalkyl and heterocycle;

$R^5$ and $R^6$ are each independently selected from the group consisting of hydrogen, alkoxy, alkyl, alkylcarbonyl, alkylsufonyl, carboxy, carboxyalkyl, carboxycycloalkyl, cycloalkyl, cycloalkyloxy, cycloalkylsulfonyl, aryl, arylalkyl, arylalkylcarbonyl, arylcarbonyl, aryloxy, aryloxyalkyl, arylsulfonyl, heteroaryl, heteroarylalkyl, heteroarylalkylcarbonyl, heteroarylcarbonyl, heteroaryloxyalkyl, heteroarylsulfonyl, heterocycle, heterocyclealkyl, heterocyclealkylcarbonyl, heterocyclecarbonyl, heterocycleoxyalkyl, heterocycleoxy, heterocyclesulfonyl and hydroxy, or $R^5$ and $R^6$ together with the atom to which they are attached form a heterocycle;

$R^7$ is selected from the group consisting of hydrogen, alkyl, carboxyalkyl, cycloalkyl, carboxycycloalkyl, aryl, arylalkyl, aryloxyalkyl, hydroxy, alkoxy, heteroaryl, heteroarylalkyl, heteroaryloxyalkyl, heterocycle, heterocyclealkyl and heterocycleoxyalkyl;

$R^8$ and $R^9$ are each independently selected from the group consisting of hydrogen and alkyl, or $R^8$ and $R^9$ taken together with the atom to which they are attached form a ring selected from the group consisting of cycloalkyl and heterocycle;

$R^{10}$ is selected from the group consisting of hydrogen, alkyl, carboxyalkyl, cycloalkyl, carboxycycloalkyl, aryl, arylalkyl, aryloxy, aryloxyalkyl, hydroxy, alkoxy, cycloalkyloxy, heteroaryl, heteroarylalkyl, heteroaryloxy, heteroaryloxyalkyl, heterocycle, heterocyclealkyl, heterocycleoxy, heterocycleoxyalkyl and $—N(R^{32}R^{33})$;

$R^{11}$ and $R^{12}$ are each independently selected from the group consisting of hydrogen and alkyl or $R^{11}$ and $R^{12}$ taken together with the atom to which they are attached form a ring selected from the group consisting of cycloalkyl and heterocycle;

$R^{13}$ is selected from the group consisting of hydroxy and $—N(R^{34}R^{35})$;

$R^{14a}$ is selected from the group consisting of carboxyalkyl, cycloalkyl, carboxycycloalkyl, aryl, arylalkyl, aryloxyalkyl, haloalkyl, heteroaryl, heteroarylalkyl, heteroaryloxyalkyl, heterocycle, heterocyclealkyl and heterocycleoxyalkyl;

$R^{14b}$ is selected from the group consisting of hydrogen, alkyl, carboxyalkyl, cycloalkyl, carboxycycloalkyl, aryl, arylalkyl, aryloxyalkyl, haloalkyl, heteroaryl, heteroarylalkyl, heteroaryloxyalkyl, heterocycle, heterocyclealkyl and heterocycleoxyalkyl;

$R^{15}$ and $R^{16}$ are each independently selected from the group consisting of hydrogen, alkyl, alkylcarbonyl, carboxyalkyl, cycloalkyl, carboxycycloalkyl, aryl, arylalkyl, arylalkylcarbonyl, arylcarbonyl, aryloxyalkyl, heteroaryl, heteroarylalkyl, heteroarylalkylcarbonyl, heteroarylcarbonyl, heteroaryloxyalkyl, heteroarylsulfonyl, heterocycle, heterocyclealkyl, heterocyclealkylcarbonyl, heterocylecarbonyl, heterocycleoxyalkyl, heterocyclesulfonyl, alkylsulfonyl, cycloalkylsulfonyl and arylsulfonyl, or $R^{15}$ and $R^{16}$ together with the atom to which they are attached form a heterocycle;

$R^{17}$ is selected from the group consisting of hydrogen, alkyl, carboxyalkyl, cycloalkyl, carboxycycloalkyl, aryl, arylalkyl, aryloxyalkyl, heteroaryl, heteroarylalkyl, heteroaryloxyalkyl, heterocycle, heterocyclealkyl and heterocycleoxyalkyl;

$R^{18}$ and $R^{19}$ are each independently selected from the group consisting of hydrogen, alkoxy, alkyl, alkylsufonyl, carboxy, carboxyalkyl, carboxycycloalkyl, cycloalkyl, cycloalkyloxy, cycloalkylsulfonyl, aryl, arylalkyl, aryloxy, aryloxyalkyl, arylsulfonyl, heteroaryl, heteroarylalkyl, heteroaryloxyalkyl, heteroarylsulfonyl, heterocycle, heterocyclealkyl, heterocycleoxyalkyl, heterocycleoxy, heterocyclesulfonyl and hydroxy, or $R^{18}$ and $R^{19}$ together with the atom to which they are attached form a heterocycle;

$R^{20}$, $R^{21}$ and $R^{22}$ are each independently selected from the group consisting of hydrogen, alkyl, aryl, arylalkyl, carboxyalkyl, carboxycycloalkyl, cycloalkyl, haloalkyl, heteroaryl, heteroarylalkyl, heterocycle and heterocyclealkyl;

$R^{23}$ and $R^{24}$ are each independently selected from the group consisting of hydrogen, alkyl, alkylcarbonyl, alkylsulfonyl, aryl, arylcarbonyl, arylsulfonyl, carboxyalkyl, carboxycycloalkyl, cycloalkyl, cycloalkylcarbonyl, cycloalkylsulfonyl, heteroaryl, heteroarylcarbonyl, heteroarylsulfonyl, heterocycle, heterocyclecarbonyl and heterocyclesulfonyl;

$R^{25}$ and $R^{26}$ are each independently selected from the group consisting of hydrogen, alkoxy, alkyl, alkylcarbonyl, alkylsulfonyl, aryl, arylcarbonyl, aryloxy, arylsulfonyl, carboxyalkyl, carboxycycloalkyl, cycloalkyl, cycloalkylcarbonyl, cycloalkyloxy, cycloalkylsulfonyl, heteroaryl, heteroarylcarbonyl, heteroaryloxy, heteroarylsulfonyl, heterocycle, heterocyclecarbonyl, heterocycleoxy, heterocyclesulfonyl and hydroxy, or $R^{25}$ and $R^{26}$ together with the nitrogen to which they are attached form a ring selected from the group consisting of heteroaryl and heterocycle;

$R^{27}$ and $R^{28}$ are each independently selected from the group consisting of hydrogen, alkyl, aryl, cycloalkyl, heteroaryl and heterocycle or $R^{27}$ and $R^{28}$ together with the atom to which they are attached form a ring selected from the group consisting of cycloalkyl and heterocycle, or $R^{27}$ and $R^{29}$ together with the atoms to which they are attached form a ring selected from the group consisting of cycloalkyl and heterocycle, or $R^{28}$ and $R^4$ together with the atoms to which they are attached form a ring selected from the group consisting of cycloalkyl and heterocycle;

$R^{29}$ and $R^{30}$ are each independently selected from the group consisting of hydrogen, alkyl, alkoxy, aryl, aryloxy, cycloalkyl, cycloalkyloxy, heteroaryl, heterocycle, and —N($R^{36}R^{37}$), or $R^{29}$ and $R^{30}$ together with the atom to which they are attached form a ring selected from the group consisting of cycloalkyl and heterocycle, or $R^{29}$ and $R^4$ together with the atoms to which they are attached form a ring selected from the group consisting of cycloalkyl and heterocycle, or $R^{29}$ and E together with the atoms to which they are attached form a ring selected from the group consisting of cycloalkyl and heterocycle;

$R^{31}$ is selected from the group consisting of hydrogen, alkyl, aryl, cycloalkyl, heterocycle and heteroaryl, or $R^{31}$ and E together with the atom to which they are attached form a ring selected from the group consisting of heteroaryl and heterocycle, or $R^{31}$ and $R^4$ together with the atoms to which they are attached form a heterocycle;

$R^{32}$ and $R^{33}$ are each independently selected from the group consisting of hydrogen, alkyl, carboxy, carboxyalkyl, cycloalkyl, cycloalkyloxy, carboxycycloalkyl, aryl, arylalkyl, aryloxy, aryloxyalkyl, heterocycle, heterocyclealkyl, heterocycleoxyalkyl, heterocycleoxy, hydroxy, alkoxy, alkylsufonyl, cycloalkylsulfonyl, arylsulfonyl, and heterocyclesulfonyl, or $R^{32}$ and $R^{33}$ together with the atom to which they are attached form a heterocycle;

$R^{34}$ and $R^{35}$ are each independently selected from the group consisting of hydrogen, alkyl, carboxy, carboxyalkyl, cycloalkyl, cycloalkyloxy, carboxycycloalkyl, aryl, arylalkyl, aryloxy, aryloxyalkyl, heterocycle, heterocyclealkyl, heterocycleoxyalkyl, heterocycleoxy, hydroxy, alkoxy, alkylsufonyl, cycloalkylsulfonyl, arylsulfonyl, and heterocyclesulfonyl, or $R^{34}$ and $R^{35}$ together with the atom to which they are attached form a heterocycle; and $R^{36}$ and $R^{37}$ are each independently selected from the group consisting of hydrogen, alkyl and aryl.

2. The method according to claim 1, wherein the inhibitor is a therapeutically suitable metabolite of a compound of formula (I).

3. The method according to claim 1, wherein the inhibitor is a compound selected from the group consisting of:
E-4-{[1-(4-chloro-phenyl)-cyclobutanecarbonyl]-amino}-adamantane-1-carboxylic acid;
E-4-[(1-phenyl-cyclopropanecarbonyl)-amino]-adamantane-1-carboxylic acid;
E-4-(2-methyl-2-phenyl-propionylamino)-adamantane-1-carboxylic acid;
E-4-{[1-(4-Chloro-phenyl)-cyclobutanecarbonyl]-amino}-adamantane-1-carboxylic acid amide;
E-4-[(1-phenyl-cyclopropanecarbonyl)-amino]-adamantane-1-carboxylic acid amide;
E-4-(2-Methyl-2-phenyl-propionylamino)-adamantane-1-carboxylic acid amide;
E-4-({[1-(4-chlorophenyl)cyclohexyl]carbonyl}amino)adamantane-1-carboxamide;
E-4-({[1-(4-chlorophenyl)cyclopropyl]carbonyl}amino)adamantane-1-carboxamide;
E-4-({[1-(4-chlorophenyl)cyclopentyl]carbonyl}amino)adamantane-1-carboxamide;
E-4-{[2-(4-chlorophenyl)-2-methylpropanoyl]amino}adamantane-1-carboxamide;
E-4-{[(1-phenylcyclopentyl)carbonyl]amino}adamantane-1-carboxamide;
E-4-({[1-(3-fluorophenyl)cyclopentyl]carbonyl}amino)adamantane-1-carboxamide;
E-4-({[1-(2-chloro-4-fluorophenyl)cyclopentyl]carbonyl}amino)adamantane-1-carboxamide;
E-4-({[1-(4-fluorophenyl)cyclopentyl]carbonyl}amino)adamantane-1-carboxamide;
E-4-({[1-(2-fluorophenyl)cyclopentyl]carbonyl}amino)adamantane-1-carboxamide;
E-4-{[(1-methylcyclohexyl)carbonyl]amino}adamantane-1-carboxamide;
E-4-({[1-(2,4-dichlorophenyl)cyclopropyl]carbonyl}amino)adamantane-1-carboxamide;

E-4-({[1-(4-methoxyphenyl)cyclopropyl]
carbonyl}amino)adamantane-1-carboxamide;
E-4-({[1-(4-methylphenyl)cyclopropyl]carbonyl}amino)
adamantane-1-carboxamide;
E-4-{[2-methyl-2-(4-pyridin-4-ylphenyl)propanoyl]
amino}adamantane-1-carboxamide;
E-4-[(2-methyl-2-thien-2-ylpropanoyl)amino]adamantane-1-carboxamide;
E-4-[(2-methyl-2-thien-3-ylpropanoyl)amino]adamantane-1-carboxamide;
E-4-({2-methyl-2-[5-(trifluoromethyl)pyridin-2-yl]
propanoyl}amino)adamantane-1-carboxamide;
E-4-[(2-methyl-2-{4-[5-(trifluoromethyl)pyridin-2
yl]phenyl}propanoyl)amino]adamantane-1-carboxamide;
E-4-({[1-(4-methoxyphenyl)cyclopentyl]
carbonyl}amino)adamantane-1-carboxamide;
E-4-{[2-(4-bromophenyl)-2-methylpropanoyl]
amino}adamantane-1-carboxamide;
E-4-[5-(aminocarbonyl)-2-adamantyl]-3-methyl-1-(2-
methylbenzyl)-2-oxopiperidine-3-carboxamide;
E-4-(aminocarbonyl)-2-adamantyl]-1-benzyl-3-methyl-
2-oxopyrrolidine-3-carboxamide;
E-4-(aminocarbonyl)-2-adamantyl]-3-methyl-1-(2-methylbenzyl)-2-oxopyrrolidine-3-carboxamide;
E-4-(aminocarbonyl)-2-adamantyl]-1-(2-chlorobenzyl)-
3-methyl-2-oxopyrrolidine-3-carboxamide;
E-4-(aminocarbonyl)-2-adamantyl]-1-(3-chlorobenzyl)-
3-methyl-2-oxopyrrolidine-3-carboxamide;
E-4-({2-methyl-2-[4-(1-methyl-1H-pyrazol-4-yl)phenyl]
propanoyl}amino)adamantane-1-carboxamide;
E-4-{[2-(3-bromophenyl)-2-methylpropanoyl]
amino}adamantane-1-carboxamide;
E-4-({2-[4-(3,5-dimethylisoxazol-4-yl)phenyl]-2-
methylpropanoyl}amino)adamantane-1-carboxamide;
E-4-{[2-methyl-2-(4-pyridin-3-ylphenyl)propanoyl]
amino}adamantane-1-carboxamide;
4-{[({(E)-4-[(2-methyl-2-thien-2-ylpropanoyl)amino]-1-
adamantyl}carbonyl)amino]methyl}benzoic acid;
E-4-({2-methyl-2-[4-(1H-pyrazol-4-yl)phenyl]
propanoyl}amino)adamantane-1-carboxamide;
E-4-(aminocarbonyl)-2-adamantyl]-3-methyl-1-(1-methyl-1-phenylethyl)-2-oxopyrrolidine-3-carboxamide;
E-4-(aminocarbonyl)-2-adamantyl]-3-methyl-2-oxo-1-
[(1R)-1-phenylethyl]pyrrolidine-3-carboxamide;
E-4-(aminocarbonyl)-2-adamantyl]-3-methyl-2-oxo-1-
[(1S)-1-phenylethyl]pyrrolidine-3-carboxamide;
E-4-{[2-methyl-2-(1,3-thiazol-2-yl)propanoyl]
amino}adamantane-1-carboxamide;
E-4-(aminocarbonyl)-2-adamantyl]-1-(4-chlorobenzyl)-
3-methylpiperidine-3-carboxamide;
E-4-{[2-(4-hydroxyphenyl)-2-methylpropanoyl]
amino}adamantane-1-carboxamide;
E-4-(aminocarbonyl)-2-adamantyl]-1-benzyl-3-methyl-
2-oxopiperidine-3-carboxamide;
E-4-{[2-methyl-2-(4-phenoxyphenyl)propanoyl]
amino}adamantane-1-carboxamide;
E-4-{[2-(1-benzothien-3-yl)-2-methylpropanoyl]
amino}adamantane-1-carboxamide;
E-4-{[2-(5-fluoropyridin-2-yl)-2-methylpropanoyl]
amino}adamantane-1-carboxamide;
E-4-[(2-methyl-2-quinoxalin-2-ylpropanoyl)amino]adamantane-1-carboxamide;
(E)-4-[(2-methyl-2-pyrazin-2-ylpropanoyl)amino]adamantane-1-carboxamide;
N-[(E)-5-(aminocarbonyl)-2-adamantyl]-3-methyl-2-
oxo-1-(2-pyridin-2-ylethyl) pyrrolidine-3-carboxamide;
methyl(E)-4-[(2-methyl-2-phenylpropanoyl)amino]adamantane-1-carboxylate;
(E)-4-({2-methyl-2-[3-(1,3-thiazol-4-ylmethoxy)phenyl]
propanoyl}amino)adamantane-1-carboxamide;
(E)-4-({2-methyl-2-[6-(methylamino)pyridin-3-yl]
propanoyl}amino)adamantane-1-carboxamide;
(E)-4-({2-methyl-2-[3-(morpholin-4-ylmethyl)phenyl]
propanoyl}amino)adamantane-1-carboxamide;
(E)-4-({2-methyl-2-[4-(trifluoromethyl)pyridin-2-yl]
propanoyl}amino)adamantane-1-carboxamide;
(E)-4-[(2-{3-[2-(1H-imidazol-1-yl)ethoxy]phenyl}-2-
methylpropanoyl)amino]adamantane-1-carboxamide;
methyl(E)-4-{[(1-phenylcyclopropyl)carbonyl]
amino}adamantane-1-carboxylate;
(E)-4-{[2-(6-fluoropyridin-3-yl)-2-methylpropanoyl]
amino}adamantane-1-carboxamide;
(E)-N-[3-(aminocarbonyl)benzyl]-4-[(2-methyl-2-phenylpropanoyl)amino]adamantane-1-carboxamide;
N-[(E)-5-(aminocarbonyl)-2-adamantyl]-1-(2-chlorobenzyl)-3-methyl-2-oxopiperidine-3-carboxamide;
N-[(E)-5-(aminocarbonyl)-2-adamantyl]-3-methyl-2-
oxo-1-(pyridin-4-ylmethyl) pyrrolidine-3-carboxamide;
(E)-4-{[2-methyl-2-(4-phenoxyphenyl)propanoyl]
amino}adamantane-1-carboxylic acid;
N-[(E)-5-(aminosulfonyl)-2-adamantyl]-1-phenylcyclopropanecarboxamide;
(E)-4-({3-[(5-cyanopyridin-2-yl)oxy]-2,2-
dimethylpropanoyl}amino)adamantane-1-carboxamide;
N-[(E)-5-(aminocarbonyl)-2-adamantyl]-3-methyl-2-
oxo-1-(1-pyridin-2-ylethyl)pyrrolidine-3-carboxamide;
(E)-4-[(2-methyl-3-phenylpropanoyl)amino]adamantane-1-carboxamide;
(E)-4-{[2-methyl-2-(6-morpholin-4-ylpyridin-3-yl)propanoyl]amino}adamantane-1-carboxamide;
methyl(E)-4-({[1-(4-chlorophenyl)cyclobutyl]
carbonyl}amino)adamantane-1-carboxylate;
N-[(E)-5-(aminocarbonyl)-2-adamantyl]-3-methyl-2-
oxo-1-(pyridin-3-ylmethyl)pyrrolidine-3-carboxamide;
(E)-4-[(2-methyl-2-{6-[(2-morpholin-4-ylethyl)amino]
pyridin-3-yl}propanoyl)amino]adamantane-1-carboxamide;
(E)-4-[(2-methyl-2-{4-[(E)-2-pyridin-4-ylvinyl]
phenyl}propanoyl)amino]adamantane-1-carboxamide;
N-[(E)-5-(aminosulfonyl)-2-adamantyl]-2-(4-chlorophenyl)-2-methylpropanamide;
(E)-4-({2-methyl-2-[3-(2-morpholin-4-ylethoxy)phenyl]
propanoyl}amino)adamantane-1-carboxamide;
(E)-4-{[2-(3-cyanopyridin-2-yl)-2-methylpropanoyl]
amino}adamantane-1-carboxamide;
(E)-4-({2-methyl-2-[6-(4-methylpiperazin-1-yl)pyridin-
3-yl]propanoyl}amino) adamantane-1-carboxamide;
N-[(E)-5-(aminocarbonyl)-2-adamantyl]-3-methyl-2-
oxo-1-(pyridin-2-ylmethyl) pyrrolidine-3-carboxamide;
(E)-N-[4-(aminosulfonyl)benzyl]-4-[(2-methyl-2-phenylpropanoyl)amino]adamantane-1-carboxamide;
(E)-4-({2-methyl-2-[4-(pentyloxy)phenyl]
propanoyl}amino)adamantane-1-carboxylic acid;
(E)-4-({2-methyl-2-[4-(1,3-thiazol-4-ylmethoxy)phenyl]
propanoyl}amino)adamantane-1-carboxylic acid;

(E)-4-[(2-methyl-2-phenylpropanoyl)amino]-N-(1,3-thia-zol-5-ylmethyl)adamantane-1-carboxamide;
(E)-4-({2-[4-(benzyloxy)phenyl]-2-methylpropanoyl}amino)adamantane-1-carboxylic acid;
(E)-4-{[2-(5-cyanopyridin-2-yl)-2-methylpropanoyl]amino}adamantane-1-carboxamide;
(E)-4-{[2-(4-chlorophenyl)-2-methylpropanoyl]amino}adamantane-1-carboxylic acid;
4-[({[(E)-4-({2-methyl-2-[5-(trifluoromethyl)pyridin-2-yl]propanoyl}amino)-1-adamantyl]carbonyl}amino)methyl]benzoic acid;
4-{[({(E)-4-[(2-methyl-2-phenylpropanoyl)amino]-1-adamantyl}carbonyl)amino]methyl}benzoic acid;
3-{[({(E)-4-[(2-methyl-2-phenylpropanoyl)amino]-1-adamantyl}carbonyl)amino]methyl}benzoic acid;
(E)-4-({[1-(4-methylphenyl)cyclopropyl]carbonyl}amino)adamantane-1-carboxylic acid;
(E)-4-[(2-methyl-2-phenylpropanoyl)amino]-N-(pyridin-4-ylmethyl)adamantane-1-carboxamide;
(E)-4-({[1-(2,4-dichlorophenyl)cyclopropyl]carbonyl}amino)adamantane-1-carboxylic acid;
(E)-N-(2-furylmethyl)-4-[(2-methyl-2-phenylpropanoyl)amino]adamantane-1-carboxamide;
3-[(E)-4-({2-methyl-2-[5-(trifluoromethyl)pyridin-2-yl]propanoyl}amino)-1-adamantyl]-1H-pyrazole-5-carboxamide;
(E)-4-[(2-methyl-2-phenylpropanoyl)amino]-N-(pyridin-3-ylmethyl)adamantane-1-carboxamide;
(E)-4-[(2-methyl-2-phenylpropanoyl)amino]-N-(pyridin-2-ylmethyl)adamantane-1-carboxamide;
(E)-4-({2-[4-(cyclohexylmethoxy)phenyl]-2-methylpropanoyl}amino)adamantane-1-carboxylic acid;
(E)-4-[(2-methyl-2-{4-[5-(trifluoromethyl)pyridin-2-yl]phenyl}propanoyl)amino]adamantine-1-carboxylic acid; and
N-[(E)-5-(aminosulfonyl)-2-adamantyl]-1-(2-chlorobenzyl)-3-methyl-2-oxopyrrolidine-3-carboxamide;
or a pharmaceutically acceptable salt, or a combination thereof.

4. The method of claim 1, wherein the patient is a mammal.

5. The method of claim 4, wherein the disorder is mediated by excessive glucocorticoid action in the mammal.

6. The method of claim 4, wherein the disorder is decline in cognitive function in Alzheimer's disease.

7. The method of claim 4, wherein the disorder is attention deficit disorder in general, attention deficit hyperactivity disorder (ADHD), or mild cognitive impairment.

8. The method of claim 4, wherein the disorder is schizophrenia.

9. A method for treating a patient suffering from a disorder selected from the group consisting of non insulin dependent type 2 diabetes, insulin resistance, obesity, metabolic syndrome, hypertension, anxiety, major depressive disorder, psychotic depression, treatment resistant depression, panic disorder, post traumatic stress disorder, depression in Cushing's syndrome, cognitive deficits associated with diabetes and cognitive deficits associated with aging, and combinations thereof, comprising administering to the patient an effective amount of a selective inhibitor of 11-beta-hydroxysteroid dehydrogenase Type 1 enzyme activity, wherein said inhibitor is a compound of formula (I), or a pharmaceutically acceptable salt, or a combination thereof,

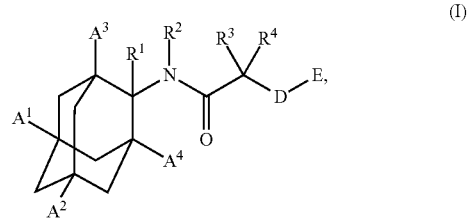

wherein
one of $A^1$, $A^2$, $A^3$ and $A^4$ is selected from the group consisting of alkyl-NH-alkyl, alkylcarbonyl, alkylsulfonyl, cycloalkyl, cycloalkylcarbonyl, cycloalkylsulfonyl, arylcarbonyl, arylsulfonyl, heteroaryl, heteroarylalkyl, heteroaryloxyalkyl, heterocyclecarbonyl, heterocyclesulfonyl, aryl, arylalkyl, aryloxyalkyl, carboxyalkyl, carboxycycloalkyl, haloalkyl, heterocyclealkyl, heterocycleoxyalkyl, $-S(O)_2-N(R^5R^6)$, $-NR^7-[C(R^8R^9)]_N-C(O)-R^{10}$, $-O-[C(R^{11}R^{12})]_p-C(O)-R^{13}$, $-OR^{14a}$, $-N(R^{15}R^{16})$, $-CO_2R^{17}$, $-C(O)-N(R^{18}R^{19})$, $-C(R^{20}R^{21})-OR^{22}$, $-C(R^{23}R^{24})-N(R^{25}R^{26})$, and heterocycle, with the exception that 5 membered heterocycles may not contain two oxygen atoms, and the remaining members of the group consisting of $A^1$, $A^2$, $A^3$ and $A^4$ are each individually selected from the group consisting of hydrogen, alkyl, alkyl-NH-alkyl, alkylcarbonyl, alkylsulfonyl, cycloalkyl, cycloalkylcarbonyl, cycloalkylsulfonyl, arylcarbonyl, arylsulfonyl, heterocyclecarbonyl, heterocyclesulfonyl, aryl, arylalkyl, aryloxyalkyl, carboxyalkyl, carboxycycloalkyl, halogen, haloalkyl, heteroaryl, heteroarylalkyl, heteroaryloxyalkyl, heterocycle, heterocyclealkyl, heterocycleoxyalkyl, $-S(O)_2-N(R^5R^6)$, $-NR^7-[C(R^8R^9)]_n-C(O)-R^{10}$, $-O-[C(R^{11}R^{12})]_p-C(O)-R^{13}$, $-OR^{14b}$, $-N(R^{15}R^{16})$, $-CO_2R^{17}$, $-C(O)-N(R^{18}R^{19})$, $-C(R^{20}R^{21})-OR^{22}$, and $-C(R^{23}R^{24})-N(R^{25}R^{26})$;

n is 0 or 1;

p is 0 or 1;

D is selected from the group consisting of a bond, $-C(R^{27}R^{28})-X-$ and $-C(R^{27}R^{28})-C(R^{29}R^3)-X-$;

E is selected from the group consisting of cycloalkyl, alkyl, aryl, heteroaryl and heterocycle, wherein the heteroaryl is appended to the parent molecular moiety through an available carbon atom, or $R^4$ and E together with the atoms to which they are attached form a ring selected from the group consisting of cycloalkyl and heterocycle;

X is selected from the group consisting of a bond, $-N(R^{31})-$, $-O-$, $-S-$, $-S(O)-$ and $-S(O)_2-$;

$R^1$ is selected from the group consisting of hydrogen and alkyl;

$R^2$ is selected from the group consisting of hydrogen, alkyl and cycloalkyl;

$R^3$ and $R^4$ are each independently selected from the group consisting of hydrogen, alkyl, carboxyalkyl, carboxycycloalkyl, cycloalkyl, haloalkyl, aryl, arylalkyl, heteroaryl, heteroarylalkyl, heterocycle and heterocyclealkyl, or $R^3$ and $R^4$ together with the atom to which they are attached form a ring selected from the group consisting of cycloalkyl and heterocycle;

$R^5$ and $R^6$ are each independently selected from the group consisting of hydrogen, alkoxy, alkyl, alkylcarbonyl, alkylsufonyl, carboxy, carboxyalkyl, carboxycycloalkyl, cycloalkyl, cycloalkyloxy, cycloalkylsulfonyl, aryl, arylalkyl, arylalkylcarbonyl, arylcarbonyl, aryloxy, aryloxyalkyl, arylsulfonyl, heteroaryl, heteroarylalkyl, heteroarylalkylcarbonyl, heteroarylcarbonyl, heteroaryloxyalkyl, heteroarylsulfonyl, heterocycle, heterocyclealkyl, heterocyclealkylcarbonyl, heterocyclecarbonyl, heterocycleoxyalkyl, heterocycleoxy, heterocyclesulfonyl and hydroxy, or $R^5$ and $R^6$ together with the atom to which they are attached form a heterocycle;

$R^7$ is selected from the group consisting of hydrogen, alkyl, carboxyalkyl, cycloalkyl, carboxycycloalkyl, aryl, arylalkyl, aryloxyalkyl, hydroxy, alkoxy, heteroaryl, heteroarylalkyl, heteroaryloxyalkyl, heterocycle, heterocyclealkyl and heterocycleoxyalkyl;

$R^8$ and $R^9$ are each independently selected from the group consisting of hydrogen and alkyl, or $R^8$ and $R^9$ taken together with the atom to which they are attached form a ring selected from the group consisting of cycloalkyl and heterocycle;

$R^{10}$ is selected from the group consisting of hydrogen, alkyl, carboxyalkyl, cycloalkyl, carboxycycloalkyl, aryl, arylalkyl, aryloxy, aryloxyalkyl, hydroxy, alkoxy, cycloalkyloxy, heteroaryl, heteroarylalkyl, heteroaryloxy, heteroaryloxyalkyl, heterocycle, heterocyclealkyl, heterocycleoxy, heterocycleoxyalkyl and —$N(R^{32}R^{33})$;

$R^{11}$ and $R^{12}$ are each independently selected from the group consisting of hydrogen and alkyl or $R^{11}$ and $R^{12}$ taken together with the atom to which they are attached form a ring selected from the group consisting of cycloalkyl and heterocycle;

$R^{13}$ is selected from the group consisting of hydroxy and —$N(R^{34}R^{35})$;

$R^{14a}$ is selected from the group consisting of carboxyalkyl, cycloalkyl, carboxycycloalkyl, aryl, arylalkyl, aryloxyalkyl, haloalkyl, heteroaryl, heteroarylalkyl, heteroaryloxyalkyl, heterocycle, heterocyclealkyl and heterocycleoxyalkyl;

$R^{14b}$ is selected from the group consisting of hydrogen, alkyl, carboxyalkyl, cycloalkyl, carboxycycloalkyl, aryl, arylalkyl, aryloxyalkyl, haloalkyl, heteroaryl, heteroarylalkyl, heteroaryloxyalkyl, heterocycle, heterocyclealkyl and heterocycleoxyalkyl;

$R^{15}$ and $R^{16}$ are each independently selected from the group consisting of hydrogen, alkyl, alkylcarbonyl, carboxyalkyl, cycloalkyl, carboxycycloalkyl, aryl, arylalkyl, arylalkylcarbonyl, arylcarbonyl, aryloxyalkyl, heteroaryl, heteroarylalkyl, heteroarylalkylcarbonyl, heteroarylcarbonyl, heteroaryloxyalkyl, heteroarylsulfonyl, heterocycle, heterocyclealkyl, heterocyclealkylcarbonyl, heterocyclecarbonyl, heterocycleoxyalkyl, heterocyclesulfonyl, alkylsufonyl, cycloalkylsulfonyl and arylsulfonyl, or $R^{15}$ and $R^{16}$ together with the atom to which they are attached form a heterocycle;

$R^{17}$ is selected from the group consisting of hydrogen, alkyl, carboxyalkyl, cycloalkyl, carboxycycloalkyl, aryl, arylalkyl, aryloxyalkyl, heteroaryl, heteroarylalkyl, heteroaryloxyalkyl, heterocycle, heterocyclealkyl and heterocycleoxyalkyl;

$R^{18}$ and $R^{19}$ are each independently selected from the group consisting of hydrogen, alkoxy, alkyl, alkylsufonyl, carboxy, carboxyalkyl, carboxycycloalkyl, cycloalkyl, cycloalkyloxy, cycloalkylsulfonyl, aryl, arylalkyl, aryloxy, aryloxyalkyl, arylsulfonyl, heteroaryl, heteroarylalkyl, heteroaryloxyalkyl, heteroarylsulfonyl, heterocycle, heterocyclealkyl, heterocycleoxyalkyl, heterocycleoxy, heterocyclesulfonyl and hydroxy, or $R^{18}$ and $R^{19}$ together with the atom to which they are attached form a heterocycle;

$R^{20}$, $R^{21}$ and $R^{22}$ are each independently selected from the group consisting of hydrogen, alkyl, aryl, arylalkyl, carboxyalkyl, carboxycycloalkyl, cycloalkyl, haloalkyl, heteroaryl, heteroarylalkyl, heterocycle and heterocyclealkyl;

$R^{23}$ and $R^{24}$ are each independently selected from the group consisting of hydrogen, alkyl, alkylcarbonyl, alkylsulfonyl, aryl, arylcarbonyl, arylsulfonyl, carboxyalkyl, carboxycycloalkyl, cycloalkyl, cycloalkylcarbonyl, cycloalkylsulfonyl, heteroaryl, heteroarylcarbonyl, heteroarylsulfonyl, heterocycle, heterocyclecarbonyl and heterocyclesulfonyl;

$R^{25}$ and $R^{26}$ are each independently selected from the group consisting of hydrogen, alkoxy, alkyl, alkylcarbonyl, alkylsulfonyl, aryl, arylcarbonyl, aryloxy, arylsulfonyl, carboxyalkyl, carboxycycloalkyl, cycloalkyl, cycloalkylcarbonyl, cycloalkyloxy, cycloalkylsulfonyl, heteroaryl, heteroarylcarbonyl, heteroaryloxy, heteroarylsulfonyl, heterocycle, heterocyclecarbonyl, heterocycleoxy, heterocyclesulfonyl and hydroxy, or $R^{25}$ and $R^{26}$ together with the nitrogen to which they are attached form a ring selected from the group consisting of heteroaryl and heterocycle;

$R^{27}$ and $R^{28}$ are each independently selected from the group consisting of hydrogen, alkyl, aryl, cycloalkyl, heteroaryl and heterocycle or $R^{27}$ and $R^{28}$ together with the atom to which they are attached form a ring selected from the group consisting of cycloalkyl and heterocycle, or $R^{27}$ and $R^{29}$ together with the atoms to which they are attached form a ring selected from the group consisting of cycloalkyl and heterocycle, or $R^{28}$ and $R^4$ together with the atoms to which they are attached form a ring selected from the group consisting of cycloalkyl and heterocycle;

$R^{29}$ and $R^{30}$ are each independently selected from the group consisting of hydrogen, alkyl, alkoxy, aryl, aryloxy, cycloalkyl, cycloalkyloxy, heteroaryl, heterocycle, and —$N(R^{36}R^{37})$, or $R^{29}$ and $R^{30}$ together with the atom to which they are attached form a ring selected from the group consisting of cycloalkyl and heterocycle, or $R^{29}$ and $R^4$ together with the atoms to which they are attached form a ring selected from the group consisting of cycloalkyl and heterocycle, or $R^{29}$ and E together with the atoms to which they are attached form a ring selected from the group consisting of cycloalkyl and heterocycle;

$R^{31}$ is selected from the group consisting of hydrogen, alkyl, aryl, cycloalkyl, heterocycle and heteroaryl, or $R^{31}$ and E together with the atom to which they are attached form a ring selected from the group consisting of heteroaryl and heterocycle, or $R^{31}$ and $R^4$ together with the atoms to which they are attached form a heterocycle;

$R^{32}$ and $R^{33}$ are each independently selected from the group consisting of hydrogen, alkyl, carboxy, carboxyalkyl, cycloalkyl, cycloalkyloxy, carboxycycloalkyl, aryl, arylalkyl, aryloxy, aryloxyalkyl, heterocycle, heterocyclealkyl, heterocycleoxyalkyl, heterocycleoxy, hydroxy, alkoxy, alkylsufonyl, cycloalkylsulfonyl, arylsulfonyl, and heterocyclesulfonyl, or $R^{32}$ and $R^{33}$ together with the atom to which they are attached form a heterocycle;

$R^{34}$ and $R^{35}$ are each independently selected from the group consisting of hydrogen, alkyl, carboxy, carboxyalkyl, cycloalkyl, cycloalkyloxy, carboxycycloalkyl, aryl, arylalkyl, aryloxy, aryloxyalkyl, heterocycle, heterocyclealkyl, heterocycleoxyalkyl, heterocycleoxy, hydroxy, alkoxy, alkylsufonyl, cycloalkylsulfonyl, arylsulfonyl, and heterocyclesulfonyl, or $R^{34}$ and $R^{35}$ together with the atom to which they are attached form a heterocycle; and $R^{36}$ and $R^{37}$ are each independently selected from the group consisting of hydrogen, alkyl and aryl.

10. The method according to claim 9, wherein the inhibitor is a compound selected from the group consisting of:

E-4-[(2-methyl-2-thien-2-ylpropanoyl)amino]adamantane-1-carboxamide;

E-4-[(2-methyl-2-thien-3-ylpropanoyl)amino]adamantane-1-carboxamide;

E-4-({2-methyl-2-[5-(trifluoromethyl)pyridin-2-yl]propanoyl}amino)adamantane-1-carboxamide;

4-{[({(E)-4-[(2-methyl-2-thien-2-ylpropanoyl)amino]-1-adamantyl}carbonyl)amino]methyl}benzoic acid;

E-4-{[2-methyl-2-(1,3-thiazol-2-yl)propanoyl]amino}adamantane-1-carboxamide;

E-4-{[2-(1-benzothien-3-yl)-2-methylpropanoyl]amino}adamantane-1-carboxamide;

E-4-{[2-(5-fluoropyridin-2-yl)-2-methylpropanoyl]amino}adamantane-1-carboxamide; and E-4-[(2-methyl-2-quinoxalin-2-ylpropanoyl)amino]adamantane-1-carboxamide;

or a pharmaceutically acceptable salt, or a combination thereof.

11. The method of claim 9, wherein the patient is a mammal.

12. The method of claim 11, wherein the disorder is mediated by excessive glucocorticoid action in a mammal.

13. The method of claim 11, wherein the disorder is selected from the group consisting of non insulin dependent type 2 diabetes, insulin resistance, obesity, metabolic syndrome, and hypertension.

14. The method of claim 11, wherein the disorder is cognitive deficits associated with aging.

15. The method of claim 11, wherein the disorder is depression.

16. The method of claim 15, wherein the depression is major depressive disorder, psychotic depression, depression in Cushing's syndrome, or treatment resistant depression.

17. The method of claim 11, wherein the disorder is anxiety, panic disorder, or post traumatic stress disorder.

18. The method of claim 11, wherein the disorder is cognitive deficits associated with diabetes.

* * * * *